US006120991A

United States Patent [19]
Carter et al.

[11] Patent Number: 6,120,991
[45] Date of Patent: Sep. 19, 2000

[54] EPILIGRIN, AN EPITHELIAL LIGAND FOR INTEGRINS

[75] Inventors: William G. Carter, Bainbridge Island; Susana G. Gil, Seattle; Maureen C. Ryan, Bellevue, all of Wash.

[73] Assignee: Fred Hutchinson Cancer Research Center, Seattle, Wash.

[21] Appl. No.: 08/600,982

[22] PCT Filed: Sep. 2, 1994

[86] PCT No.: PCT/US94/10261

§ 371 Date: Feb. 22, 1996

§ 102(e) Date: Feb. 22, 1996

[87] PCT Pub. No.: WO95/06660

PCT Pub. Date: Mar. 9, 1995

Related U.S. Application Data

[63] Continuation-in-part of application No. 08/115,918, Sep. 2, 1993, abandoned, and a continuation-in-part of application No. 08/292,065, Aug. 17, 1994, abandoned, which is a continuation of application No. 08/154,638, Nov. 18, 1993, abandoned, which is a continuation of application No. 07/654,103, Feb. 8, 1991, abandoned, which is a continuation-in-part of application No. 07/607,137, Oct. 30, 1990, abandoned.

[51] Int. Cl.[7] ..................................................... C12Q 1/68
[52] U.S. Cl. ........................ 435/6; 435/325; 435/320.1; 536/23.5
[58] Field of Search .......................... 435/6, 91.2, 252.3, 435/320.1; 536/23.5, 24.1, 24.33

[56] References Cited

U.S. PATENT DOCUMENTS

| | | | |
|---|---|---|---|
| 4,016,036 | 4/1977 | Green | 195/1.8 |
| 4,304,866 | 12/1981 | Green | 435/240 |
| 4,769,317 | 9/1988 | Hefton | 435/1 |

OTHER PUBLICATIONS

Database, EMBL, Accession L20478, May 5, 1994, Aberdam D., "Mus musculus nicein chain A (NicA) mRNA sequence."

Baudoin, C. et al., "The 150 kDa sub–unit of the basement membrane component nicein is a truncated isoform of laminin chain A," *J. Invest. Dermatol.* 102(4):549, Apr., 1994.

Aberdam, D. et al., "Developmental Expression of Nicein Adhesion Protein (Laminin–5) Subunits Suggests Multiple Morphogenic Roles," *Cell Adhes. and Comm.* 2:115–129, 1994.

Kefalides, N.A., *Int. Rev. Connect. Tissue Res.* 6:63–104, 1973.

Vracko, R., *Am. J. Pathol.* 77:314–338, 1974.

Timpl, R. and Martin, G., In: Immunochemistry of Collagen (Furthmayr, H., Ed.), vol. II, pp. 119–150, CRC Press, Boca Raton, FL, 1982.

Laurie, G.W. and Leblond, C.P., *Histochem. Cytochem.* 31:159–163, 1983.

Yurchenko, P. and Schittny, J.C., *FASEB J.* 4:1577–1590, 1990.

(List continued on next page.)

*Primary Examiner*—Scott W. Houtteman
*Attorney, Agent, or Firm*—Christensen O'Connor Johnson & Kindness PLLC

[57] ABSTRACT

Nucleic acid sequences are disclosed encoding an E170 epithelial ligand and capable of hybridizing under stringent conditions to the nucleotide sequences derived from cDNA clones shown in the figure. Also disclosed are vectors containing the nucleic acid sequences, and cells transformed with the vectors. Methods are given for purifying and utilizing epiligrin, an epithelial glycoprotein complex, and its component glycoproteins, and for raising antibodies against components of this complex. Assay methods are further provided for identification of functional epiligrin in tissues.

8 Claims, 68 Drawing Sheets

OTHER PUBLICATIONS

Orkin, R.W. et al., *J. Exp. Med.* 145:204–220, 1977.
Timpl, R. et al., *J. Biol. Chem.* 254:9933–9937, 1979.
Chung, A.E. et al., *Cell* 16:277–287, 1979.
Carlin, B. et al., *J. Biol. Chem.* 256:5209–5214, 1981.
Kanwar, Y.S. and Farquhar, M.G., *Proc. Natl. Sci., USA*, 76:4493–4497, 1979.
Hassell, J.R. et al., *J. Biol. Chem.* 260:8098–8105, 1985.
Laemmli, U.K., *Nature* 277:680–685, 1970.
Kleinman, H.K. et al., *Biochemistry* 25:312–318, 1986.
Staehlin, L.A., *Int. Rev. Cytol.* 39:191–283, 1974.
Jones, J.C.R. et al., *Cell Motil. and Cytoskeleton* 6:560–569, 1986.
Shienvold, F.L. and Kelly, D.E., *Cell Tissue Res.* 172:289–307, 1976.
Griepp, E.B. and Robbins, E.S., "Epithelium in Cell and Tissue Biology," L. Weiss, Ed.), Urban & Swarzenburg, Inc., Baltimore, MD, 1988.
Burridge, K. et al., *Ann. Rev. Cell Biol.*, 4:487–525, 1988.
Stepp et al., *Proc. Natl. Acad. Sci.* 87:8970–8974, 1990.
Carter, W.G., *J. Cell Biol.* 111:3141–3154, 1990.
Carter, W.G. et al., *J. Cell Biol.*, 110:1387–1404, 1990.
Keene, D.R., et al., *J. Cell Biol.* 104:611–620, 1987.
Keene, et al., *J. Cell Biol.* 104:611–620, 1987.
Sakai, L.Y. et al., *J. Cell Biol.* 103:1577–1586, 1986.
Stanley, J.R., *Clin. Invest.* 94:617–623, 1989.
Tanaka, T. et al., *J. Invest. Dermatol.* 94:617–623, 1990.
Engall, E. et al., *Cell Regulation* 1:731–740, 1990.
Elices, M.J. et al., *J. Cell Biol.* 112:169–181, 1991.
Green, H. et al., *Proc. Nat. Acad. Sci., USA*, 76:5665–5668, 1979.
Rheinwald and H. Green, *Nature* 265:421–424, 1977.
Kamalti, T. et al., *Development* 106:283–293, 1989.
Kamalti, T. et al., *Exp. Cell Res.* 185:453–463, 1989.
Haake, A.R. and Lane, A.T., *In Vitro Develop. Biol.* 25:560–592, 1989.
Pillai, S. et al., *J. Cell Physiol.* 134(2):229–237, 1988.
Wilke, M.S. et al., *J. Natl. Cancer Inst.* 80:1299–1304, 1988.
Adams, J.C. and Watt, F.M., *J. Cell Biol.* 107(5):1927–1938, 1988.
Michel, S. et al., *J. Invest. Dermatol.* 88:301–305, 1987.
Eckert, R.L. and Green, H., *Cell* 46:583–589, 1986.
Eckert, R.L. and Rorke, E.A., *Environ. Health Perspect.* 80:109–116, 1989.
Watt, F.M., *J. Cell Biol.* 98:16–21, 1984.
Murphy, G.F., et al., *J. Invest. Dermatol.* 82:453–457, 1984.
Simon, M. and Green, H., *J. Invest. Dermatol.* 92:721–724, 1989.
Parentau, N.L. et al., *Proc. Natl. Acad. Sci., USA* 84:7571–7575, 1987.
Hronis, T.S. et al., *Cancer Res.* 44:5797–5804, 1984.
Cline, P.R. and Rice, R.H., *Canc. Res.* 43:3203–3207, 1983.
Watt, F.M., *J. Invest. Dermatol.* 81(1 Suppl.):100s–103s, 1983.
Simon, M. and Green, H., *Cell* 36:827–834, 1984.
Simon, M. and Green, H., *Cell* 40:677–683, 1985.
Martin, G. and Timpl, R., *Ann. Rev. Cell Biol.* 3:57–85, 1987.
Beck, K. et al., *FASEB* 4:148–160, 1990.
Hynes, R.O., *Cell* 48:549–554, 1987.
Rouslahti, E., *Ann. Rev. Biochem.* 57:375–413, 1988.
Hemler, M.E., *Immunol. Today* 9:109, 1988.
Buck, C.F. and Horwitz, A.F., *Ann. Rev. Cell Biol.* 3:179–205, 1990.
Tamura, R.N. et al., *J. Cell Biol.* 111:1593–1604, 1990.
Wayner, E.A. et al., *J. Cell Biol.*, 107:1881–1891, 1988.
DeLuca, M. et al., *Proc. Natl. Acad. Sci. USA*, 87:6888–6892, 1990.
Wayner, E.A. and Carter, W.G., *J. Cell Biol.* 105:1873–1884, 1987.
Elices, M.J. and Hemler, M.E., *Proc. Natl. Acad. Sci. USA* 86:9906–9910, 1989.
Lotz, M.M. et al., *Cell Regulation* 1:249–257, 1990.
Sonnenberg, A. et al., *J. Cell Biol.* 110:2145–2155, 1990.
Gehlsen, K.R. et al., *J. Biol. Chem.* 264:19034–19038, 1989.
Adams, J.C. and Watt, F.M., *Cell* 63:425–435, 1990.
Stanely, J.R., *J. Clin. Invest.* 83:1443–1448, 1989.
Kaufmann, R. et al., *J. Cell Biol.* 109:1807–1815, 1989.
Larjava, H. et al., *J. Cell Biol.* 110:803–815, 1990.
Hadley et al., *J. Cell Biol.* 101:1511–1522, 1985.
Carey, D. and Todd, M., unpublished results and L. Reid, unpublished results cited in Kleinman et al., #13, above.
Bernard, B.A. et al., *Canc. Res.* 45:1707–1716, 1985.
Said, J.M. et al., *J. Invest. Dermatol.* 82:449–452, 1984.
Murphy, G.F. et al., *J. Invest. Dermatol.* 82:453–457, 1984.
Levitt, M.L. et al., *Cancer Res.* 50:120–128, 1990.
Peterson, L.L. et al., *J. Invest. Dermatol.* 81(1 Suppl.):45s–100s, 1983.
Kvedar, J.C. et al., *Arch. Pathol. Lab. Med.* 110:183–188, 1986.
Elsayed, A. et al., *Gynecol. Oncol.* 26:25–34, 1987.
Harris, H. and Bramwell, M.E., *J. Cell Sci.* 87:383–388, 1987.
Bernard, B.A. et al., *Br. J. Dermatol.* 112:647–653, 1985.
Schaumberg-Lever, W.F., *J. Invest. Dermatol.* 64:47–49, 1979.
Holubar, K. et al., *J. Invest. Dermatol.* 64:220–225, 1975.
Honigsmann, H., et al., *J. Invest. Dermatol.* 66:262, 1976.
Nieboer, C. et al., *Br. J. Hematol.* 106:419–422, 1983.
Fine, J.D. et al., *J. Invest. Dermatol.* 82:39–43, 1984.
Yaoita, H. et al., *Invest. Dermatol.* 76:288–292, 1981.
Stanley, J.R. et al., *Cell* 24:897–903, 1981.
Nisengard, R.J. et al., *Oral Surgery* 40:365–375, 1975.
Woodley, D.T. et al., *N. Engl. J. Med.* 310:1007–1013, 1984.
Fine, J.D., *J. Invest. Dermatol.* 82:39–43, 1984.
Fine, J.D., *Collagen Rel. Res.* 5:369–377, 1985.
Kaur, P. and McDougall, J.K., *J. Virol.* 62:1917–1924, 1988.
Kaur, P. et al., *J. Gen. Virol.* 70:1261–1266, 1989.
Carter, W.G., *J. Biol. Chem.* 257:13805–13815, 1982.
Oi and L. Herzenberg, In: *Selected Methods in Cellular Immunology* (B.B. Mishell and S.M. Shiigi, Eds.), W.H. Freeman & Co. Publishers, San Francisco, CA, pp. 351–373, 1980.
Taggart and Samloff, *Science* 219:1228–1230, 1983.
Neylakh, A.A. et al., *Exp. Cell Res.* 149:387–396, 1983.
Aumailley, M. et al., *Exp. Cell Res.* 188:55–60, 1990.
Katz, S.I., *J. Amer. Acad. Dermatol.* 11:1025–1037, 1984.
Mar. H. and Wight, T.N., In: *Colloidal Gold: Principles, Methods, and Applications*, vol. 2 (Ed. M.A. Hayat), Acad. Press, Inc., N.Y., 1989.
Boyce, S.T. and Ham, R.G., *J. Tiss. Cult. Meth.* 9:83–93, 1985.
Towbin et al., *Proc. Natl. Acad. Sci. USA* 76:4350–4354, 1979.
Michel, S.R. et al., *J. Invest. Dermatol.* 88:301–305, 1987.
Wolpert, L., *J. Cell Sci.*, Suppl. 10:1–9, 1988.
Plantefaber, L.C. and Hynes, R.O., *Cell* 56:281–290, 1989.
Izzard, C.S. and Lochner, L.R., *J. Cell Sci.* 21:129–159, 1976.

Potten, C.S. and Morris, R.J., *J. Cell Sci.* 10:45–62, 1988.
Hemler, M.E. et al., *J. Biol. Chem.* 264:6529–6535, 1989.
Hemler, M.E. et al., *J. Biol. Chem.* 263:7660–7665, 1988.
Ekblom, P., *FASEB J.* 3:2141–2150, 1989.
Dang, N.H. et al., *J. Exp. Med.* 172:649–652, 1990.
Sanes, J.R. *J. Exp. Med.* 111:1685–1699, 1990.
Hogervorst, F. et al., *EMBO J.* 9:765–770, 1990.
Gordon, J.I., *J. Cell Biol.* 108:1187–1194, 1989.
Sonnenberg, A. et al., *Nature* 336:487–489, 1988.
Tew, J.G. et al., *Immunol. Rev.* 117:185–211, 1990.
Simon, M. and Green, H., "Participation of Membrane–Associated Proteins in the Formation of the Cross–Linked Envelope of the Keratinocyte," *Cell* 36:827–834, 1984.
Simon, M. and Green, H., "Enzymatic Cross–Linking of Involucrin and Other Proteins by Keratinocyte Particulates in Vitro," *Cell* 40:677–683, 1985.
Martin, G. and Timpl, R., "Laminin and Other Basement Membrane Components," *Ann. Rev. Cell Biol.* 3:57–85, 1987.
Hemler, M.E., "Adhesive protein receptors on hematopoietic cells," *Immunol. Today* 9:109–113, 1988.
Carter, W.G. et al., "The Role of Integrins $\alpha 2\beta 1$ and $\alpha 3\beta 1$ in Cell–Cell and Cell–Substrate Adhesion of Human Epidermal Cells," *J. Cell Biol.* 110:1387–1404, 1990.
Carter, W.G. et al., "Epiligrin, a New Cell Adhesion Ligand for Integrin $\alpha 3\beta 1$ in Epithelial Basement Membranes," *Cell* 65:599–610, 1991.
Domloge–Hultsch, N. et al., "Epiligrin, the Major Human Keratinocyte Integrin Ligand, Is a Target in Both an Acquired Autoimmune and an Inherited Subepidermal Blistering Skin Disease," *J. Clin. Invest.* 90:1628–1633, 1992.

Henikoff, S. and Henikoff, J.G., "Amino acid substitution matrices from protein blocks," *Proc. Natl. Acad. Sci. USA* 89:10915–10919, 1992.
Maniatis, T. et al., "Agarose Gel Electrophoresis," In: *Molecular Cloning: A Laboratory Manual*; Cold Spring Harbor Laboratory, Cold Spring Harbor, New Hork, pp 150–185, 382–386, 1982.
Rousselle, P. et al., "Kalinin: An Epithelium–Specific Basement Membrane Adhesion Molecule That Is a Component of Anchoring Filaments," *J. Cell Biol.* 114(3):567–576, 1991.
Sanger, F. et al., "DNA sequencing with chain–terminating inhibitors," *Proc. Natl. Acad. Sci. USA* 74(12):5463–5467, 1977.
Verrando, P. et al., "Monoclonal Antibody GB3, A New Probe for the Study of Human Basement Membranes and Hemidesmosomes," *Exp. Cell. Res.* 170:116–128, 1987.
Verrando, P. et al., "Monoclonal Antibody GB3 Defines a Widespread Defect of Several Basement Membranes and a Keratinocyte Dysfunction in Patients with Lethal Junctional Epidermolysis Bullosa," *Lab. Invest.* 64(1):85–92, 1991.
Wayner, E.A. et al., "Epiligrin, A Component of Epithelial Basement Membranes, Is An Adhesive Ligand for $\alpha 3\beta 1$ Positive T Lymphocytes," *J. Cell Biol.* 121(5):1141–1152, 1993.
Young, R.A. and Davis, R.W., "Efficient isolation of genes by using antibody probes," *Proc. Natl. Acad. Sci. USA* 80:1194–1198, 1983.
Dean et al., *Affinity Chromotography*, IRL Press, 1985.
Creighton, *Protein Function*, IRL Press, 1990.
Enerstein, *J. Investigative Dermatol.* 91:34–38, 1988.

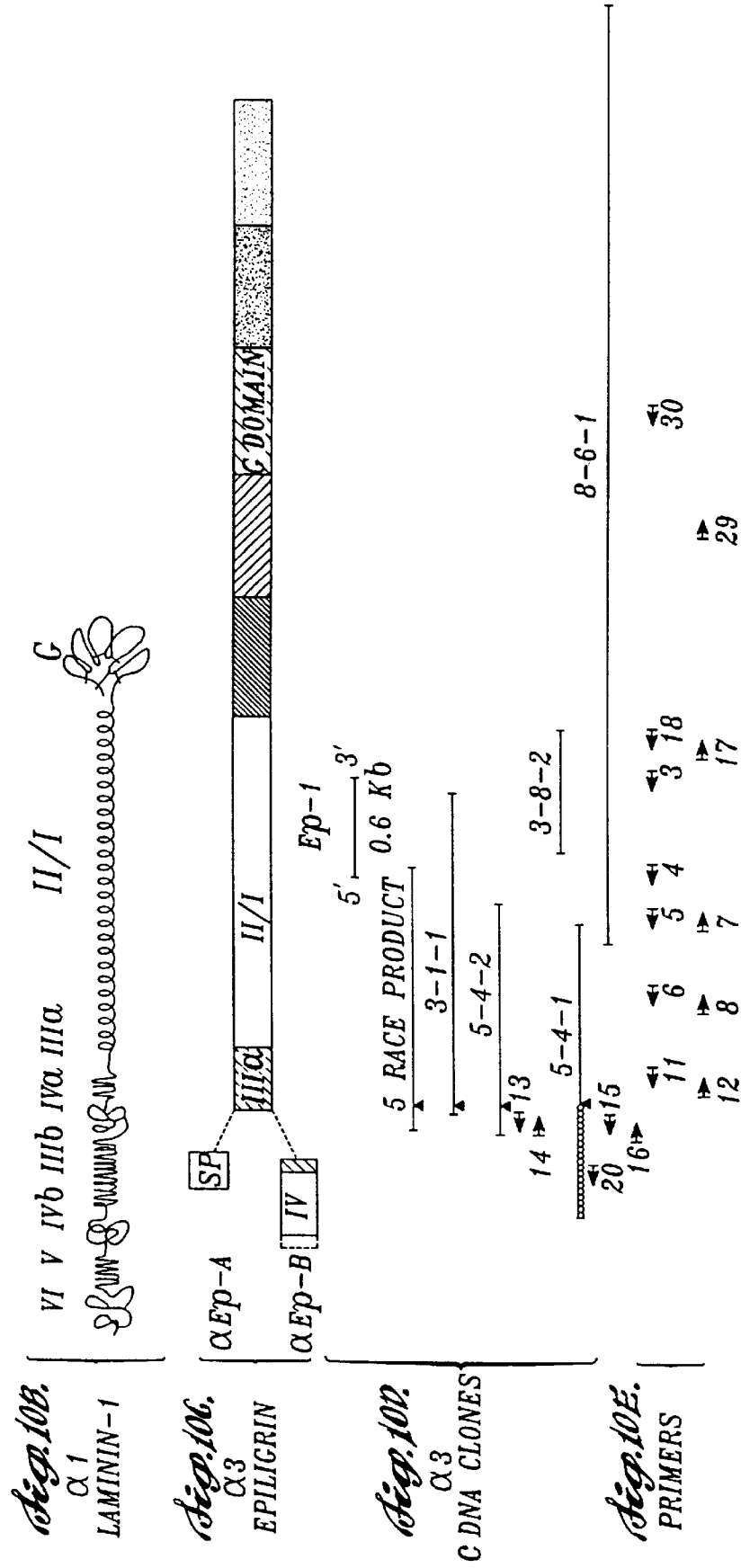

```
CGGGGATGCC TCCAGCAGTG ACCCGGTCAG CCTGCAGCAT GGGATGGCTG TGGATCTTTG   60
GGGCAGCCCT GGGGCAGTGT CTGGGCTACA GTTCACAGCA GCAAAGGGTG CCATTCTTC   120
AGCCTCCCGG TCAAAGTCAA CTGCAAGCGA GTTATGTGGA GTTTAGACCC AGCCAGGGTT  180
GTAGCCCTGG ATACTATCGG GATCATAAAG GCTTGTATAC CGGACGGTGT GTTCCCCTGC  240
AATTGCAACG GACATTCAAA TCAATGCCAG GATGGCTCAG GCATATGTGT TAACTGTCAG  300
CACAACACCG CGGGAGCACT GTCATCGCTG CCAGGAGGGC TACTATGGCA ACGCCGTCCA  360
CGGATCCTGC AGGCCCTGCC CATGTCCTCA CACTAACAGC TTGCCTCTGC CTGTGTGGTG  420
AATGGGGAG ACGTACGGCG CTCCTGCAAA GCTGGGTACA CAGGAACCCA GTGTGTAAGG  480
TGTGCACCGG GATATTTCGG GAATTCGGAG AAATTCGGAA GTAGCTGCCA ACCATGCAGT  540
TGTAACAGCA ATGGCCAGCT GGGCAGCTGT CATCCCCTGA CTGGAGGCTG CATAAACCAA  600
GAAACCAAAG ATAACAACCC TGCAGAAGAA TGTGATGATT GCGACACCTG TGTGATGACC  660
CTCC 664
```

Fig. 10F.

```
CGGGGATGCC TCCAGCAGTG ACCCGGTCAG CCTGCAGCAT GGGATGGCTG TGGATCTTTG   60
GGGCAGCCCT GGGGCAGTGT CTGGGCTACA GTTCACAGCA GCAAAGGGTG CCATTCTTC  120
AGCCTCCCGG TCAAAGTCAA CTGCAAGCGA GTTATGTGGA GTTTAGACCC AGCCAGGGTT  180
GTAGCCCTGG ATACTATCGG GATCATAAAG GCTTGTATAC CGGACGGTGT GTTCCCCTGC  240
AATTGCAACG GACATTCAAA TCAATGCCAG GATGGCTCAG GCATATGTGT TAACTGTCAG  300
CACAACACCG CGGGAGCACT GTCATCGCTG CCAGGAGGGC TACTATGGCA ACGCCGTCCA  360
CGGATCCTGC AGGCCCTGCC CATGTCCTCA CACTAACAGC TTGCCTCTGC CTGTGTGGTG  420
AATGGGGGAG ACGTACGGCG GAATCCCCAG GCTGGGTACA CAGGAACCCA GTGTGTAAGG  480
TGTGCACCGG GATATTTCGG GGGCAGCTGT CATCCCCTGA AAATTCGGAG GTAGCTGCCA ACCATGCAGT  540
TGTAACAGCA ATGGCCAGCT GGGCAGCTGT CATCCCCTGA CATAAACCAA  600
GAAACCAAAG ATAACAACCC TGCAGAAGAA TGTGATGATT GCGACACCTG TGTGATGACC  660
CTCCTGAACG ACCTGGCCAC CATGGGGCGAG CAGCTCCGCC TGGTCAAGTC TCAGCTGCAG  720
```

*Fig. 11A.*

```
GGCCTGAGTG CCAGGCGCAGG GCTTCTGGAG CAGATGAGGC ACATGGAGAC CCAGGCCAAG   780
GACCTGAGGA ATCAGTTGCT CAACTACCGT TCTGCCATTT CAAATCATGG ATCAAAAATA   840
GAAGGCCTGG AAAGAGAACT GACTGATTTG AATCAAGAAT TTGAGACTTT GCAAGAAAAG   900
GCTCAAGTAA ATTCCAGAAA AGCACAAACA TTAAACAACA ATGTTAATCG GGCAACACAA   960
AGCGCAAAAG AACTGGATGT GAAGATTAAA AATGTCATCC GGAATGTGCA CATTCTTTTA  1020
AAGCAGATCT CTGGGACAGA AACAACGTGC GAACTGCGGA CTTCAGGTGA CTTTTCCAGA  1080
GAGTGGGCTG AAGCCCAGCG CATGATGAGG GAACTGCGGA ACAGGAACTT TGCTGAACCG  1140
CTCAGAGAAG CAGAAGCTGA TAAAAGGGAG TCGCAGCTCT GCTGCTTGCTA ACAGTATCCG  1200
```

```
GAAAAATTAG CTGCCAGTTT AAATGAAGCA AGACAAGAAC TAAGTGACAA AGTAAGAGAA    1560
CTTTCCAGAT CTGCTGGCAA AACATCCCTT GTGGAGGAGG CAGAAAAGCA CGCGCGGTCC    1620
TTACAAGAGC TGGCAAAGCA GCTGGAAGAG ATCAAGAGAA ACGCCAGCGG GGATGAGCTG    1680
GTGCGCTGTG CTGTGGATGC CGCCACCGCC TACGAGAACA TCCTCAATGC CATCAAAGCG    1740
GCCGAGGACC GAGCCAACAG GGCTCGCAGT GCATCTGAAT CTGCCCTCCA GACAGTGATA    1800
AAGGAAGATC TGCCAAGAAA AGCTAAAACC CTGAGTTCCA AAGAAGTCAG ACTGTTAAAG    1860
AAGCCAAGAT GACACAAAAG AAGCTAAAAG AAGAAGTCAG TCCAGCTCTC AACAACCTAC    1920
AGCAAACCCT GAATATTGTG ACAGTTCAGA AAGAAGTGAT AGACACCAAT CTCACAACTC    1980
TCCGAGATGG TCTC                                                     1994
```

| ENZYME | NO. OF CLEAVAGE SITES | POSITION OF CLEAVAGE SITE(#) WITHIN NUCLEOTIDE SEQUENCE (0–1994) |
|---|---|---|
| AccI | 1 | |
| AccII | 1 | |
| AhaIII | 3 | |
| AIwNI | 4 | |
| ApaLI | 2 | |
| BaII | 2 | |
| BamHI | 1 | |
| BanI | 1 | |
| BanII | 1 | |
| BglI | 5 | |
| BglII | 3 | |
| BsaI | 2 | |
| Bsp1286 | 5 | |
| BspMII | 1 | |
| Bsu36I | 1 | |
| CvnI | 1 | |
| DraI | 3 | |
| DraII | 4 | |
| EaeI | 3 | |
| EagI | 1 | |
| EarI | 1 | |
| Eco52I | 1 | |
| Eco81I | 1 | |
| EcoNI | 1 | |
| EccO109 | 4 | |
| HaeII | 1 | |
| HgiAI | 4 | |
| HincII | 2 | |
| HpaI | 1 | |
| MamI | 1 | |

Fig. 1E.

| PRIMER | 5'-3' SEQUENCE | STRAND | ANNEALING TEMP.(°C) | SEQ.ID.NO. |
|---|---|---|---|---|
| MR-3 | TGCCATTGAGGATGTTCTCGTAGG | (-) | 60 | 3 |
| MR-4 | ACGTAAGCTTAGCCACGAAGGTCACTGAGTT | (-) | 57 | 4 |
| MR-5 | ATATGTCCACAAGTCACCTGAAGGCACG | (-) | 55-57 | 5 |
| MR-6 | TGCACCTGAGACTTGACCAG | (-) | 57 | 6 |
| MR-7 | ATGTCATCCCGGAATGTCCAC | (+) | 55-57 | 7 |
| MR-8 | TACCACACCTGTCTGTCATG | (+) | 55 | 8 |
| MR-11 | ACGGGCGTTGCCCATAGTAC | (-) | 50 | 9 |
| MR-12 | TAGCCCTGGATACTATCG | (+) | 50 | 10 |

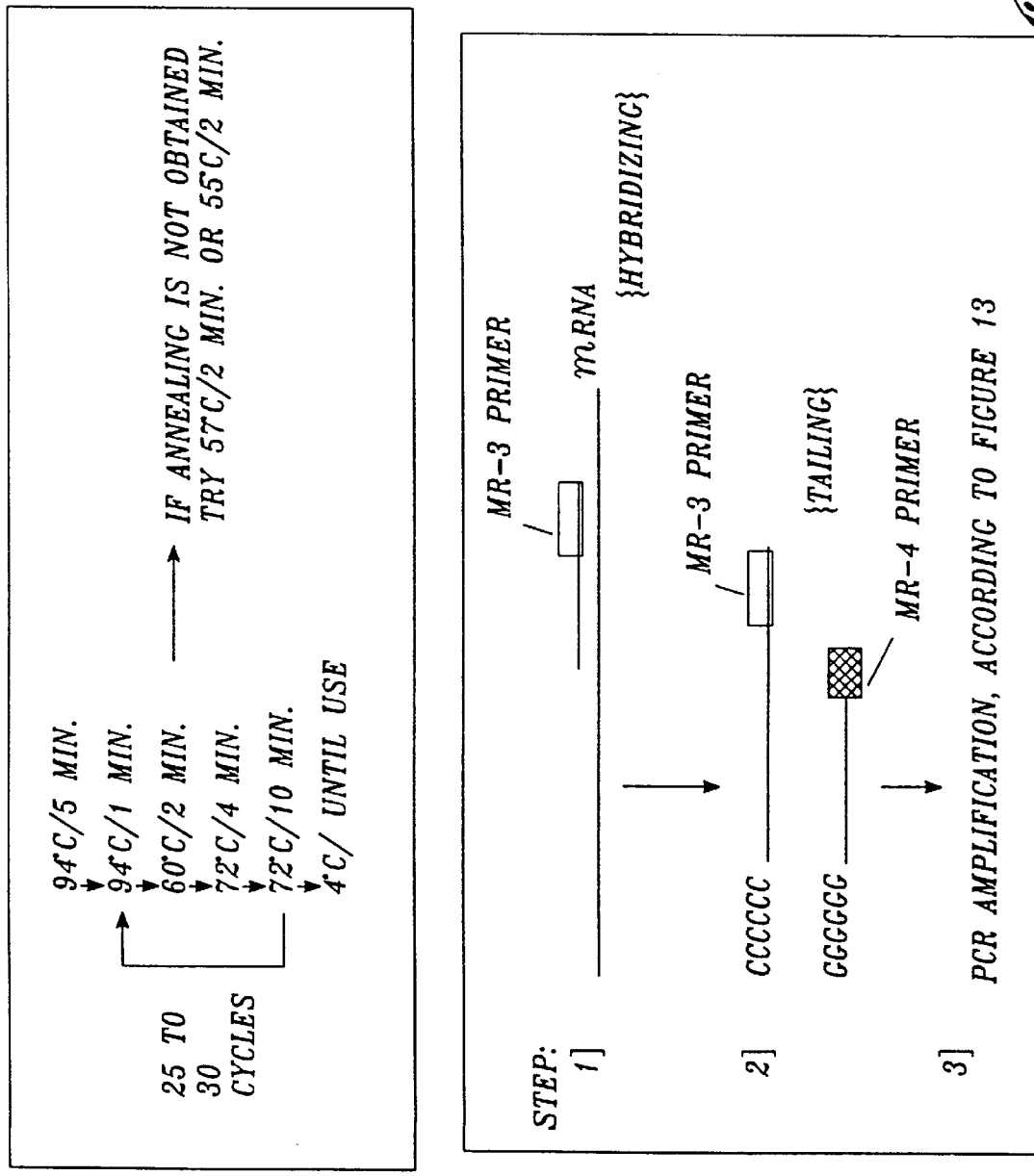

Fig.15A.

```
AGCCAGCGGA CGTCCAGGAA CCGGGATGCC TCCAGCAGTG AGGCGGTCAG CCTGCAGC         58
ATG GGA CTG TGG ATC TTT GGG GCA GCC CTG TGT CCC GGT CAA                106
TAC AGT TCA CAG CAG CAA AGG GTG CCA TTT CTT AGA CCT AGC GGC             154
AGT CAA CTG CAA GCG AGT TAT GTG GAG TTT GTG CAG CCC CAG GGT TGT         202
AGC CCT GGA TAC TAT CGG GAT CAT AAA GGC TTG TAT ACC GGA CGG TGT         250
GTT CCC TGC AAT GGA CAT TCA AAC GGA CAT CAA TGC CAG GAT GGC TCA         298
GGC ATA TGT GTT AAC TGT CAG CAC CAC AAC ACC GCG GAG CAC TGT GAA         346
CGC TGC CAG GAG GGC TAC TAT ACT AAC AGC GTC TTT GCC ACT GGG TGC AGG     394
GCC TGC CCA TGT CCT CAC AAC AGC TGC TCC AAA GCT GGC TAC ACA GGA ACA     442
AAT GGG GGA GAC GTG CGG GGA TAT TTC AAC AAT CCC CAG AAA TTC             490
CAG TGT GAA AGG TGT GCA CCG TGC AGT TGT AAC AGC CAG CTG GGC             538
GGA GGT AGC TGC CAA CCA ACT GGA GAC TGT GAT ATG GGC CAG GAA GAT ACC     586
AGC TGT CAT CCC CTG ACT GAA GAA TGC GAG GCC AGC GGG CTG CGC AAG         634
AGC AGC CCT GCA AAC GAC CTG GCC ATG GCC AAG GAC CAG GGG AGG AAT GAT     682
CTC CTG AAC GAC CAG GGC CTG AGT AGT GCA CTG CTT CTG GAG TTG CTC AAC     730
TCT CAG ATG CTG CAG GCC ACC CAG GCC AAG GAC CAG GGG AGG AAT CAG ATA     778
AGG CAC ATG GAG CTG GCC ATT TCA AAT CAT GGA TCA AAA ATA GAA GGC CTC AAC 826
TAC CGT TCT GCC ATT TCA AAT CAT GAA TTT CAA GAA TTT GAG ACT CTG AAG     874
AGA GAA CTG ACT GAT TTG AAT CAA GAA CAA ACA TTG CAA GAA AAG            922
GCT CAA GTA AAT TCC AGA AAA GCA CAA CAA ACA TTA AAC AAC AAT GTT AAT     970
```

Fig.15B.

```
CGG GCA CAA AGC GCA AAA GAA CTG GAT GTG AAG ATT AAA AAT GTC  1018
ATC CGG AAT GTG CAC ATT CTT TTA AAG CAG ATC TCT GGG ACA GAT GGA  1066
GAG GGA AAC AAC GTG ATG CCT TCA GAC TTT TCC AGA GAG GCT GAA  1114
GCC CAG CGC ATG AGG AGG GAA AAC AGG GAG CAG AAC TTT GGA AAG CAC  1162
CTC AGA GAA GCA GAA GCT GAT AAA ACC CAC CAG AAC TCG CTC TTG CTG AAC  1210
CGG ATA AGG ACC TGG CAG AAA TTA AAT GAA CAC CAG GGG GAG AAC CTT  1258
GCT AAC AGT ATC CGG GAT TCT CAG CAG GCA TAC GAA GCC AAA AAA CTT AGT  1306
GAC CTT CGT GCT CGG CTG CAG AAC GAG GCA GCT GCC CAA AAG CAG AGT  1354
AAT GGC TTG AAC CAA ATA AAT TCC CTG GGA AGA GAG AGT TTG GAT GCC ATT CAG CAG AGA  1402
CAA GTG AAA GAA GAC TCA CAG CAA AAC ACC AAA GCG CTG AAG TAT CTA  1450
ACC ACT GCA AAA AGC CAG TCT TTG TAT GAA GTA AGA GAA ATT GCT GCC AGT TCC CAG CTG  1498
ATG GAG AAA AGA CAA AGC CAG CTA GTG GAC GAG GAG GCA GAA AAG CTT TCC AGA TCT  1546
GAA GCA AGA CAA TCC CTT GTG GCA CAG ATC GCC CAC CGG GGG TCC  1594
GCT GGC AAA ACA GCA TCC AAA GCG CTG TGT AAA GCG GAC ATC AAG AGA TCC TCC  1642
TTA CAA GAG CTC CTG GCA AAG CAG GAG ATC GCC GAC GTG ACC AAC GCC TAC GAG  1690
GGG GAT GAG CTG CGC ATC AAA GAC TGT GCC CAG ACA ATA AAG GAA AGG GCT  1738
AAC ATC CTC AAT GCC TCT GAA GCG CTC CTC CAG GAT ATA AAG GAA CTG CTG  1786
GCC AGT GCA TCT GAA TCT GCC AAC AGT CCC CAG CTG AGT GAT AAA CTG TTA AAT  1834
CCA AGA AAA GCT AAA ACC CTG AGT TCC AAC GTC ACA GCT GAT AAG CTG TTA AAT  1882
```

Fig.16C.

| | | | | | | | | | | | |
|---|---|---|---|---|---|---|---|---|---|---|---|
| GAA | GCC | AAG | ATG | ACA | CAA | AAG | AAG | CTA | AAG | CAA | GAA | GTC | AGT | CCA | GCT | 1930 |
| CTC | AAC | AAC | CAG | CTA | CAG | CAA | ACC | CTG | AAT | ATT | GTG | ACA | GTT | CTT | CAG | AAA | GAA | 1978 |
| GTG | ATA | GAC | ACC | AAT | CTC | ACA | ACT | CTC | CGA | ATT | GAT | GGT | CAT | GGG | ATA | 2026 |
| CAG | AGA | GGT | GAT | ATT | GCT | ATG | AGT | AGT | AGT | CTT | AAG | AGC | ATG | GTC | 2074 |
| AGA | AAG | GCC | AAC | GAC | ACA | GAT | AGA | ATT | AAG | GAT | CTG | CTG | GAT | GGG | CTC | AAC | CCC | 2122 |
| ATC | CAG | ACA | GAT | GTG | GAA | AAG | GCT | CTG | ACC | GCA | TAT | GAT | AAG | AGG | ACA | CAG | 2170 |
| AAC | GAA | GAC | TTC | AAA | AAA | CTA | CCT | TTG | TGG | CGC | AAG | ATT | GAA | GTG | AAT | 2218 |
| AAG | TTA | ACC | AAC | AAA | CTG | CCC | TTG | AAC | ATC | TCT | GCC | TCT | ACT | GAC | AGT | ATC | 2266 |
| AAC | CAA | CAG | CTA | ATT | CAG | CAG | GCC | AGA | GAT | GCC | AGT | GTC | GAT | AAC | ATG | GAC | AGA | 2314 |
| ATA | CGA | GAA | CTA | CCT | AAT | GGT | AAA | GAA | AAT | TCT | GGA | TAT | GGG | GGT | ACA | AGT | TAT | GCT | 2362 |
| GTC | CCC | ATG | AGG | TTC | AAT | GCC | ACC | TGT | GTC | TAC | CGG | TCC | ATC | GAG | TAC | CTG | GCA | 2410 |
| AAT | GAC | CTG | GAA | GAT | TTG | AGA | GAA | TAT | ACA | GGT | TAT | TCC | TTT | TTT | CTC | 2458 |
| CAA | CAG | CCC | AAC | TCA | AGA | AAA | GAT | GCC | CAG | ATC | TTG | ACC | AGA | AGT | ACT | GAG | ATG | TGT | GTG | 2506 |
| ATG | GAC | CTT | ATG | GGA | AAT | CCC | CAG | AAA | TTT | CAG | AGT | TAT | CAG | GGC | ATG | GCA | 2554 |
| GTT | GTG | GAT | GGC | CAG | CTC | GAC | GTG | GGA | GCC | ACA | TCC | AGT | GAA | ACT | TTT | GAC | CGT | GAG | 2602 |
| GCT | GAA | CTC | CAA | GTG | GAC | CAG | AAA | ATT | AAA | CCA | GAA | TTT | AAG | GAG | 2650 |
| GCA | GTT | AAT | GAT | CGG | GTG | GGA | GCC | AGA | TCC | AGT | TAT | CCA | CTC | TTT | GCA | CCC | AGG | 2698 |
| CTT | AAT | TAC | ACC | AAA | GGA | GCC | ACA | TCC | AGT | AAT | ACA | CTT | AAT | TTG | GAT | 2746 |
| GTC | TAT | GAC | ATG | CGG | GAT | AGA | AAT | AGC | CAG | GAA | ACA | AAT | TTG | GAT | 2794 |
| CCT | GAA | AAT | GTT | GTA | TTT | TAT | GTT | GGA | GGT | TAC | CCA | CCT | GAT | TTT | AAA | 2842 |

FIG. 15D.

```
CTT CCC AGT CGA CTA AGT TTC CCT CCA TAC AAA GGT TGT ATT GAA TTA    2890
GAT GAC CTC AAT GAA ACT GTT CTG AGC TTG TAC AAC TTC AAA AAA ACA    2938
TTC AAT CTC AAC ACA AAT ACT GAA GTG GAG CCT ACG AGG AAG AAG GAA    2986
GAG TCA GAC ACA AAT AAT TAT TTT GAA GGT TGT CGA GTT CAG ACC CCA    3034
ACT CAA CCA CAT GCT CCC ATC ACC TTT GGA TAT ACA ATT CAG ACC        3082
ACC GTG GAT AGA GGC TTG CTG AAG AGA GGA TTT GAT AAC GGG TTC        3130
ATA TCT CTA AAT ATA GAA AAT GGA AGA ATA GAA TAC AAA CTG            3178
AAT TCA GAC CAT TCG CAA GTT ACG CTG ATC GGA GAC GTG GTG AAC AAC    3226
GGC AGA GAC CAT TCG CAA GTT AGA CTG ATC AAA AGA AAG AAG AAC        3274
ATG TGG ATA AAT GTG GAC TAT TCT ACG GGA CCT GAG AAA CGT GAA AAG    3322
TTT GAT TTC AGC ACA TAT TCT CTA AGT TTG CTT GGC GGC AAA ATT AGG    3370
GAA AGA TTC AAC ACC ATT TCT ACG GTC AAG AAT GGA ATT ATT GCC ATC    3418
TTG AAA AAC ATT CCA CCT TTC AGA TGC CCA TCA GGA AAA AAT AAT        3466
ACC AAA AAG TGC AGT GGT CTT TTG GAT CTT TTA TTC ACC CCT ACT        3514
TCC AGA CTC TCG GAA CAA CGC CCC GGC CTG TAC TTA CAG CCC AGT GGC    3562
GAC CAC CTC CAG GCC AGC AAA GAA AAA ATC CTG CTT CAA GGA CAA GGC    3610
ATA TTA GAT CAT CAG ACA TTG CCA AGT AAG ACA AGG AGG GTA TCG CCA    3658
GAA GAT GGT TAC ATT GAA ATG ATG AGC ATG AAC CCT ACG GCC TAT GGC    3706
TTT AAA TCT CCA CAG ACG TAT ATG CAT TTA GGT CTT AGC ATA TCT TCT    3754
```

Fig.15E.

| | | | | | | | | | | | | |
|---|---|---|---|---|---|---|---|---|---|---|---|---|
| GTA | ATA | AGC | GAC | AAC | TCT | GGA | CTA | CGG | CTT | CTC | ATC | GAT | GAC | CAG | CTT | 3802 |
| CTG | AGA | AAT | AGC | AAA | AGG | CTA | AAA | CAC | ATT | TCA | AGT | GAT | GAC | CAG | TCT | 3850 |
| CTG | CGT | CTG | GGC | GGG | AGC | TTT | CCT | GGT | AAT | TCA | AGC | CGG | CAG | TCT | 3898 |
| GTC | CAG | AGG | TTA | TCA | CTG | AGT | TCC | CTG | GTC | GAA | ATT | GAT | TTG | GTT | TTT | 3946 |
| TCT | CTC | AAG | AGA | GAT | GTG | CTT | AAA | GGT | GGA | GGC | CTA | TGC | AGT | TTA | AAC | 3994 |
| CCT | TTT | CTA | ATG | TTG | CTT | AAA | CAG | TTG | ACC | AGG | TTT | AAA | AAC | ACC | AAG | 4042 |
| ACT | TTT | CGT | ATC | AAC | CAG | CTG | TTG | CAG | ACA | GAC | CCA | TCA | GCC | TCC | CCA | 4090 |
| AGG | AGC | GTG | AAG | CAT | GTG | TGG | CAA | GAT | GCT | TTT | CCA | CCA | ATT | CCC | AAG | ACC | 4138 |
| CAG | AGC | AAT | CAG | GGA | GCC | CTC | CCT | CAG | GAG | TGC | GGG | GAC | CTG | AGG | AGC | CAC | 4186 |
| TTG | CTA | AAG | CTT | AAG | CTG | CAG | ACA | TCC | CTT | TAT | AAA | CTG | TCA | CAG | TTT | 4234 |
| GCT | GTG | GAC | ATG | CCT | ACA | TTT | GCT | GGG | AAA | ACG | GTG | TTT | CAC | ACG | 4282 |
| GGC | ACT | AAG | ATG | AAC | TCC | ATG | GAT | AAA | TGG | CAC | GTG | GGA | CGT | CTG | 4330 |
| GTC | TTT | GCA | CTG | GGG | TTG | GTT | GTG | CAT | GCC | GTG | TCA | AAA | AGC | CAG | AAG | 4378 |
| GAG | AAA | TGC | AAT | GAT | CGC | ACC | ATC | AGC | AGG | GCC | CGG | CAT | GAT | GGC | CAT | GAT | 4426 |
| GGG | GAA | AAG | GGG | TTG | GTT | ACC | AAG | AGA | CTC | CCA | ACA | GCC | GGA | GGA | 4474 |
| AGT | TTG | CCT | GGA | AAC | TTT | CAG | CTG | AGA | AGC | CTG | TCA | AAA | TTT | AAT | TTG | 4522 |
| GGA | TCA | CCT | CCA | TCA | GGG | TTT | GGT | TCT | TGG | TTT | TGC | CCC | ACA | TAC | AGC | CTG | 4570 |
| GTG | GGA | TGC | CTG | AAG | AAC | TTC | GGG | GTG | TCT | TGT | TTG | CCT | TTG | GAG | 4618 |
| CCT | TCT | TCA | AGC | TTC | TCT | GAA | GAA | GGT | CAT | TGG | CCT | TTG | 4666 |
| AAA | GGC | ATT | TAT | TTC | TCT | GAA | GGA | GGA | CCC | CAC | GCT | CAC | 4714 |

```
TCT GTA TTG TTG GGG CCA GAA TTT AAG CTT GTT TTC AGC ATC CGC CCA       4762
AGA AGT CTC ACT GGG ATC CTA ATA CAC ATC GGA AGT CAG CCC GGG AAG       4810
CAC TTA TGT GTT TAC CTG GAG ACC GCA GGA AAG GTC ACG GCC TCT ATG GAC   4858
AGT GGG GCA GGT GGG ACC TCA ACG TCG GTC ACA CCA AAG CAG TCT CTG       4906
TGT GAT GGA CAG TGG CAC TCG GTG GCA GTC ACC ATA AAA CAA CAC ATC       4954
CTG CAC CTG GAA CTG GAC ACA GAC AGT TAC ACA GCT GGA CAG ATC           5002
CCC TTC CCA CCT GCC AGC ACT CAA CTA CAC CTT GGA GGT GCT               5050
CCA GCC AAT TTG ACG ACA CTG AGG ATC CCT GTG TGG AAA TCA TTC TTT       5098
GGC TGT CTG AGG AAT ATT CAT GTC CAG GGG CCT GTC ATC CCT GTC ACT       5146
GAA GCC TTG GAA GTC CAG GGG CCT GTC AGT CTG AAT GGT TGT CCT GAC       5194
CAG TAACCCAAGC CTATTTCACA GCAAGGAAAT TCACCCTTCAA AAGCACTGAT           5247
TACCCAATGC ACCTCCCTCC CCAGCTCGAG ATCATTCTTC AATTAGGACA CAAACCAGAC     5307
AGGTTTAATA GCGAATCTAA TTTTGAATTC TGACCATGGA TACCCATCAC TTTGGCATTC     5367
AGTGCTACAT GTGTATTTTA TATAAAAATC CCATTTCTTG AAGATAAAAA AATTGTTATT     5427
CAAATTGTTA TGCACAGAAT GTTTTTGGTA ATATTAATTT CCACTAAAAA ATTAAATGTC     5487
TTTTAAAAA                                                              5496
```

Fig. 15F.

|  Ep-1 Immune Serum | Pre-Immune Serum |
|---|---|
| P1E1 Ag / Cond. Media | Cond. Media / P1E1 Ag |

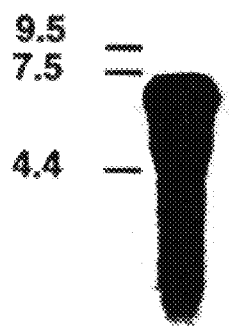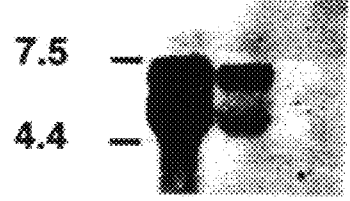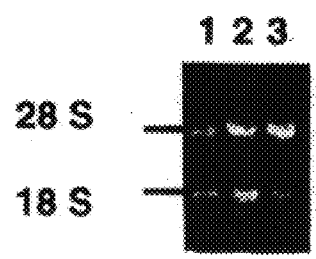
fig. 17A.    fig. 17B.

```
ATG  GGA  TGG  CTG  TGG  ATC  TTT  GGG  GCA  GCC  CTG  GGG  CAG  TGT  CTG  GGC      48
Met  Gly  Trp  Leu  Trp  Ile  Phe  Gly  Ala  Ala  Leu  Gly  Gln  Cys  Leu  Gly
 1              5                   10                  15

TAC  AGT  CAG  CAA  AGG  GTG  CCA  TTT  CTT  CAG  CCT  GGT  CAA                      96
Tyr  Ser  Gln  Gln  Arg  Val  Pro  Phe  Leu  Gln  Pro  Gly  Gln
              20                  25                  30

AGT  CAA  CTG  CAA  GCG  AGT  TAT  GTG  GAG  TTT  AGA  CCC  AGC                     135
Ser  Gln  Leu  Gln  Ala  Ser  Tyr  Val  Glu  Phe  Arg  Pro  Ser
              35                  40                  45
```

*Fig. 18A.*

| | | | | | | | | | | |
|---|---|---|---|---|---|---|---|---|---|---|
| CCC<br>Pro<br>1 | ACC<br>Thr | TCC<br>Ser | TAC<br>Tyr | CTG<br>Leu<br>5 | GGG<br>Gly | GAC<br>Asp | AAG<br>Lys | GTT<br>Val | TCT<br>Ser<br>10 | TCA<br>Ser | TAT<br>Tyr | GGT<br>Gly | TAC<br>Tyr<br>15 | CTC<br>Leu | 48 |
| ACT<br>Thr | TAC<br>Tyr | CAA<br>Gln | GCC<br>Ala<br>20 | AAG<br>Lys | TTT<br>Phe | TGG<br>Leu<br>25 | TCC<br>Ser | GGC<br>Gly | TTT<br>Phe | CCT<br>Pro | TTG<br>Leu | GGC<br>Gly | ATG<br>Met | GTT<br>Val<br>30 | CTG<br>Leu | 96 |
| GAA<br>Glu | AAG<br>Lys<br>35 | CCG<br>Pro | GAT<br>Asp | GTA<br>Val | CAG<br>Gln | CTC<br>Leu<br>40 | ACT<br>Thr | GGT<br>Gly | GGT<br>Gly | GAC<br>Asp | ATG<br>Met<br>45 | ATC<br>Ile | ATC<br>Ile | 144 |
| TAT<br>Tyr | GAG<br>Glu<br>50 | CAC<br>His | GTC<br>Val | GGA<br>Gly | GAG<br>Glu | ACA<br>Thr | CCA<br>Pro<br>55 | CGG<br>Arg | GAC<br>Asp | CAC<br>His | CAT<br>His | CAG<br>Gln | ATG<br>Met<br>60 | TCC<br>Ser | ATC<br>Ile | 192 |
| GTG<br>Val<br>65 | CAC<br>His | GTC<br>Val | GGA<br>Gly<br>70 | GAG<br>Glu | AAC<br>Asn | ACC<br>Thr | CAT<br>His | GCA<br>Ala<br>75 | CGG<br>Arg | CCA<br>Pro | GAC<br>Asp | CGT<br>Arg | AGC<br>Ser | CGA<br>Arg<br>80 | 240 |
| GTG<br>Val | TCT<br>Ser | AGG<br>Arg | GGA<br>Gly | TTC<br>Phe | ATG<br>Met<br>85 | CTG<br>Leu | CTG<br>Leu<br>90 | TCT<br>Ser | GGA<br>Gly | AGC<br>Ser | CGT<br>Arg | GCA<br>Ala | CCA<br>Pro<br>80 | | 288 |
| CGC<br>Arg | ATC<br>Ile | CAA<br>Gln<br>100 | GGC<br>Gly | CTA<br>Leu | ATG<br>Met | TTC<br>Phe | TAC<br>Tyr | GTG<br>Val<br>105 | GAG<br>Glu | ACT<br>Thr | CAA<br>Gln | AGG<br>Arg | CTG<br>Leu | CTC<br>Leu | ACC<br>Thr<br>110 | GCC<br>Ala | GAT<br>Asp<br>95 | 336 |
| GAG<br>Glu | GTG<br>Val | GGG<br>Gly<br>115 | GAG<br>Glu | GCC<br>Ala | TCT<br>Ser | GAC<br>Asp | ACA<br>Thr | CAA<br>Gln | GGA<br>Gly | AGT<br>Ser | GGG<br>Gly<br>125 | CTC<br>Leu | ATA<br>Ile | GCA<br>Ala | TGC<br>Cys<br>120 | 384 |
| CTT<br>Leu | GCT<br>Ala<br>130 | GTG<br>Val | GAA<br>Glu | ATC<br>Ile | TGT<br>Cys | GCC<br>Ala | CCT<br>Pro | TGC<br>Cys<br>135 | CCC<br>Pro | TAC<br>Tyr<br>140 | AGT<br>Ser | GCT<br>Ala | GGT<br>Gly | GAC<br>Asp | TCT<br>Ser | 432 |
| TGT<br>Cys<br>145 | | | | | | | | | | | | | | | | 435 |

*Fig. 18B.*

```
  1 CAG GGT TGT AGC CCT GGA TAC TAT CGG GAT CAT AAA GGC TTG TAT ACC   48
    Gln Gly Cys Ser Pro Gly Tyr Tyr Arg Asp His Lys Gly Leu Tyr Thr
      1           5              10              15

17 GGA CGG TGT GTT CCC TGC AAT TGC AAT CAT GGA AAT TCA CAA TGC CAG   96
    Gly Arg Cys Val Pro Cys Asn Cys Asn His Gly Asn Ser Gln Cys Gln
                    20              25              30

33 GAT GGC TCA ATA GGC CCC ATA AAC TGC GTT CAG CAT AAT ACC GCA CAG  144
    Asp Gly Ser Ile Gly Pro Ile Asn Cys Val Gln His Asn Thr Ala Gln
                35              40              45

49 CAC TGT GGC CAG GAG GTT CAG GAG CAC AAC TAT GGC TAT TGT CAC GGA  192
    His Cys Gly Gln Glu Val Gln Glu His Asn Tyr Gly Tyr Cys His Gly
             50              55              60

65 TCC TGC TGC CAG TGC TGT CAC ACT TAT TAC GCC AAC AGC TTT GTC CAC  240
    Ser Cys Cys Gln Cys Cys His Thr Tyr Tyr Ala Asn Ser Phe Val His
     65              70              75              80

81 TGT GTG GGA GAC CGG GGT GGA GCC AGG CGG TGC TAT ACT GGG TAC TAC  288
    Cys Val Gly Asp Arg Gly Gly Ala Arg Arg Cys Tyr Thr Gly Tyr Tyr
                 85              90              95

97 ACA GGA AAT CAG CAG TGC TGT GCA CCA AAC AGC GCT GGG AAT CCC GCC  336
    Thr Gly Asn Gln Gln Cys Cys Ala Pro Asn Ser Ala Gly Asn Pro Ala
            100             105             110

113 AAA TTC GGC AGC TGT CAT CCC CAA CTG AGC AAC AGC TTC TAC GCC TTC  384
    Lys Phe Gly Ser Cys His Pro Gln Leu Ser Asn Ser Phe Tyr Ala Phe
        115             120             125

129 CTG GGC CTG CAT CAT CCC ACT GAA AAT AGC TGC AGC GCC GGT GCA AAT  432
    Leu Gly Leu His His Pro Thr Glu Asn Ser Cys Ser Ala Gly Ala Asn
    130             135             140

145 CCC AGC GAT AAA GAA TGT GAT GAT GGC AGC GCA CAA GGC CTA GAA GAT  468
    Pro Ser Asp Lys Glu Cys Asp Asp Gly Ser Ala Gln Gly Leu Glu Asp
    145             150             155
```

*Fig. 18C.*

```
Met Gly Trp Leu Trp Ile Phe Gly Ala Ala Leu Gly Gln Cys Leu Gly
 1                   5                  10                  15
Tyr Ser Ser Gln Gln Gln Arg Val Pro Phe Leu Gln Pro Pro Gly Gln
                20                  25                  30
Ser Gln Leu Gln Ala Ser Tyr Val Glu Phe Arg Pro Ser
                35                  40                  45
```

Fig. 19A.

```
                                                Gln Gly Cys
Ser Pro Gly Tyr Tyr Arg Asp His Lys Gly Leu Tyr Thr Gly Arg Cys
        50              55              60
Val Pro Cys Asn Cys Asn Gly His Ser Asn Gln Cys Gln Asp Gly Ser
        65              70              75              80
Gly Ile Cys Val Asn Cys Gln His Asn Thr Ala Gly Glu His Cys Glu
        85              90              95
Arg Cys Gln Glu Gly Tyr Tyr Gly Asn Ala Val His Gly Ser Cys Arg
        100             105             110
Ala Cys Pro Cys Pro His Thr Asn Ser Phe Ala Thr Gly Cys Val Val
        115             120             125
Asn Gly Gly Asp Val Arg Cys Ser Cys Lys Ala Gly Tyr Thr Gly Thr
        130             135             140
```

*Fig. 19B.*

```
Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
                180                 185                 190

Ser Ser Pro Ala Glu Glu Cys Asp Asp Cys Asp Ser Cys Val Met Thr
195                 200                 205
```

*Fig. 19C.*

```
                            Cys Asp Ser Cys Val Met Thr
                                        205

Leu Leu Asn Asp Leu Ala Thr Met Gly Glu Gln Leu Arg Leu Val Lys
210                     215                     220

Ser Gln Leu Gln Gly Leu Ser Ala Ser Ala Gly Leu Leu Glu Gln Met
225                     230                     235                     240

Arg His Met Glu Thr Gln Ala Lys Asp Leu Arg Asn Gln Leu Leu Asn
            245                     250                     255

Tyr Arg Ser Ala Ile Ser Asn His Gly Ser Lys Ile Glu Gly Leu Glu
260                     265                     270

Arg Glu Leu Thr Asp Leu Asn Gln Glu Phe Glu Thr Leu Gln Glu Lys
            275                     280                     285

Ala Gln Val Asn Ser Arg Lys Ala Gln Thr Leu Asn Asn Asn Val Asn
290                     295                     300

Arg Ala Thr Gln Ser Ala Lys Glu Leu Asp Val Lys Ile Lys Asn Val
305                     310                     315                     320
```

Fig. 19D.

```
Ile Arg Asn Val His Ile Leu Leu Lys Gln Ile Ser Gly Thr Asp Gly
                325                 330                 335
Glu Gly Asn Val Pro Ser Gly Asp Phe Ser Arg Glu Trp Ala Glu
                340                 345                 350
Ala Gln Arg Met Met Arg Glu Leu Arg Asn Arg Asn Phe Gly Lys His
                355                 360                 365
Leu Arg Glu Ala Glu Ala Asp Lys Arg Glu Ser Gln Leu Leu Leu Asn
                370                 375                 380                 400
Arg Ile Arg Thr Trp Gln Lys Thr His Gln Gly Glu Asn Asn Gly Leu
                385                 390                 395
Ala Asn Ser Ile Arg Asp Ser Leu Asn Glu Tyr Glu Ala Lys Leu Ser
                405                 410                 415
Asp Leu Arg Ala Arg Leu Gln Glu Ala Ala Gln Ala Lys Gln Ala
                420                 425                 430
Asn Gly Leu Asn Gln Glu Asn Gly Arg Ala Leu Gly Ala Ile Gln Arg
                435                 440                 445
```

Fig. 19E.

Gln Val Lys Glu Ile Asn Ser Leu Gln Ser Asp Phe Thr Lys Tyr Leu
450                 455                 460                 480

Thr Thr Ala Asp Ser Ser Leu Leu Gln Thr Asn Ile Ala Leu Gln Leu
465                 470                 475                 480

Met Glu Lys Ser Gln Lys Glu Tyr Glu Lys Leu Ala Ala Ser Leu Asn
                485                 490                 495

Glu Ala Arg Gln Glu Leu Ser Asp Lys Val Arg Glu Leu Ser Arg Ser
            500                 505                 510

Ala Gly Lys Thr Ser Leu Val Glu Glu Ala Glu Lys His Ala Arg Ser
        515                 520                 525

Leu Gln Glu Leu Ala Lys Gln Leu Glu Glu Ile Lys Arg Asn Ala Ser
    530                 535                 540

Gly Asp Glu Leu Val Arg Cys Ala Val Asp Ala Ala Thr Ala Tyr Glu
545                 550                 555                 560

Asn Ile Leu Asn Ala Ile Lys Ala Ala Glu Asp Ala Ala Asn Arg Ala
                565                 570                 575

*Fig. 19F.*

```
Ala Ser Ala Ser Glu Ser Ala Leu Gln Thr Val Ile Lys Glu Asp Leu
            580                 585                 590
Pro Arg Lys Ala Lys Thr Leu Ser Ser Asn Ser Asp Lys Leu Leu Asn
        595                 600                 605
Glu Ala Lys Met Thr Gln Lys Lys Leu Lys Gln Glu Val Ser Pro Ala
            610                 615                 620
Leu Asn Asn Leu Gln Gln Thr Leu Asn Ile Val Thr Val Gln Lys Glu
        625                 630                 635                 640
Val Ile Asp Thr Asn Leu Thr Thr Leu Arg Asp Gly Leu His Gly Ile
            645                 650                 655
Gln Arg Gly Asp Ile Asp Ala Met Ile Ser Ser Ala Lys Ser Met Val
        660                 665                 670
Arg Lys Ala Asn Asp Ile Thr Asp Glu Val Leu Asp Gly Leu Asn Pro
            675                 680                 685
Ile Gln Thr Asp Val Glu Arg Ile Lys Asp Thr Tyr Gly Arg Thr Gln
        690                 695                 700
```

*Fig.19G.*

```
Asn Glu Asp Phe Lys Lys Ala Leu Thr Asp Ala Asp Asn Ser Val Asn
705                 710                 715                 720
Lys Leu Thr Asn Lys Leu Pro Asp Leu Trp Arg Lys Ile Glu Ser Ile
            725                 730                 735
Asn Gln Gln Leu Leu Pro Leu Gly Asn Ile Ser Asp Asn Met Asp Arg
        740                 745                 750
Ile Arg Glu Leu Ile Gln Gln Ala Arg Asp Ala Ala Ser Lys Val Ala
    755                 760                 765
Val Pro Met Arg Phe Asn Gly Lys Ser Gly Val Glu Val Arg Leu Pro
770                 775                 780
Asn Asp Leu Glu Asp Leu Lys Gly Tyr
785                 790
```

*Fig. 19H.*

Thr Ser Leu Ser Leu Phe Leu
                    795         800

Gln Arg Pro Asn Ser Arg Glu Asn Gly Gly Thr Glu Asn Met Phe Val
            805                 810                 815

Met Tyr Leu Gly Asn Lys Asp Ala Ser Arg Asp Tyr Ile Gly Met Ala
        820                 825                 830

Val Val Asp Gly Gln Leu Thr Cys Val Tyr Asn Leu Gly Asp Arg Glu
    835                 840                 845

Ala Glu Leu Gln Val Asp Gln Ile Leu Thr Lys Ser Glu Thr Lys Glu
850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
            885                 890                 895

Fig. 19I.

Val Tyr Asp Met Asp Gly Arg Asn Ser Asn Thr Leu Leu Asn Leu Asp
              900             905             910

Pro Glu Asn Val Val Phe Tyr Val Gly Gly Tyr Pro Pro Asp Phe Lys
              915             920             925

Leu Pro Ser Arg Leu Ser Phe Pro Pro Tyr Lys Gly Cys Ile Glu Leu
              930             935             940

Asp Asp Leu Asn Glu Asn Val Leu Ser Leu Tyr Asn Phe Lys Lys Thr
              945             950             955             960

Phe Asn Leu Asn Thr Thr Glu Val Glu Pro Cys
              965             970

Fig. 19J.

```
                                            Arg Arg Arg Lys Glu
                                                        975

Glu Ser Asp Lys Asn Tyr Phe Glu Gly Thr Gly Tyr Ala Arg Val Pro
            980                 985                 990

Thr Gln Pro His Ala Pro Ile Pro Thr Phe Gly Gln Thr Ile Gln Thr
        995                 1000                1005

Thr Val Asp Arg Gly Leu Leu Phe Ala Glu Asn Gly Asp Arg Phe
    1010                1015                1020

Ile Ser Leu Asn Ile Glu Asp Gly Lys Leu Met Val Arg Tyr Lys Leu
    1025                1030                1035            1040

Asn Ser Glu Leu Pro Lys Glu Arg Gly Val Gly Asp Ala Ile Asn Asn
            1045                1050                1055

Gly Arg Asp His Ser Ile Gln Ile Lys Ile Gly Lys Leu Gln Lys Arg
        1060                1065                1070
```

Met Trp Ile Asn Val Asp Val Gln Asn Thr Ile Ile Asp Gly Glu Val
1075                          1080                     1085

Phe Asp Phe Ser Thr Tyr Tyr Leu Gly Gly Ile Pro Ile Ala Ile Arg
1090                     1095                     1100

Glu Arg Phe Asn Ile Ser Thr Pro Ala Phe Arg Gly Cys Met Lys Asn
1105                     1110                     1115          1120

Leu Lys Lys Thr Ser Gly Val Val Arg Leu Asn Asp Thr Val Gly Val
                1125                     1130                     1135

Thr Lys Lys Cys
        1140 fig.19L.

```
Ser Glu Asp Trp Lys Leu Val Arg Ser Ala Ser Phe
                1145                1150
Ser Arg Gly Gly Gln Leu Ser Phe Thr Asp Leu Gly Leu Pro Pro Thr
        1155                1160                1165
Asp His Gln Ala Ser Phe Gly Phe Gln Thr Phe Gln Pro Ser Gly
        1170                1175            1180
Ile Leu Leu Asp His Gln Thr Trp Thr Arg Asn Leu Gln Val Thr Leu
        1185                1190                1195            1200
Glu Asp Gly Tyr Ile Glu Leu Ser Thr Ser Asp Ser Gly Gly Pro Ile
            1205                1210                1215
Phe Lys Ser Pro Gln Thr Tyr Met Asp Gly Leu Leu His Tyr Val Ser
            1220                1225                1230
Val Ile Ser Asp Asn Ser Gly Leu Arg Leu Leu Ile Asp Asp Gln Leu
            1235                1240                1245
```

Fig. 19M.

Leu Arg Asn Ser Lys Arg Leu Lys His Ile Ser Ser Ser Arg Gln Ser
1250                    1255                    1260

Leu Arg Leu Gly Gly Ser Asn Phe Glu Gly Cys Ile Ser Asn Val Phe
1265                    1270                    1275              1280

Val Gln Arg Leu Ser Leu Ser Pro Glu Val Leu Asp Leu Thr Ser Asn
                1285                    1290                    1295

Ser Leu Lys Arg Asp Val Ser Leu Gly Gly Cys Ser Leu Asn Lys Pro
        1300                    1305                    1310

Pro Phe Leu Met Leu Leu Lys Gly Ser Thr Arg Phe Asn Lys Thr Lys
                1315                    1320                1325

Thr Phe Arg Ile Asn Gln Leu Leu Gln Asp Thr Pro Val Ala Ser Pro
1330                    1335                    1340

Arg Ser Val Lys Val Trp Gln Asp Ala Cys
1345                    1350

FIG. 19N.

```
                                    Ser Pro Leu Pro Lys Thr
                                    1355            1360

Gln Ala Asn His Gly Ala Leu Gln Phe Gly Asp Ile Pro Thr Ser His
            1365                1370                1375

Leu Leu Phe Lys Leu Pro Gln Glu Leu Leu Lys Pro Arg Ser Gln Phe
            1380                1385                1390

Ala Val Asp Met Gln Thr Thr Ser Ser Arg Gly Leu Val Phe His Thr
            1395                1400                1405

Gly Thr Lys Asn Ser Phe Met Ala Leu Tyr Leu Ser Lys Gly Arg Leu
            1410                1415                1420

Val Phe Ala Leu Gly Thr Asp Gly Lys Lys Leu Arg Ile Lys Ser Lys
            1425                1430                1435                1440

Glu Lys Cys Asn Asp Gly Lys Trp His Thr Val Val Phe Gly His Asp
            1445                1450                1455
```

Fig. 190.

Gly Glu Lys Gly Arg Leu Val Val Asp Gly Leu Arg Ala Arg Glu Gly
1460                          1465                      1470

Ser Leu Pro Gly Asn Ser Thr Ile Ser Ile Arg Ala Pro Val Tyr Leu
1475                          1480                      1485

Gly Ser Pro Pro Ser Gly Lys Ser Leu Pro Thr Asn Ser Phe
1490                          1495                      1500

Val Gly Cys Leu Lys Asn Phe Gln Leu Asp Ser Lys Pro Leu Tyr Thr
1505                          1510                      1515                      1520

Pro Ser Ser Ser Phe Gly Val Ser Ser Cys
1525                          1530

Fig. 19F.

Leu Gly Gly Pro Leu Glu
1535

Lys Gly Ile Tyr Phe Ser Glu Gly Gly His Val Val Leu Ala His
1540                          1545                1550

Ser Val Leu Leu Gly Pro Glu Phe Lys Leu Val Phe Ser Ile Arg Pro
1555                          1560                1565

Arg Ser Leu Thr Gly Ile Leu Ile His Ile Gly Ser Gln Pro Gly Lys
1570                          1575                1580

His Leu Cys Val Tyr Leu Glu Ala Gly Lys Val Thr Ala Ser Met Asp
1585                          1590                1595                1600

Ser Gly Ala Gly Gly Thr Ser Val Thr Ser Val Ala Val Thr Pro Lys Gln Ser Leu
                              1605                1610                1615

Cys Asp Gly Gln Trp His Ser Val Ala Val Thr Ile Lys Gln His Ile
1620                          1625                1630

Leu His Leu Glu Leu Asp Thr Asp Ser Ser Tyr Thr Ala Gly Gln Ile
1635                          1640                1645

*Fig. 19Q.*

Pro Phe Pro Pro Ala Ser Thr Gln Glu Pro Leu His Leu Gly Gly Ala
     1650                1655                1660

Pro Ala Asn Leu Thr Thr Leu Arg Ile Pro Val Trp Lys Ser Phe Phe
     1665                1670                1675                1680

Gly Cys Leu Arg Asn Ile His Val Asn His Ile Pro Val Pro Val Thr
             1685                1690                1695

Glu Ala Leu Glu Val Gln Gly Pro Val Ser Leu Asn Gly Cys Pro Asp
     1700                1705                1710

Gln

Fig. 19R.

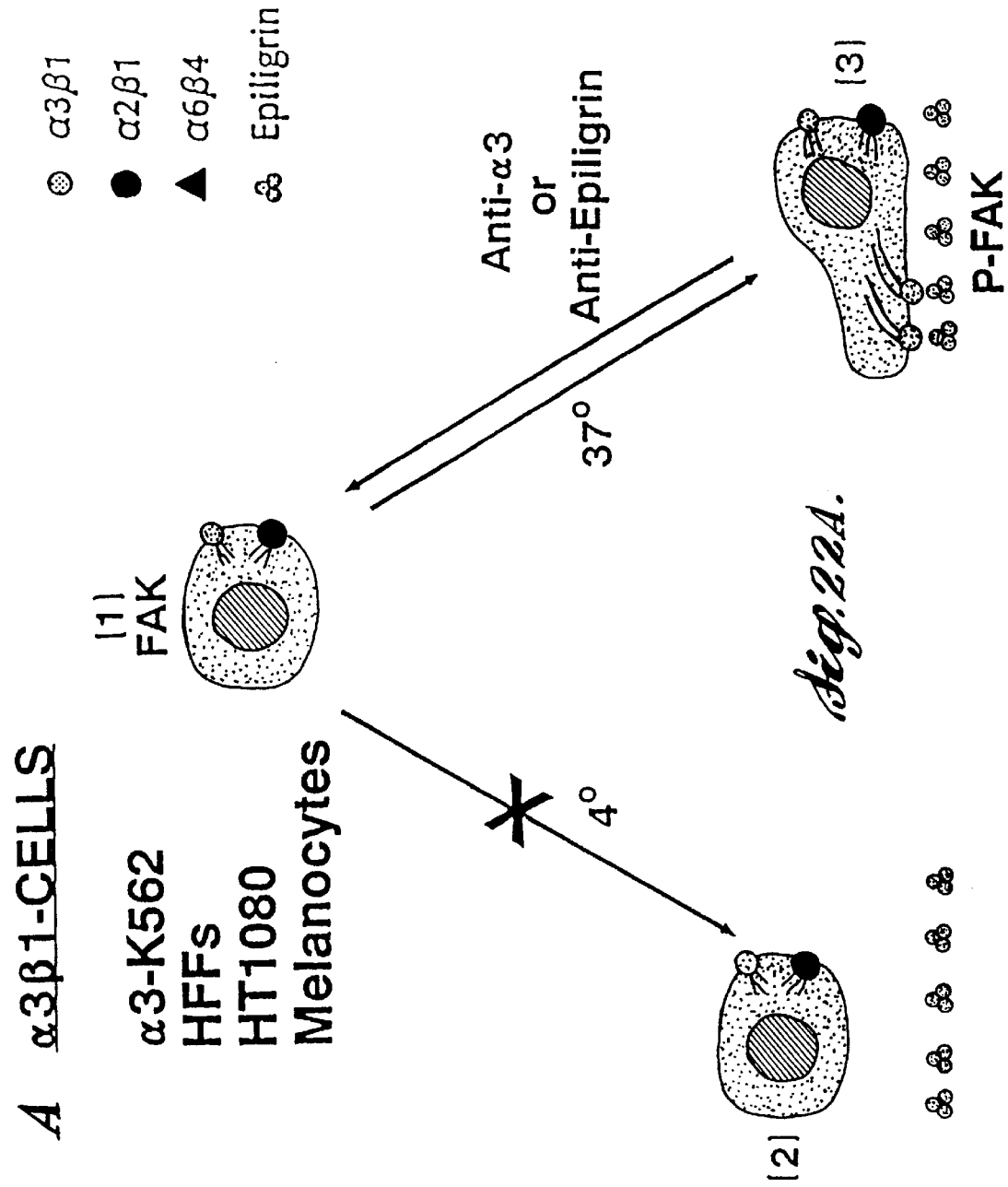

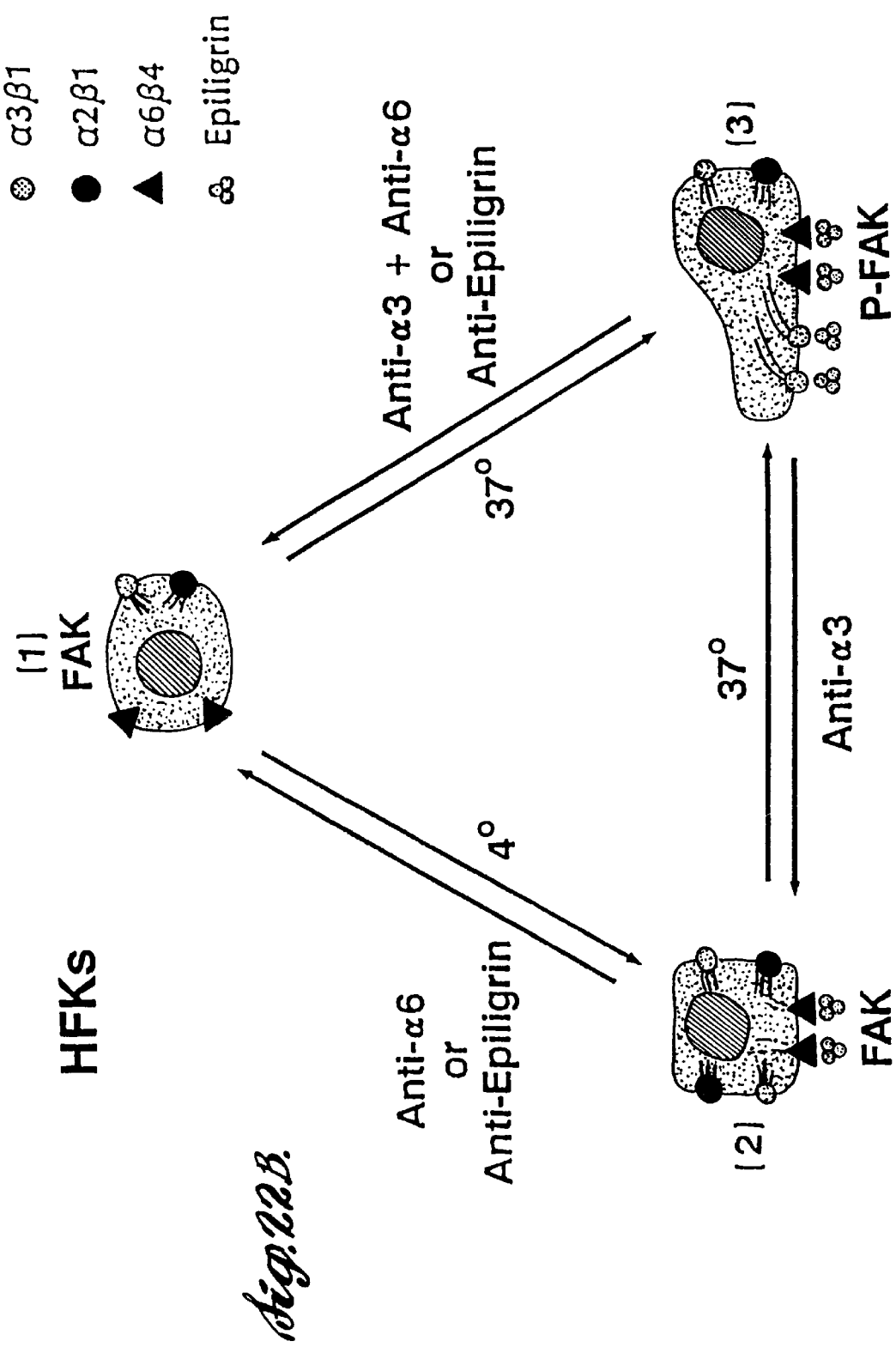

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 24 base pairs (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see FIGURE 12B (iii) HYPOTHETICAL: NO (vi) ORIGINAL SOURCE:
            (A) ORGANISM: Homo sapiens (xi) SEQUENCE DESCRIPTION: SEQ ID NO:1:

TGGCATTGAG GATGTTCTCG TAGG                                              24

(2) INFORMATION FOR SEQ ID NO:2:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see FIGURE 12B (iii) HYPOTHETICAL: NO (vi) ORIGINAL SOURCE:
            (A) ORGANISM: Homo sapiens (xi) SEQUENCE DESCRIPTION: SEQ ID NO:2:

ACGTAAGCTT AGCACGAAGG TCACTGAGTT                                        30

(2) INFORMATION FOR SEQ ID NO:3:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see FIGURE 12B (iii) HYPOTHETICAL: NO (vi) ORIGINAL SOURCE:
            (A) ORGANISM: Homo sapiens (xi) SEQUENCE DESCRIPTION: SEQ ID NO:3:

ATATGTCGAC AAGTCACCTG AAGGCACG                                          28

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see FIGURE 12B (iii) HYPOTHETICAL: NO (vi) ORIGINAL SOURCE:
            (A) ORGANISM: Homo sapiens (xi) SEQUENCE DESCRIPTION: SEQ ID NO:4:

TGGACGTGAG ACTTGACCAG                                                   20

```
(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION:  PCR primer; see FIGURE 12B (iii) HYPOTHETICAL: NO (vi) ORIGINAL SOURCE:
        (A) ORGANISM: Homo sapiens (xi) SEQUENCE DESCRIPTION: SEQ ID NO:5:

ATGTCATCCG GAATGTGCAC                                                       20

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION:  PCR primer; see FIGURE 12B (iii) HYPOTHETICAL: NO (vi) ORIGINAL SOURCE:
        (A) ORGANISM: Homo sapiens (xi) SEQUENCE DESCRIPTION: SEQ ID NO:6:

TACGACACCT GTGTGATG                                                         18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION:  PCR primer; see FIGURE 12B (iii) HYPOTHETICAL: NO (vi) ORIGINAL SOURCE:
        (A) ORGANISM: Homo sapiens (xi) SEQUENCE DESCRIPTION: SEQ ID NO:7:

ACGGCGTTGC CATAGTAG                                                         18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION:  PCR primer; see FIGURE 12B (iii) HYPOTHETICAL: NO (vi) ORIGINAL SOURCE:
        (A) ORGANISM: Homo sapiens
```

```
        (xi) SEQUENCE DESCRIPTION: SEQ ID NO:8:

TAGGCCTGGA TACTATCG                                                    18

(2) INFORMATION FOR SEQ ID NO:9:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA to mRNA
           (A) DESCRIPTION:  PCR primer; see TABLE 1

(iii) HYPOTHETICAL: NO (vi) ORIGINAL SOURCE:
           (A) ORGANISM: Homo sapiens (xi) SEQUENCE DESCRIPTION: SEQ ID NO:9:

AGCACGAAGG TCACTGAGTT                                                  20

(2) INFORMATION FOR SEQ ID NO:10:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: cDNA to mRNA
           (A) DESCRIPTION:  PCR primer; see TABLE 1

(iii) HYPOTHETICAL: NO (vi) ORIGINAL SOURCE:
           (A) ORGANISM: Homo sapiens (xi) SEQUENCE DESCRIPTION: SEQ ID NO:10:

AAGTCACCTG AAGGCACG                                                    18

(2) INFORMATION FOR SEQ ID NO:11:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA to mRNA
           (A) DESCRIPTION:  PCR primer; see TABLE 1

(iii) HYPOTHETICAL: NO (vi) ORIGINAL SOURCE:
           (A) ORGANISM: Homo sapiens (xi) SEQUENCE DESCRIPTION: SEQ ID NO:11:

TGGACGTGCG ACTTGACCAG                                                  20

(2) INFORMATION FOR SEQ ID NO:12:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: cDNA to mRNA
           (A) DESCRIPTION:  PCR primer; see TABLE 1
```

(iii) HYPOTHETICAL: NO (vi) ORIGINAL SOURCE:
             (A) ORGANISM: Homo sapiens (xi) SEQUENCE DESCRIPTION: SEQ ID NO:12:

AACTCGCTTG CAGTTGAC                                                    18

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:13:

GATGGCTGTG GATCTTTG                                                    18

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:14:

TCCACAGCAA GTGCTATG                                                    18

(2) INFORMATION FOR SEQ ID NO:15:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:15:

ATGACAGTGC TGTCTGGAC                                                   19

(2) INFORMATION FOR SEQ ID NO:16:

(i) SEQUENCE CHARACTERISTICS:
            (A) LENGTH: 20 base pairs
            (B) TYPE: nucleic acid

```
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:16:

TCTCCGAGAT GGTCTTCATG                                            20

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:17:

TTATCTGCAT CAGTCAGAGC                                            20

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:18:

TGACCAGTGA GCTGTACATC                                            20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA
            (A) DESCRIPTION:  PCR primer; see TABLE 1

(iii) HYPOTHETICAL: NO (vi) ORIGINAL SOURCE:
            (A) ORGANISM: Homo sapiens (xi) SEQUENCE DESCRIPTION: SEQ ID NO:19:

AGAGACCATT CGATTCAGAT                                            20
```

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION: PCR primer; see TABLE 1

(iii) HYPOTHETICAL: NO (vi) ORIGINAL SOURCE:
        (A) ORGANISM: Homo sapiens (xi) SEQUENCE DESCRIPTION: SEQ ID NO:20:

| | |
|---|---:|
| AGCTTCTGAG AAATAGCAAA | 20 |

(2) INFORMATION FOR SEQ ID NO:21:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION: cDNA sequence corresponding FIGURE 10F (iii) HYPOTHETICAL: NO (vi) ORIGINAL SOURCE:
        (A) ORGANISM: Homo sapiens (xi) SEQUENCE DESCRIPTION: SEQ ID NO:21:

| | |
|---|---:|
| CGGGGATGCC TCCAGCAGTG ACCCGGTCAG CCTGCAGCAT GGGATGGCTG TGGATCTTTG | 60 |
| GGGCAGCCCT GGGGCAGTGT CTGGGCTACA GTTCACAGCA GCAAAGGGTG CCATTTCTTC | 120 |
| AGCCTCCCGG TCAAAGTCAA CTGCAAGCGA GTTATGTGGA GTTTAGACCC AGCCAGGGTT | 180 |
| GTAGCCCTGG ATACTATCGG GATCATAAAG GCTTGTATAC CGGACGGTGT GTTCCCCTGC | 240 |
| AATTGCAACG GACATTCAAA TCAATGCCAG GATGGCTCAG GCATATGTGT TAACTGTCAG | 300 |
| CACAACACCG CGGGAGCACT GTCATCGCTG CCAGGAGGGC TACTATGGCA ACGCCGTCCA | 360 |
| CGGATCCTGC AGGCCCTGCC CATGTCCTCA CACTAACAGC TTGCCTCTGC CTGTGTGGTG | 420 |
| AATGGGGGAG ACGTACGGCG CTCCTGCAAA GCTGGGTACA CAGGAACCCA GTGTGTAAGG | 480 |
| TGTGCACCGG GATATTTCGG GAATCCCCAG AAATTCGGAG GTAGCTGCCA ACCATGCAGT | 540 |
| TGTAACAGCA ATGGCCAGCT GGGCAGCTGT CATCCCCTGA CTGGAGGCTG CATAAACCAA | 600 |
| GAAACCAAAG ATAACAACCC TGCAGAAGAA TGTGATGATT GCGACACCTG TGTGATGACC | 660 |
| CTCC | 664 |

(2) INFORMATION FOR SEQ ID NO:22:

(i) SEQUENCE CHARACTERISTICS:
        (A) LENGTH: 1994 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION: cDNA sequence corresponding to FIGURES
            11A-11C (iii) HYPOTHETICAL: NO (vi) ORIGINAL SOURCE:

(A) ORGANISM: Homo sapiens (xi) SEQUENCE DESCRIPTION: SEQ ID NO:22:

```
CGGGGATGCC TCCAGCAGTG ACCCGGTCAG CCTGCAGCAT GGGATGGCTG TGGATCTTTG      60

GGGCAGCCCT GGGGCAGTGT CTGGGCTACA GTTCACAGCA GCAAAGGGTG CCATTTCTTC     120

AGCCTCCCGG TCAAAGTCAA CTGCAAGCGA GTTATGTGGA GTTTAGACCC AGCCAGGGTT     180

GTAGCCCTGG ATACTATCGG GATCATAAAG GCTTGTATAC CGGACGGTGT GTTCCCCTGC     240

AATTGCAACG GACATTCAAA TCAATGCCAG GATGGCTCAG GCATATGTGT TAACTGTCAG     300

CACAACACCG CGGGAGCACT GTCATCGCTG CCAGGAGGGC TACTATGGCA ACGCCGTCCA     360

CGGATCCTGC AGGCCCTGCC CATGTCCTCA CACTAACAGC TTGCCTCTGC CTGTGTGGTG     420

AATGGGGGAG ACGTACGGCG CTCCTGCAAA GCTGGGTACA CAGGAACCCA GTGTGTAAGG     480

TGTGCACCGG GATATTTCGG GAATCCCCAG AAATTCGGAG GTAGCTGCCA ACCATGCAGT     540

TGTAACAGCA ATGGCCAGCT GGGCAGCTGT CATCCCCTGA CTGGAGGCTG CATAAACCAA     600

GAAACCAAAG ATAACAACCC TGCAGAAGAA TGTGATGATT GCGACACCTG TGTGATGACC     660

CTCCTGAACG ACCTGGCCAC CATGGGCGAG CAGCTCCGCC TGGTCAAGTC TCAGCTGCAG     720

GGCCTGAGTG CCAGCGCAGG GCTTCTGGAG CAGATGAGGC ACATGGAGAC CCAGGCCAAG     780

GACCTGAGGA ATCAGTTGCT CAACTACCGT TCTGCCATTT CAAATCATGG ATCAAAAATA     840

GAAGGCCTGG AAAGAGAACT GACTGATTTG AATCAAGAAT TTGAGACTTT GCAAGAAAAG     900

GCTCAAGTAA ATTCCAGAAA AGCACAAACA TTAAACAACA ATGTTAATCG GGCAACACAA     960

AGCGCAAAAG AACTGGATGT GAAGATTAAA AATGTCATCC GGAATGTGCA CATTCTTTTA    1020

AAGCAGATCT CTGGGACAGA TGGAGAGGGA ACAACGTGC CTTCAGGTGA CTTTTCCAGA     1080

GAGTGGGCTG AAGCCCAGCG CATGATGAGG GAACTGCGGA ACAGGAACTT TGGAAAGCAC    1140

CTCAGAGAAG CAGAAGCTGA TAAAAGGGAG TCGCAGCTCT TGCTGAACCG GATAAGGACC    1200

TGGCAGAAAA CCCACCAGGG GGAGAACAAT GGGCTTGCTA ACAGTATCCG GGATTCTTTA    1260

AATGAATACG AAGCCAAACT CAGTGACCTT CGTGCTCGGC TGCAGGAGGC AGCTGCCCAA    1320

GCCAAGCAGG CAAATGGCTT GAACCAAGAA AACGAGAGAG CTTTGGGAGC CATTCAGAGA    1380

CAAGTGAAAG AAATAAATTC CCTGCAGAGT GATTTCACCA AGTATCTAAC CACTGCAGAC    1440

TCATCTTTGT TGCAAACCAA CATTGCGCTG CAGCTGATGG AGAAAAGCCA GAAGGAATAT    1500

GAAAAATTAG CTGCCAGTTT AAATGAAGCA AGACAAGAAC TAAGTGACAA AGTAAGAGAA    1560

CTTTCCAGAT CTGCTGGCAA AACATCCCTT GTGGAGGAGG CAGAAAAGCA CGCGCGGTCC    1620

TTACAAGAGC TGGCAAAGCA GCTGGAAGAG ATCAAGAGAA ACGCCAGCGG GGATGAGCTG    1680

GTGCGCTGTG CTGTGGATGC CGCCACCGCC TACGAGAACA TCCTCAATGC CATCAAAGCG    1740

GCCGAGGACC GAGCCAACAG GGCTCGCAGT GCATCTGAAT CTGCCCTCCA GACAGTGATA    1800

AAGGAAGATC TGCCAAGAAA AGCTAAAACC CTGAGTTCCA ACAGTGATAA ACTGTTAAAG    1860

AAGCCAAGAT GACACAAAAG AAGCTAAAGC AAGAAGTCAG TCCAGCTCTC AACAACCTAC    1920

AGCAAACCCT GAATATTGTG ACAGTTCAGA AAGAAGTGAT AGACACCAAT CTCACAACTC    1980

TCCGAGATGG TCTC                                                      1994
```

(2) INFORMATION FOR SEQ ID NO:23:

(i) SEQUENCE CHARACTERISTICS:
(A) LENGTH: 5496 base pairs
(B) TYPE: nucleic acid
(C) STRANDEDNESS: single -continued

```
          (D) TOPOLOGY: linear (ii) MOLECULE TYPE: cDNA to mRNA
          (A) DESCRIPTION:Sequence of cDNA to 3EpA cDNA; see FIGURES
              15A-15F (iii) HYPOTHETICAL: NO (iv) ANTI-SENSE: NO (vi) ORIGINAL SOURCE:
          (A) ORGANISM: Homo sapiens (ix) FEATURE:
          (A) NAME/KEY: CDS
          (B) LOCATION: 59..5200

(xi) SEQUENCE DESCRIPTION: SEQ ID NO:23:

AGCCAGCGGA CGTCCAGGAA CCGGGATGCC TCCAGCAGTG AGGCGGTCAG CCTGCAGC              58

ATG GGA TGG CTG TGG ATC TTT GGG GCA GCC CTG GGG CAG TGT CTG GGC            106
Met Gly Trp Leu Trp Ile Phe Gly Ala Ala Leu Gly Gln Cys Leu Gly
 1               5                  10                  15

TAC AGT TCA CAG CAG CAA AGG GTG CCA TTT CTT CAG CCT CCC GGT CAA            154
Tyr Ser Ser Gln Gln Gln Arg Val Pro Phe Leu Gln Pro Pro Gly Gln
                 20                  25                  30

AGT CAA CTG CAA GCG AGT TAT GTG GAG TTT AGA CCC AGC CAG GGT TGT            202
Ser Gln Leu Gln Ala Ser Tyr Val Glu Phe Arg Pro Ser Gln Gly Cys
         35                  40                  45

AGC CCT GGA TAC TAT CGG GAT CAT AAA GGC TTG TAT ACC GGA CGG TGT            250
Ser Pro Gly Tyr Tyr Arg Asp His Lys Gly Leu Tyr Thr Gly Arg Cys
     50                  55                  60

GTT CCC TGC AAT TGC AAC GGA CAT TCA AAT CAA TGC CAG GAT GGC TCA            298
Val Pro Cys Asn Cys Asn Gly His Ser Asn Gln Cys Gln Asp Gly Ser
 65                  70                  75                  80

GGC ATA TGT GTT AAC TGT CAG CAC AAC ACC GCG GGA GAG CAC TGT GAA            346
Gly Ile Cys Val Asn Cys Gln His Asn Thr Ala Gly Glu His Cys Glu
                 85                  90                  95

CGC TGC CAG GAG GGC TAC TAT GGC AAC GCC GTC CAC GGA TCC TGC AGG            394
Arg Cys Gln Glu Gly Tyr Tyr Gly Asn Ala Val His Gly Ser Cys Arg
                100                 105                 110

GCC TGC CCA TGT CCT CAC ACT AAC AGC TTT GCC ACT GGC TGT GTG GTG            442
Ala Cys Pro Cys Pro His Thr Asn Ser Phe Ala Thr Gly Cys Val Val
        115                 120                 125

AAT GGG GGA GAC GTG CGG TGC TCC TGC AAA GCT GGG TAC ACA GGA ACA            490
Asn Gly Gly Asp Val Arg Cys Ser Cys Lys Ala Gly Tyr Thr Gly Thr
130                 135                 140

CAG TGT GAA AGG TGT GCA CCG GGA TAT TTC GGG AAT CCC CAG AAA TTC            538
Gln Cys Glu Arg Cys Ala Pro Gly Tyr Phe Gly Asn Pro Gln Lys Phe
145                 150                 155                 160

GGA GGT AGC TGC CAA CCA TGC AGT TGT AAC AGC AAT GGC CAG CTG GGC            586
Gly Gly Ser Cys Gln Pro Cys Ser Cys Asn Ser Asn Gly Gln Leu Gly
                165                 170                 175

AGC TGT CAT CCC CTG ACT GGA GAC TGC ATA AAC CAA GAA CCC AAA GAT            634
Ser Cys His Pro Leu Thr Gly Asp Cys Ile Asn Gln Glu Pro Lys Asp
            180                 185                 190

AGC AGC CCT GCA GAA GAA TGT GAT GAT TGC GAC AGC TGT GTG ATG ACC            682
Ser Ser Pro Ala Glu Glu Cys Asp Asp Cys Asp Ser Cys Val Met Thr
                195                 200                 205

CTC CTG AAC GAC CTG GCC ACC ATG GGC GAG CAG CTC CGC CTG GTC AAG            730
Leu Leu Asn Asp Leu Ala Thr Met Gly Glu Gln Leu Arg Leu Val Lys
        210                 215                 220

TCT CAG CTG CAG GGC CTG AGT GCC AGC GCA GGG CTT CTG GAG CAG ATG            778
Ser Gln Leu Gln Gly Leu Ser Ala Ser Ala Gly Leu Leu Glu Gln Met
```

```
                 225                  230                235                 240
AGG CAC ATG GAG ACC CAG GCC AAG GAC CTG AGG AAT CAG TTG CTC AAC        826
Arg His Met Glu Thr Gln Ala Lys Asp Leu Arg Asn Gln Leu Leu Asn
                        245                250                255

TAC CGT TCT GCC ATT TCA AAT CAT GGA TCA AAA ATA GAA GGC CTG GAA        874
Tyr Arg Ser Ala Ile Ser Asn His Gly Ser Lys Ile Glu Gly Leu Glu
                    260                265                270

AGA GAA CTG ACT GAT TTG AAT CAA GAA TTT GAG ACT TTG CAA GAA AAG        922
Arg Glu Leu Thr Asp Leu Asn Gln Glu Phe Glu Thr Leu Gln Glu Lys
                275                280                285

GCT CAA GTA AAT TCC AGA AAA GCA CAA ACA TTA AAC AAC AAT GTT AAT        970
Ala Gln Val Asn Ser Arg Lys Ala Gln Thr Leu Asn Asn Asn Val Asn
                290                295                300

CGG GCA ACA CAA AGC GCA AAA GAA CTG GAT GTG AAG ATT AAA AAT GTC       1018
Arg Ala Thr Gln Ser Ala Lys Glu Leu Asp Val Lys Ile Lys Asn Val
305                310                315                320

ATC CGG AAT GTG CAC ATT CTT TTA AAG CAG ATC TCT GGG ACA GAT GGA       1066
Ile Arg Asn Val His Ile Leu Leu Lys Gln Ile Ser Gly Thr Asp Gly
                        325                330                335

GAG GGA AAC AAC GTG CCT TCA GGT GAC TTT TCC AGA GAG TGG GCT GAA       1114
Glu Gly Asn Asn Val Pro Ser Gly Asp Phe Ser Arg Glu Trp Ala Glu
                    340                345                350

GCC CAG CGC ATG ATG AGG GAA CTG CGG AAC AGG AAC TTT GGA AAG CAC       1162
Ala Gln Arg Met Met Arg Glu Leu Arg Asn Arg Asn Phe Gly Lys His
                355                360                365

CTC AGA GAA GCA GAA GCT GAT AAA AGG GAG TCG CAG CTC TTG CTG AAC       1210
Leu Arg Glu Ala Glu Ala Asp Lys Arg Glu Ser Gln Leu Leu Leu Asn
            370                375                380

CGG ATA AGG ACC TGG CAG AAA ACC CAC CAG GGG GAG AAC AAT GGG CTT       1258
Arg Ile Arg Thr Trp Gln Lys Thr His Gln Gly Glu Asn Asn Gly Leu
385                390                395                400

GCT AAC AGT ATC CGG GAT TCT TTA AAT GAA TAC GAA GCC AAA CTC AGT       1306
Ala Asn Ser Ile Arg Asp Ser Leu Asn Glu Tyr Glu Ala Lys Leu Ser
                        405                410                415

GAC CTT CGT GCT CGG CTG CAG GAG GCA GCT GCC CAA GCC AAG CAG GCA       1354
Asp Leu Arg Ala Arg Leu Gln Glu Ala Ala Ala Gln Ala Lys Gln Ala
                    420                425                430

AAT GGC TTG AAC CAA GAA AAC GAG AGA GCT TTG GGA GCC ATT CAG AGA       1402
Asn Gly Leu Asn Gln Glu Asn Glu Arg Ala Leu Gly Ala Ile Gln Arg
                435                440                445

CAA GTG AAA GAA ATA AAT TCC CTG CAG AGT GAT TTC ACC AAG TAT CTA       1450
Gln Val Lys Glu Ile Asn Ser Leu Gln Ser Asp Phe Thr Lys Tyr Leu
            450                455                460

ACC ACT GCA GAC TCA TCT TTG TTG CAA ACC AAC ATT GCG CTG CAG CTG       1498
Thr Thr Ala Asp Ser Ser Leu Leu Gln Thr Asn Ile Ala Leu Gln Leu
465                470                475                480

ATG GAG AAA AGC CAG AAG GAA TAT GAA AAA TTA GCT GCC AGT TTA AAT       1546
Met Glu Lys Ser Gln Lys Glu Tyr Glu Lys Leu Ala Ala Ser Leu Asn
                        485                490                495

GAA GCA AGA CAA GAA CTA AGT GAC AAA GTA AGA GAA CTT TCC AGA TCT       1594
Glu Ala Arg Gln Glu Leu Ser Asp Lys Val Arg Glu Leu Ser Arg Ser
                    500                505                510

GCT GGC AAA ACA TCC CTT GTG GAG GAG GCA GAA AAG CAC GCG CGG TCC       1642
Ala Gly Lys Thr Ser Leu Val Glu Glu Ala Glu Lys His Ala Arg Ser
                515                520                525

TTA CAA GAG CTG GCA AAG CAG CTG GAA GAG ATC AAG AGA AAC GCC AGC       1690
Leu Gln Glu Leu Ala Lys Gln Leu Glu Glu Ile Lys Arg Asn Ala Ser
            530                535                540

GGG GAT GAG CTG GTG CGC TGT GCT GTG GAT GCC GCC ACC GCC TAC GAG       1738
```

-continued

```
Gly Asp Glu Leu Val Arg Cys Ala Val Asp Ala Ala Thr Ala Tyr Glu
545                 550                 555                 560

AAC ATC CTC AAT GCC ATC AAA GCG GCC GAG GAC GCA GCC AAC AGG GCT      1786
Asn Ile Leu Asn Ala Ile Lys Ala Ala Glu Asp Ala Ala Asn Arg Ala
                565                 570                 575

GCC AGT GCA TCT GAA TCT GCC CTC CAG ACA GTG ATA AAG GAA GAT CTG      1834
Ala Ser Ala Ser Glu Ser Ala Leu Gln Thr Val Ile Lys Glu Asp Leu
                580                 585                 590

CCA AGA AAA GCT AAA ACC CTG AGT TCC AAC AGT GAT AAA CTG TTA AAT      1882
Pro Arg Lys Ala Lys Thr Leu Ser Ser Asn Ser Asp Lys Leu Leu Asn
            595                 600                 605

GAA GCC AAG ATG ACA CAA AAG AAG CTA AAG CAA GAA GTC AGT CCA GCT      1930
Glu Ala Lys Met Thr Gln Lys Lys Leu Lys Gln Glu Val Ser Pro Ala
        610                 615                 620

CTC AAC AAC CTA CAG CAA ACC CTG AAT ATT GTG ACA GTT CAG AAA GAA      1978
Leu Asn Asn Leu Gln Gln Thr Leu Asn Ile Val Thr Val Gln Lys Glu
625                 630                 635                 640

GTG ATA GAC ACC AAT CTC ACA ACT CTC CGA GAT GGT CTT CAT GGG ATA      2026
Val Ile Asp Thr Asn Leu Thr Thr Leu Arg Asp Gly Leu His Gly Ile
                645                 650                 655

CAG AGA GGT GAT ATT GAT GCT ATG ATC AGT AGT GCA AAG AGC ATG GTC      2074
Gln Arg Gly Asp Ile Asp Ala Met Ile Ser Ser Ala Lys Ser Met Val
                660                 665                 670

AGA AAG GCC AAC GAC ATC ACA GAT GAG GTT CTG GAT GGG CTC AAC CCC      2122
Arg Lys Ala Asn Asp Ile Thr Asp Glu Val Leu Asp Gly Leu Asn Pro
            675                 680                 685

ATC CAG ACA GAT GTG GAA AGA ATT AAG GAC ACC TAT GGG AGG ACA CAG      2170
Ile Gln Thr Asp Val Glu Arg Ile Lys Asp Thr Tyr Gly Arg Thr Gln
        690                 695                 700

AAC GAA GAC TTC AAA AAG GCT CTG ACT GAT GCA GAT AAC TCG GTG AAT      2218
Asn Glu Asp Phe Lys Lys Ala Leu Thr Asp Ala Asp Asn Ser Val Asn
705                 710                 715                 720

AAG TTA ACC AAC AAA CTA CCT GAT CTT TGG CGC AAG ATT GAA AGT ATC      2266
Lys Leu Thr Asn Lys Leu Pro Asp Leu Trp Arg Lys Ile Glu Ser Ile
                725                 730                 735

AAC CAA CAG CTG TTG CCC TTG GGA AAC ATC TCT GAC AAC ATG GAC AGA      2314
Asn Gln Gln Leu Leu Pro Leu Gly Asn Ile Ser Asp Asn Met Asp Arg
                740                 745                 750

ATA CGA GAA CTA ATT CAG CAG GCC AGA GAT GCT GCC AGT AAG GTT GCT      2362
Ile Arg Glu Leu Ile Gln Gln Ala Arg Asp Ala Ala Ser Lys Val Ala
            755                 760                 765

GTC CCC ATG AGG TTC AAT GGT AAA TCT GGA GTC GAA GTC CGA CTG CCA      2410
Val Pro Met Arg Phe Asn Gly Lys Ser Gly Val Glu Val Arg Leu Pro
        770                 775                 780

AAT GAC CTG GAA GAT TTG AAA GGA TAT ACA TCT CTG TCC TTG TTT CTC      2458
Asn Asp Leu Glu Asp Leu Lys Gly Tyr Thr Ser Leu Ser Leu Phe Leu
785                 790                 795                 800

CAA AGG CCC AAC TCA AGA GAA AAT GGG GGT ACT GAG AAT ATG TTT GTG      2506
Gln Arg Pro Asn Ser Arg Glu Asn Gly Gly Thr Glu Asn Met Phe Val
                805                 810                 815

ATG TAC CTT GGA AAT AAA GAT GCC TCC CGG GAC TAC ATC GGC ATG GCA      2554
Met Tyr Leu Gly Asn Lys Asp Ala Ser Arg Asp Tyr Ile Gly Met Ala
                820                 825                 830

GTT GTG GAT GGC CAG CTC ACC TGT GTC TAC AAC CTG GGG GAC CGT GAG      2602
Val Val Asp Gly Gln Leu Thr Cys Val Tyr Asn Leu Gly Asp Arg Glu
            835                 840                 845

GCT GAA CTC CAA GTG GAC CAG ATC TTG ACC AAG AGT GAG ACT AAG GAG      2650
Ala Glu Leu Gln Val Asp Gln Ile Leu Thr Lys Ser Glu Thr Lys Glu
        850                 855                 860
```

-continued

```
GCA GTT ATG GAT CGG GTG AAA TTT CAG AGA ATT TAT CAG TTT GCA AGG    2698
Ala Val Met Asp Arg Val Lys Phe Gln Arg Ile Tyr Gln Phe Ala Arg
865                 870                 875                 880

CTT AAT TAC ACC AAA GGA GCC ACA TCC AGT AAA CCA GAA ACA CCC GGA    2746
Leu Asn Tyr Thr Lys Gly Ala Thr Ser Ser Lys Pro Glu Thr Pro Gly
            885                 890                 895

GTC TAT GAC ATG GAT GGT AGA AAT AGC AAT ACA CTC CTT AAT TTG GAT    2794
Val Tyr Asp Met Asp Gly Arg Asn Ser Asn Thr Leu Leu Asn Leu Asp
        900                 905                 910

CCT GAA AAT GTT GTA TTT TAT GTT GGA GGT TAC CCA CCT GAT TTT AAA    2842
Pro Glu Asn Val Val Phe Tyr Val Gly Gly Tyr Pro Pro Asp Phe Lys
    915                 920                 925

CTT CCC AGT CGA CTA AGT TTC CCT CCA TAC AAA GGT TGT ATT GAA TTA    2890
Leu Pro Ser Arg Leu Ser Phe Pro Pro Tyr Lys Gly Cys Ile Glu Leu
930                 935                 940

GAT GAC CTC AAT GAA AAT GTT CTG AGC TTG TAC AAC TTC AAA AAA ACA    2938
Asp Asp Leu Asn Glu Asn Val Leu Ser Leu Tyr Asn Phe Lys Lys Thr
945                 950                 955                 960

TTC AAT CTC AAC ACA ACT GAA GTG GAG CCT TGT AGA AGG AGG AAG GAA    2986
Phe Asn Leu Asn Thr Thr Glu Val Glu Pro Cys Arg Arg Arg Lys Glu
            965                 970                 975

GAG TCA GAC AAA AAT TAT TTT GAA GGT ACG GGC TAT GCT CGA GTT CCA    3034
Glu Ser Asp Lys Asn Tyr Phe Glu Gly Thr Gly Tyr Ala Arg Val Pro
        980                 985                 990

ACT CAA CCA CAT GCT CCC ATC CCA ACC TTT GGA CAG ACA ATT CAG ACC    3082
Thr Gln Pro His Ala Pro Ile Pro Thr Phe Gly Gln Thr Ile Gln Thr
    995                 1000                1005

ACC GTG GAT AGA GGC TTG CTG TTC TTT GCA GAA AAC GGG GAT CGC TTC    3130
Thr Val Asp Arg Gly Leu Leu Phe Phe Ala Glu Asn Gly Asp Arg Phe
1010                1015                1020

ATA TCT CTA AAT ATA GAA GAT GGC AAG CTC ATG GTG AGA TAC AAA CTG    3178
Ile Ser Leu Asn Ile Glu Asp Gly Lys Leu Met Val Arg Tyr Lys Leu
1025                1030                1035                1040

AAT TCA GAG CTA CCA AAA GAG AGA GGA GTT GGA GAC GCC ATA AAC AAC    3226
Asn Ser Glu Leu Pro Lys Glu Arg Gly Val Gly Asp Ala Ile Asn Asn
            1045                1050                1055

GGC AGA GAC CAT TCG ATT CAG ATC AAA ATT GGA AAA CTC CAA AAG CGT    3274
Gly Arg Asp His Ser Ile Gln Ile Lys Ile Gly Lys Leu Gln Lys Arg
        1060                1065                1070

ATG TGG ATA AAT GTG GAC GTT CAA AAC ACT ATA ATT GAT GGT GAA GTA    3322
Met Trp Ile Asn Val Asp Val Gln Asn Thr Ile Ile Asp Gly Glu Val
    1075                1080                1085

TTT GAT TTC AGC ACA TAT TAT CTG GGA GGA ATT CCA ATT GCA ATC AGG    3370
Phe Asp Phe Ser Thr Tyr Tyr Leu Gly Gly Ile Pro Ile Ala Ile Arg
1090                1095                1100

GAA AGA TTT AAC ATT TCT ACG CCT GCT TTC CGA GGC TGC ATG AAA AAT    3418
Glu Arg Phe Asn Ile Ser Thr Pro Ala Phe Arg Gly Cys Met Lys Asn
1105                1110                1115                1120

TTG AAG AAA ACC AGT GGT GTC GTT AGA TTG AAT GAT ACT GTG GGA GTA    3466
Leu Lys Lys Thr Ser Gly Val Val Arg Leu Asn Asp Thr Val Gly Val
            1125                1130                1135

ACC AAA AAG TGC TCG GAA GAC TGG AAG CTT GTG CGA TCT GCC TCA TTC    3514
Thr Lys Lys Cys Ser Glu Asp Trp Lys Leu Val Arg Ser Ala Ser Phe
        1140                1145                1150

TCC AGA GGA GGA CAA TTG AGT TTC ACT GAT TTG GGC TTA CCA CCT ACT    3562
Ser Arg Gly Gly Gln Leu Ser Phe Thr Asp Leu Gly Leu Pro Pro Thr
    1155                1160                1165

GAC CAC CTC CAG GCC TCA TTT GGA TTT CAG ACC TTT CAA CCC AGT GGC    3610
Asp His Leu Gln Ala Ser Phe Gly Phe Gln Thr Phe Gln Pro Ser Gly
1170                1175                1180
```

```
ATA TTA TTA GAT CAT CAG ACA TGG ACA AGG AAC CTG CAG GTC ACT CTG      3658
Ile Leu Leu Asp His Gln Thr Trp Thr Arg Asn Leu Gln Val Thr Leu
1185                 1190                1195                1200

GAA GAT GGT TAC ATT GAA TTG AGC ACC AGC GAT AGC GGC GGC CCA ATT      3706
Glu Asp Gly Tyr Ile Glu Leu Ser Thr Ser Asp Ser Gly Gly Pro Ile
             1205                1210                1215

TTT AAA TCT CCA CAG ACG TAT ATG GAT GGT TTA CTG CAT TAT GTA TCT      3754
Phe Lys Ser Pro Gln Thr Tyr Met Asp Gly Leu Leu His Tyr Val Ser
                 1220                1225                1230

GTA ATA AGC GAC AAC TCT GGA CTA CGG CTT CTC ATC GAT GAC CAG CTT      3802
Val Ile Ser Asp Asn Ser Gly Leu Arg Leu Leu Ile Asp Asp Gln Leu
         1235                1240                1245

CTG AGA AAT AGC AAA AGG CTA AAA CAC ATT TCA AGT TCC CGG CAG TCT      3850
Leu Arg Asn Ser Lys Arg Leu Lys His Ile Ser Ser Ser Arg Gln Ser
             1250                1255                1260

CTG CGT CTG GGC GGG AGC AAT TTT GAG GGT TGT ATT AGC AAT GTT TTT      3898
Leu Arg Leu Gly Gly Ser Asn Phe Glu Gly Cys Ile Ser Asn Val Phe
1265                1270                1275                1280

GTC CAG AGG TTA TCA CTG AGT CCT GAA GTC CTA GAT TTG ACC AGT AAC      3946
Val Gln Arg Leu Ser Leu Ser Pro Glu Val Leu Asp Leu Thr Ser Asn
                 1285                1290                1295

TCT CTC AAG AGA GAT GTG TCC CTG GGA GGC TGC AGT TTA AAC AAA CCA      3994
Ser Leu Lys Arg Asp Val Ser Leu Gly Gly Cys Ser Leu Asn Lys Pro
         1300                1305                1310

CCT TTT CTA ATG TTG CTT AAA GGT TCT ACC AGG TTT AAC AAG ACC AAG      4042
Pro Phe Leu Met Leu Leu Lys Gly Ser Thr Arg Phe Asn Lys Thr Lys
             1315                1320                1325

ACT TTT CGT ATC AAC CAG CTG TTG CAG GAC ACA CCA GTG GCC TCC CCA      4090
Thr Phe Arg Ile Asn Gln Leu Leu Gln Asp Thr Pro Val Ala Ser Pro
1330                1335                1340

AGG AGC GTG AAG GTG TGG CAA GAT GCT TGC TCA CCA CTT CCC AAG ACC      4138
Arg Ser Val Lys Val Trp Gln Asp Ala Cys Ser Pro Leu Pro Lys Thr
1345                1350                1355                1360

CAG GCC AAT CAT GGA GCC CTC CAG TTT GGG GAC ATT CCC ACC AGC CAC      4186
Gln Ala Asn His Gly Ala Leu Gln Phe Gly Asp Ile Pro Thr Ser His
         1365                1370                1375

TTG CTA TTC AAG CTT CCT CAG GAG CTG CTG AAA CCC AGG TCA CAG TTT      4234
Leu Leu Phe Lys Leu Pro Gln Glu Leu Leu Lys Pro Arg Ser Gln Phe
             1380                1385                1390

GCT GTG GAC ATG CAG ACA ACA TCC TCC AGA GGA CTG GTG TTT CAC ACG      4282
Ala Val Asp Met Gln Thr Thr Ser Ser Arg Gly Leu Val Phe His Thr
             1395                1400                1405

GGC ACT AAG AAC TCC TTT ATG GCT CTT TAT CTT TCA AAA GGA CGT CTG      4330
Gly Thr Lys Asn Ser Phe Met Ala Leu Tyr Leu Ser Lys Gly Arg Leu
1410                1415                1420

GTC TTT GCA CTG GGG ACA GAT GGG AAA AAA TTG AGG ATC AAA AGC AAG      4378
Val Phe Ala Leu Gly Thr Asp Gly Lys Lys Leu Arg Ile Lys Ser Lys
1425                1430                1435                1440

GAG AAA TGC AAT GAT GGG AAA TGG CAC ACG GTG GTG TTT GGC CAT GAT      4426
Glu Lys Cys Asn Asp Gly Lys Trp His Thr Val Val Phe Gly His Asp
             1445                1450                1455

GGG GAA AAG GGG CGC TTG GTT GTG GAT GGA CTG AGG GCC CGG GAG GGA      4474
Gly Glu Lys Gly Arg Leu Val Val Asp Gly Leu Arg Ala Arg Glu Gly
                 1460                1465                1470

AGT TTG CCT GGA AAC TCC ACC ATC AGC ATC AGA GCG CCA GTT TAC CTG      4522
Ser Leu Pro Gly Asn Ser Thr Ile Ser Ile Arg Ala Pro Val Tyr Leu
         1475                1480                1485

GGA TCA CCT CCA TCA GGG AAA CCA AAG AGC CTC CCC ACA AAC AGC TTT      4570
Gly Ser Pro Pro Ser Gly Lys Pro Lys Ser Leu Pro Thr Asn Ser Phe
```

```
      1490              1495              1500
GTG GGA TGC CTG AAG AAC TTT CAG CTG GAT TCA AAA CCC TTG TAT ACC     4618
Val Gly Cys Leu Lys Asn Phe Gln Leu Asp Ser Lys Pro Leu Tyr Thr
1505                1510              1515              1520

CCT TCT TCA AGC TTC GGG GTG TCT TCC TGC TTG GGT GGT CCT TTG GAG     4666
Pro Ser Ser Ser Phe Gly Val Ser Ser Cys Leu Gly Gly Pro Leu Glu
                1525              1530              1535

AAA GGC ATT TAT TTC TCT GAA GAA GGA GGT CAT GTC GTC TTG GCT CAC     4714
Lys Gly Ile Tyr Phe Ser Glu Glu Gly Gly His Val Val Leu Ala His
            1540              1545              1550

TCT GTA TTG TTG GGG CCA GAA TTT AAG CTT GTT TTC AGC ATC CGC CCA     4762
Ser Val Leu Leu Gly Pro Glu Phe Lys Leu Val Phe Ser Ile Arg Pro
        1555              1560              1565

AGA AGT CTC ACT GGG ATC CTA ATA CAC ATC GGA AGT CAG CCC GGG AAG     4810
Arg Ser Leu Thr Gly Ile Leu Ile His Ile Gly Ser Gln Pro Gly Lys
    1570              1575              1580

CAC TTA TGT GTT TAC CTG GAG GCA GGA AAG GTC ACG GCC TCT ATG GAC     4858
His Leu Cys Val Tyr Leu Glu Ala Gly Lys Val Thr Ala Ser Met Asp
1585              1590              1595              1600

AGT GGG GCA GGT GGG ACC TCA ACG TCG GTC ACA CCA AAG CAG TCT CTG     4906
Ser Gly Ala Gly Gly Thr Ser Thr Ser Val Thr Pro Lys Gln Ser Leu
                1605              1610              1615

TGT GAT GGA CAG TGG CAC TCG GTG GCA GTC ACC ATA AAA CAA CAC ATC     4954
Cys Asp Gly Gln Trp His Ser Val Ala Val Thr Ile Lys Gln His Ile
            1620              1625              1630

CTG CAC CTG GAA CTG GAC ACA GAC AGT AGC TAC ACA GCT GGA CAG ATC     5002
Leu His Leu Glu Leu Asp Thr Asp Ser Ser Tyr Thr Ala Gly Gln Ile
        1635              1640              1645

CCC TTC CCA CCT GCC AGC ACT CAA GAG CCA CTA CAC CTT GGA GGT GCT     5050
Pro Phe Pro Pro Ala Ser Thr Gln Glu Pro Leu His Leu Gly Gly Ala
    1650              1655              1660

CCA GCC AAT TTG ACG ACA CTG AGG ATC CCT GTG TGG AAA TCA TTC TTT     5098
Pro Ala Asn Leu Thr Thr Leu Arg Ile Pro Val Trp Lys Ser Phe Phe
1665              1670              1675              1680

GGC TGT CTG AGG AAT ATT CAT GTC AAT CAC ATC CCT GTC CCT GTC ACT     5146
Gly Cys Leu Arg Asn Ile His Val Asn His Ile Pro Val Pro Val Thr
                1685              1690              1695

GAA GCC TTG GAA GTC CAG GGG CCT GTC AGT CTG AAT GGT TGT CCT GAC     5194
Glu Ala Leu Glu Val Gln Gly Pro Val Ser Leu Asn Gly Cys Pro Asp
            1700              1705              1710

CAG TAACCCAAGC CTATTTCACA GCAAGGAAAT TCACCTTCAA AAGCACTGAT          5247
Gln

TACCCAATGC ACCTCCCTCC CCAGCTCGAG ATCATTCTTC AATTAGGACA CAAACCAGAC    5307

AGGTTTAATA GCGAATCTAA TTTTGAATTC TGACCATGGA TACCCATCAC TTTGGCATTC    5367

AGTGCTACAT GTGTATTTTA TATAAAAATC CCATTTCTTG AAGATAAAAA AATTGTTATT    5427

CAAATTGTTA TGCACAGAAT GTTTTGGTA ATATTAATTT CCACTAAAAA ATTAAATGTC     5487

TTTTAAAAA                                                            5496

(2) INFORMATION FOR SEQ ID NO:24:

(i) SEQUENCE CHARACTERISTICS:
        (A) LENGTH: 1713 amino acids
        (B) TYPE: amino acid
        (D) TOPOLOGY: linear (ii) MOLECULE TYPE: protein
        (A) DESCRIPTION: E170 protein as translated from sequence
            of FIGURES 15A-15F, and as shown also in FIGURES
            19A-19R
```

(xi) SEQUENCE DESCRIPTION: SEQ ID NO:24:

```
Met Gly Trp Leu Trp Ile Phe Gly Ala Ala Leu Gly Gln Cys Leu Gly
  1               5                  10                  15

Tyr Ser Ser Gln Gln Gln Arg Val Pro Phe Leu Gln Pro Pro Gly Gln
                 20                  25                  30

Ser Gln Leu Gln Ala Ser Tyr Val Glu Phe Arg Pro Ser Gln Gly Cys
             35                  40                  45

Ser Pro Gly Tyr Tyr Arg Asp His Lys Gly Leu Tyr Thr Gly Arg Cys
         50                  55                  60

Val Pro Cys Asn Cys Asn Gly His Ser Asn Gln Cys Gln Asp Gly Ser
 65                  70                  75                  80

Gly Ile Cys Val Asn Cys Gln His Asn Thr Ala Gly Glu His Cys Glu
                 85                  90                  95

Arg Cys Gln Glu Gly Tyr Tyr Gly Asn Ala Val His Gly Ser Cys Arg
             100                 105                 110

Ala Cys Pro Cys Pro His Thr Asn Ser Phe Ala Thr Gly Cys Val Val
         115                 120                 125

Asn Gly Gly Asp Val Arg Cys Ser Cys Lys Ala Gly Tyr Thr Gly Thr
130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                 165                 170                 175

Ser Cys His Pro Leu Thr Gly Asp Cys Ile Asn Gln Glu Pro Lys Asp
             180                 185                 190

Ser Ser Pro Ala Glu Glu Cys Asp Asp Cys Asp Ser Cys Val Met Thr
         195                 200                 205

Leu Leu Asn Asp Leu Ala Thr Met Gly Glu Gln Leu Arg Leu Val Lys
            210                 215                 220

Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
                 245                 250                 255

Tyr Arg Ser Ala Ile Ser Asn His Gly Ser Lys Ile Glu Gly Leu Glu
             260                 265                 270

Arg Glu Leu Thr Asp Leu Asn Gln Glu Phe Glu Thr Leu Gln Glu Lys
         275                 280                 285

Ala Gln Val Asn Ser Arg Lys Ala Gln Thr Leu Asn Asn Asn Val Asn
        290                 295                 300

Arg Ala Thr Gln Ser Ala Lys Glu Leu Asp Val Lys Ile Lys Asn Val
305                 310                 315                 320

Ile Arg Asn Val His Ile Leu Leu Lys Gln Ile Ser Gly Thr Asp Gly
                 325                 330                 335

Glu Gly Asn Asn Val Pro Ser Gly Asp Phe Ser Arg Glu Trp Ala Glu
             340                 345                 350

Ala Gln Arg Met Met Arg Glu Leu Arg Asn Arg Asn Phe Gly Lys His
         355                 360                 365

Leu Arg Glu Ala Glu Ala Asp Lys Arg Glu Ser Gln Leu Leu Leu Asn
     370                 375                 380

Arg Ile Arg Thr Trp Gln Lys Thr His Gln Gly Glu Asn Asn Gly Leu
385                 390                 395                 400

Ala Asn Ser Ile Arg Asp Ser Leu Asn Glu Tyr Glu Ala Lys Leu Ser
```

```
                    405                 410                 415
Asp Leu Arg Ala Arg Leu Gln Glu Ala Ala Gln Ala Lys Gln Ala
                420                 425                 430

Asn Gly Leu Asn Gln Glu Asn Glu Arg Ala Leu Gly Ala Ile Gln Arg
                435                 440                 445

Gln Val Lys Glu Ile Asn Ser Leu Gln Ser Asp Phe Thr Lys Tyr Leu
    450                 455                 460

Thr Thr Ala Asp Ser Ser Leu Leu Gln Thr Asn Ile Ala Leu Gln Leu
465                 470                 475                 480

Met Glu Lys Ser Gln Lys Glu Tyr Glu Lys Leu Ala Ala Ser Leu Asn
                485                 490                 495

Glu Ala Arg Gln Glu Leu Ser Asp Lys Val Arg Glu Leu Ser Arg Ser
                500                 505                 510

Ala Gly Lys Thr Ser Leu Val Glu Glu Ala Glu Lys His Ala Arg Ser
                515                 520                 525

Leu Gln Glu Leu Ala Lys Gln Leu Glu Glu Ile Lys Arg Asn Ala Ser
                530                 535                 540

Gly Asp Glu Leu Val Arg Cys Ala Val Asp Ala Ala Thr Ala Tyr Glu
545                 550                 555                 560

Asn Ile Leu Asn Ala Ile Lys Ala Ala Glu Asp Ala Ala Asn Arg Ala
                565                 570                 575

Ala Ser Ala Ser Glu Ser Ala Leu Gln Thr Val Ile Lys Glu Asp Leu
                580                 585                 590

Pro Arg Lys Ala Lys Thr Leu Ser Ser Asn Ser Asp Lys Leu Leu Asn
                595                 600                 605

Glu Ala Lys Met Thr Gln Lys Lys Leu Lys Gln Glu Val Ser Pro Ala
                610                 615                 620

Leu Asn Asn Leu Gln Gln Thr Leu Asn Ile Val Thr Val Gln Lys Glu
625                 630                 635                 640

Val Ile Asp Thr Asn Leu Thr Thr Leu Arg Asp Gly Leu His Gly Ile
                645                 650                 655

Gln Arg Gly Asp Ile Asp Ala Met Ile Ser Ser Ala Lys Ser Met Val
                660                 665                 670

Arg Lys Ala Asn Asp Ile Thr Asp Glu Val Leu Asp Gly Leu Asn Pro
                675                 680                 685

Ile Gln Thr Asp Val Glu Arg Ile Lys Asp Thr Tyr Gly Arg Thr Gln
                690                 695                 700

Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
                725                 730                 735

Asn Gln Gln Leu Leu Pro Leu Gly Asn Ile Ser Asp Asn Met Asp Arg
                740                 745                 750

Ile Arg Glu Leu Ile Gln Gln Ala Arg Asp Ala Ala Ser Lys Val Ala
                755                 760                 765

Val Pro Met Arg Phe Asn Gly Lys Ser Gly Val Glu Val Arg Leu Pro
                770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
                805                 810                 815

Met Tyr Leu Gly Asn Lys Asp Ala Ser Arg Asp Tyr Ile Gly Met Ala
                820                 825                 830
```

```
Val Val Asp Gly Gln Leu Thr Cys Val Tyr Asn Leu Gly Asp Arg Glu
        835                 840                 845

Ala Glu Leu Gln Val Asp Gln Ile Leu Thr Lys Ser Glu Thr Lys Glu
850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
                885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
        915                 920                 925

Leu Pro Ser Arg Leu Ser Phe Pro Pro Tyr Lys Gly Cys Ile Glu Leu
930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Arg Lys Glu
                965                 970                 975

Glu Ser Asp Lys Asn Tyr Phe Glu Gly Thr Gly Tyr Ala Arg Val Pro
            980                 985                 990

Thr Gln Pro His Ala Pro Ile Pro Thr Phe Gly Gln Thr Ile Gln Thr
        995                 1000                1005

Thr Val Asp Arg Gly Leu Leu Phe Phe Ala Glu Asn Gly Asp Arg Phe
        1010                1015                1020

Ile Ser Leu Asn Ile Glu Asp Gly Lys Leu Met Val Arg Tyr Lys Leu
1025                1030                1035                1040

Asn Ser Glu Leu Pro Lys Glu Arg Gly Val Gly Asp Ala Ile Asn Asn
                1045                1050                1055

Gly Arg Asp His Ser Ile Gln Ile Lys Ile Gly Lys Leu Gln Lys Arg
            1060                1065                1070

Met Trp Ile Asn Val Asp Val Gln Asn Thr Ile Ile Asp Gly Glu Val
        1075                1080                1085

Phe Asp Phe Ser Thr Tyr Tyr Leu Gly Gly Ile Pro Ile Ala Ile Arg
        1090                1095                1100

Glu Arg Phe Asn Ile Ser Thr Pro Ala Phe Arg Gly Cys Met Lys Asn
1105                1110                1115                1120

Leu Lys Lys Thr Ser Gly Val Val Arg Leu Asn Asp Thr Val Gly Val
                1125                1130                1135

Thr Lys Lys Cys Ser Glu Asp Trp Lys Leu Val Arg Ser Ala Ser Phe
            1140                1145                1150

Ser Arg Gly Gly Gln Leu Ser Phe Thr Asp Leu Gly Leu Pro Pro Thr
        1155                1160                1165

Asp His Leu Gln Ala Ser Phe Gly Phe Gln Thr Phe Gln Pro Ser Gly
        1170                1175                1180

Ile Leu Leu Asp His Gln Thr Trp Thr Arg Asn Leu Gln Val Thr Leu
1185                1190                1195                1200

Glu Asp Gly Tyr Ile Glu Leu Ser Thr Ser Asp Ser Gly Gly Pro Ile
            1205                1210                1215

Phe Lys Ser Pro Gln Thr Tyr Met Asp Gly Leu Leu His Tyr Val Ser
                1220                1225                1230

Val Ile Ser Asp Asn Ser Gly Leu Arg Leu Leu Ile Asp Asp Gln Leu
        1235                1240                1245
```

```
Leu Arg Asn Ser Lys Arg Leu Lys His Ile Ser Ser Ser Arg Gln Ser
    1250                1255                1260

Leu Arg Leu Gly Gly Ser Asn Phe Glu Gly Cys Ile Ser Asn Val Phe
1265                1270                1275                1280

Val Gln Arg Leu Ser Leu Ser Pro Glu Val Leu Asp Leu Thr Ser Asn
                1285                1290                1295

Ser Leu Lys Arg Asp Val Ser Leu Gly Gly Cys Ser Leu Asn Lys Pro
            1300                1305                1310

Pro Phe Leu Met Leu Leu Lys Gly Ser Thr Arg Phe Asn Lys Thr Lys
        1315                1320                1325

Thr Phe Arg Ile Asn Gln Leu Leu Gln Asp Thr Pro Val Ala Ser Pro
    1330                1335                1340

Arg Ser Val Lys Val Trp Gln Asp Ala Cys Ser Pro Leu Pro Lys Thr
1345                1350                1355                1360

Gln Ala Asn His Gly Ala Leu Gln Phe Gly Asp Ile Pro Thr Ser His
                1365                1370                1375

Leu Leu Phe Lys Leu Pro Gln Glu Leu Leu Lys Pro Arg Ser Gln Phe
            1380                1385                1390

Ala Val Asp Met Gln Thr Thr Ser Ser Arg Gly Leu Val Phe His Thr
        1395                1400                1405

Gly Thr Lys Asn Ser Phe Met Ala Leu Tyr Leu Ser Lys Gly Arg Leu
    1410                1415                1420

Val Phe Ala Leu Gly Thr Asp Gly Lys Lys Leu Arg Ile Lys Ser Lys
1425                1430                1435                1440

Glu Lys Cys Asn Asp Gly Lys Trp His Thr Val Val Phe Gly His Asp
                1445                1450                1455

Gly Glu Lys Gly Arg Leu Val Val Asp Gly Leu Arg Ala Arg Glu Gly
            1460                1465                1470

Ser Leu Pro Gly Asn Ser Thr Ile Ser Ile Arg Ala Pro Val Tyr Leu
        1475                1480                1485

Gly Ser Pro Pro Ser Gly Lys Pro Lys Ser Leu Pro Thr Asn Ser Phe
    1490                1495                1500

Val Gly Cys Leu Lys Asn Phe Gln Leu Asp Ser Lys Pro Leu Tyr Thr
1505                1510                1515                1520

Pro Ser Ser Ser Phe Gly Val Ser Cys Leu Gly Gly Pro Leu Glu
                1525                1530                1535

Lys Gly Ile Tyr Phe Ser Glu Glu Gly Gly His Val Val Leu Ala His
            1540                1545                1550

Ser Val Leu Leu Gly Pro Glu Phe Lys Leu Val Phe Ser Ile Arg Pro
        1555                1560                1565

Arg Ser Leu Thr Gly Ile Leu Ile His Ile Gly Ser Gln Pro Gly Lys
    1570                1575                1580

His Leu Cys Val Tyr Leu Glu Ala Gly Lys Val Thr Ala Ser Met Asp
1585                1590                1595                1600

Ser Gly Ala Gly Gly Thr Ser Thr Ser Val Thr Pro Lys Gln Ser Leu
                1605                1610                1615

Cys Asp Gly Gln Trp His Ser Val Ala Val Thr Ile Lys Gln His Ile
            1620                1625                1630

Leu His Leu Glu Leu Asp Thr Asp Ser Ser Tyr Thr Ala Gly Gln Ile
        1635                1640                1645

Pro Phe Pro Pro Ala Ser Thr Gln Glu Pro Leu His Leu Gly Gly Ala
    1650                1655                1660

Pro Ala Asn Leu Thr Thr Leu Arg Ile Pro Val Trp Lys Ser Phe Phe
```

```
                1665            1670            1675            1680
Gly Cys Leu Arg Asn Ile His Val Asn His Ile Pro Val Pro Val Thr
                    1685            1690            1695

Glu Ala Leu Glu Val Gln Gly Pro Val Ser Leu Asn Gly Cys Pro Asp
        1700            1705            1710

Gln
```

(2) INFORMATION FOR SEQ ID NO:25:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION: Sequence of 3EpA cDNA encoding amino-terminal
            region of E170;

(iii) HYPOTHETICAL: NO (vi) ORIGINAL SOURCE:
        (A) ORGANISM: Homo sapiens (ix) FEATURE:
        (A) NAME/KEY: CDS
        (B) LOCATION: 1..135

(xi) SEQUENCE DESCRIPTION: SEQ ID NO:25:

```
ATG GGA TGG CTG TGG ATC TTT GGG GCA GCC CTG GGG CAG TGT CTG GGC    48
Met Gly Trp Leu Trp Ile Phe Gly Ala Ala Leu Gly Gln Cys Leu Gly
 1               5                  10                  15

TAC AGT TCA CAG CAG CAA AGG GTG CCA TTT CTT CAG CCT CCC GGT CAA    96
Tyr Ser Ser Gln Gln Gln Arg Val Pro Phe Leu Gln Pro Pro Gly Gln
             20                  25                  30

AGT CAA CTG CAA GCG AGT TAT GTG GAG TTT AGA CCC AGC                135
Ser Gln Leu Gln Ala Ser Tyr Val Glu Phe Arg Pro Ser
             35                  40                  45
```

(2) INFORMATION FOR SEQ ID NO:26:

(i) SEQUENCE CHARACTERISTICS:
        (A) LENGTH: 45 amino acids
        (B) TYPE: amino acid
        (D) TOPOLOGY: linear (ii) MOLECULE TYPE: protein
        (A) DESCRIPTION: Sequence of amino terminal region of E170
            encoded by 3EpA cDNA; see FIGURE 18A (xi) SEQUENCE DESCRIPTION: SEQ ID NO:26:

```
Met Gly Trp Leu Trp Ile Phe Gly Ala Ala Leu Gly Gln Cys Leu Gly
 1               5                  10                  15

Tyr Ser Ser Gln Gln Gln Arg Val Pro Phe Leu Gln Pro Pro Gly Gln
             20                  25                  30

Ser Gln Leu Gln Ala Ser Tyr Val Glu Phe Arg Pro Ser
             35                  40                  45
```

(2) INFORMATION FOR SEQ ID NO:27:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: cDNA to mRNA (A) DESCRIPTION: Sequence of region of 3EpB cDNA encoding
    amino terminal region of E170; see FIGURE 18B (iii) HYPOTHETICAL: NO (vi) ORIGINAL SOURCE:
    (A) ORGANISM: Homo sapiens (ix) FEATURE:
    (A) NAME/KEY: CDS
    (B) LOCATION: 1..435

(xi) SEQUENCE DESCRIPTION: SEQ ID NO:27:

```
CCC ACC TCC TAC CTG GGG GAC AAG GTT TCT TCA TAT GGT GGT TAC CTC      48
Pro Thr Ser Tyr Leu Gly Asp Lys Val Ser Ser Tyr Gly Gly Tyr Leu
 1               5                  10                  15

ACT TAC CAA GCC AAG TCC TTT GGC TTG CCT GGC GAC ATG GTT CTT CTG      96
Thr Tyr Gln Ala Lys Ser Phe Gly Leu Pro Gly Asp Met Val Leu Leu
             20                  25                  30

GAA AAG AAG CCG GAT GTA CAG CTC ACT GGT CAG CAC ATG TCC ATC ATC     144
Glu Lys Lys Pro Asp Val Gln Leu Thr Gly Gln His Met Ser Ile Ile
         35                  40                  45

TAT GAG GAG ACA AAC ACC CCA CGG CCA GAC CGG CTG CAT CAT GGA CGA     192
Tyr Glu Glu Thr Asn Thr Pro Arg Pro Asp Arg Leu His His Gly Arg
     50                  55                  60

GTG CAC GTG GTC GAG GGA AAC TTC AGA CAT GCC AGC AGC CGT GCC CCA     240
Val His Val Val Glu Gly Asn Phe Arg His Ala Ser Ser Arg Ala Pro
 65                  70                  75                  80

GTG TCT AGG GAG GAG CTG ATG ACA GTG CTG TCT GGA CTG GCA GAT GTG     288
Val Ser Arg Glu Glu Leu Met Thr Val Leu Ser Gly Leu Ala Asp Val
                 85                  90                  95

CGC ATC CAA GGC CTC TAC TTC ACA GAG ACT CAA AGG CTC ACC CTG AGC     336
Arg Ile Gln Gly Leu Tyr Phe Thr Glu Thr Gln Arg Leu Thr Leu Ser
            100                 105                 110

GAG GTG GGG CTA GAG GAA GCC TCT GAC ACA GGA AGT GGG CGC ATA GCA     384
Glu Val Gly Leu Glu Glu Ala Ser Asp Thr Gly Ser Gly Arg Ile Ala
        115                 120                 125

CTT GCT GTG GAA ATC TGT GCC TGC CCC CCT GCC TAC GCT GGT GAC TCT     432
Leu Ala Val Glu Ile Cys Ala Cys Pro Pro Ala Tyr Ala Gly Asp Ser
    130                 135                 140

TGT                                                                 435
Cys
145
```

(2) INFORMATION FOR SEQ ID NO:28:

(i) SEQUENCE CHARACTERISTICS:
        (A) LENGTH: 145 amino acids
        (B) TYPE: amino acid
        (D) TOPOLOGY: linear (ii) MOLECULE TYPE: protein
        (A) DESCRIPTION: Amino terminal region of E170 encoded by
            3EpB; see FIGURE 18B.

(xi) SEQUENCE DESCRIPTION: SEQ ID NO:28:

```
Pro Thr Ser Tyr Leu Gly Asp Lys Val Ser Ser Tyr Gly Gly Tyr Leu
 1               5                  10                  15

Thr Tyr Gln Ala Lys Ser Phe Gly Leu Pro Gly Asp Met Val Leu Leu
             20                  25                  30

Glu Lys Lys Pro Asp Val Gln Leu Thr Gly Gln His Met Ser Ile Ile
         35                  40                  45

Tyr Glu Glu Thr Asn Thr Pro Arg Pro Asp Arg Leu His His Gly Arg
     50                  55                  60
```

```
Val His Val Val Glu Gly Asn Phe Arg His Ala Ser Ser Arg Ala Pro
 65                  70                  75                  80

Val Ser Arg Glu Glu Leu Met Thr Val Leu Ser Gly Leu Ala Asp Val
                 85                  90                  95

Arg Ile Gln Gly Leu Tyr Phe Thr Glu Thr Gln Arg Leu Thr Leu Ser
            100                 105                 110

Glu Val Gly Leu Glu Glu Ala Ser Asp Thr Gly Ser Gly Arg Ile Ala
        115                 120                 125

Leu Ala Val Glu Ile Cys Ala Cys Pro Pro Ala Tyr Ala Gly Asp Ser
    130                 135                 140

Cys
145

(2) INFORMATION FOR SEQ ID NO:29:

(i) SEQUENCE CHARACTERISTICS:
         (A) LENGTH: 468 base pairs
         (B) TYPE: nucleic acid
         (C) STRANDEDNESS: single
         (D) TOPOLOGY: linear (ii) MOLECULE TYPE: DNA (genomic)
         (A) DESCRIPTION: Sequences shared by 3EpA and 3EpB cDNAs in
             the amino terminal coding region; see FIGURE 18C (iii) HYPOTHETICAL: NO (iv) ANTI-SENSE: NO (vi) ORIGINAL SOURCE:
         (A) ORGANISM: Homo sapiens (ix) FEATURE:
         (A) NAME/KEY: CDS
         (B) LOCATION: 1..468

(xi) SEQUENCE DESCRIPTION: SEQ ID NO:29:

CAG GGT TGT AGC CCT GGA TAC TAT CGG GAT CAT AAA GGC TTG TAT ACC        48
Gln Gly Cys Ser Pro Gly Tyr Tyr Arg Asp His Lys Gly Leu Tyr Thr
  1               5                  10                  15

GGA CGG TGT GTT CCC TGC AAT TGC AAC GGA CAT TCA AAT CAA TGC CAG        96
Gly Arg Cys Val Pro Cys Asn Cys Asn Gly His Ser Asn Gln Cys Gln
             20                  25                  30

GAT GGC TCA GGC ATA TGT GTT AAC TGT CAG CAC AAC ACC GCG GGA GAG       144
Asp Gly Ser Gly Ile Cys Val Asn Cys Gln His Asn Thr Ala Gly Glu
         35                  40                  45

CAC TGT GAA CGC TGC CAG GAG GGC TAC TAT GGC AAC GCC GTC CAC GGA       192
His Cys Glu Arg Cys Gln Glu Gly Tyr Tyr Gly Asn Ala Val His Gly
     50                  55                  60

TCC TGC AGG GCC TGC CCA TGT CCT CAC ACT AAC AGC TTT GCC ACT GGC       240
Ser Cys Arg Ala Cys Pro Cys Pro His Thr Asn Ser Phe Ala Thr Gly
 65                  70                  75                  80

TGT GTG GTG AAT GGG GGA GAC GTG CGG TGC TCC TGC AAA GCT GGG TAC       288
Cys Val Val Asn Gly Gly Asp Val Arg Cys Ser Cys Lys Ala Gly Tyr
                 85                  90                  95

ACA GGA ACA CAG TGT GAA AGG TGT GCA CCG GGA TAT TTC GGG AAT CCC       336
Thr Gly Thr Gln Cys Glu Arg Cys Ala Pro Gly Tyr Phe Gly Asn Pro
            100                 105                 110

CAG AAA TTC GGA GGT AGC TGC CAA CCA TGC AGT TGT AAC AGC AAT GGC       384
Gln Lys Phe Gly Gly Ser Cys Gln Pro Cys Ser Cys Asn Ser Asn Gly
        115                 120                 125

CAG CTG GGC AGC TGT CAT CCC CTG ACT GGA GAC TGC ATA AAC CAA GAA       432
Gln Leu Gly Ser Cys His Pro Leu Thr Gly Asp Cys Ile Asn Gln Glu
```

-continued

```
                130                 135                 140
CCC AAA GAT AGC AGC CCT GCA GAA GAA TGT GAT GAT                            468
Pro Lys Asp Ser Ser Pro Ala Glu Glu Cys Asp Asp
145                 150                 155

(2) INFORMATION FOR SEQ ID NO:30:

(i) SEQUENCE CHARACTERISTICS:
        (A) LENGTH: 156 amino acids
        (B) TYPE: amino acid
        (D) TOPOLOGY: linear (ii) MOLECULE TYPE: protein
        (A) DESCRIPTION: Amino terminal region of E170 encoded by
            the sequences shown in FIGURE 18C.

(xi) SEQUENCE DESCRIPTION: SEQ ID NO:30:

Gln Gly Cys Ser Pro Gly Tyr Tyr Arg Asp His Lys Gly Leu Tyr Thr
1               5                   10                  15

Gly Arg Cys Val Pro Cys Asn Cys Asn Gly His Ser Asn Gln Cys Gln
                20                  25                  30

Asp Gly Ser Gly Ile Cys Val Asn Cys Gln His Asn Thr Ala Gly Glu
            35                  40                  45

His Cys Glu Arg Cys Gln Glu Gly Tyr Tyr Gly Asn Ala Val His Gly
        50                  55                  60

Ser Cys Arg Ala Cys Pro Cys Pro His Thr Asn Ser Phe Ala Thr Gly
65                  70                  75                  80

Cys Val Val Asn Gly Gly Asp Val Arg Cys Ser Cys Lys Ala Gly Tyr
                85                  90                  95

Thr Gly Thr Gln Cys Glu Arg Cys Ala Pro Gly Tyr Phe Gly Asn Pro
            100                 105                 110

Gln Lys Phe Gly Gly Ser Cys Gln Pro Cys Ser Cys Asn Ser Asn Gly
        115                 120                 125

Gln Leu Gly Ser Cys His Pro Leu Thr Gly Asp Cys Ile Asn Gln Glu
    130                 135                 140

Pro Lys Asp Ser Ser Pro Ala Glu Glu Cys Asp Asp
145                 150                 155
```

EPILIGRIN, AN EPITHELIAL LIGAND FOR INTEGRINS

This application is a continuation of pending international application No. PCT/US94/10261, filed Sep. 2, 1994. This is a continuation-in-part of application Ser. No. 08/115,918, filed Sep. 2, 1993 (abandoned); and is a continuation-in-part of pending application Ser. No. 08/292,065, filed Aug. 17, 1994 (abandoned), which is a continuation of application Ser. No. 08/154,638, filed Nov. 18, 1993 (abandoned), which is a continuation of application Ser. No. 07/654,103, filed Feb. 8, 1991 (abandoned), which is a continuation-in-part of application Ser. No. 07/607,137, filed Oct. 30, 1990 (abandoned); the benefits of the filing dates of which are hereby claimed under 35 U.S.C. § 120.

1. FIELD OF THE INVENTION

The invention relates generally to epithelial cell receptors and ligands which are useful for adhering epithelial cells to a substratum.

2. BACKGROUND OF THE INVENTION

The invention is predicated upon a basic understanding of epithelial cells and tissues studied. Such epithelia, which cover free surfaces and line body cavities and ducts, have been studied microscopically for at least three centuries. Recently the biochemistry and molecular biology of epithelial cells and tissues have been extensively investigated. However, the seemingly simple question of how the cells in epithelial tissues are driven to become specialized has remained unanswered. The present invention provides reagents that allow us for the first time to unravel the inter- and intracellular signals that direct epithelial cell differentiation. More fundamentally, the subject reagents permit one to finally decipher what has been a tangled web of suspected interactions involving a wide variety of cell types, some of them non-epithelial, in order to understand and modulate at a molecular level how the cells are driven to differentiate to fulfill specialized functions in the body. Pertinent background information concerning these heretofore disparate systems follows.

2.1 Abbreviations

By way of introduction, the following abbreviations are used in this disclosure: BPA, bullous pemphigoid antigen; CD3, cellular determinant #3, a lymphocyte surface antigen marker; CP, cicatrical pemphigoid, an autoimmune dermatological disease; EBA, epidermolysis bullosa acquisita, an autoimmune dermatological disease; ECM, extracellular matrix; FAs, focal adhesions; HD-BSA, heat denatured bovine serum albumin; HFK(s), human foreskin keratinocyte(s); HFK-ECM, human foreskin keratinocyte-extracellular matrix; kDa, kilodaltons of molecular mass as determined by SDS-PAGE; MAbs, monoclonal antibodies; Mr, molecular radius by SDS-PAGE, approximating molecular mass; SACs, stable anchoring contacts; and SDS-PAGE, sodium dodecyl sulfate-polyacrylamide gel electrophoresis.

E200, E170, E145, E135, E100, and E36 refer to the constituent and associated glycoproteins of the subject epithelial ligand complex epiligrin, having apparent molecular weights of 200±20 kDa, 170±20 kDa, 145±20 kDa, 135±15 kDa, 100±10 kDa, and 36±5 kDa, respectively.

Ep-1, 1-1, and 8-6 refer to the disclosed cDNA clones deposited under ATCC accession numbers 75540, 75539, and 75538, respectively.

Throughout the specification, the notation "(#)" is used to refer to the documents listed in the appended Citations section.

2.2 Epithelial Cells

The invention is predicated upon a basic understanding of epithelial cells and tissues studied. Such epithelia, which cover free surfaces and line body cavities and ducts, have been studied microscopically for at least three centuries. Recently the biochemistry and molecular biology of epithelial cells and tissues have been extensively investigated. However, the seemingly simple question of how the cells in epithelial tissues are driven to become specialized has remained unanswered. The present invention provides reagents that allow us for the first time to unravel the inter- and intracellular signals that direct epithelial cell differentiation. More fundamentally, the subject reagents permit one to finally decipher what has been a tangled web of suspected interactions involving a wide variety of cell types, some of them nonepithelial, in order to understand and modulate at a molecular level how these cells are driven to differentiate to fulfill their specialized functions in the body. Pertinent background information concerning these heretofore disparate systems follows.

The significance of epithelial tissues as a protective barrier is readily apparent in the body as the lining of body cavities, blood vessels, digestive tract, mammary glands, urogenital, endocrine, reticuloendothelial systems, respiratory surfaces, placenta, and surrounding the nerves and brain. The epithelia also forms the basis for the epidermis, cornea, and conjunctiva.

2.3 Epithelial tissues are rather unique in their ability for continuous regulated self-renewal, and in their ability to polarize and control cellular division and the subsequent differentiation of the daughter cells. In attempting to explain how epithelial cells may decide how and when to differentiate, it has been suggested that perhaps gradients of growth factors or interactions with extracellular matrix (ECM) may influence the cells. However, the biochemical mechanisms remain largely unknown.

2.4 The epithelial basement membrane is a common histological feature of columnar, stratified, and squamous epithelia. Another prominent feature is a proliferative basal (stem) cell layer resting on a basement membrane. When viewed through the light microscope, an epithelial basement membrane may include lucent and dense regions termed, respectively, the Lamina lucida and Lamina densa, which are sandwiched between an overlying cellular stroma (stroma), made up of basal stem cells and fibroblasts, and an underlying collagenous matrix. Basement membranes are thin but continuous sheets that separate epithelium from stroma and surround nerves, muscle fibers, smooth muscle cells, and fat cells (1–4). The molecular composition of the basement membrane varies with specialized cellular functions and with the developmental stages, shape, structure, and architecture of different epithelia (5). In the simplest model, basement membranes contain at least type IV collagen (1, 6–8), laminin (7–8), entactin (9), and heparin sulfate proteoglycans (10–11). When co-electrophoresed in SDS-PAGE (12) under reducing conditions, purified EHS tumor laminin was reported to have apparent molecular sizes of 400 kDa and 200 kDa, entactin was 158 kDa, and nidogen was 100 kDa (Kleinman et al., *Biochemistry* 25:312–318 (1986)).

2.5 The human skin, for example, is an epithelial tissue composed of the epidermis and the dermis. The dermis is relatively acellular and composed of secreted cell products, e.g., collagens and heparin-sulfate- and chondroitin-sulfate-proteoglycans. In contrast, the epidermis is essentially cellular, containing a layer of cells resting on a basement membrane, termed the basal (stem) cells that are covered by a layer of cornified cells, termed the stratum corneum. Central questions in skin biology have been, (1) how do the cells in the basal layer commit to become cornified, and (2) how do cells decide which daughter cells will become cornified, and which will remain in the basal layer to provide the germinal basis for future generations of cells? Histological examination provides little insight. The viable inner malpighian layers of the skin, from which the cornified cells arise, are composed of the basal cell layer, the stratum spinosum and the stratum granulosum. The cell types in these areas include at least keratinocytes, melanocytes, Merkel cells, Langerhans cells, and migratory immune cells. Cell division in the basal (stem) cell layer forms the basis for the continuous self-renewal of the skin, and it is thought that decisions on the fate of the daughter cells are made in this layer.

2.6 Two types of daughter cells appear to be created by cell division in the basal (stem) cell layers of the skin. The first daughter cell, which will continue to divide; and the second daughter cell, which will differentiate and ultimately become cornified. Distinctive cellular features that may define stages in the differentiation of the second daughter cell include at least the acquisition first, of a flattened cell shape with cytoplasmic keratohyalin granules, ivolucrin, and cytokeratin filaments (characteristics of cells in the stratum spinosum); second, of greater amounts of cytoplasmic keratin and a submembranous envelope formed of proteins cross-linked by epidermal transglutaminase (characteristics of cells in the stratum granulosum); and third, the acquisition of distinguishing features associated with cornified anuclear cells such as extensively cross-linked dense submembranous envelopes (i.e., characteristics of cells in the stratum corneum). The molecular mechanisms determining "first daughter" and "second daughter" status, as well as the mechanisms which control epidermal cell differentiation into cornified anuclear cells, are largely unknown, but these mechanisms appear to be coordinated; i.e., cells enter and leave the malpighian layer at approximately the same rate; they appear to be polarized, i.e., from the basal (stem) cell layer to the apical cornified layers; and they appear to be self-regulating, i.e., processes by which the cornified layers are renewed can effectively compensate for variation in the rate of mechanical sloughing of cells from the surface in different parts of the body. The molecular processes by which this remarkable coordination of cells is achieved in skin or other epithelial tissues are largely unknown, at present.

2.7 The attachment of proliferating, basal (stem) cells to the basement membrane occurs at limited points of cellular contact. Contact of epithelial cells, in general, with the basement membrane has been thought to have potential functional significance for maintaining cellular polarization necessary for asymmetric cell division, e.g., to give rise to the distinctively different types of daughter cells, as well as for sustaining the continuous morphogenetic process through which progeny of stem cells differentiate into cornified epithelial cells in skin or into Schwann cells and cells of the spinous strata surrounding nerves. However, there has been (and is currently) a lack of detailed knowledge regarding the cellular biology and molecular biochemistry involved in these postulated polarization and morphogenetic processes. Thus, the mechanisms controlling proliferation of stem cells and commitment of the daughter cells to differentiation are largely unknown.

2.8 The ultrastructure of the attachment points where basal cells are in contact with the basement membrane exhibits characteristic features that are identifiable in appropriately fixed and stained tissues (and cultures). The ultra-structural features have been termed hemidesmosomes (14–16), focal adhesions (17, 18), and hemidesmosome-like stable anchoring contacts (SACs) (19). Focal adhesions and SAC/hemidesmosomes are structurally and functionally distinct adhesion structures (19, 20). Focal adhesions have been observed in motile cells in association with actin-containing stress fibers (20, 21), while SACs appear to be distinguished as a structural component of stationary cells which only form in vitro after cells stop migrating. The function of SACs and focal adhesions is currently not clear, either with respect to their possible role in motility or to other possible roles in the cell biology of the epidermis. However, it has been observed that the lamina densa may be connected to stroma through anchoring fibrils (22), such as those observed in cells which appear to be linked to hemidesmosomes (23–25). SAC/hemidesmosome structures have also been observed to be associated with cytoplasmic intermediate filaments (26, 27) which have a bullous pemphigoid antigen (BPA) identifiable by indirect immunofluoresence.

2.9 Studies of basal cell interactions with basement membranes have been complicated by lack of suitable in vitro model systems as well as by changes occurring in the structure, shape, and composition of basement membranes during development and acquisition of specialized cellular functions (5). There has been a near total lack of in vitro models by which basal (stem) cells might be studied. Keratinocytes are one in vitro epithelial model system. These cells are not basal (stem) cells, but they do represent a major cellular constituent of epidermis. Human keratinocytes have been isolated and cultured from stratified or squamous epithelia in vitro under controlled conditions either using fibroblast feeder layers and conditioned medium (28–30); medium containing at least epidermal growth factor (31); keratinocyte growth medium (KGM) containing at least hydrocortisone, low-calcium, insulin, and insulin-like growth factor-1 (32, 33) serum-free (34, 35) or supplemented MCDB 153 basal nutrient medium (36). One recent study has suggested that 85–90% of keratinocyte clones, derived from growing and cloning normal human skin keratinocytes, may be derived from the basal (stem) cell layer and 10–15% from the suprabasal layers of the epidermis (36). The presumptive "suprabasal" keratinocytes expressed markers of terminal differentiation (i.e., ivolucrin) but still possessed the ability to synthesize DNA. These findings suggested to the investigators that some "suprabasal" keratinocytes may exist in an altered state of "non-terminal" differentiation wherein they are still capable of cell division (36). Others have termed possibly related strains of keratinocytes "nondifferentiating keratinocytes" (37). Ivolucrin is one marker for keratinocyte differentiation in vitro. It is a cytosolic protein of human keratinocytes with a reported apparent Mr of 140 kDa on SDS-PAGE (38); the gene has recently been reportedly cloned (39) and its regulation studied in cells in vitro (40). Ivolucrin is useful as a marker for an early stage in the terminal differentiation of keratinocytes since it is synthesized shortly after keratinocytes leave the basal (stem) cell layer, at a time when cellular enlargement has begun, but before onset of envelope cross-linking (41, 42). Ivolucrin has been reported to have undergone a relatively rapid evolution with the possibility of 3 alleles in monkeys (43, 44). Cytokeratins are a second useful marker for keratinocyte differentiation in vitro. There are at least five cytokeratins which may be expressed by keratinocytes in vitro using Western immunoblot analysis and commercially available monoclonal antibodies AE1 and AE3: these include cytokeratins No. 5 (58 kDa), No. 6 (56 kDa); No. 14/15 (50 kDa); No. 16 (48 kDa); and No. 17 (46 kDa) (45).

Keratinocyte differentiation can be induced in vitro, at least to the extent that the cells change morphology into cells resembling cornified epithelia. This process can be induced in tissue culture with calcium or with ionophores (46, 47). When such keratinocyte differentiation is induced in tissue culture, epidermal transglutaminase can become activated in the cells with coincident development of a cross-linked submembranous protein envelope. During cross-linking, cytosolic ivolucrin becomes associated with the submembranous protein envelope as do two other proteins which are reportedly found in keratinocytes but not in fibroblasts. These two proteins have reported apparent molecular sizes on SDS-PAGE of 210 kDa and 195 kDa (48). In an in vitro reconstituted system it was suggested that addition of ivolucrin promoted cross-linking of proteins (49). Thus, while keratinocytes are useful as an in vitro model for some molecular processes involved in epithelial differentiation, they are not basal (stem) cells and are clearly distinguished from them with at least ivolucrin as a marker. In addition, the past studies of keratinocytes has not approached at a molecular level the possible interactions which may occur between receptors in basal (stem) cells and ligands in the basement membrane.

2.10 Ligands which mediate the binding of basal (stem) cells to the epithelial basement membrane are largely unknown. The known basement membrane components in the lamina lucida layer of the epithelium include at least laminin, nidogen, and heparin sulfate proteoglycan, and in the lamina densa they include types IV and VII collagen (5, 50, 51). The possible cellular receptors which may bind to these ligands include at least the integrin adhesion receptors (for reviews see 52–55).

2.11 Integrins are a family of receptor glycoproteins with two noncovalently associated polypeptide chains of different molecular sizes (the larger termed the a chain and the smaller the b), forming a structure termed a heterodimer. The respective chains have amino acid sequence homology, and the integrins serve a similar function at least as receptors for cellular adhesion to extracellular matrix glycoproteins. Six a chains and at least four b chains have recently been identified, giving at least 24 different theoretical heterodimers which could act as receptors for cellular adhesion. An alignment of the α6 chain amino acid sequence with the $\alpha_3$ chain reportedly showed approximately 37% identity (#56). The molecular events and mechanisms governing control of the biosynthesis and assembly of the different a and b chains in different cells and tissues are largely unknown, as is the possible existence of several of the theoretical integrin structures. In T-lymphocytes, as opposed to epithelial cells, the activation of cells with interleukin-2 is correlated with induction of expression of the $\alpha_3\beta_1$ integrin on the cell surface (#57).

2.12 Biological functions of integrins in tissues and cells include (1) the possible mediation of the attachment of T- and B-lymphocytes and platelets to basement membrane via integrins $\alpha_3\beta_1$, $\alpha_2\beta_1$ and $\alpha_6\beta_4$ and (2) a possible role in hemostasis and homeostasis for these integrins, the latter by contributing to the maintenance of the structure of the integument and epithelia (#s 19–21; 57, 58).

2.13 Possible associations between integrins and laminin ligands include reports that the $\alpha_2\beta_1$ integrin is a collagen receptor in human fibrosarcoma cells (59, 60) with affinity for laminin in some cells (61, 62). Laminin is a disulfide-bonded glycoprotein complex composed of three distinct polypeptide chains. Laminin was first isolated from mouse Engelbreth-Holm-Swarn (Elts) tumor (#7), and the subunits were originally designated as follows: A (400 kDa), B1 (220 kDa), and B2 (210 kDa). However, in light of many recent reports describing multiple isoforms of laminin, the original subunits of EHS laminin (laminin-1) have now been designated as α1 (400 kDa), β1 (220 kDa), and γ1 (210 kDa) (#125).

$\alpha_6\beta_4$ integrin has also been suggested as a laminin receptor in human colon carcinoma cells (63), but it reportedly does not bind to the E8 domain of laminin, a ligand domain of laminin that interacts with $\alpha_6\beta_1$ integrin (64). $\alpha_3\beta_1$ is reportedly one of the most widely expressed integrins in tissues and in cultured epithelial and non-epithelial cells. It also has been suggested as a possible nonspecific laminin receptor in cells (57, 65). The reports of an association of $\alpha_3\beta_1$ with laminin either have not determined the apparent binding affinity of the interaction or have determined the association by assays which permit only a relational comparison, i.e., relatively strong or weak. Laminin is reportedly a poor ligand for adhesion of cultured human foreskin keratinocytes (20, 21). In tissue culture, antibody reactive with $\alpha_3\beta_1$ reportedly substantially inhibited adhesion of human foreskin keratinocytes to HFK-extracellular matrix. In contrast, antibody reactive with $\alpha_6\beta_4$ had only a minor effect, but when both antibodies were added together, adhesion of HFK to HFK-ECM was reportedly completely inhibited (20) but no ligand was identified. Thus, it is not apparent whether the interactions of $\alpha_3\beta_1$, and $\alpha_6\beta_4$ with laminin are physiologically meaningful, whether laminin is a ligand, or what the physiologically meaningful ligands for these integrins may be in skin.

2.14 The distribution of the $\alpha_6\beta_4$, $\alpha_3\beta_1$, and $\alpha_2\beta_1$ integrins in tissues is varied. The $\alpha_6\beta_4$ form of integrin is limited primarily in epithelial and Schwann cells surrounding myelinated nerves (64) and is down-regulated in differentiated spinal cells (20, 21, 66). SAC/hemidesmosome structures have also been observed to be associated with bullous pemphigoid antigen (27, 67). In contrast, the $\alpha_3\beta_1$ and $\alpha_2\beta_1$ integrins are widely expressed in tissue and particularly evident in proliferating epithelial cells (20, 21) and in transformed cells and activated lymphoblastoid cells. At the ultrastructural level, the $\alpha_6\beta_4$, $\alpha_3\beta_1$ and $\alpha_2\beta_1$ integrins have been visualized by association with focal adhesions (rather than SACs) and actin-containing stress fibers in motile cells (20, 21). In addition, $\alpha_3\beta_1$ (68) and possibly $\beta_2\beta_1$, have been implicated in cell-cell adhesion because they have been observed to relocate from areas of cell-substrate contact to areas of cell-cell contact in cells, and because antibodies to the $\beta_1$ integrin polypeptide inhibit cell-cell contact in cells in vitro (20, 21, 69). In general, $\alpha_6\beta_4$, $\alpha_3\beta_1$ and $\alpha_2\beta_1$, appear only in the proliferating basal cell layer; $\alpha_6\beta_4$ appears to be restricted to regions of the stem cell basal plasma membrane (58, 20, 21); $\alpha_3\beta_1$ appears on basal lateral and apical regions of the stem cell plasma membrane; and $\alpha_2\beta_1$ appears primarily on the apical and lateral regions of the stem cell plasma membrane (59, 20, 21). Thus, while integrins $\alpha_3\beta_1$ and $\alpha_6\beta_4$ have been recognized as glycoproteins involved in cell-substrate contact in vitro, the available information has created a tangled web which does not permit a determination of which interactions may be physiologically meaningful in vivo.

2.15 Integrins are reported to play a possible role in lymphocyte activation. It has been reported recently that in T-lymphocytes, the interaction of cells containing $\alpha_3\beta_1$ integrin with collagen and a second signal such as initiated by binding of antibody to CD3 to the cell surface integrin may trigger cellular activation. Whether such effects may also be triggered by integrins in non-lymphoid cells is not known, at present. It has been reported that a complex substrate composed of a gel formed from purified laminin, type IV collagen, heparin sulfate proteoglycan, entactin and nidogen induced clustering of melanocytes (13), formation of tubular structures by Sertoli cells (70), in vivo growth of neurons (71), and in vitro growth of Schwann cells and liver cells (72). However, it is not known whether the complex substrate induced these effects, or whether the complex substrate favored the growth of a few cells which already possessed these features. Epithelial cells grown with this complex substrate, in general, were reported to assume a much greater polarity than on plastic, collagen, laminin, or fibronectin, but again the molecular basis for this reported change is at present unclear.

2.16 Malignant transformation of normal human keratinocytes in vitro has been reported to impair their ability to differentiate, stratify, and form cornified epithelia in vitro, and these properties were correlated with inability of the cells to synthesize ivolucrin and re-expression of fetal cytokeratins (73). Studies of ivolucrin tissue distribution in cases of skin and lung carcinoma have also suggested that basal cell carcinomas may be negative for ivolucrin with low transglutaminase activity while squamous cell carcinomas may be positive for ivolucrin (74–77). In these respects the transformed keratinocytes and basal cell carcinomas seemed to resemble basal (stem) cells. However, the validity of such interpretations based on ivolucrin has been brought into doubt by the finding that ivolucrin is universally present in both benign acne and keratotic lesions as well as in malignant lesions in skin (78) or cervical tissues (79).

2.17 The mechanisms by which cancer cells of epithelial origin arise are largely unknown, and since these mechanisms are unknown it is difficult to structure treatments to restore normal growth control to malignant cells. Recently it has been reported that malignant human cells may be induced to assume a non-malignant phenotype in vitro by fusion with diploid human keratinocytes. The non-malignant phenotype in the fused cells was reportedly correlated with the continued expression of ivolucrin as a marker of keratinocyte terminal differentiation, i.e., cells which reportedly lost the ability to produce ivolucrin during in vitro culture also reacquired the ability to grow progressively in animals (80).

2.18 Mechanisms involved in psoriasis and autoimmune dermatological diseases are also largely unknown. However, it is reported that epidermal tissues may show decreased transglutaminase activity and premature appearance of ivolucrin in the basal cell layer (81), suggesting a possible premature terminal differentiation of basal (stem) cells in this disease, but not suggesting any mechanisms by which this condition may be caused or corrected. Similarly, bullous pemphigoid (BP), cicatrical pemphigoid (CP), and epidemolysis bullosa acquisita (EBA), are autoimmune dermatological diseases where autoantibodies have been reported (in some patients) that bind to antigens in pathological and normal basement membranes. In BP and CP, using immunoelectron microscopy, immunoreactants have been reported to be in skin, and associated with the lamina lucida (82–86) while, in contrast, EPA immunoreactants reportedly are localized just below the Lamina densa (87). Autoantibodies present in some BP patients' sera also reportedly bound antigens in the Lamina lucida (88, 89) and in EBA they reportedly bound to antigens in the Lamina densa (87, 90). The apparent molecular sizes on SDS-PAGE reported for the BP antigens were 220 kDa and 240 kDa (91) and the EBA were 290 kDa and 145 kDa (90). Using suction blisters and split skin techniques to separate the basal layer from the basement membrane, BP antigens (BPA) were reportedly identified in the "roofs" of the blisters and split skin (i.e., associated with the cells and not with the basement membrane) while CP antigens were reportedly located in the "floors" (i.e., associated with the basement membrane) (92, 93). BPA has been associated by immunoelectron microscopy with ultrastructural elements resembling SACs (26, 27). These ultrastructural studies have made the association between the presence of immunoreactants in the Lamina lucida and the antibodies that are present (in some patients) to the antigens presumed to be present on the basal surfaces of the basal (stem) cells in BP, but it is not clear at present what significance these findings may have for understanding these autoimmune diseases. Similarly, it is not clear at present how these findings may relate to the cell biology and biochemistry of normal epithelia.

2.19 Epiligrin is a recently elucidated epithelial basement membrane component that mediates cell adhesion via integrins $\alpha_3\beta_1$ and $\alpha_6\beta_4$ (113). Epiligrin, a complex of several glycoproteins, is located in the lamina lucida of the basement membrane where the complex comes in direct contact with the overlying epithelial cells. A major constituent of this complex is a 170 kDa protein (EI70) that is encoded by the LamA3 gene (#135). E170 is the $\alpha_3$ chain of epiligrin, not to be confused with the $\alpha_3$ chain of integrin (#135).

Epiligrin and nicein, a similar glycoprotein complex, have been shown to be absent from the basement membrane of patients with the gravis form of junctional epidermolysis bullosa (#114, 121, 126, 135). Junctional epidermolysis bullosa is a blistering disorder of the skin that is characterized by a separation of basal cells from the basement membrane due to a decreased number of hemidesmosomes (#126–128). These data establish that epiligrin interactions with integrin $\alpha_6\beta_4$ in hemidesmosomes are important for anchorage of basal cells to the basement membrane. Furthermore, it was shown that epidermotrophic T-lymphocytes can interact with epiligrin via integrin $\alpha_3\beta_1$ and this interaction may mediate T cell infiltration of the epidermis during pathogenic cutaneous inflammation (#123). Taken together, these results indicated that epiligrin interactions with both integrin $\alpha_3\beta_1$ and $\alpha_6\beta_4$ are physiologically important. Similar observations were made in studies by Weitzman et al. (1993), Niessen et al. (1994), and Rousselle and Aumailley (1994) (#s 129–131).

Epiligrin is the major adhesion ligand present in epidermal basement membranes and it has been shown to mediate basal cell adhesion via integrins $\alpha_3\beta_1$ in focal adhesions and $\alpha_6\beta_4$ in hemidesmosome adhesion structures (113, 133).

3. SUMMARY OF THE INVENTION

The present invention is predicated upon the discovery that adhesion of epithelial and lymphoid cells is modified by epiligrin, an epithelial ligand complex composed of disulfide-linked glycoproteins of 200±20 kDa, 170±20 kDa, 145±20 kDa, 135±15 kDa, and 100±10 kDa, with an associated intracellular 36±15 kDa glycoprotein. Epiligrin, as well as constituent epithelial ligand glycoproteins and peptides disclosed herein, are ligands for the $\alpha_3\beta_1$ and $\alpha_6\beta_4$ integrins. Epiligrin and its constituents are useful for modifying adhesion of epithelial and lymphoid cells. Certain embodiments of the invention thereby provide reagents and methods for restoring normal growth in epithelial cells, e.g., in autoimmune disease and carcinoma. Other embodiments provide reagents and methods for inhibiting the binding of activated lymphoid cells to epithelial cells through the integrins, e.g., for controlling inflammation in epithelial tissues.

The present claims are directed to nucleic acids that encode E170 epithelial ligand glycoproteins, and particularly to such nucleic acids capable of hybridizing under stringent conditions to one or more of the disclosed "Ep-1" (ATCC No. 75540), "1-1" (ATCC No. 75539; deposited under the strain designation "NAS-3 1-1"), and "8-6" (ATCC No. 75538; deposited under the strain designation "NAS-3 8-6") nucleotide sequences. The gene encoding E170 is called LamA3, and is located at human chromosome 18q11.2. The subject nucleic acids are useful in expression systems for production of E170 epithelial ligand glycoproteins, and they also find use as diagnostic and therapeutic agents in identifying and treating patients with the gravis form of junctional epidermolysis bullosa and other epithelial diseases. The claims are directed also to antibodies directed against proteins, as well as to the epiligrin complex itself and the proteins encoded by the claimed nucleic acids.

4. BRIEF DESCRIPTION OF THE DRAWINGS

FIGS. 6A–6F demonstrate the attachment of human foreskin fibroblasts HFK-ECM (FIGS. 6D–6F) but not other ECM components.

Figure 7:
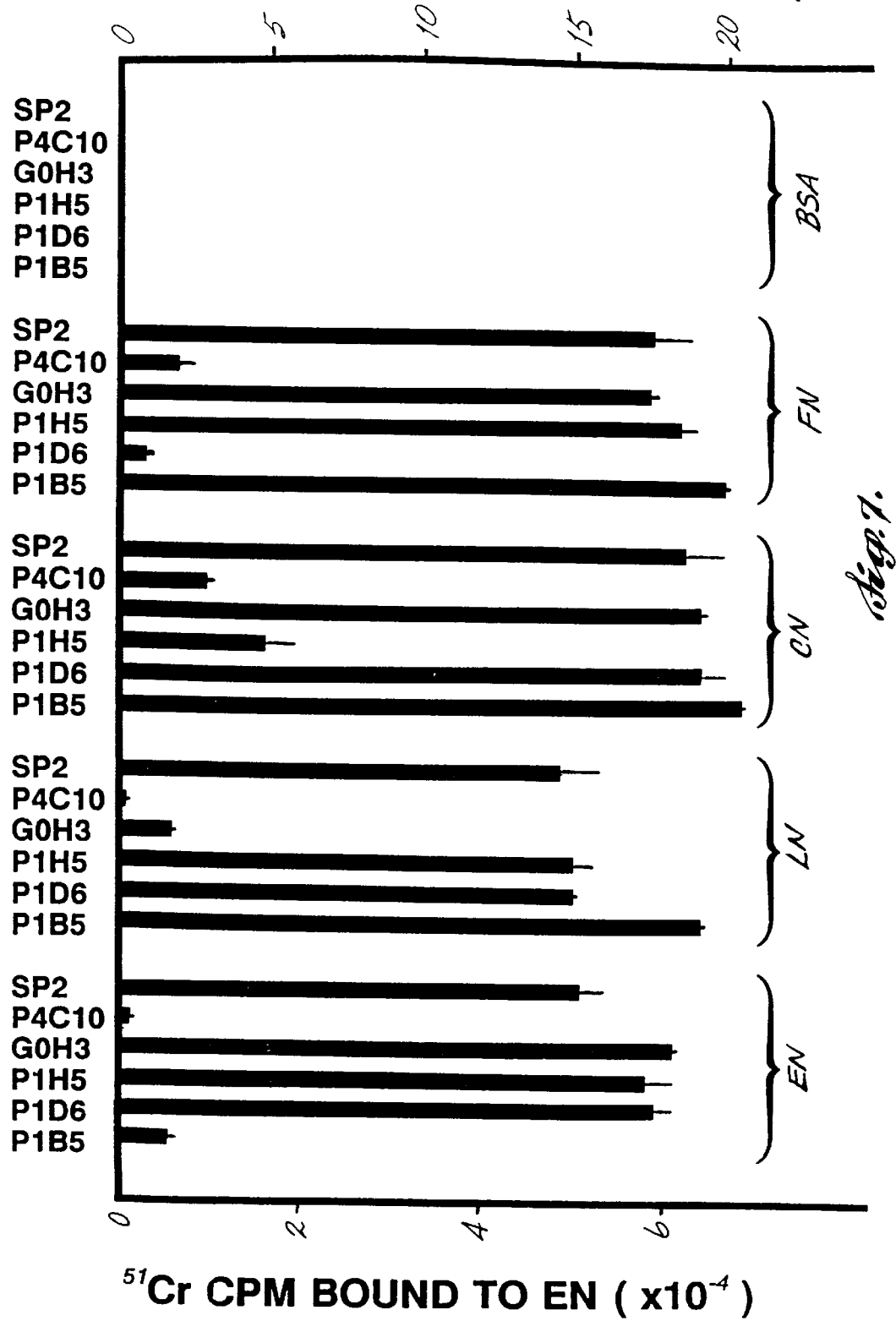

FIG. 7 illustrates a specific test cell assay for epiligrin in which specific adherence of cells to epiligrin is modulated.

Figure 8A:
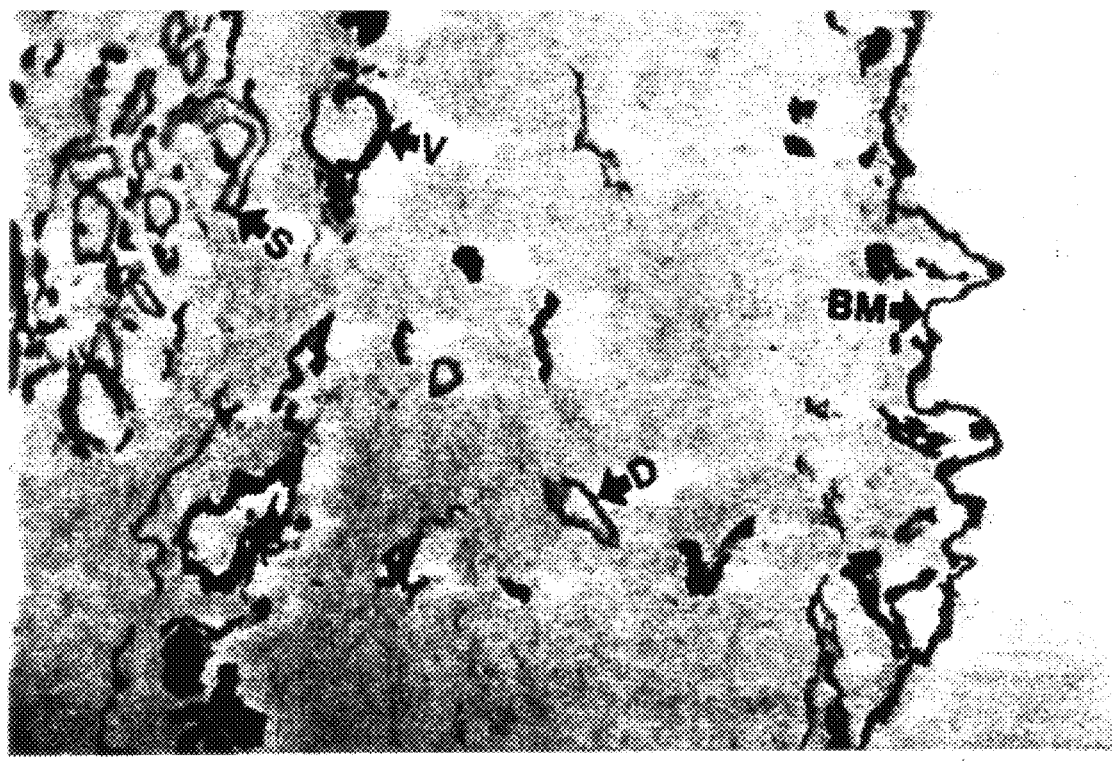
Figure 8B:
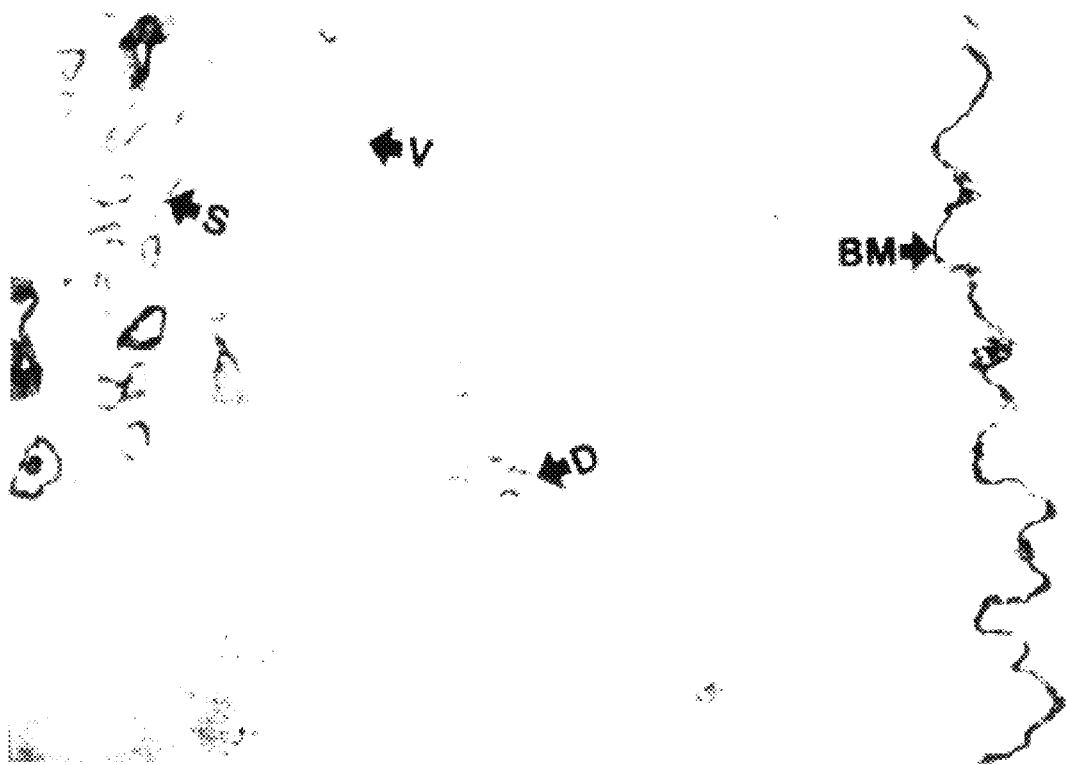
Figure 8C:
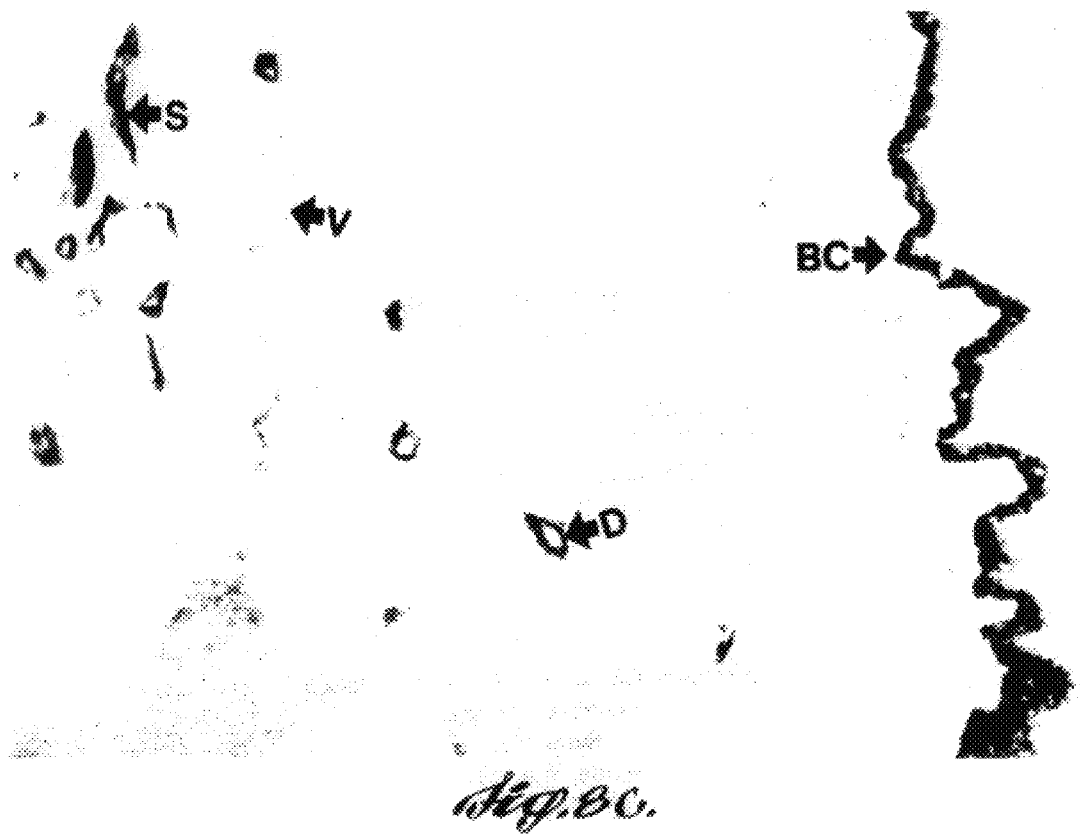
Figure 8D:
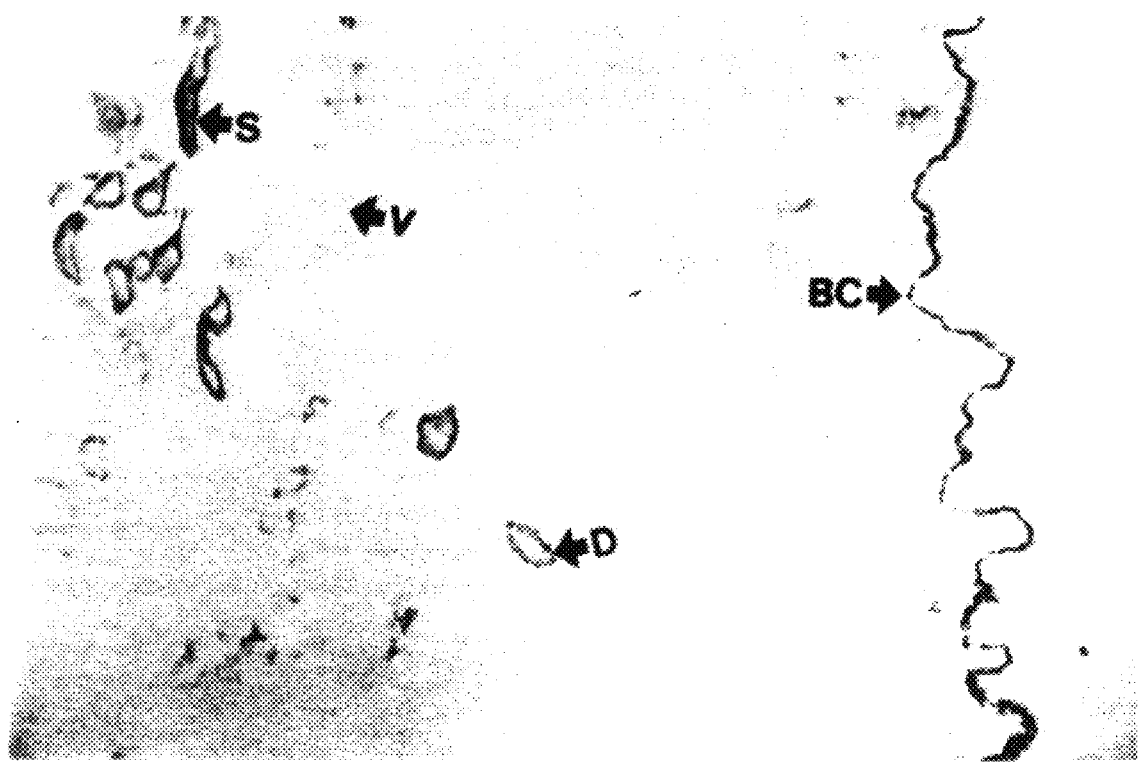
Figure 8E:
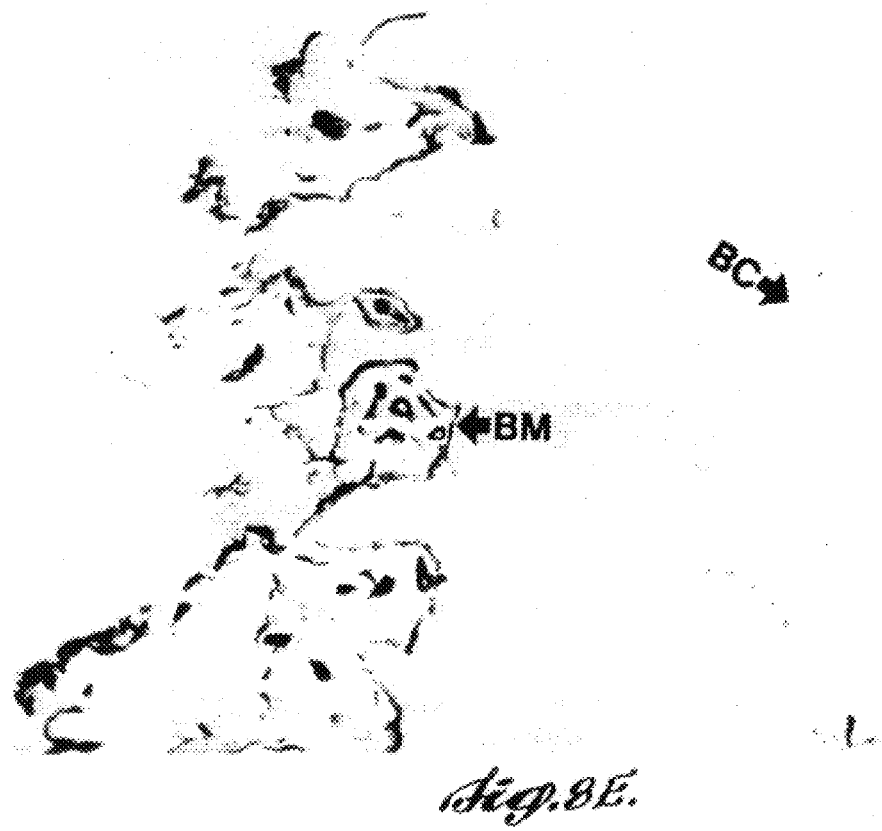
Figure 8F:
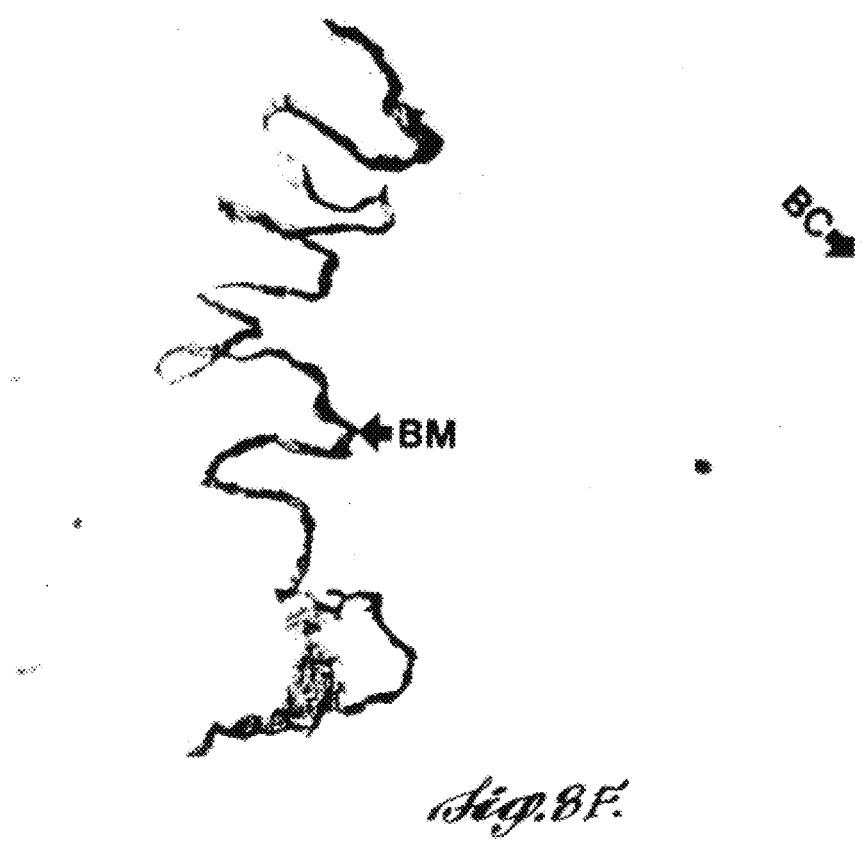
Figure 8G:
Figure 8H:
Figure 8I:
Figure 8J:
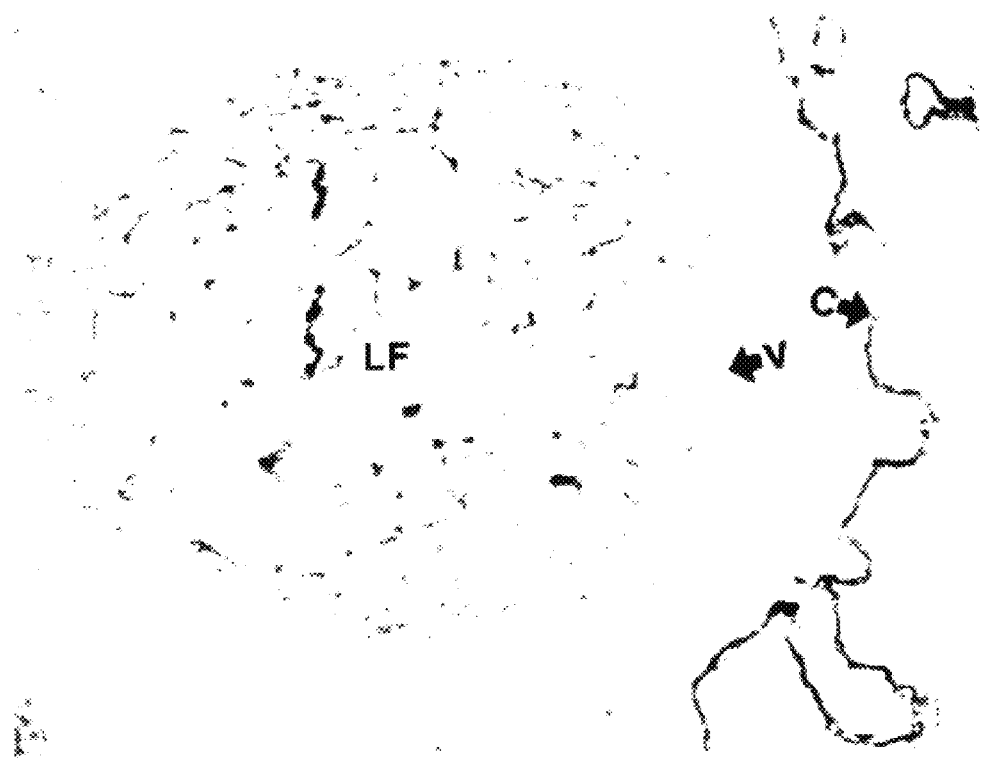
Figure 8K:
Figure 8L:
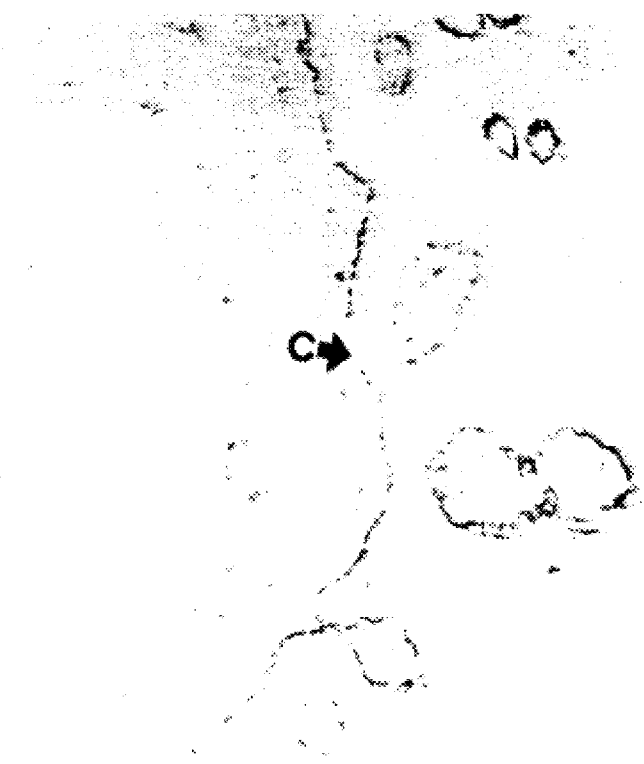
Figure 8M:
Figure 8N:
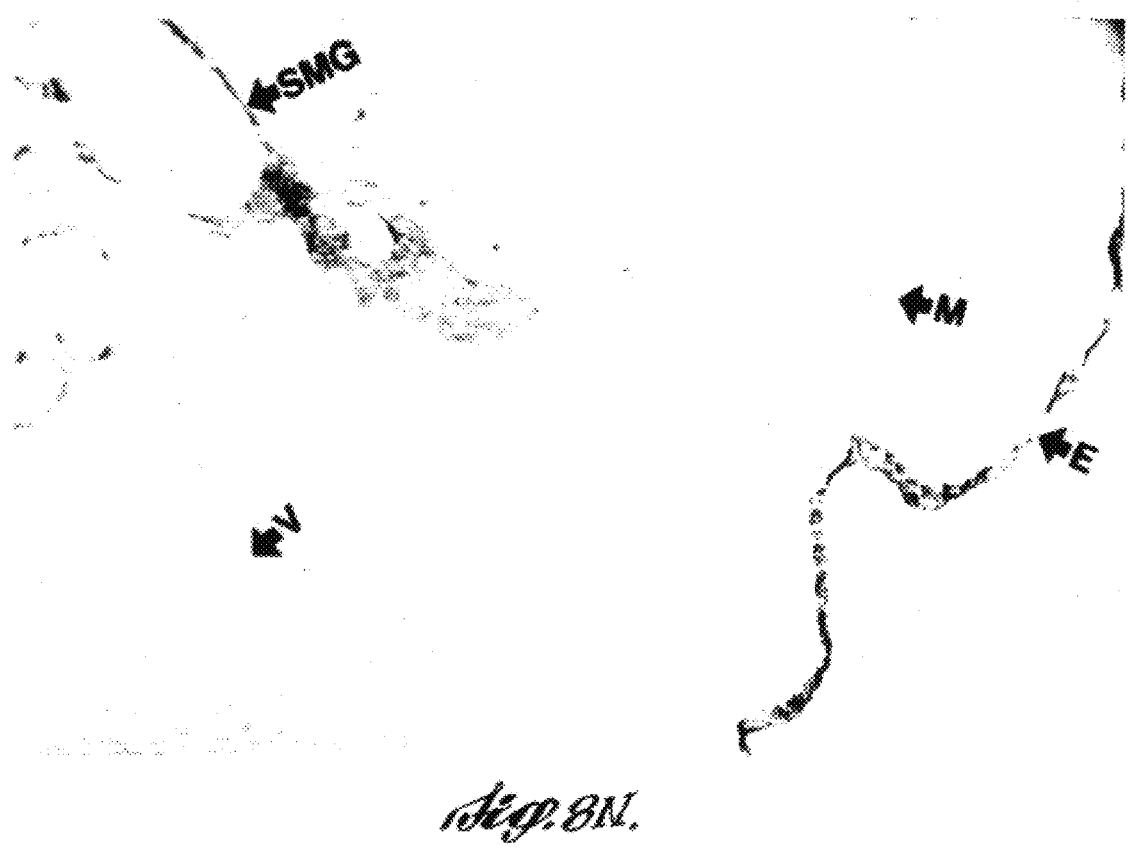
Figure 30:
Figure 32:

FIGS. 8A–8P illustrate the localization of epiligrin in epithelial basement membranes of skin, tonsil, and lung, and shows epiligrin distribution in sweat glands, lymphoid follicle germinal centers, and in submucosal glands.

FIGS. 9A–9F illustrate the ultrastructural localization of epiligrin in epithelium.

Figure 10A:
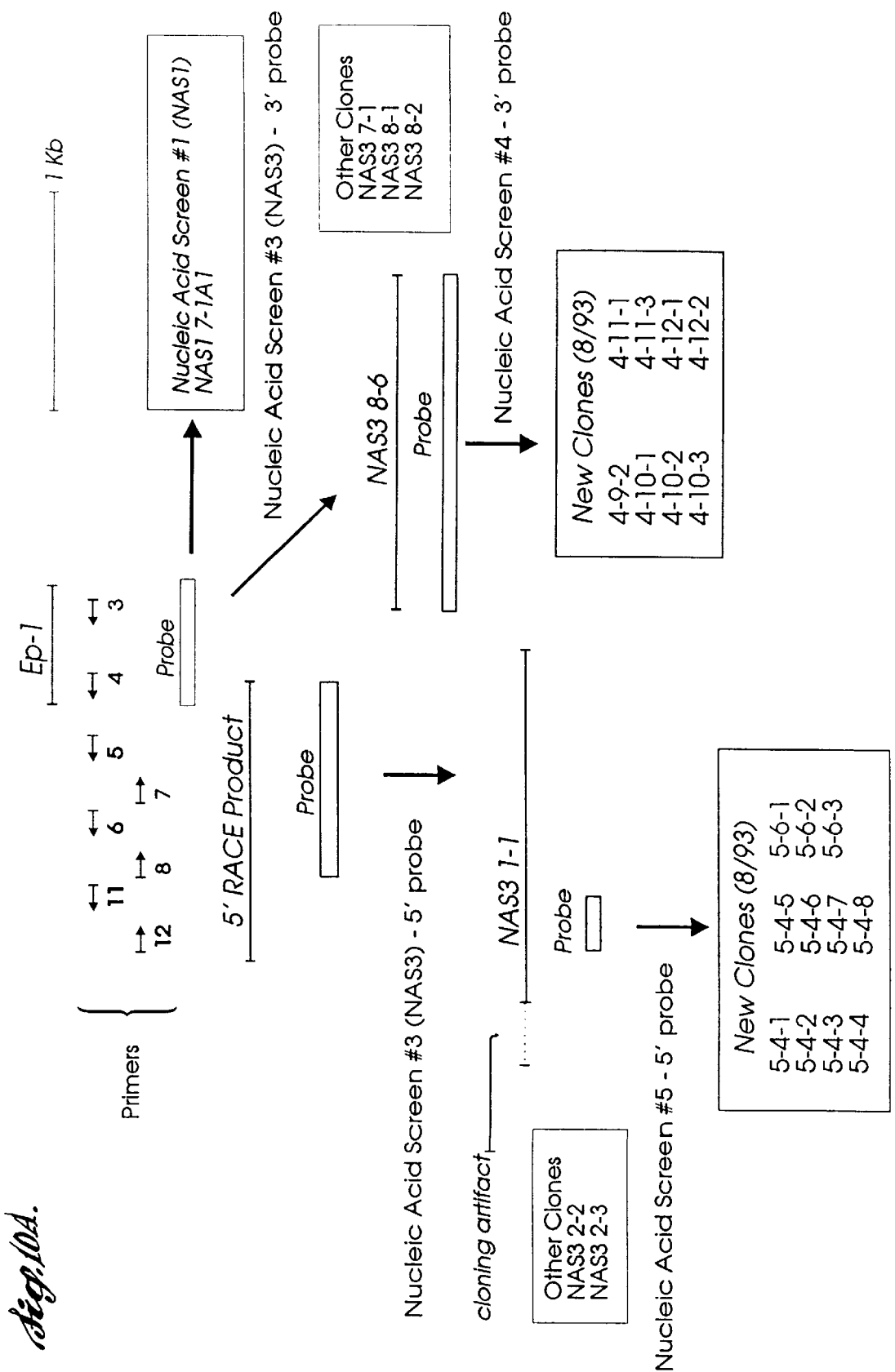

FIG. 10A schematically depicts the strategy used to clone the E170 component of epiligrin.

FIGS. 10B–10C depict a comparison of the domains of $\alpha 1$ laminin-1 and $\alpha_3$ epiligrin, as well as the overlapping cDNA clones (FIG. 10D) used in Example 15 to compile the nucleotide sequence encoding E170 epithelial ligand glycoprotein, i.e., as shown in FIGS. 10F, 11A–11C, and 15A–15F. FIG. 10E shows the location of primers used in sequencing.

FIG. 10F shows the nucleotide sequence of E170 epithelial ligand glycoprotein cDNA clone "1-1" from position 1 to position 664 (SEQ ID NO: 21). (The sequence of clone 1-1 was edited to remove a common cloning artifact, the first 150 bp of the Ep-1 cDNA consisting of a cloned fragment of a rRNA.)

FIGS. 11A–11C show 1994 bp (SEQ ID NO: 22) of the nucleotide sequence of E170 epithelial ligand glycoprotein compiled from cloned cDNAs as depicted in FIG. 10A. PCR primers used in cDNA cloning were: MR-12 (corresponding to nucleotides 183–198 in FIG. 11A), MR-11 (nucleotides 340–357 in FIG. 11A), MR-8 (nucleotides 640–657 in FIG. 11A), MR-6 (nucleotides 700–719 in FIG. 11A), MR-7 (nucleotides 992–1012 in FIG. 11B), MR-5 (complement to nucleotides 1055–1073 in FIG. 11B), MR-4 (nucleotides 1277–1296 in FIG. 11B) and MR-3 (nucleotides 1709–1723 in FIG. 11C). The positions at which different cDNA clones begin are position 1, where "1-1" begins, and position 1216, where EP-1 begins. Clone EP-1 ends at position 1742. FIG. 11A shows the sequence from position 1 to position 720. FIG. 11B shows the sequence from position 721 to position 1500. FIG. 11C shows the sequence from position 1501 to position 1994.

FIGS. 11D–11E show schematically the positions of restriction endonuclease sites within the E170 nucleotide sequence shown in FIGS. 11A–11C.

Figures 12A, 12B:
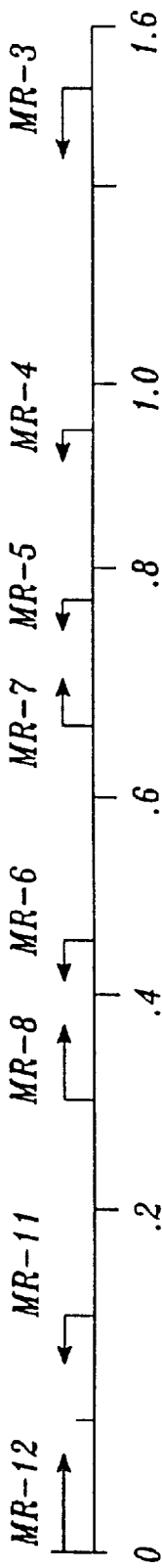

FIG. 12A shows the relative positions of the primers within the EP-1 E170 sequence.

FIG. 12B shows the nucleotide sequences of 8 primers (SEQ ID NOS:1–8) useful in PCR methods for isolating nucleic acids encoding E170 epithelial ligand glycoprotein, as described in Example 15.

FIG. 13 depicts schematically the steps in a representative PCR assay method for isolating nucleic acids encoding E170 epithelial ligand glycoprotein.

FIG. 14 depicts schematically the steps in a representative 5' RACE system for PCR cloning of cDNAs encoding E170 epithelial ligand glycoprotein, as described in Example 15.

FIGS. 15A–15F depict the nucleotide sequence compiled from sequencing cDNA clones corresponding to the $\alpha 3_{EpA}$ transcript (SEQ ID NO:23).

Figure 16A:
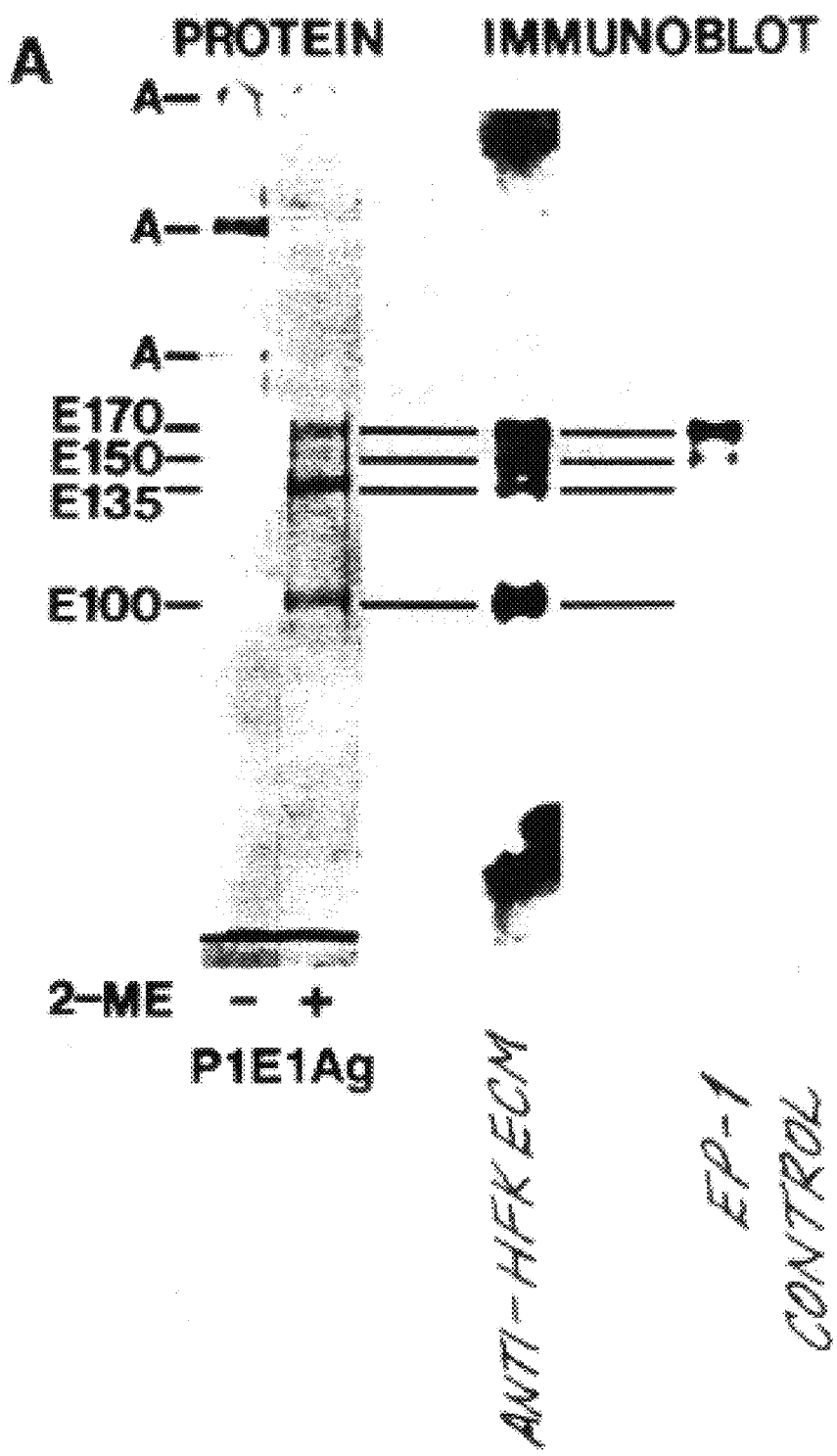

FIGS. 16A–16B show experiments demonstrating that the clone Ep-1 expresses a fusion protein that corresponds to at least a portion of the 170 kDa subunit of epiligrin.

FIGS. 17A–17B show a Northern blot analysis of $\alpha 3_{Ep}$ mRNA and illustrates that two distinct transcripts are detectable.

FIGS. 18A–18C illustrate the sequence variability in domain IIIa, near the amino-terminal portion of the protein encoded by $\alpha 3_{Ep}$ (SEQ ID NOS:26–30).

FIGS. 19A–19R show the amino acid sequence encoded by $\alpha 3_{EpA}$ (SEQ ID NO:24).

FIGS. 20A–20H illustrate the localization of epiligrin mRNA and protein in 48 hour human wounds, using in situ hybridization with probes derived from $\alpha 3_{Ep}$.

Figure 20A:
Figure 20B:
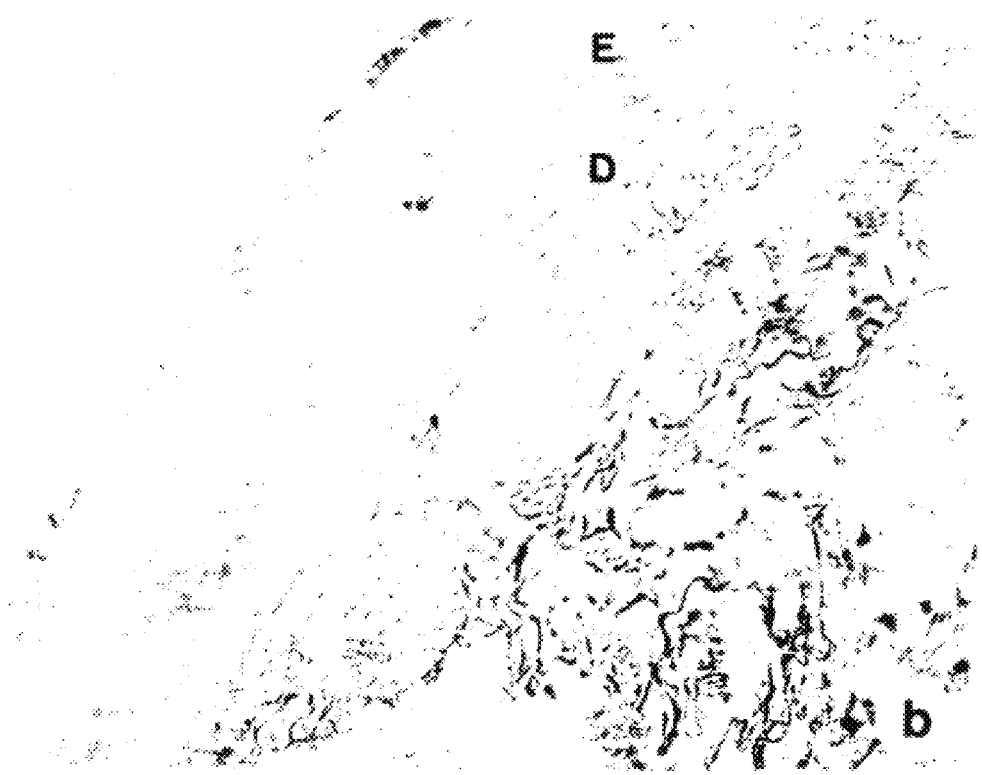
Figure 20C:
Figure 20D:
Figure 20E:
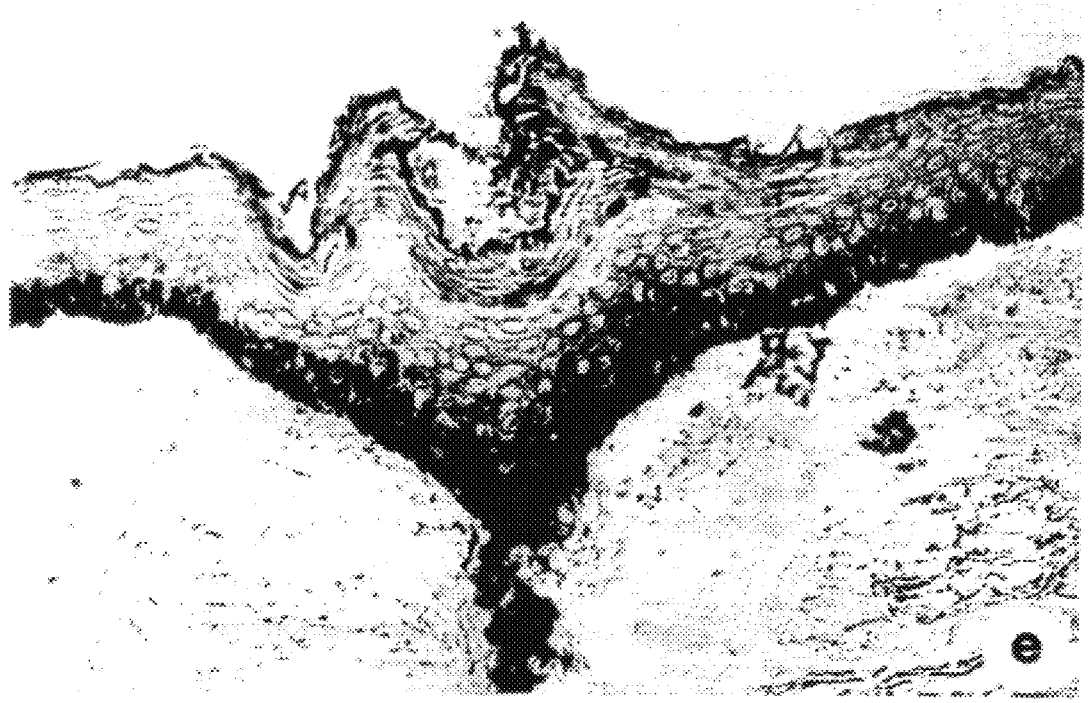
Figure 20F:
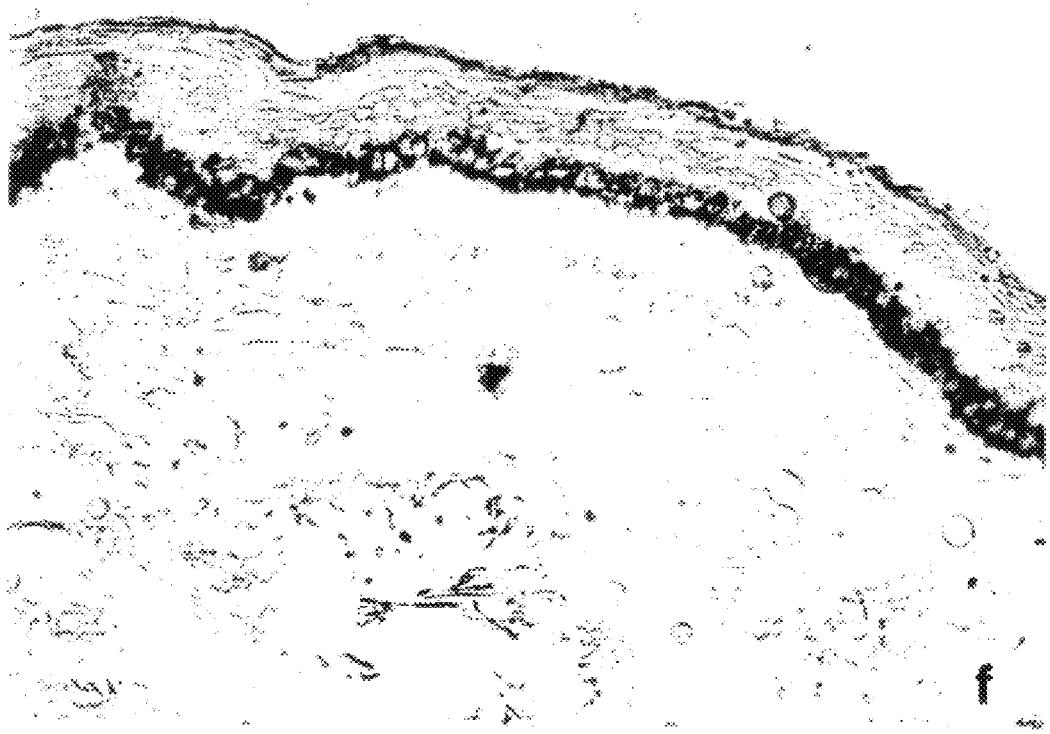
Figure 20G:
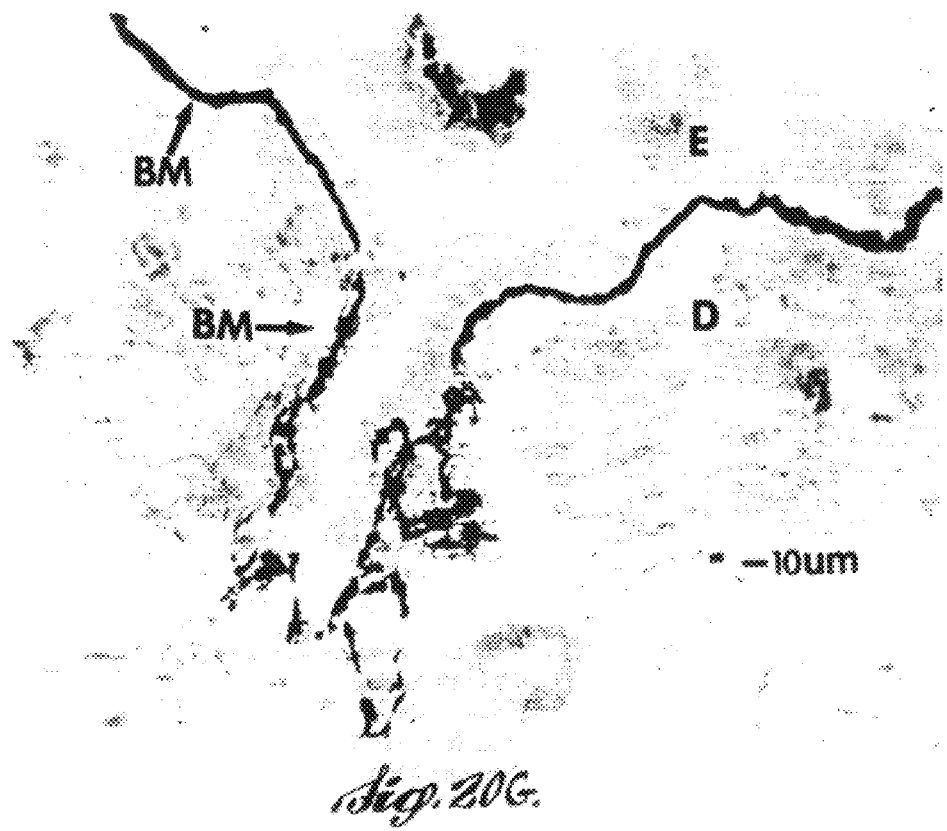
Figure 20H:

FIGS. 20A, 20C, and 20E show the wound site, as compared to normal skin shown in FIGS. 20B, 20D, and 20FFF. FIGS. 20A–20B are labeled with epiligrin anti-sense probe, FIGS. 20C–20D with epiligrin sense probe, and FIGS. 20E–20F with keratin anti-sense probe. FIGS. 20G and 20H show wound sites labeled with anti-epiligrin and anti-$\alpha 3$ antibodies, respectively.

Figure 21:
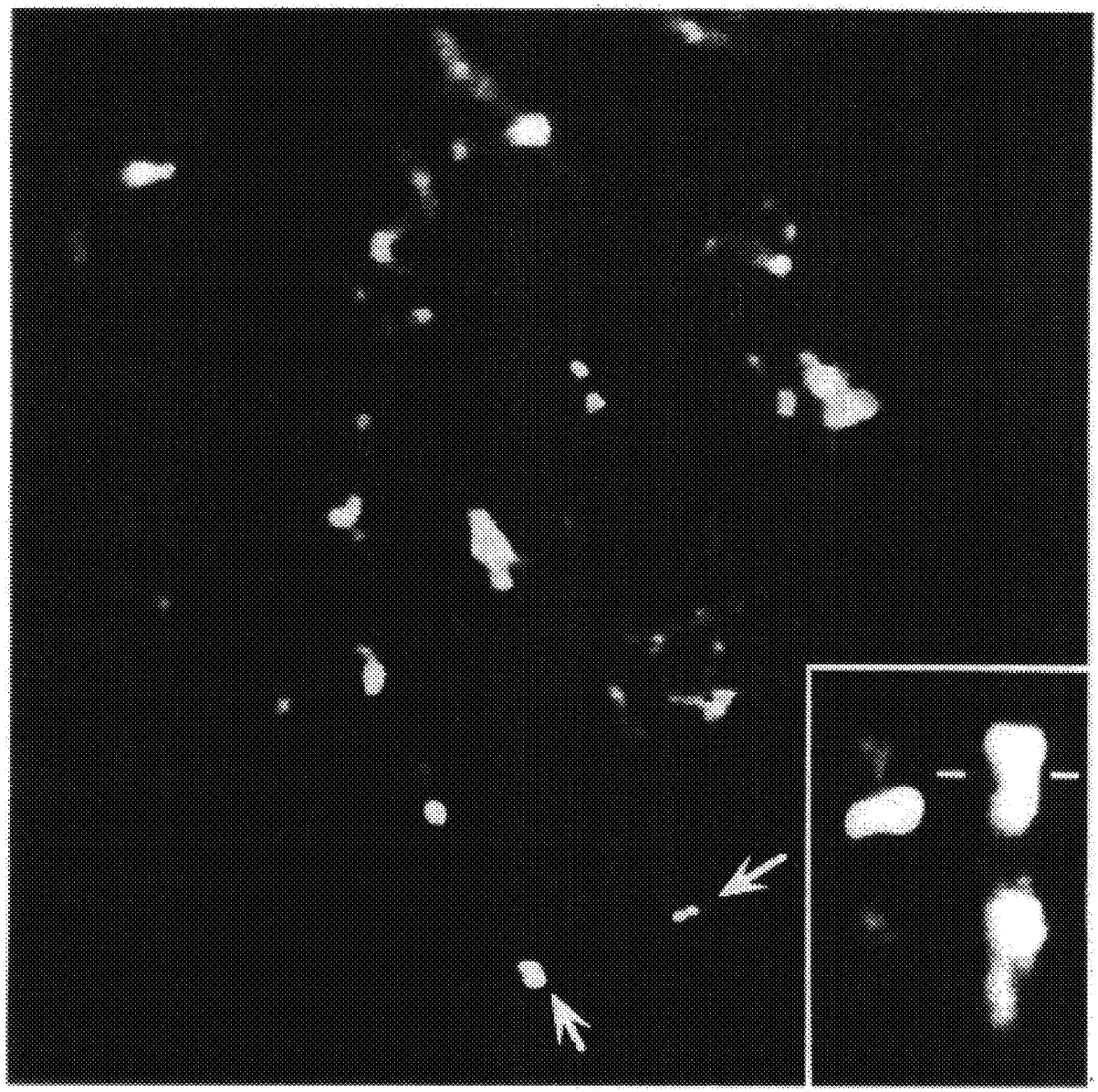

FIG. 21 shows the localization of the human LamA3 gene to chromosome 18q11.2.

FIGS. 22A–22B are graphical representations depicting that integrins $\alpha_6\beta_4$ and $\alpha_3\beta_1$ mediate anchorage and motility, respectively, on epiligrin via distinct signal pathways, as described in Example 18.

5. DETAILED DESCRIPTION OF THE PREFERRED EMBODIMENT

The scientific literature contains several examples wherein the discovery of ubiquitous extracellular proteins (e.g., laminin and fibronectin) led to the subsequent identification and purification of the cellular receptors binding these ligands. In contrast, in the present case the inventors recognized that existing background art which identified laminin as a putative ligand for binding two of these cellular receptors, $\alpha_3\beta_4$ and $\alpha_6\beta_4$ integrins, probably described physicochemically minor binding interactions. The inventors had previously observed that the $\alpha_3$ $\beta_1$ and $\alpha_6\beta_4$ integrins were co-distributed in epithelial tissues including human skin; however, the significance of this observation was not readily apparent and the distribution could have been due to both cellular receptors binding to laminin in the tissues. However, in distinction to the teachings in the literature, they reasoned that (a) laminin was not the ligand, and (b) that the two cellular receptors co-distributed because they shared some other (new) extracellular matrix complex as a ligand. With this recognition of the problem, they sought to identify the novel ligand. Because it was not possible to investigate this problem in tissue sections of human biopsy material, they recognized that it would be necessary to select the proper cell type for study in vitro. Since they had previously observed that the two forms of integrin were present together on cells in regions of human skin that contained keratinocytes, fibroblasts, and other specialized epithelial cells, they focused on those regions as a possible source of cells for in vitro study. In considering among these possible different cell types the inventors recognized that human fetal keratinocytes (HFKs) expressed both the $\alpha_3\beta_1$ and $\alpha_6\beta_4$ integrins. Although keratinocytes were recognized by the literature to be a differentiated form of epithelial cell, both with respect to their microscopic appearance and their biosynthetic activities, the inventors reasoned that cultures of these cells might synthesize and secrete the novel extracellular matrix ligand, and might be suitable for in vitro study. (In fact, as the detailed description of the invention (appearing below) shows, if they had chosen to study fibroblasts or continuous epithelial cell lines, they would not have succeeded in identifying the ligand which is an embodiment of this invention.) Armed with this recognition of the problem and its possible solution, the inventors succeeded in identifying the novel ligand for the $\alpha_3\beta_1$ and $\alpha_6\beta_4$ integrins. Surprisingly, the cellular receptors and ligands identified and isolated from keratinocytes in tissue culture were the same as those utilized by the basal (stem) cells in epithelial tissue.

In the research described below, the molecular mechanisms by which epithelial cells establish contact with the basement membrane are elucidated, the cell receptor and its extracellular basement membrane ligand are identified and substantially purified, and the mechanisms are unraveled through which growth and differentiation are controlled in the epithelium. The novel ligand which is a subject of the invention is termed "epiligrin." Research from other laboratories has identified GB3 antigen/nicein (Verrando et al., 1987, 1988) and kalinin (Rouselle et al., 1991; Marinkovich et al., 1993) which are probably identical to epiligrin. Epiligrin is a covalently linked glycoprotein complex that mediates epithelial cell attachment to the basement membrane through $\alpha_3\beta_1$ integrin acting as a cellular receptor. In this application, the terms "epiligrin" and "epithelial ligand glycoproteins" are used interchangeably to refer to the same glycoprotein complex. Individual protein components of epiligrin are sometimes referred to as "epithelial ligand glycoproteins." Epiligrin is present in the lamina lucida of basement membrane and is associated with those cell membrane ultrastructural features previously termed focal adhesions. These focal adhesions are located on the basal surface of the cells in areas of contact with the basement membrane substratum, and they are also involved in cell motility. Epiligrin also interacts with the $\alpha_6\beta_4$ integrin, a cellular receptor that is present in ultrastructural membrane features previously termed hemidesmosomes and stable adhesion complexes. The invention provides an understanding, for the first time, of how these two different ultrastructural features (frozen in time by fixation for electron microscopy) can function in a living cell to mediate adhesion, control of cell growth, and determination of the fate of daughter cells derived from cell division in the basal layer of the epithelium.

Burgeson et al. (#125) have proposed nomenclature that categorizes epiligrin as a kind of "laminin." Accordingly, the inventors have denoted the gene encoding E170 as "LamA3." However, following this nomenclature can convey the misleading impression that E170 is demonstrably similar to the $\alpha_3$ chains of laminin 5, 6, and 7. First, there is no published sequence available for the Burgeson scheme's $\alpha_3$ chain of laminin-5, laminin-6, or laminin-7 which would provide any way of comparing those sequences with the $\alpha3_{EpA}$ and $\alpha3_{EpB}$ sequence. Second, the new nomenclature is based on the unproven assumption that $\alpha_3$ chains of laminin-5, laminin-6, and laminin-7 are indistinguishable. In contrast, the Applicants' data clearly show that there are two distinct $\alpha3_{Ep}$ transcripts, suggesting that there is heterogeneity in the $\alpha_3$ polypeptide chains (135). In addition, the $\alpha_3$ chain described for nicein (#137) contains a significantly smaller G domain and is reported to have a different structural organization than the Applicants observed for the $\alpha3_{EpA}$ or $\alpha3_{EpB}$ transcripts of epiligrin. This suggests the possible existence of a third $\alpha3_{Ep}$ transcript (#137), but no nucleotide sequences for nicein are known, and nicein may be encoded by a locus distinct from LamA3.

The $\alpha_3\beta_1$, integrin which binds epiligrin is one of the most widely expressed of all integrins in tissue, but its physiological ligand has not been identified until now. Novel test cell assays, extracellular matrix compositions, and immunochemical reagents were created which allowed identification for the first time of epiligrin, in basement membranes as the physiologically significant ligand for plasma membrane-based $\alpha_3\beta_1$ and $\alpha_6\beta_4$ integrins. Only a few epithelial cells in culture (e.g., keratinocytes) express significant quantities of epiligrin, and this glycoprotein complex is of a large molecular size and has poor solubility in aqueous solutions. Epiligrin's size and poor solubility have undoubtedly contributed to the lack of previous recognition of this ligand in binding to integrins.

The role of the $\alpha_6\beta_4$ integrin as a receptor for the epithelia ligand (i.e., in stable adhesion complexes) is less impressive than the adhesion mediated by the $\alpha_3\beta_1$ integrin but is potentially more significant. The findings described below indicate that $\alpha_6\beta_4$ integrin is involved in cellular adhesion to basement membranes, and it may also localize the focal adhesions in a pattern which encircles the regions of the stable anchoring contracts. This process of encirclement, as well as the localization of $\alpha_6\beta_4$ integrin in cell-cell adhesion sites, determines the fate of the daughter cells formed by division in the basal (stem) cell layer of the epithelium.

Migration of epithelial cells is an important aspect of at least wound healing, inflammation, and tumor metastasis. Focal adhesions containing $\alpha_3\beta_1$ integrin are involved in cell movement, and the stable anchoring contacts containing $\alpha_6\beta_4$ integrin are involved in stopping cell movement. Epiligrin binds to both $\alpha_3\beta_1$ and $\alpha_6\beta_4$ integrins. This inventive recognition, pursuant to the present disclosure, allows one skilled in the art to identify specific binding partners to epiligrin (as disclosed in greater detail, below), and provides for the first time compositions which can modify movement and adhesion of cells of epithelial origin. The invention also provides, for the first time, an understanding at the molecular level of how polarized self-regulated growth and differentiation are achieved in epithelial tissues through the binding of the transmembrane integrins in the plasma membrane to extracellular epiligrin, the epithelial ligand complex, and possibly through intracellular signaling accomplished by the 36±15 kDa epiligrin glycoprotein. These events occur at discrete plasma membrane sites in the stable anchoring contacts, and a second cytoplasmic polypeptide was also discovered to be a recognized SACs protein termed bullous pemphigoid antigen. Armed with the new information and understanding provided in the present disclosure, one skilled in the art is able to recognize how malignant carcinoma cells may arise through loss of the control mechanisms provided by epiligrin, and how it is possible to consider reestablishing these normal control mechanisms in carcinoma cells by using the understanding provided by the invention to select for epiligrin derivatives and other pharmaceutical agents that induce the cells to correct their defect in epithelial ligand regulation.

Conclusions based on the following findings and on reinterpretation of previous reports in light of the new insights gained from the present invention are: (i) Purified epiligrin was shown to induce cell adhesion and localization of the $\alpha_3\beta_1$ integrin in focal adhesions better than laminin, fibronectin, or collagen. Further, cell adhesion to epiligrin was specifically inhibited with monoclonal antibodies to $\alpha_3\beta_1$ integrin. (ii) Epiligrin was the major component of the extracellular matrix synthesized by human foreskin keratinocytes. In cultures of stationary keratinocytes, epiligrin was deposited and co-distributed with the transmembrane $\alpha_6\beta_4$ integrin and with cytoplasmic bullous pemphigoid antigens which are recognized components of hemidesmosome-like stable adhesion complexes. All three of these components in the stable adhesion complexes were resistant to sequential extraction with detergent, 2 M urea/1 M NaCl, and 8 M urea. In contrast, the $\beta_1$-containing integrins in the focal adhesions were not stable to this extraction. The $\alpha_3\beta_1$ integrin-containing focal adhesions were observed to form rings around the periphery of the $\alpha_6\beta_4$ integrin containing stable anchoring contacts. (iii) In tissue, epiligrin localized in most epithelial basement membranes, but not in the basement membranes of muscle, or endothelium. At the ultrastructural level, epiligrin localized to the lamina lucida of the epidermal/dermal basement membrane of skin. Consistently, epiligrin localized with the $\alpha_3\beta_1$, integrin in the basal plasma membrane, as well as with the $\alpha_6\beta_4$ integrin-containing hemidesmosomes of basal (stem) cells. These data indicate that epiligrin is the ligand for which $\beta_3\beta_1$ and $\alpha_6\beta_4$ act as receptors.

The subject epiligrin derived from HFK is an epithelial ligand glycoprotein complex that includes at least three major covalently linked disulfide-bonded glycoproteins having apparent molecular sizes of 170 kDa, 145 kDa, and 135 kDa. A glycoprotein of 36 kDa is also associated with the epiligrin complex. Other observed components of epiligrin include a 100 kDa protein that is antigenically related to the 145 kDa protein, and a 200 kDa protein that is antigenically related to the 170 kDa protein. The individual epithelial ligand glycoproteins are visible following reduction and SDS-PAGE (under reducing conditions). These constituent glycoproteins are at times referred to herein by reference to their apparent molecular weight on SDS-PAGE, i.e., E200, E170, E145, E135, E100, and E36, respectively. The 145 kDa protein in some instances is referred to as E145/100. The subject epithelial ligand complex has the ability to bind to $\alpha_6\beta_4$ and $\alpha_3\alpha_1$ integrins and thereby modify cellular adhesion to a substratum (#s 113, 133, 134).

Skilled artisans will recognize a variety of epithelial cells from which the subject epiligrin and its constituent glycoproteins may be purified, or substantially pure nucleic acids prepared. The following direction is provided with regard to representative sources of constituent epiligrin glycoproteins. E36 may be found in the culture supernatant (CS) and extracellular matrix of HFK cells (HFK-ECM); E100 accumulates in CS; E170 is usually not found in CS but may be found in a Triton X-100 extract of HFK-ECM as well as in the insoluble HFK-ECM fraction after the Triton X-100 extraction; and E200, E140, and E130 are usually not found in CS or the Triton X-100 soluble fraction of HFK-ECM, but only in the Triton X-100 insoluble fraction of HFK-ECM. A variety of biochemical and immunochemical methods may be utilized to purify the subject epiligrin glycoproteins, e.g., affinity chromatography in buffers containing Triton X-100 and/or mixtures of ionic, nonionic, or zwitterionic detergents. Treatment with proteases (e.g., trypsin) may be useful for preparation of soluble epithelial ligand glycopeptides, some of which, while failing to mediate cellular adhesion to a surface may still retain the ability to block cellular adherence to epithelial ligand coated surfaces. The following immunochemical direction is provided with regard to the antigenic relatedness of the subject epiligrin glycoproteins: E200 appears to be antigenically related to E170; E145 appears antigenically related to E100; and E135 does not appear to be related to other glycoproteins in the epithelial ligand complex. The inventors currently believe that E170 may be derived from E200 by proteolytic degradation (and/or processing) and, in a similar manner, E100 may be derived from E145.

Epiligrin antigens are associated with the basal surfaces of basal (stem) cells in epithelia at limited points of cellular contact with basement membranes. Embodiments of the invention also relate to the isolation of epiligrin glycoprotein complexes for modifying adhesion of cells to substrata and for achieving polarized and self-regulated growth and differentiation in cells of epithelial origin. Other embodiments relate to antibodies to the epiligrin glycoprotein complex for modifying cellular adhesion to substrata and for identifying epiligrin-like antigens in biological fluids, as well as epiligrin antigens for identifying antibodies in patient samples. Still other embodiments relate to nucleotide sequences of E170 epithelial ligand glycoprotein useful as specific probes for measuring the presence of epithelial ligand mRNA in a tissue, as well as the level of expression in different cells in the tissue. Embodiments of the invention provide compositions and test methods for identifying diseased epithelial cells, and for distinguishing at least between the epithelial abnormalities in such autoimmune dermatological diseases as bullous pemphigoid, cicatrical pemphigoid, and epidemolysis bullosa acquisita.

The subject test methods and compositions are useful for determining the level of expression of epiligrin in a tissue. Expression of epiligrin is a hallmark of a regenerating epithelial tissue (see Example 15). The level of expression of E170 epiligrin glycoprotein was found to provide a tool useful for distinguishing between regenerating epithelial tissues (where expression was high) and non-regenerative epithelial tissues or malignant tissues (where expression was low). Diagnostic histopathology is frequently complicated because it is not easy to distinguish tissue repair (e.g., resulting from traumatic injury or infection) from an abnormality that might be a neoplastic or preneoplastic event. Examining the levels of E170 epithelial ligand expression (e.g., using immuno-histochemical techniques, in situ hybridization with an oligonucleotide or cDNA probes, or PCR of isolated tissue mRNA), is useful for distinguishing between repair and malignant (or premalignant) changes in epithelial tissues.

The invention provides nucleic acids capable of hybridizing under stringent conditions to at least one nucleotide sequence selected from the group consisting of the nucleotide sequence shown in FIGS. 11A–11C (SEQ ID NO:22), the cDNA clone Ep-1 (ATCC No. 75540) shown in FIG. 10F, the cDNA clone 1-1 (ATCC No. 75539), and the cDNA clone 8-6 (ATCC No. 75538), or the nucleotide sequences shown in FIGS. 15A–15F (SEQ ID NO:23). The subject nucleic acids are preferably capable of encoding an E170 epithelial ligand glycoprotein. A partial nucleotide sequence of nucleic acid encoding E170 epithelial ligand glycoprotein is provided in FIGS. 11A–11C (SEQ ID NO:22) compiled from the cDNAs shown in FIG. 10D as schematically depicted in FIG. 10A. The entire nucleotide region encoding E170 is depicted in FIGS. 15A–15F, and corresponds to the sequence of $\alpha 3_{EpA}$, one of the two distinct $\alpha 3_{Ep}$ transcripts discovered by the Applicants. FIGS. 15A–15F (SEQ ID NO:23) consist of a composite sequence derived from the several overlapping clones shown in FIG. 10D Although only a single (+) strand of the cDNA is shown in FIGS. 10F (SEQ ID NO:21), 11A–11C (SEQ ID NO:22), and 15A–15F (SEQ ID NO:23), those skilled in the art will recognize that the complementary (−) strands are thereby disclosed as well. According to the convention used herein to describe PCR primers, the "(−) strand" is complementary to E170 mRNA.

By nucleic acid molecule is meant DNA, RNA, and/or synthetic nucleotide sequences such as oligonucleotides that are the same as, homologous with, or complementary to, at least one helical turn (about 10 to 15 nucleotides) of the illustrated E170 epithelial ligand glycoprotein nucleotide sequence. At least two alternative forms of E170 transcripts are disclosed herein in HFK cells, one mRNA of about 5 kb and another of about 6 kb. Both mRNA species are identifiable to those skilled in the art in RNA from HFK by standard Northern blotting methods (e.g., using radiolabeled Ep-1 as a probe as illustrated in Example 15). The invention relates to at least four classes of E170 encoding nucleotide sequences, 1) alternative splicing transcript sequences, 2) sequences resulting from genetic polymorphism of E170, 3) sequences resulting from translocation of E170 in tumorigenesis and genetic diseases, and 4) sequences of E170 family members having greater than 75% homology with E170 over a conserved region of at least 30 nucleotides. In all cases the latter four classes of E170 nucleotide sequences are identifiable as hybridizing under stringent conditions with an E170 nucleotide sequence of FIGS. 11A–11C (SEQ ID NO:22), e.g., cDNA clone 1-1, Ep-1, or 8-6, while the several clones depicted in FIG. 10D encompass the entire nucleotide sequence encoding an E170 epithelial ligand glycoprotein, skilled artisans will recognize that additional cDNA clones may be obtained using nucleotide sequences contained within the subject cDNAs as probes and primers for obtaining additional cDNA clones. An illustrative example of a PCR cloning method for obtaining additional cDNA clones through PCR cloning is provided in Example 15, below. PCR primers are additionally provided in FIG. 12B (SEQ ID NOS:1–8) and Table 1 (SEQ ID NOS:9–20), below, and the steps of an illustrative PCR method are outlined in FIG. 13.

TABLE I

Primers for PCR Primer-extended Sequencing

| | | |
|---|---|---|
| Primer 4 (SEQUENCE ID NO: 9): | 5' AGCACGAAGGTCACTGAGTT | 3' |
| Primer 5 (SEQUENCE ID NO: 10): | 5' AAGTCACCTGAAGGCACG | 3' |
| Primer 6 (SEQUENCE ID NO: 11): | 5' TGGACGTGCGACTTGACCAG | 3' |
| Primer 13 (SEQUENCE ID NO: 12): | 5' AACTCGCTTGCAGTTGAC | 3' |
| Primer 14 (SEQUENCE ID NO: 13): | 5' GATGGCTGTGGATCTTTG | 3' |
| Primer 15 (SEQUENCE ID NO: 14): | 5' TCCACAGCAAGTGCTATG | 3' |
| Primer 16 (SEQUENCE ID NO: 15): | 5' ATGACAGTGCTGTCTGGAC | 3' |
| Primer 17 (SEQUENCE ID NO: 16): | 5' TCTCCGAGATGGTCTTCATG | 3' |
| Primer 18 (SEQUENCE ID NO: 17): | 5' TTATCTGCATCAGTCAGAGC | 3' |
| Primer 20 (SEQUENCE ID NO: 18): | 5' TGACCAGTGAGCTGTACATC | 3' |
| Primer 29 (SEQUENCE ID NO: 19): | 5' AGAGACCATTCGATTCAGAT | 3' |
| Primer 30 (SEQUENCE ID NO: 20): | 5' AGCTTCTGAGAAATAGCAAA | 3' |

The PCR method in FIG. 13 was used successfully to isolate mRNA encoding E170 from normal epidermal tissue as well as from cells of patients with Epidermolysis bullosa. Primers MR-4 and MR-7 and primers MR-5 and MR-7 (FIGS. 12A–12B; SEQ ID NOS:1–8) and the primers shown in Table 1 (SEQ ID NOS:9–20) have also been used for PCR amplification and isolation of genomic DNA from normal and patient samples. The latter isolated genomic DNA contained both intron and exon sequences. The intron coded for a junctional amino acid sequence between an EGF-like region and a helix region in E170, and the exon was recognized by the presence of non-coding sequence and stop codons.

The subject nucleic acid capable of hybridizing under stringent conditions to a nucleotide sequence in FIGS. 11A–11C (SEQ ID NO:22) and FIGS. 15A–15F (SEQ ID NO:23), (e.g., cDNA clones "Ep-1", 3-1-1, 5-4-2, 3-8-6, 5-4-1, 3-8-2, or 8-6-1), find a variety of in vitro and in vivo uses. For instance, in a preferred embodiment the nucleic acids are useful (as illustrated in Example 15) in expression systems that produce E170 epithelial ligand glycoprotein. The expressed epiligrin glycoproteins, in turn, find a variety of uses: e.g., as adhesive agents for cells; as antigens for production of antibodies; and, as antigens useful in detection of patient autoantibodies such as those described in the serum of patients with acquired subepidermal blistering diseases (Domologe-Hultsch et al., citation #114, incorporated herein by reference).

In another example, the subject nucleotide sequences of the subject nucleic acids are useful for constructing antisense oligonucleotides (as illustrated in Example 15 below). The antisense oligonucleotides have nucleotide sequences capable of hybridizing under stringent conditions with the subject nucleic acids and are complementary with a nucleotide sequence encoding an E170 epithelial ligand glycoprotein. The subject antisense nucleotides have been used successfully for in situ hybridization, as shown in FIG. 21. The subject antisense nucleotides may be further characterized by their ability to transiently inhibit expression of an epiligrin gene in a cell, e.g., by transiently binding and inhibiting translation of an mRNA encoding an epiligrin constituent. Epithelial cells whose expression of epiligrin was transiently blocked by antisense oligonucleotides did not adhere as strongly to HFK-ECM in vitro, and they became more rounded in appearance and form multicellular aggregates in suspension. The cells in the aggregates were observed to be differentiating. Thus, it is considered most likely that one or more regulatory feedback mechanisms exist in epithelial cells through which the binding of epiligrin to its $\alpha_3\beta_1$ receptor transduces a signal through a second messenger pathway that stops cellular proliferation and induces differentiation. It is thought highly likely that abnormalities in the latter signal transduction pathway will exist in certain epithelial cells because of defects in expression levels of epiligrin, or abnormalities in one or more epiligrin glycoproteins or in the epithelial $\alpha_3\beta_1$ integrin. The affected cells may exhibit a phenotype of either uncontrolled growth or premature differentiation. Antisense nucleic acids (e.g., oligonucleotides) may thus be useful for inducing epithelial differentiation in diseased cells that are exhibiting uncontrolled growth resulting from a failure to properly regulate epiligrin expression. In an additional use for the subject antisense nucleic acids, expression of E170 epiligrin glycoprotein was increased in rapidly dividing cells in the migratory tongue of epithelium in wound sites (Example 16). Exuberant (uncontrolled) wound healing is a frequent condition in scarring and keloid formation, and poor quality wound healing is also a problem encountered in large wound sites, e.g., in bum patients and in diabetic and paraplegic patients with dicubitous ulcers. In the latter ulcers a thin tongue of migrating epithelium may form across a wound site, but the cells frequently fail to properly initiate terminal differentiation. Antisense nucleic acids may be useful therapeutically for inducing epithelial differentiation in ulcers, and for restoring normal differentiation to prevent keloid formation and scarring conditions. The subject antisense nucleic acids may be introduced into a host cell by transfection (e.g., of an oligonucleotide) or by transduction of a nucleic acid encoding an antisense nucleic acid (e.g., using retroviral vectors). The subject antisense nucleic acids are all characterized by their ability to hybridize under stringent conditions with a (+) or a (−) strand of a nucleic acid encoding an E170 epithelial ligand glycoprotein, e.g., as represented in FIG. 10F (SEQ ID NO:21), FIGS. 11A–11C (SEQ ID NO:22), and FIG. 15A–15F (SEQ ID NO:23).

Methods are disclosed in Example 16, below, for up-regulating expression of epiligrin through the addition of TGFα or TGFβ to epithelial cells. These methods may be useful for increasing expression of epiligrin in patients suffering diminished synthetic capacity, e.g., in patients with a variety of blistering disorders and idiopathic urticarias (hives). Skilled practitioners will note that an effective dosage of TGFα or TGFβ may be determined in screening assays (i.e., in vitro and in vivo in animal models) where the dosage in contact with the epithelial cells is escalated in a stepwise manner until synthesis of an epiligrin glycoprotein is increased (i.e., as measured by mRNA or protein). Also, a variety of systemic and topical methods for application may be tested by examining the levels of expression of an epiligrin glycoprotein in the treated cells before and after the treatment.

The subject nucleic acids also find use in gene therapy for inducing overexpression of epiligrin in diseased cells, and for gene replacement therapy in genetic disease. For example, junctional epidermolysis bullosa gravis can be a lethal genetic disease of infants that is associated with failure to normally express epiligrin. Gene transfer may be accomplished using vectors (e.g., a retroviral vector) containing a construct that has in serial array: a promoter, a subject nucleic acid that encodes one or more epithelial ligand glycoproteins, e.g., E170, and a polyA tail. In genetic replacement therapy for treating lethal junctional epidermolysis bullosa gravis, constitutive expression of epiligrin in vivo may result in establishment of epithelium-basement membrane integrity in diseased epidermal tissues as well as in the lung, urogenital tract, gastrointestinal tract, and other sites of epiligrin expression (representatively illustrated in the Examples, below).

These and other aspects of the invention are described below:

5.1 Definition of Terms

The following terms used herein are intended to have the meanings set forth below:

"Epithelial ligand glycoprotein" means a constituent glycoprotein of the epithelial ligand complex epiligrin.

"Substantially-pure" means of a purity sufficient that more than 70% of the polypeptides in the preparation can be determined by SDS-PAGE and protein staining to be the composition so specified.

"Covalently linked" means polypeptides chemically bonded to one another, as through for example (but not limited to) disulfide-bonds, thiol-ester bonds, ester bonds, amide bonds, or the like.

"Capable of binding" means physical interaction between two materials, such as between a specific binding partner and a ligand, where the interaction is sufficiently strong to permit measurement of a chemical association (or dissociation) constant (i.e., Ka or Kd).

"Capable of hybridizing under stringent conditions" means annealing of a nucleic acid molecule to at least a region of the disclosed E170 epithelial ligand glycoprotein nucleic acid sequence (whether as cDNA, cRNA, mRNA, or genomic DNA), or to its complementary strand under standard conditions, e.g., high temperature and/or low salt content, which tend to disfavor hybridization of noncomplementary nucleotide sequences. A suitable protocol is described in Maniatis, T., et al. (#118 which is hereby incorporated by reference), at pages 387–389, wherein following the hybridization step filters are washed in 0.1×SSC, 68° C. for 2 hours. Other protocols for achieving stringent hybridization are well-known to those skilled in the art, and can be selected from those presented in Maniatis (#118). Such hybridizing molecules may be related to the disclosed sequence by deletion, point mutation, base substitute, frameshift, alternative ORFs, mRNA splicing or processing, or post-transcriptional modification (e.g., methylation and the like).

"Substratum" means an insoluble material upon which cells may be deposited by gravity.

"Non-adhesive substratum" means a substratum to which fewer than 20% of the cells will bind in 24 hours at 37° C. and from which 80% of the cells can be removed by washing with medium, e.g., such a substratum is provided by microbiological grade polystyrene plastic petri dishes.

"Epithelial cells" means, in this disclosure, the cells originating through mitosis in epithelial tissues which cover the free surfaces of the body and line the body cavities and ducts, as well as cells of epithelial origin such as malignant carcinoma cells. Further examples of epithelial cells as they are commercially available are provided in Table 2, below, as listed in the "Catalogue of Cell Lines and Hybridomas", 6th Edition, 1988, the American Type Culture Collection, Rockville, Md.

"Modulate" means to effect an increase or decrease of a specified parameter to a measurable extent.

"Adhesion assay" means an assay conducted with test cells, such as HT1080 in Example 6 below, to measure adhesion of cells to a protein-coated "non-adhesive" substratum under defined test conditions of tissue culture.

"Differentiation" means a staged process, e.g., in development, through which a cell progressively acquires distinguishably new phenotypic attributes.

"Confluent cell culture" means a culture in which more than 85% of the cells are observed microscopically to be in physical contact with their neighboring cell.

"Resistant to digestion" means that no substantial change in physical properties is observed following incubation of the polypeptide with an enzyme for a substantial period of time.

"Co-migrate" means substantially the same electrophoretic migration when two polypeptides are either run together in the same lane of an SDS-PAGE gel, or when they are run side-by-side in adjacent lanes.

"Molecular size" means the apparent molecular radius of the polypeptide as observed under denaturing conditions in SDS-PAGE, and as recorded in kilodaltons (kDa±) of mass as determined by comparison with other polypeptides of known molecular mass.

TABLE 2

Examples of Commercially-Available Human Epithelial Cells

| Tissue | Name/ATCC No. | Description |
| --- | --- | --- |
| Endometrium | RL95-2/CRL1671 | Adenosquamous carcinoma |
| Skin | WM-115/CRL1675 | epitheloid melanoma |
|  | WS-1/CRL1502 | fetal skin |
| Pancreas | AsPC-1/CRL1682 | adenocarcinoma |
|  | PANC-1/CRL1469 | epitheloid carcinoma |
| Stomach | AGS/CRL1739 | adenocarcinoma |
| Bladder | UM-UC-3/CRL1749 | bladder carcinoma |
|  | HT-1197/CRL1473 | bladder carcinoma |
| Colon | CCD841CoN/CRL1790 | fetal epithelial-like |
|  | NCI-H548/CCL249 | adenocarcinoma |
| Tongue | SCC-9/CRL1629 | squamous cell carcinoma |
| Kidney | ACHN/CRL1611 | adenocarcinoma |
| Cervix | C-41/CRL1595 | carcinoma |
|  | CaSki/CRL1550 | epidermoid carcinoma |
| Ovary | PA-1/CRL1572 | teratocarcinoma |
| Epidermis | A-431/CRL1555 | epidermoid carcinoma |
| Breast | ZR-75-1/CRL1500 | mammary carcinoma |
|  | MCF-7/HTB22 | adenocarcinoma |
| Pharynx | Detroit 562/CCL138 | carcinoma |
| Adrenal cortex | SW-13/CCL105 | adenocarcinoma |
| Lung | WI-38/CCL75 | fetal diploid |

5.2 Keratinocyte Extracellular Matrix and Immunoprecipitation of Epiligrin: The Major Glycoprotein Complex in Adhesive HFK-ECM For this study, the extracellular matrix synthesized and secreted by HFKs shall be referred to as HFK-ECM and that synthesized and secreted by HFFs as HFF-ECM. Endogenous HFK-ECM is that which is intracellular or plasma membrane associated. HFK-ECM secreted into the conditioned culture medium during the time course of an assay, or that which can be purified from culture dishes or glass cover slips (after the removal and/or extraction of the HFKs, as by the three-step extraction procedure detailed below), is referred to as exogenous HFK-ECM.

To identify a physiologically significant ligand for $\alpha_3\beta_1$ and/or $\alpha_6\beta_4$ integrins in epithelial cells, we first examined the composition of the ECM produced by HFK. Radiolabeled HFK-ECM and HFK were prepared by incubating HFK in culture dishes for 15 hours in KGM containing $^{35}$S-methionine, $^3$H-glucosamine, or $^{35}SO_4^{-2}$, and 1 mg/ml HD-BSA (Sigma) as a carrier protein. Radiolabeled HFKs were sequentially extracted in a sequential three-step extraction procedure, as described previously (Wayner and Carter, 1987): (1) with 1% (w/v) Triton X-100 (Sigma; to solubilize membranes and cytoplasmic constituents) and 2 mM N-ethylmaleimide (Sigma, to prevent intramolecular crosslinking); (2) with a solution containing 2 M Urea and 1 M NaCl (to remove nuclear and cytoskeletal components); and (3) with 8 M Urea (to solubilize residual cellular components). All extraction buffers contained 1 mM phenylmethyl sulfonyl fluoride (PMSF; Sigma Chemical Co., St. Louis, Mo.) as a protease inhibitor, and 2 mM N-ethylmaleimide (Sigma) as an inhibitor of intramolecular cross-linking. The constituent radiolabeled glycoproteins were separated by SDS-PAGE (12) and visualized by fluorography. The results of the sequential extraction procedure are presented in FIG. 1 where lanes 1–3 show the glycoproteins extracted in the steps 1, 2, and 3 (above), respectively.

Figure 1E:
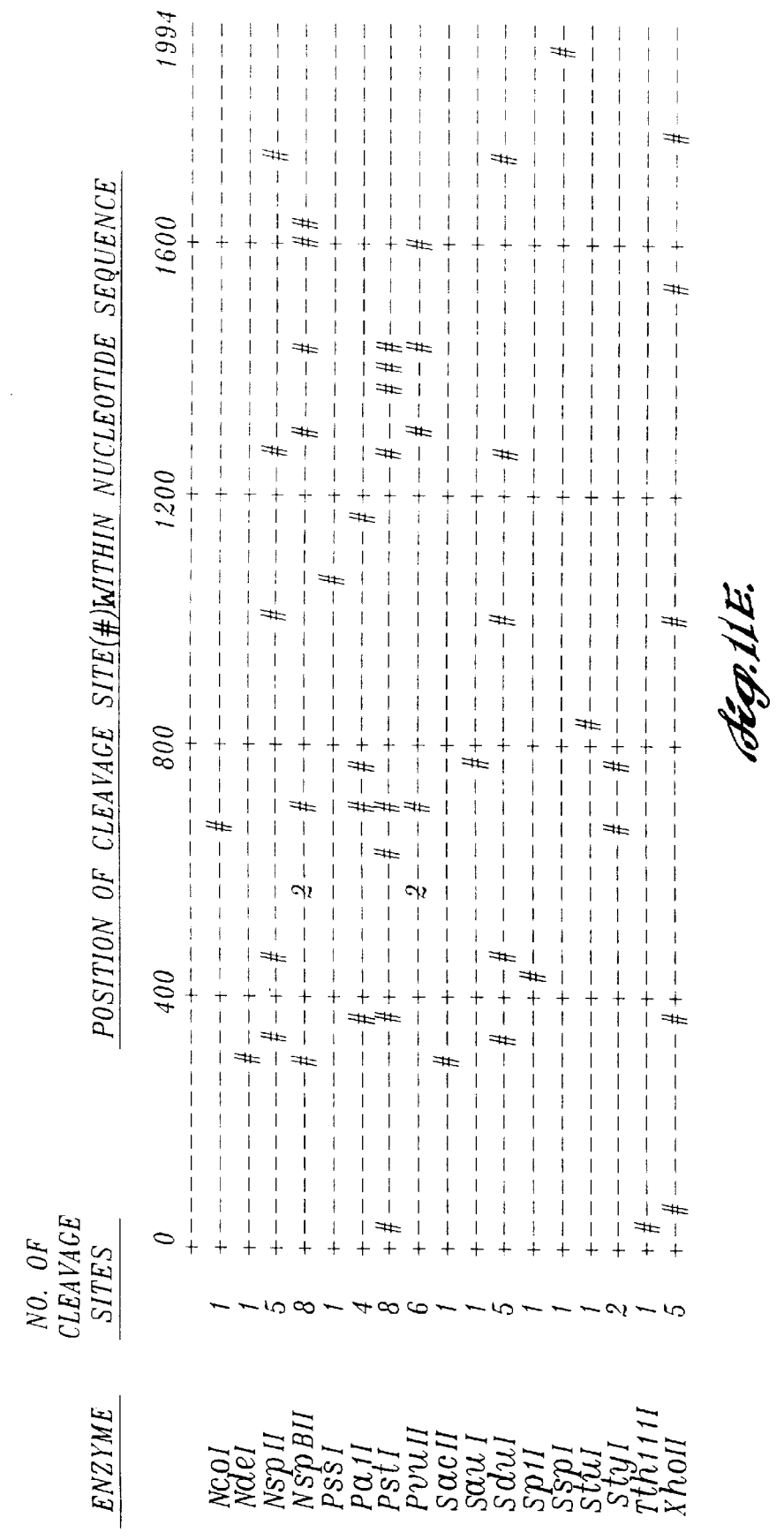
Figure 1:
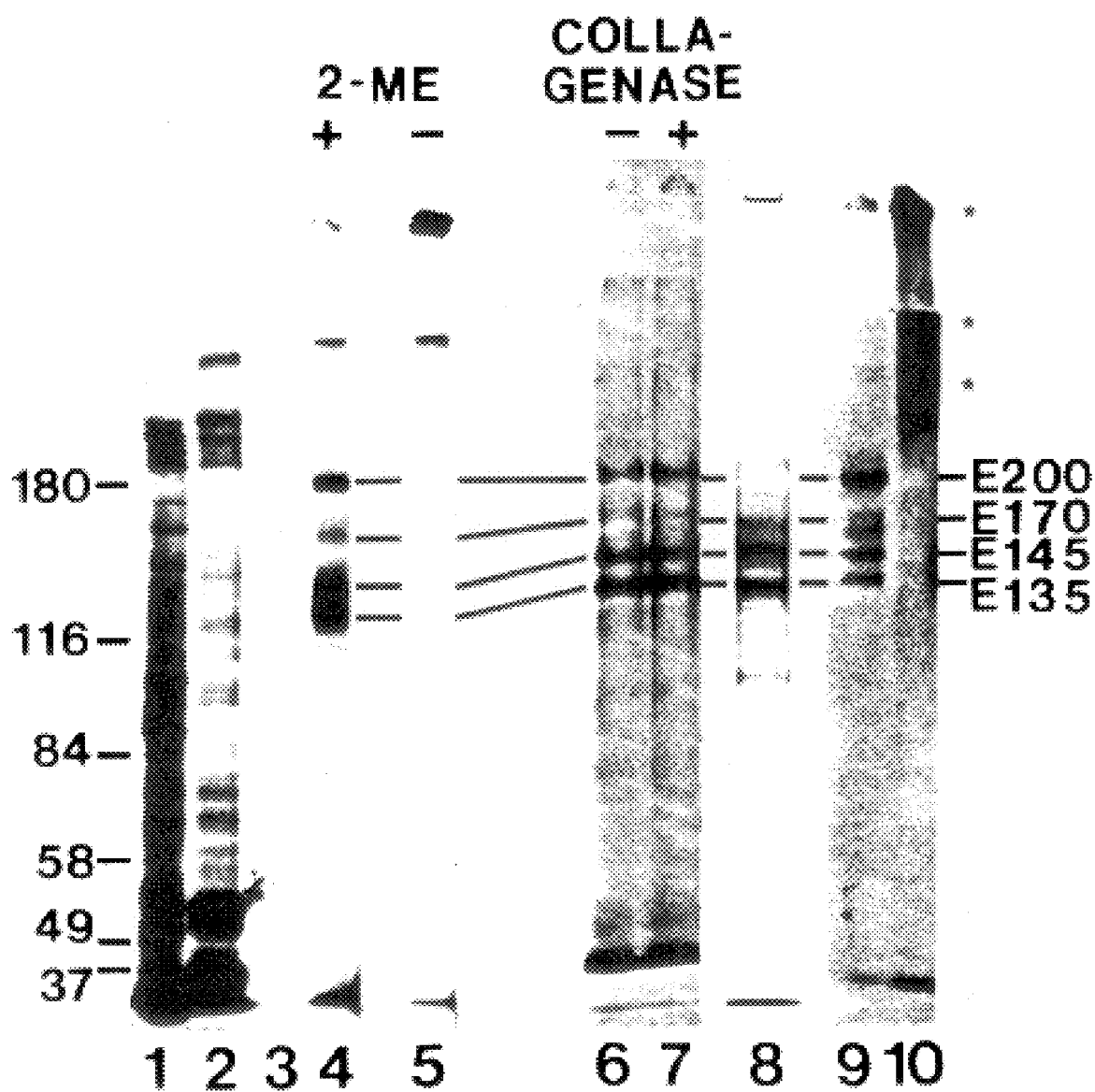
FIG. 1 shows glycoproteins extracted as the epithelial ligand glycoprotein complex (epiligrin) from extracellular matrix.
Figure 3:
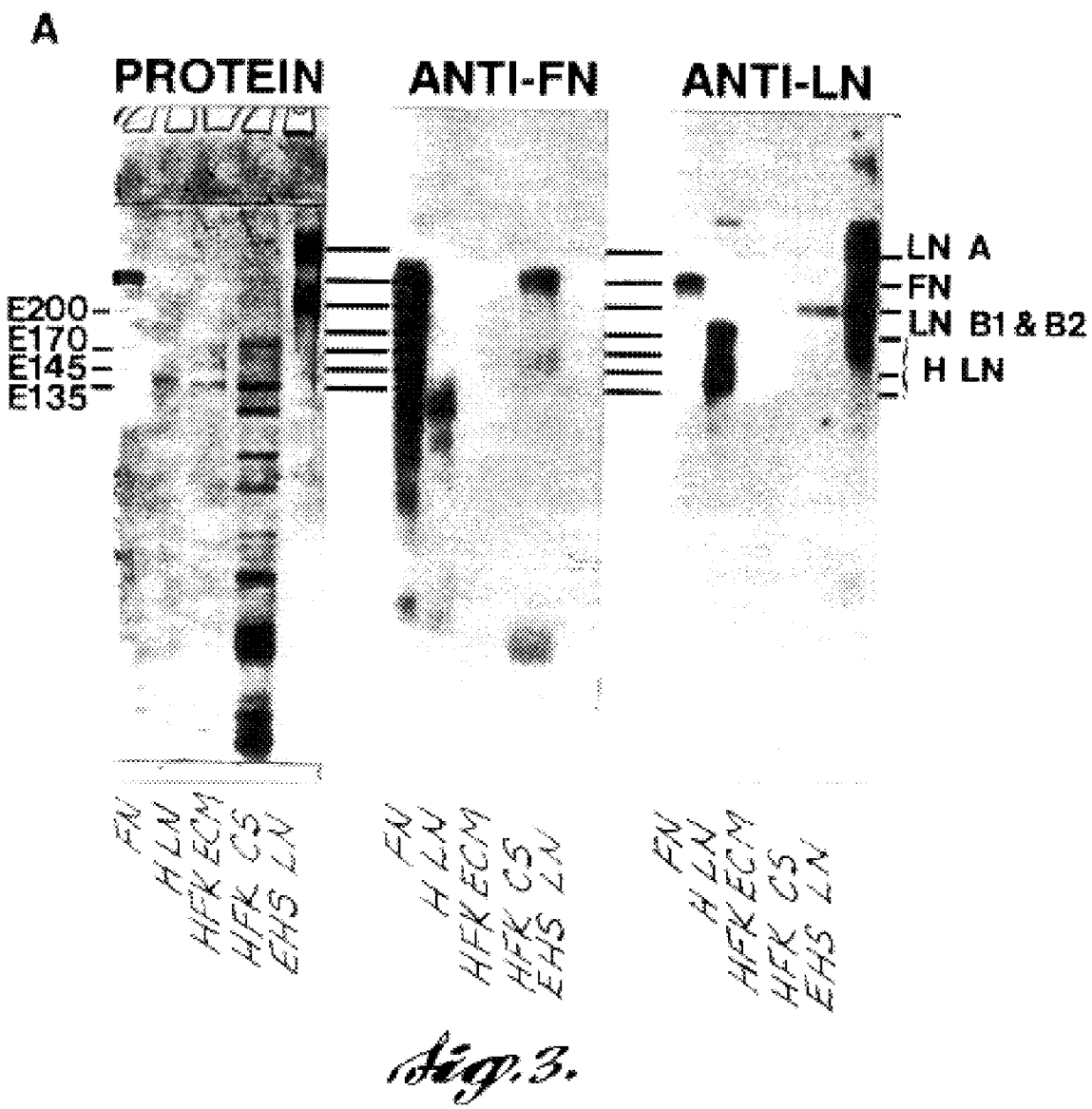
FIG. 3 shows that the purified HFK-ECM does not contain fibronectin or laminin.

To examine the nature of the 8 M urea-insoluble HFK-ECM glycoproteins remaining on culture dishes after the extraction step 3, 0.5% (w/v) SDS was added to the culture dishes, and glycoproteins were physically dissociated by mechanical scraping with a rubber policeman. The glycoproteins obtained in this manner did not enter an 8% SDS-PAGE gel (FIG. 1, lane 5) unless they were reduced on SDS-PAGE under reducing conditions (i.e., with 2-mercaptoethanol; 2ME) and visualized by fluorography. They consisted essentially of at least five major glycoproteins visualized by protein staining with Coomassie brilliant blue (FIG. 1, lane 8) or following biosynthetically radiolabeled with $^{35}$S-methionine (FIG. 1, lane 4), or $^3$H-glucosamine (FIG. 1, lane 9); these glycoproteins having apparent Mr of 200 kDa, 170 kDa, 145 kDa, 135 kDa, and 36 kDa (FIG. 1, lane 9). (Migration of molecular mass standards are indicated in the left margin of FIG. 1 (i.e., 180, 116, 84, 58, 49, and 37 kDa).) The HFK-ECM glycoproteins detected with protein stain showed slightly decreased amounts of the 200 kDa glycoprotein (FIG. 1, lane 8). The five major glycoproteins were designated E200, E170, E145, E135, and E36, based on relative molecular mass under reducing conditions on 8% SDS-PAGE. The E170 band was inconsistently resolved into two bands (FIG. 1, lane 9). Under non-reducing conditions the five glycoproteins did not enter the polyacrylamide gel (FIG. 1, lane 5), indicating that they were subunits of one or more high molecular mass complexes, cross-linked by intermolecular disulfide bonds. This mass (or masses) is known as epiligrin. Although the glycoprotein subunits were not labeled with $^{38}SO_4^{-2}$, three additional sulfate-labeled components, probably glycosaminoglycan or proteoglycan, were also present in the exogenous HFK-ECM (FIG. 1, lane 10, marked with *). In control experiments, metabolic labeling for different times did not detect any precursor product relationship among the five glycoprotein subunits of the complex. However, antigenic similarities suggest that E200 is a precursor to E170. Comparison of the molecular masses of the five glycoprotein subunits in the complex to known basement membrane components failed to detect any obvious relationships. To evaluate further any possible relationship between the exogenous HFK-ECM glycoproteins and the collagens, non-reduced and reduced (2-mercaptoethanol; Sigma) $^{35}$S-methionine biosynthetically radiolabeled HFK-ECM was treated at 37° C. for 18 hours with 100 units/ml collagenase (Advanced Biofactures, Form III) under conditions which degrade collagen standards, as described previously (98). The collagenase-digested radiolabeled HFK-ECM was extracted using the same three-step extraction procedure described above, and the glycoproteins were separated using SDS-PAGE and visualized by fluorography. None of the five major glycoprotein components in HFK-ECM was digested with collagenase either when non-reduced (FIG. 1, lanes 6 and 7) or reduced prior to digestion, indicating that they were not collagens. In addition, the HFK-ECM glycoproteins (FIG. 3, HFK-ECM) did not co-migrate on 8% SDS-PAGE with purified protein standards of EHS sarcoma laminin (FIG. 3, EHS-LN; LN A; LN B1 and B2), fibronectin (FN); when visualized by staining for protein with Coomassie blue (FIG. 3, PROTEIN), entactin, or tenascin, but E170 did co-migrate with pepsinized human placental laminin (FIG. 3, compare HFK-ECM to H LN). In contrast (and as expected), proteins in conditioned medium from HFK cells (HFK CS, FIG. 3) contained a multiplicity of proteins, some of which co-migrated with the protein standards (FIG. 3, HFK CS). To further evaluate any possible relationship between fibronectin (or laminin) and the components in exogenous HFK-ECM, three types of experiments were conducted. First, the glycoproteins in exogenous HFK-ECM were separated on SDS-PAGE, blotted onto nitrocellulose as described previously (98) and tested for their immunoblot reactivity with rabbit antibodies directed toward laminin (Anti-LN, FIG. 3) or fibronectin (Anti-FN; FIG. 3). Anti-FN bound to antigens in HFK-conditioned medium (HFK CS) and in purified fibronectin (FN) but not in human placental laminin (H LN), sarcoma EHS laminin (EHS LN) or HFK-ECM; anti-LN bound to antigens in HFK-CS, H LN, and EHS-LN but not in FN or HFK-ECM (FIG. 3). In summary, immunoblotting of HFK-ECM with antilaminin or anti-fibronectin (FIG. 3, Panel "Anti-LN and Anti-FN") failed to detect any relationship between these known extracellular matrix glycoproteins and the glycoproteins in HFK-ECM. Second, polyvalent antibodies to laminin or fibronectin were also used to prepare an immunoprecipitate of exogenous HFK-ECM. Immunoprecipitation with antibodies against laminin, fibronectin, tenascin, entactin, or bullous pemphigoid antigen (BPA) failed to detect any immunological cross-reaction among those known BM proteins and the five major glycoprotein subunits of the HFK-ECM. Third, HFK-ECM was scraped from the substratum and used to immunize rabbits to induce antiserum. The resultant antisera did not react with laminin or fibronectin, but did react with E170, E145, and E135 in the HFK-ECM.

In order to further characterize the HFK-ECM, we prepared monoclonal antibodies (MAbs) against the HFK-ECM glycoprotein complex using HFKs as an immunogen.

5.3 Binding Partners as Exemplified by Monoclonal Antibody to HFK-ECM

Binding partners as exemplified by MAbs to HFK-ECM were produced by the methods of Oi and Herzenberg (99) and Taggart and Samloff (100) as described (59). Spleen cells from RBF/DN mice immunized with cultured HFKs were fused with NS-1/FOX-NY myeloma cells. Viable heterokaryons were selected in RPMI 1640 medium supplemented with adenine/aminopterine/thymidine.

Figure 2:
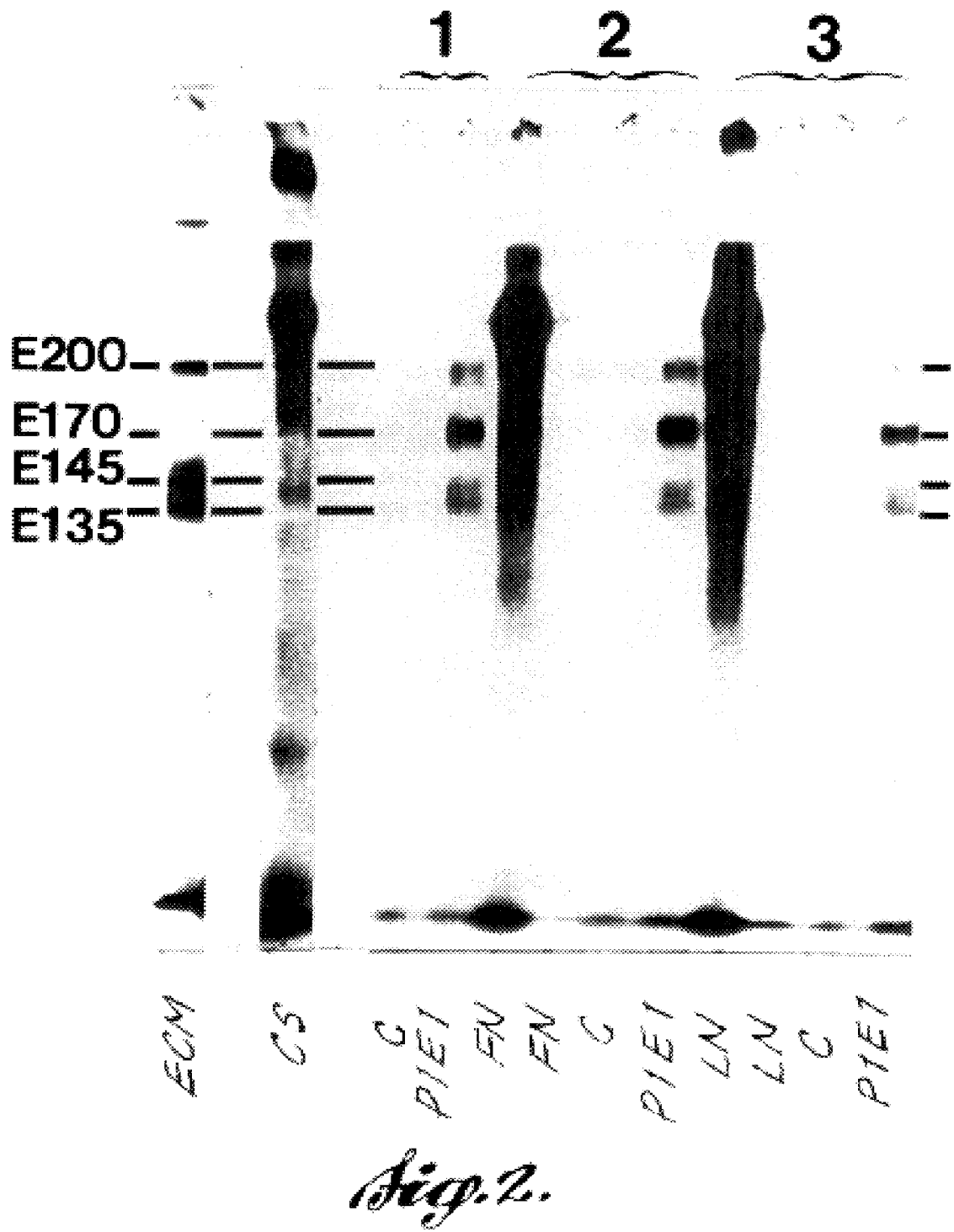
FIG. 2 depicts glycoproteins in the epiligrin complex which are not related to known basement membrane components.

Hybridomas P1E1 (ATCC No. HB10590) and P1H8 (ATCC No. HB10682) producing antibody specifically directed to HFK-ECM were selected using immunofluorescence microscopy and HFK-ECM or HFF-ECM on glass cover slips. We selected MAbs P1E1 and P1H8 that reacted with HFK-ECM but not HFF-ECM produced by the dermal fibroblasts. P1E1 and P1H8 were cloned by limiting dilution. P1E1 and P1H8 (with rabbit anti-mouse IgG) immunoprecipitated five relatively minor disulfide-bonded subunits from the conditioned culture medium of $^{35}$S-methionine-labeled HFKs. The results presented in FIG. 2 show examples of three (1, 2, 3) such immunoprecipitation experiments conducted with P1E1 in which HFK cells were metabolically radiolabeled with $^{35}$S-methionine, as described above, and antigens in the conditioned medium (FIG. 2; CS) and HFK-ECM (FIG. 2; ECM) were immunoprecipitated. The five subunits of the P1E1 antigen(s) co-migrated with the five major glycoprotein subunits of the exogenous HFK-ECM (FIG. 2, compare ECM in the far left lane of the figure with P1E1, experiment 1). The E170 subunit in FIG. 2 in the precipitated P1E1 antigen was increased relative to the other subunits in all three experiments, suggesting that E170 contained the epitope recognized by the P1E1 MAb. In a similar manner, the E36 component of glycoprotein complex was increased in the immunoprecipitate prepared in this manner between radiolabeled HFK-CS and P1H8, suggesting that E36 may contain the antigenic epitope for P1H8. The possibility that the glycoprotein complex recognized by P1E1 may contain antigens previously identified was once more evaluated, this time utilizing immunoprecipitation techniques. Preclearing of HFK conditioned culture medium (FIG. 2; CS) by immunoprecipitation with polyvalent anti-fibronectin (FIG. 2, experiment 2; FN), polyvalent anti-entactin, or mouse monoclonal anti-tenascin prior to precipitation with P1E1 had no effect on subsequent precipitation of P1E1 antigens. However, preclearing (i.e., immunoprecipitating) with polyvalent anti-laminin (FIG. 2; experiment 3, LN) removed E200 and 50% of the other subunits from the P1E1 precipitate. Since none of the glycoproteins (i.e., E200, E170, E145, E135, or E36) reacted with anti-laminin antibodies by Western immunoblotting after SDS-PAGE (FIG. 3), we conclude that: (a) E200 in the complex is not laminin; and (b) glycoprotein complex may be associated with laminin so that it forms a complex that can be precipitated with the anti-laminin antibody. This type of interaction of laminin has not been reported previously, and the composition of the precipitate differs significantly from previously reported complexes of laminin interacting with other glycoproteins.

In summary, the P1E1 and P1H8 antigens correspond in molecular sizes to the glycoproteins in exogenous HFK-ECM, which consists of at least five subunits: E200, E170, E145, E135, and E36, which are visualized on SDS-PAGE after reduction, and that are distinct from any previously identified adhesion ligand(s) present in basement membranes or extracellular matrix. The complex recognized by P1E1 and P1H8 is the major component of exogenous HFK-ECM and also a minor component in HFK-conditioned culture medium. Based on the unique characteristics of this complex, and in order to simplify the following discussion, we shall henceforth refer to the covalently linked glycoprotein complex as "epithelial ligand" or "epiligrin."

5.4 Epiligrin Distribution in Motile and Non-Motile HFKs

The organization of epiligrin deposited in HFK-ECM was examined by immunofluorescence microscopy, using MAb P1E1 and P1H8 and antibodies directed toward other extracellular matrix adhesive ligands. It was found that P1H8 stained only cells which were permeabilized to allow staining of cytoplasmic proteins, indicating that the P1H8 antigen was a cytoplasmic constituent of cells expressing $\alpha_3\beta_1$ integrin. Subsequent studies, detailed below, utilized only the P1E1 MAb.

HFKs were grown for 24 hours on glass cover slips coated with either fibronectin (FIGS. 4A–4B) or BSA (FIGS. 4C–4K), as described above (see "Cellular Adhesion to Extracellular Matrix Adhesive Ligand-Coated Substrates"). Glass cover slips and cells were then incubated with mouse or rat MAbs or rabbit polyclonal primary antibodies diluted in 1% heat HD-BSA overnight as previously described (21). The cover slips were washed with PBS; incubated with dilutions of affinity-purified, species-specific, FITC-conjugated goat anti-mouse/rat IgG or rhodamine-conjugated goat anti-rabbit IgG secondary antibodies (respectively) for 1 hour, washed with PBS, and fixed with 2% formaldehyde prior to immunofluorescence microscopy. The organization of epiligrin was dependent on the ligand to which the HFKs were attached. When HFKs attached to fibronectin (FIG. 4A), collagen, or laminin, the cells migrated over the ligand surface leaving trails of epiligrin.

Figure 4A:
FIGS. 4A–4K illustrate the SACs "ring structures" in which epiligrin is deposited in ECM.
Figure 4B:
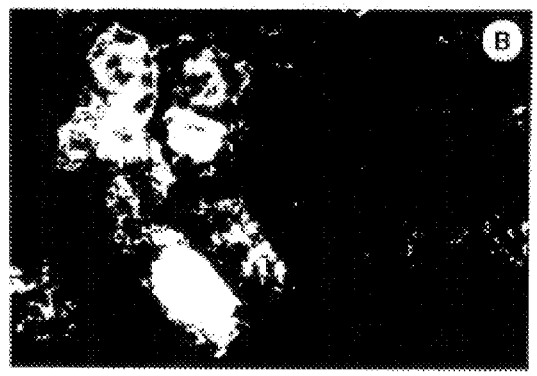
Figure 4C:
Figure 4D:
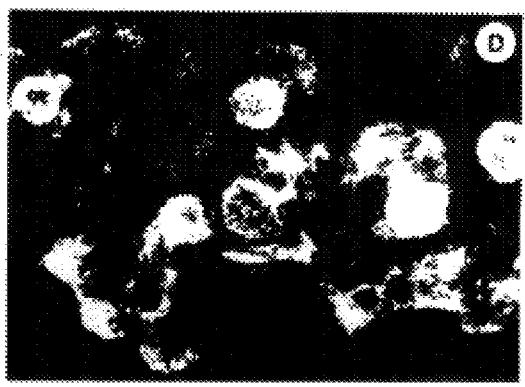
Figure 4E:
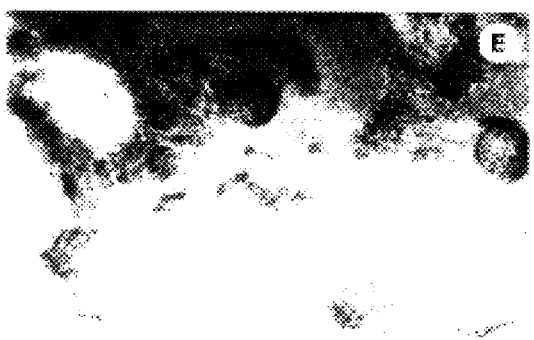
Figure 4F:
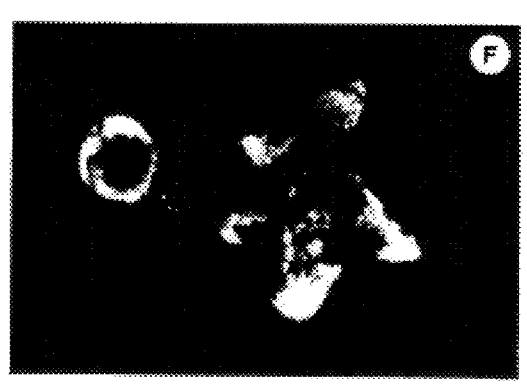
Figure 4G:
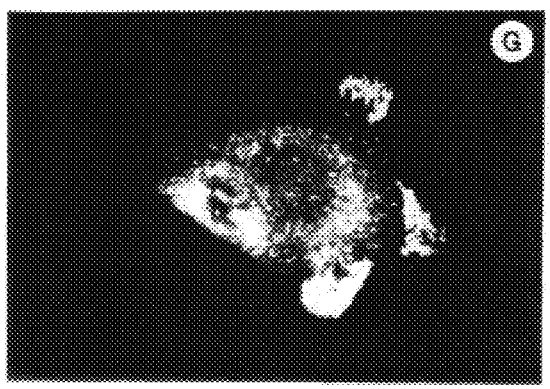
Figure 4H:
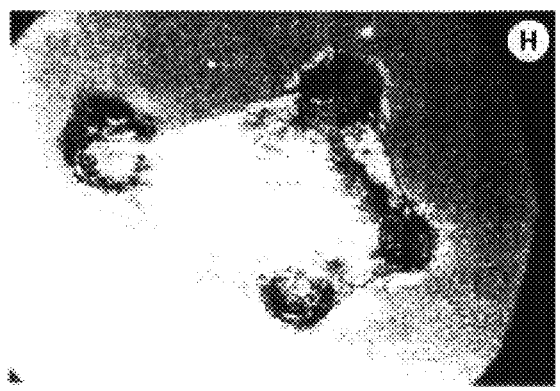
Figure 4I:
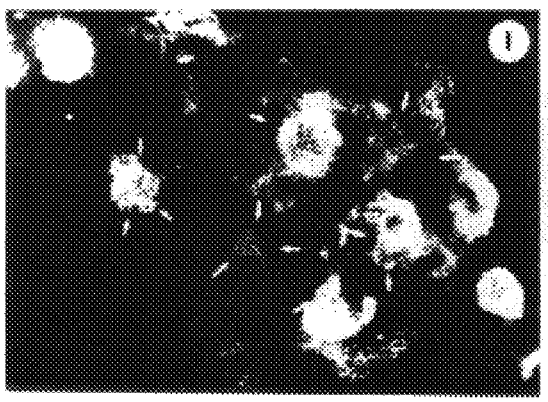
Figure 4J:
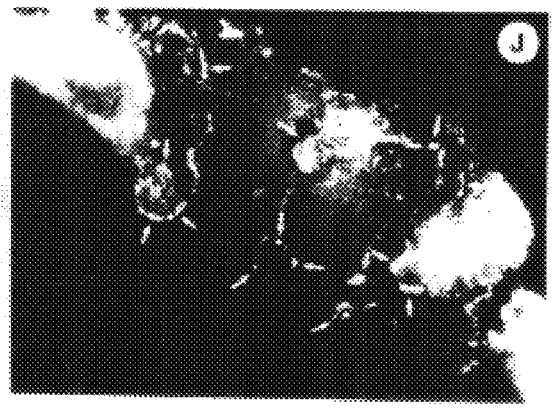
Figure 4K:

To investigate whether the $\alpha_3$- and $\alpha_6$-containing integrins (i.e., $\alpha_3\beta_1$ and $\alpha_6\beta_4$) were associated with epiligrin on the cell surface, tests were conducted simultaneously to visualize the integrin and its putative ligand on HFKs using a double immunofluorescence technique. Epiligrin (P1E1, FIGS. 4A, 4C, 4F, and 4I) was localized relative to $\alpha_6$ (FIGS. 4B and 4D; GoH3), BPA (FIG. 4G) and $\alpha_3\beta_1$, (FIG. 4J; P1F2). SACs and FAs were identified in each field by interference reflection microscopy (FIGS. 4E, 4H, and 4K). Arrows in panels I, J, K identify $\alpha_3\beta_1$ in FAs in relation to epithelial ligand in SACs. HFKs were incubated with: (1) mouse MAb anti-$\alpha_6$ (GoH3); followed by (2) incubation with rhodamine-conjugated goat-antimouse IgG and IgM; after which the cells were fixed and reacted with (3) biotinylated with mouse P1E1 MAb; followed by (4) fluorescein Avidin. In migrating HFK cells, $\alpha_6\beta_4$ was expressed on the apical surface of the cells and at the trailing edge. Small quantities of $\alpha_6\beta_4$ co-distributed with the epiligrin antigen in the trails of these cells (FIG. 4B).

As described (20), when HFKs are grown on BSA-coated surfaces, the cells migrate less and form hemidesmosome-like stable anchoring contacts (SACs) on their basal surface. In the present study, by immunofluorescence microscopy, all the SACs on the basal surface of the stationary HFK cells contained $\alpha_6\beta_4$ and most contained BPA. As seen in FIG. 4C, HFKs grown on BSA deposited epiligrin antigen on the substrata in "ring-like structures" characteristic of SACs. The distribution of epiligrin antigen (P1E1; FIGS. 4A, 4C, and 4F) in relation to $\alpha_6$ (GoH3; FIGS. 4B and 4D), and BPA (FIG. 4G) was most strikingly similar in the "ring structures." To further distinguish SACs from focal adhesions, interference reflection microscopy (IRM) was performed basically as described (Izzard and Lochner, 1976) and was used to identify focal adhesions (FAs) in the same field as the two color immunofluorescence which identified the SACs. FAs were also localized by the antibody exclusion technique (101). Epiligrin (identified by P1E1) in $\alpha_6\beta_4$/BPA-SACs corresponded to contact sites with the adhesion surface as determined by interference reflection microscopy (FIGS. 4E and 4H). The co-localization and similar stabilities indicated that the deposits of epiligrin were at adhesion sites linked to $\alpha_6\beta_4$/BPA-SACs.

Figure 5A:
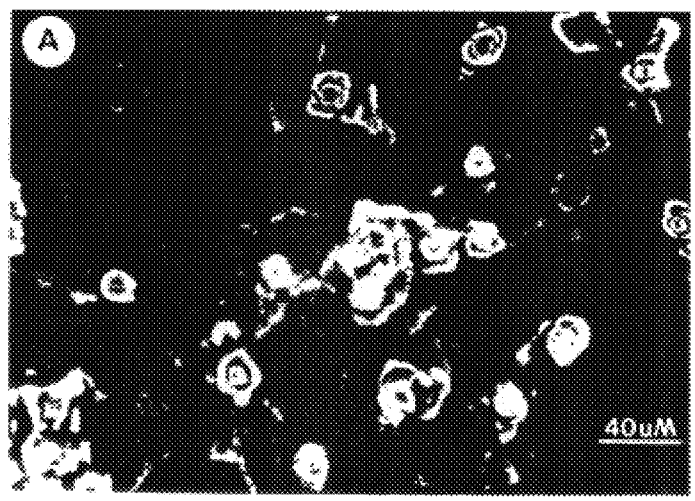
FIGS. 5A–5F depict the co-localization of $\alpha_6\beta_4$ (GoH3, FIG. 5B), he subject epithelial ligand integrins (P1E1, FIGS. 5A, 5C and 5E), BPA FIG. 5D), and $\alpha_3\beta_1$ (P1 F2, FIG. 5F) in the SACs contained in the purified FK-ECM.
Figure 5B:
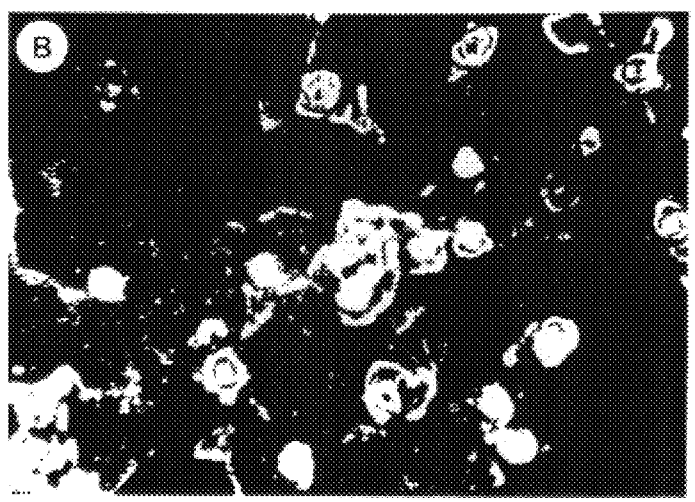
Figure 5C:
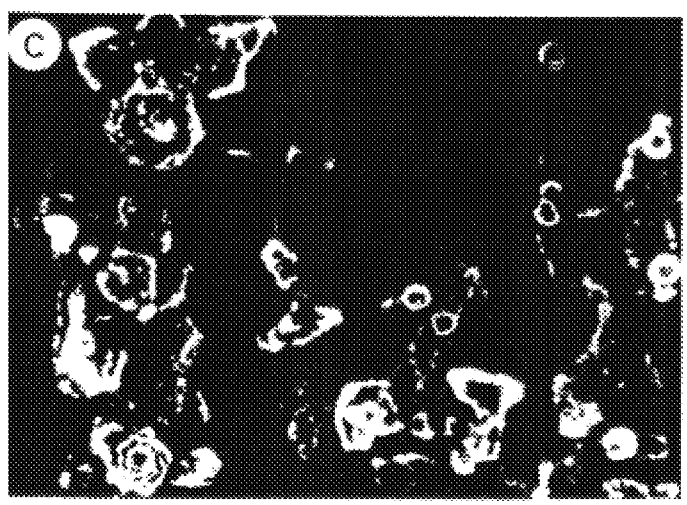

As an additional test for the localization of epiligrin in SACs, since we had previously observed that $\alpha_6\beta_4$ and BPA in SACs are extraordinarily stable and are resistant to sequential extraction with 1% Triton X-100 detergent and 2M urea/1 M NaCl, while the $\beta_1$-containing integrins in focal adhesions are soluble under these extraction conditions (20), we therefore next examined the distribution of epiligrin, $\alpha_6\beta_4$, BPA, and $\alpha_3\beta_1$ in HFK SACs extracted in this manner. HFKs were grown for 24 hours on surfaces coated with BSA, then extracted with 1% Triton X-100 detergent followed by 2 M urea containing 1 M NaCl. The adherent cell residue containing SACs was stained with anti-epiligrin (P1E1, FIGS. 5A, 5C, and 5E), anti-$\alpha_6(\beta_4)$ (GoH3, FIG. 5B), anti-BPA (FIG. 5D), and anti-$\alpha_3$ $\beta_1$, (FIG. 5F; P1F2). Consistently, we observed that epiligrin antigen was present in sequentially extracted HFK SACs (P1E1; FIGS. 5A, 5C, and 5E). In these studies $\alpha_6$, $\alpha_3$, $\beta_1$, epiligrin, or BPA antigen was visualized using a double immunofluorescence technique. Epiligrin co-distributed with the $\alpha_6$ (GoH3, FIG. 5B), and BPA (FIG. 5D) in the extracted HFK-ECM. The co-distribution of epiligrin with $\alpha_6\beta_4$ and BPA in both non-extracted and sequentially extracted HFKs (Triton X-100, 2 M urea/1 M NaCl, above) indicated a stable linkage between the cytoplasmic intermediate filament BPA, the intrinsic membrane $\alpha_6\beta_4$ integrin and the extracellular epiligrin glycoprotein complex ligand, as major constituents of hemidesmosome-like SACs.

5.5 The Epithelial Ligand Complex Epiligrin is a Ligand for a $\alpha_3\beta_1$-FAs We have previously reported that $\alpha_3\beta_1$ in HFK-ECM is localized into FAs in proximity to, but excluded from, $\alpha_6\beta_4$/BPA-SACs (20, 21). HFKs that deposited epithelial ligand in SAC, usually localized $\alpha_3\beta_1$ to FAs at the periphery of SACs as detected by interference reflection microscopy (FIGS. 4I–4K). Epiligrin was not detectable by immunofluorescence in the $\alpha_3\beta_1$-FAs probably due to physical exclusion of anti-$\alpha_3\beta_1$ antibodies from the adhesion sites (20, 21, 101). In contrast to the results obtained above with extraction of $\alpha_6\beta_4$/BPA/epiligrin in SACs, the $\alpha_3\beta_1$ integrin in FAs was readily solubilized with 1% Triton X-100 detergent (FIGS. 5E–5F), further distinguishing the organization and stability of FAs from SACs (20). We consistently observed $\alpha_3\beta_1$ integrins in FAs encircling the $\alpha_6\beta_4$ integrins in the SACs suggesting to us a functional relationship and/or common ligand for both integrins in the SAC and FA adhesion structures.

To further evaluate the role of $\alpha_3\beta_1$ in adhesion to epiligrin in isolation from the $\alpha_6\beta_4$ integrin, we first sought to identify cells by immunofluorescence microscopy that did not express $\alpha_6\beta_4$ or epiligrin antigen, but did express $\alpha_3\beta_1$. Nine different cell populations were examined, including: HFFs; HT1080 fibrosarcoma; Tera-2 teratocarcinoma; T-47D mammary carcinoma cells; Ovcar-4 ovarian carcinoma; and FEPE1 L-8, FE-A, T-47D and FE-H18L, four HSK cell lines resulting from papillomavirus transformation. Examination of the nine cell lines and primary HFKs (for comparison) by immunofluorescence microscopy with P1E1 identified only one—the primary HFKs, that produced significant quantities of epiligrin antigen (thus, further justifying our initial belief that HFK may produce an ECM that is unique from other ECMs). In contrast to primary HFKs, human foreskin fibroblasts (HFFs), HT-1080 fibrosarcoma, Tera-2 teratocarcinoma, and T-47D mammary tumor carcinoma cells, while positive for $\alpha_3\beta_1$, were all negative for expression of epiligrin. Ovcar-4, an ovarian carcinoma cell line, and FEPE1L-8, FE-A, and FE-H18L, the human papilloma virus-transformed-HFKs (94, 95), expressed epithelial ligand but at low levels relative to HFKs. Expression of $\alpha_6\beta_4$ was also investigated with immunofluorescence microscopy. of the nine cell lines and primary HFKs cells, only the HFKs, T-47D, FEPE1L8, FE-A, and FE-H18L cells expressed $\alpha_6\beta_4$. Thus, HFF and HT1080 fibrosarcoma cells expressed $\alpha_3\beta_1$, but not epithelial ligand or $\alpha_6\beta_4$ and provided us a model system to study the interactions of $\alpha_3\beta_1$ with the epithelial ligand glycoprotein complex.

Figure 6A:
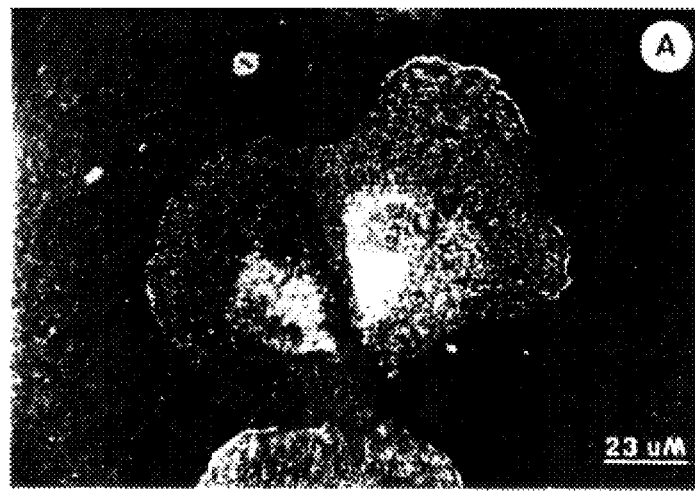
Figure 6B:
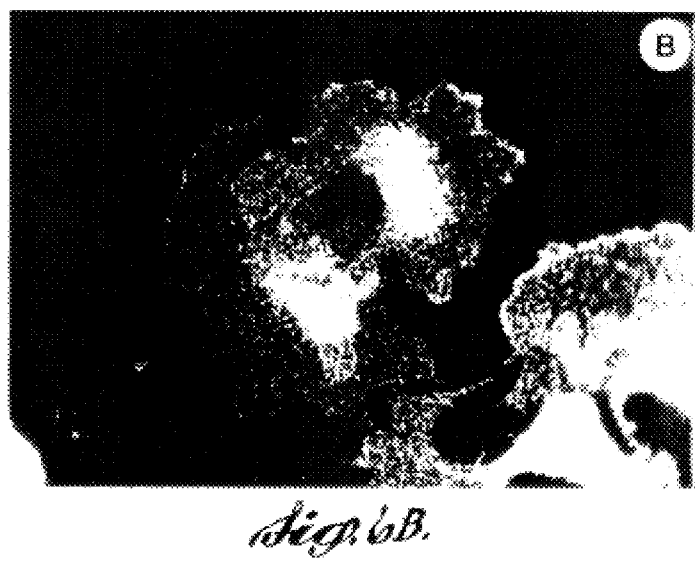
Figure 6C:
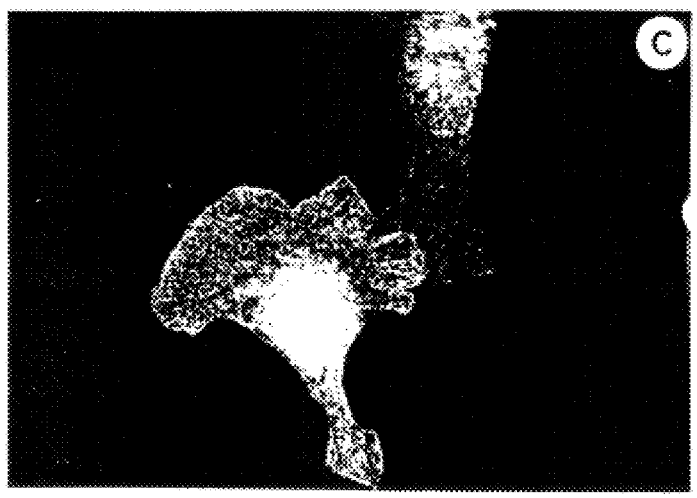
Figure 6D:
Figure 6E:
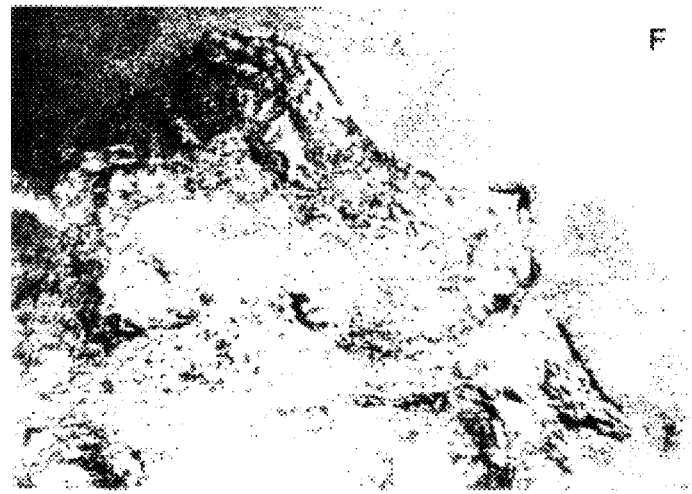
Figure 6F:
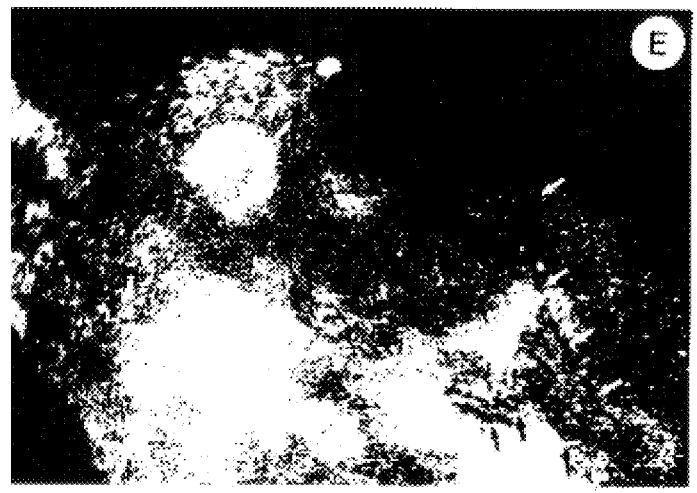

We previously observed that HFFs localized the $\alpha_5\beta_1$ and $\alpha_2\beta_1$ integrins in focal adhesions when the cells were attached to fibronectin- and collagen-coated surfaces respectively (21), and this property was considered to be associated with ligand-induced receptor redistribution on the cell surface. The $\alpha_3\beta_1$ integrin was not previously examined during the interaction of these cells with fibronectin or collagen. To study $\alpha_3\beta_1$, integrin redistribution, HFFs were attached to surfaces coated with fibronectin (FIG. 6A), type I collagen (FIG. 6B), laminin (FIG. 6C), or HFK-ECM (FIGS. 6D–6F) for 1 hour. The fixed and permeabilized cells were stained with anti-$\alpha_3\beta_1$ (P1F2, FIGS. 6A–6D). FIGS. 6D–6F are all the same field. The field in FIG. 6E was stained for epiligrin (P1E1), and FAs were detected by interference reflection microscopy as shown in FIG. 6D. Arrows in FIGS. 6D–6F indicate localization of $\alpha_3\beta_1$ in FAs that contact the adhesion surface and exclude anti-epiligrin antibody. When HFFs attached to fibronectin or collagen, they distributed $\alpha_3\beta_1$, over the entire cell surface with no localization of $\alpha_3\beta_1$ in FAs (FIGS. 6A and 6B). When attached to surfaces coated with laminin, the laminin induced thin FAs that were weakly positive for $\alpha_3\beta_1$ (FIG. 6C). Thus, neither fibronectin, collagen, nor laminin appears to constitute a major ligand capable of redistributing the $\alpha_3\beta_1$ integrin on the surface of human foreskin fibroblasts in vitro. In contrast, HFFs that attached to HFK-ECM for only 1 hour localized $\alpha_3\beta_1$ into FAs as determined by interference reflection microscopy and exclusion of the P1E1 antibody (FIGS. 6D–6F). The $\alpha_3\beta_1$ co-distributed with epiligrin in both FAs and the ring structures characteristic of SACs. These results indicated that epiligrin, as the major component of HFK-ECM, controlled the formation of $\alpha_3\beta_1$-FAs better than any previously identified ECM ligand.

5.6 Immunopurification of Epiligrin

Epiligrin was immunopurified from conditioned culture medium. This was accomplished in a stepwise fashion, first, by affinity-purification of MAb P1E1 from hybridoma culture medium on Protein G-Sepharose (Pharmacia, Piscataway, N.J.). Second, the purified monoclonal antibody was covalently coupled to Affigel-10 (Bio-Rad Laboratories, Richmond, Calif.; forming the P1E1-affinity-column). Third, conditioned culture medium from confluent cultures of HFKs was passed over a gelatin-Sepharose column (Pharmacia) to remove fibronectin. Fourth, the flow-through from the gelatin sepharose column was then passed over the P1E1-affinity-column. Unbound protein was removed by washing with PBS; and then the bound epithelial ligand antigen was eluted with 3 M KSCN and dialyzed against PBS. The epiligrin purified on the P1E1 affinity-column contained the complex of E200, E170, E145, and E135 covalently linked subunits as well as the E36 and E100, although lower levels of E200 were present than in HFK-ECM.

5.7 Specificity of an Integrin $\alpha_3\beta_1$-Mediated Cellular Adherence to Epiligrin Soluble, purified epiligrin glycoprotein complex was coated on non-adhesive polystyrene plastic surfaces to examine its ability to promote adhesion of HT1080 cells through the $\alpha_3\beta_1$ receptor. Inhibition of cell adhesion to various ligands was performed as previously described (20, 21, 59). The specificity of the adhesion for $\alpha_3\beta_1$ was evaluated by testing for inhibition of adhesion with anti-$\alpha_3\beta_1$ MAb (P1B5). For comparison, epiligrin (EN; 1 μg/ml), human plasma fibronectin (FN) 10 μg/ml), type I collagen (CN; 10 μg/ml), EHS laminin (LN; 10 μg/ml), or BSA (5 mg/ml) were coated on non-adhesive plastic surfaces (2 hours), washed, and blocked with heat denatured BSA for 1 hour. The cells were labeled with $Na_2\,^{51}CrO_2$ (New England Nuclear; 50 μCi/ml for 2–4 hours) and were allowed to adhere (in the presence of the following inhibitory antibodies) to the protein-coated surfaces in the presence of the hybridoma supernatants for 1.5 hours. The inhibitory antibodies indicated in FIG. 7 include: SP2 as a control, non-inhibitory antibody. P4C10, inhibits cell adhesion via all $\beta_1$-containing integrins. GoH3, anti-$\alpha_6(\beta_1)$ laminin receptor in HT1080. P1H5, anti-$\alpha_2\beta_1$ collagen receptor. P1D6, anti-$\alpha_5\beta_1$ fibronectin receptor. P1B5, anti-$\alpha_3\beta_1$ epiligrin receptor. The bars in FIG. 7 represent the mean values of three assays. Unattached cells were removed by washing and the adherent cells dissolved in SDS/NaOH and quantitated in a gamma counter. The results presented in FIG. 7 show that purified epiligrin mediated adhesion of HT1080 cells to the previously non-adhesive plastic surface, and the cellular adhesion to epiligrin-coated plastic was blocked in a specific manner by the P1B5 MAb to the $\alpha_3\beta_1$ integrin. More specifically, the data presented in FIG. 7 show that HT1080 cells attached to epiligrin-, fibronectin-, and collagen-coated and non-adhesive plastic surfaces and laminin (FIG. 7). Antibodies against the $\alpha_5\beta_1$, (P1D6) fibronectin receptor, the $\alpha_2\beta_1$ (P1H5) collagen receptor, and the $\alpha_6\beta_1$, (GoH3) laminin receptor (64, 102) specifically inhibited HT1D80 adhesion to their corresponding ligands but had no inhibitory effect on adhesion to epiligrin. Anti-$\beta_1$ MAb (P4C10) inhibited cell adhesion to all ligands involving $\beta_1$-containing integrins.

The testing was next expanded to include cells other than HT1080. P1B5 (anti-$\alpha_3\beta_1$) was found to inhibit the adhesion of HFK and FE-H18L cells to epiligrin. These results established $\alpha_3\beta_1$, as a primary receptor for cell adhesion to epiligrin. Further, the MAb inhibition results clearly distinguish cellular adhesion to laminin via $\alpha_6\beta_1$ from epiligrin via a $\alpha_3\beta_1$. These findings will establish a test cell assay system useful for identifying epiligrin produced by other epithelial cells.

5.8 Epiligrin Localization in Normal Epithelial Basement Membrane

We compared the distributions of epiligrin to laminin, $\alpha_3\beta_1$, and $\beta_1$ by immunoperoxidase staining of cryostat sections of normal skin, tonsil (below), and lung (below) (FIGS. 8A–8P). The results show cryostat sections of the SKIN (human neonatal foreskin) (FIGS. 8A–8D) and SPLIT SKIN (skin from a patient with junctional epidermolyses bullosis that spontaneously separates between the BM and basal cells) (FIGS. 8E–8H). TONSIL (FIGS. 8I–8L) and LUNG (FIGS. 8M–8P) were stained with the indicated antibodies (ANTI-EPILIGRIN LIGAND, etc.). (The magnification in FIGS. 8A–8P prior to photographic enlargement was 160×.) (Arrows and letter abbreviations are used in FIGS. 8A–8P to identify the following structures: BM=epidermal basement membrane; S=epithelial sweat glands in dermis; D=duct of sweat gland in dermis; V=venule; BC=basal cells of epidermis; C=BM of capsular epithelium; LF=lymphoid follicles (germinal centers); E=BM of ciliated epithelium in bronchus; M=bundles of smooth muscle cells adjacent bronchus; and SMG=submucosal glands.)

The distribution of receptors and ligands in tissue was determined by immunoperoxidase microscopy of the cryostat sections. Cryostat sections (μ) were prepared from human tissues embedded in OCT medium after snap freezing in isopentant/liquid nitrogen. All sections were fixed with 2% formaldehyde in 0.1 M NaCacodylate pH 7.2 in 0.1 M sucrose for 20 minutes and then permeabilized with 1% Triton X-100 for 15 minutes. The sections were incubated with primary antibodies and peroxidase-conjugated secondary antibodies.

In skin (FIGS. 8A–8D), antibodies against epiligrin, laminin, $\alpha_3\beta_1$ and $\beta_4$ localized to the BM region separating the epidermis and dermis and to epithelial sweat glands (S) and ducts (D) in the dermis. Epiligrin antigen was not present in laminin-positive endothelial BMs in venules (V) in the dermis.

5.9 Epiligrin Antigen Localization in Diseased Epithelial Basement Membrane

Split skin from a patient with junctional epidermolyses bullosa (JEB) was also analyzed by immunoperoxidase staining in FIGS. 8E–8H for epiligrin antigen, laminin, $\alpha_3\beta_1$, and $\beta_4$. JEB is an inherited disorder that results in disruption of basal cell attachment to the BM with a corresponding decrease in hemidesmosomes (103, 104). In cryostat sections of skin from a patient with JEB (FIGS. 8E–8H), the basal epidermis spontaneously separated from the BM. Epiligrin antigen and laminin both localized to the BM floor of the split skin indicating that epiligrin was a component of the BM. In contrast, $\alpha_3\beta_1$ and $\beta_4$ localized to the roof of the split in the basal cells (BC).

5.10 Epiligrin Localization in Lymphoid Tissues

In tonsil (FIGS. 8I–8L), P1E1 (ANTI-EPILIGRIN) localized to lymphoid follicles (LF), or germinal centers as a fine filamentous network, possibly in reticular fibers, and the basement membrane of the lymph node capsular epithelium (C). In contrast, laminin (ANTI-LAMININ (R5922), FIG. 8I) was weakly expressed in the lymphoid follicles and capsular BM and strongly expressed in the venous sinuses (V). Both $\alpha_3\beta_1$, and $\beta_4$ were expressed in basal cells associated with the capsular BM. However, neither $\alpha_3\beta_1$ nor $\beta_4$ was detectable as major components of lymphoid follicles.

5.11 Epiligrin Localization in Lung Tissues

In lung (FIGS. 8M–8P), epiligrin and laminin localized to the BM of ciliated epithelium (E) and submucosal glands (SMG) in the bronchus. $\alpha_3\beta_1$ was adjacent to epiligrin antigen in the basal plasma membranes of the ciliated epithelial cells. In contrast, $\beta_4$ was only sporadically expressed along the basal plasma membrane (E). Both laminin and $\alpha_3\beta_1$ were strongly expressed in bundles of smooth muscle cells (M) and veins (V) while epiligrin was absent.

5.12 Epiligrin Localization in Other Tissues and Organs

Epiligrin was absent from BM of heart muscle, mesothelium, brain, and glomerulus and tubules in kidney, while laminin was expressed. Epiligrin was present in the BM separating the intestinal epithelium from the lamina propria. These results identified epiligrin as a component of epithelial BMs particularly in organs of endodermal and ectodermal (but not neural) origin. Epiligrin was not present in muscle, neural, and endothelial BMs.

5.13 Epiligrin, $\alpha_3\beta_1$ and $\beta_4$ Localize at the Cell-Basement Membrane Junction The ultrastructural localization of epiligrin, $\alpha_3\beta_1$, and $\beta_4$ was determined by immunoelectron microscopy of human skin. Electron micrographs are presented in FIGS. 9A–9F of immunoperoxidase-stained human neonatal foreskin which was stained with the following antibodies and achieving the following results: (FIG. 9A) control staining with SP2 culture (supernatant is negative; hemidesmosomes and desmosomes are detectable), (FIG. 9B) P1F2 ($\alpha_3\beta_1$ is detectable on the apical, lateral, and basal membranes; staining was also observed in desmosomes); (FIG. 9C) and (FIG. 9D) E31 (the $\beta_4$ subunit is localized to the basal surface and increased staining localized to hemidesmosomes at the origin of keratin filaments); and (FIG. 9E) and (FIG. 9F) P1E1 (epiligrin is present in the lamina lucida along the entire basal membrane but particularly adjacent hemidesmosomes). (Abbreviations used in FIGS. 9A–9F include: BM=basement membrane; IC=intercellular contacts; BS=basal membrane surface; KF=intermediate filaments; HD=hemidesmosomes; D=desmosomes; and C=collagen filaments.)

Figure 9A:
Figure 9B:
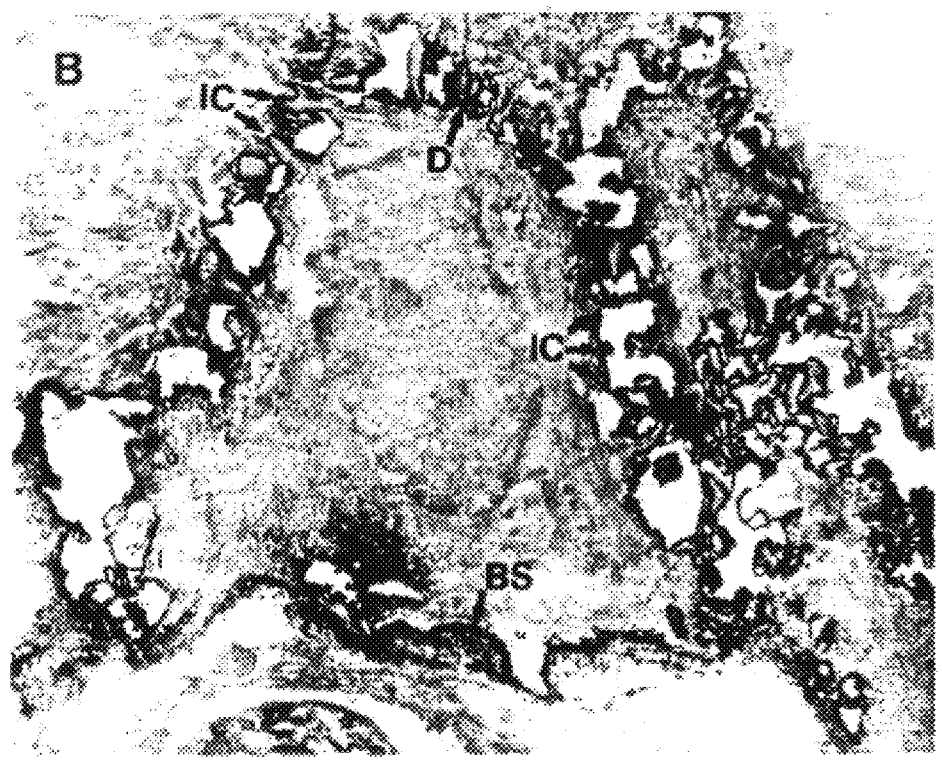
Figure 9C:
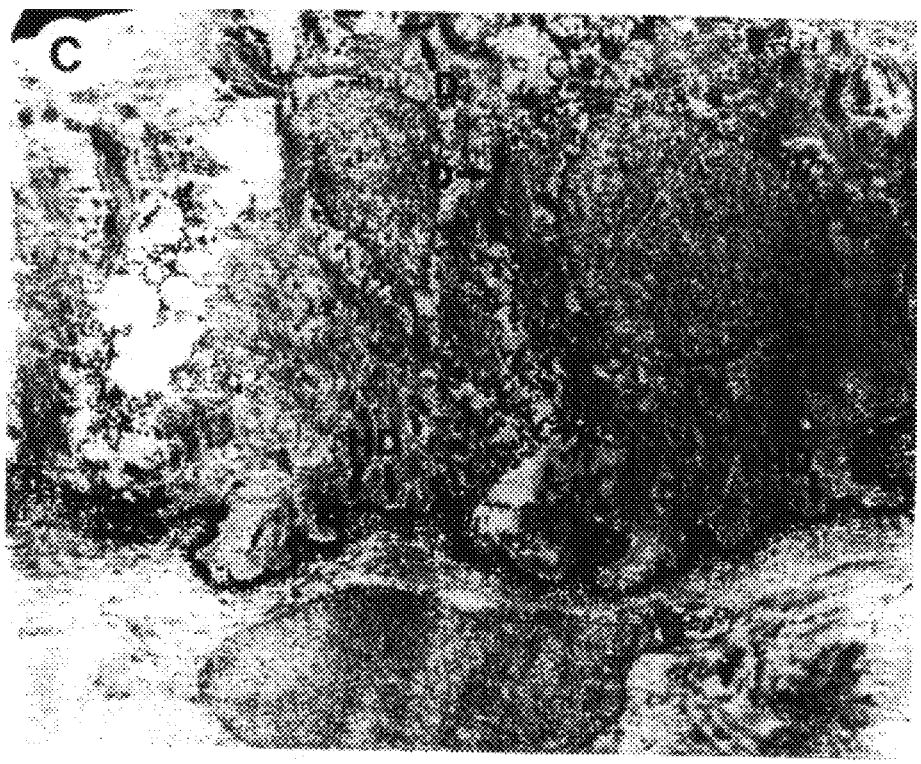
Figure 9D:
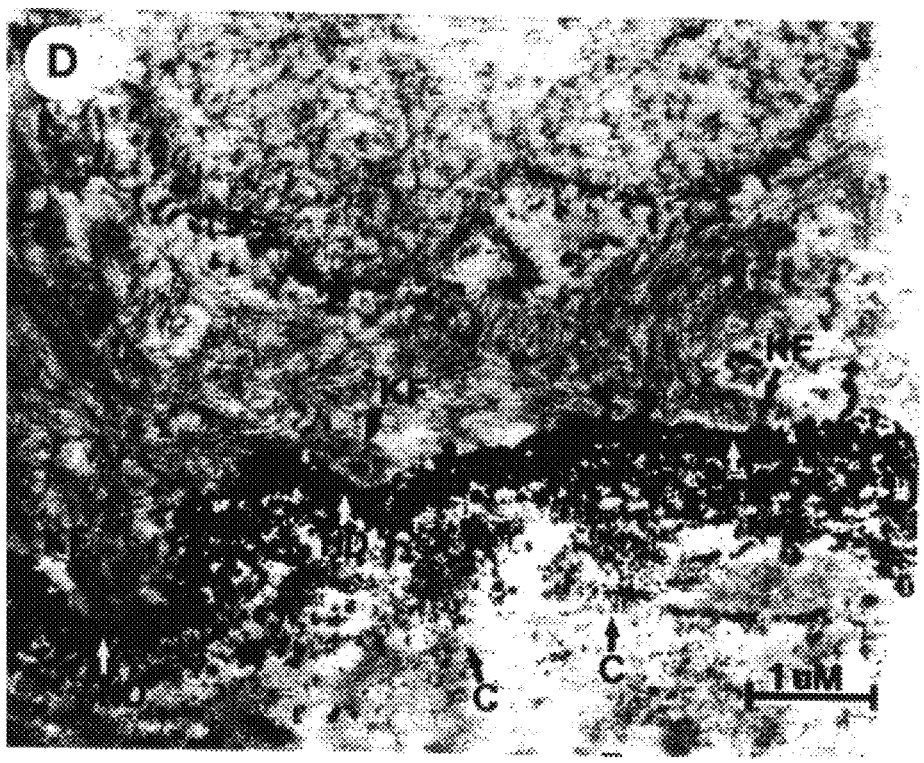

We reported previously that $\alpha_6\beta_4$-containing SACs in HFKs are homologous to hemidesmosomes in skin (20). Consistent with this suggestion and the report of Stepp et al. (19), immunoelectron microscopy localized $\beta_4$ to hemidesmosomes at origins for intermediate filaments (FIGS. 9C–9D).

For immunoelectron microscopy, tissue was fixed (30 minutes in 3% paraformaldehyde/0.5% glutaraldehyde in PBS) prior to freezing and cryostat sectioning ($6\mu$), followed by immunoperoxidase staining with P1F2 and P1E1. Because MAb 3E1 required milder fixation conditions, tissue was cryostat sectioned, then fixed (2% paraformaldehyde in PBS for 15 minutes) followed by peroxidase staining and further fixation (2.0% paraformaldehyde and 2.5% glutaraldehyde in 0.1 M Ca-codylate buffer). All tissue sections were post-fixed for 1 hour in 1% osmium tetroxide, alcohol dehydrated and infiltrated with Epon 812-tm resin (Polysciences, Warrington, Pa.) as described (105). Thin sections were cut (600–800 Å). No uranyl acetate staining was performed.

Figure 9E:
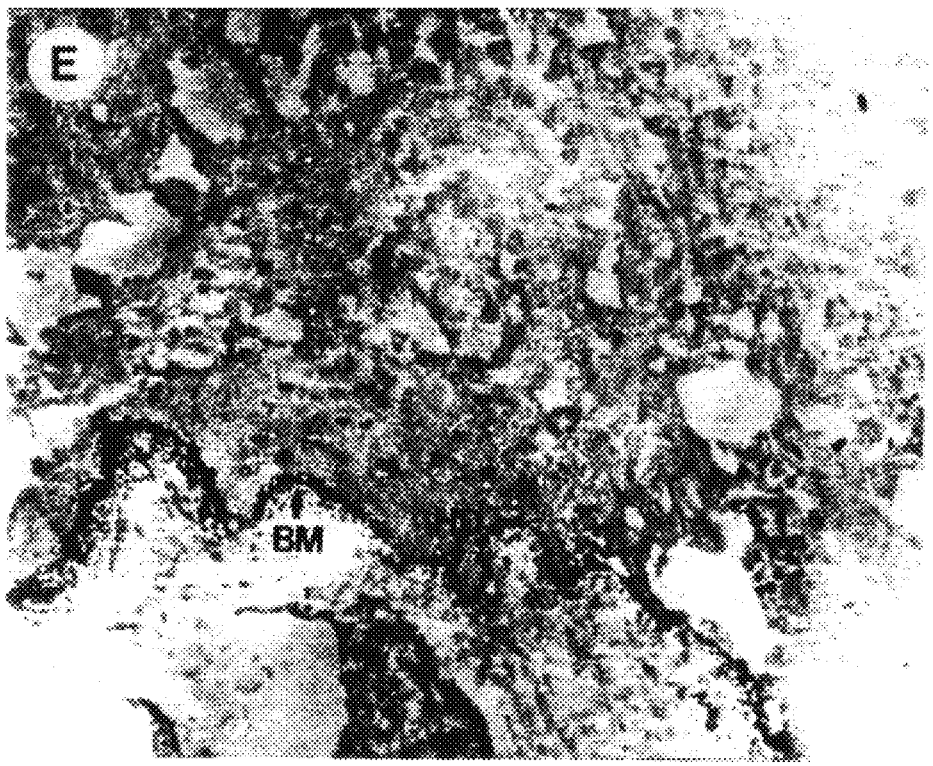
Figure 9F:
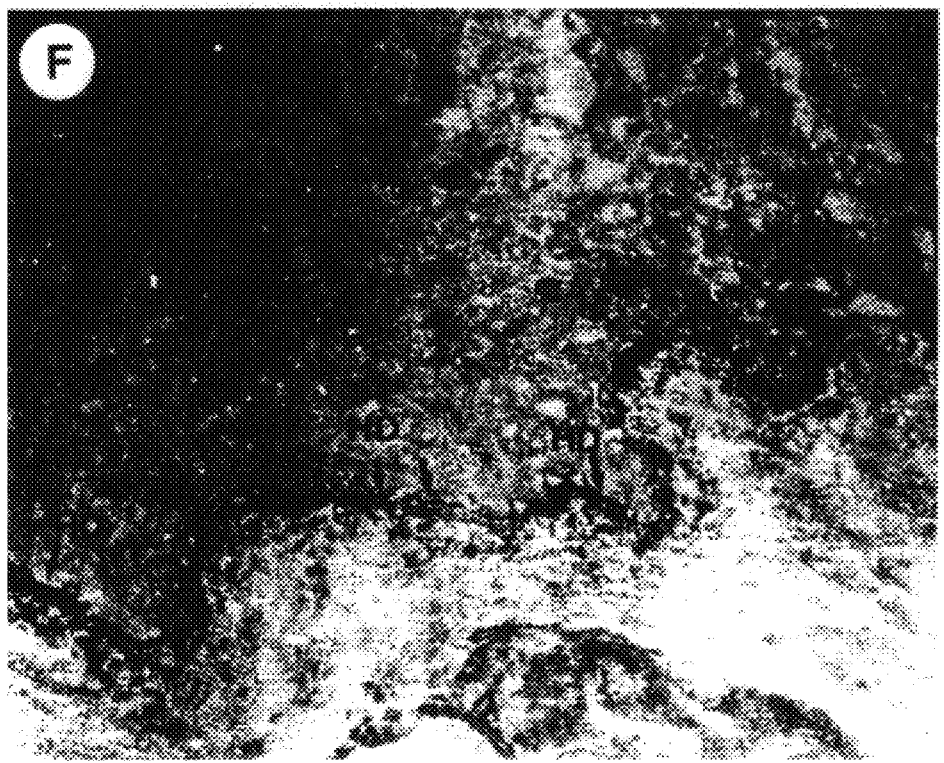

Consistently, epiligrin localized in the lamina lucida of epidermal BM (FIGS. 9E–9F). Epiligrin appeared to directly contact the entire basal surface of the basal cell plasma membrane but was elevated in concentration adjacent $\beta_4$-containing hemidesmosomes. $\alpha_3\beta_1$ localized along the basal membrane as well as the lateral and apical membranes of basal cells (FIG. 9A), consistent with the dual roles for $\alpha_3\beta_1$, in adhesion to epithelial ligand glycoprotein complex and in cell-cell adhesion (21). In many fields, we observed $\alpha_3\beta_1$ localization in desmosomes indicating an association of $\alpha_3\beta_1$ and epiligrin with desmosomes. Nonspecific staining of controls (FIG. 9A) was not detectable while hemidesmosomes and desmosomes were identifiable with anti-$\alpha_3\beta_1$ and P1E1.

The foregoing is exemplified by the representative examples that follow. Specific protocols are described in the appended Materials and Methods section.

EXAMPLES

6. Example 1

Process for Preparing HFK-ECM and HFF-ECM

Human foreskin keratinocytes (HFKs) were prepared as described by Boyce and Ham (106) and maintained by serial passage in serum-free keratinocyte growth medium (KGM; Clonetics, San Diego, Calif.) containing insulin, 10 ng/ml epidermal growth factor hydrocortisone, and 50 $\mu$g/ml bovine pituitary extract.

Keratinocytes have a distinctive composition of glycoproteins which is extracted with SDS sample buffer (12) and is visualized by SDS-PAGE (12): namely, (a) cytokeratins glycoproteins No. 5 (58 kDa); No. 6 (56 kDa); No. 14/15 (50 kDa); No. 16 (48 kDa); and, No. 17 (46 kDa); (b) and the ivolucrin glycoprotein. Several or all of these keratins are visualized by protein staining, e.g., with Coomassie brilliant blue, or alternatively by Western immunoblotting (107) with monoclonal antibodies AE1 and AE3 (45). Ivolucrin is visualized at an apparent Mr of approximately 140 kDa in human keratinocytes by SDS-PAGE (107). Keratinocytes also have a distinctive ultrastructure in tissue culture visible by electron microscopy where the cellular colonies are 5 to 6 cells thick with characteristic keratin filaments, tonofilaments, and numerous desmosomes.

Human foreskin fibroblasts (HFFs) were prepared by protease/collagenase digestion (Methods in Enzymology). For preparation of HFK-ECM or HFF-ECM of HFK or HFF cells, respectively, were seeded in KGM into 7.5 cm diameter tissue culture plastic dishes, and the dishes were incubated at 37° C. in a humidified atmosphere consisting of 95% air/5% CO2 preferably for 1–3 days. The HFK-ECM or HFF-ECM was prepared by a three-step extraction procedure. First, the adherent HFK and HFF cells and their membrane and cytoplasmic constituents were removed by extraction with detergent in the continuous presence of protease inhibitors and 2 mM N-ethylmalaeimide (to inhibit intramolecular cross-linking). Suitable detergents and concentrations for this first step include for example 1% (v/v) Triton X-100-tm anionic detergent (Sigma), Empigen BB-tm Zwitterionic detergent or 100 mM octyl glucoside. Suitable protease inhibitors include diisopropyl fluorophosphate (DFP; Sigma), benzamidine, polybrene, kallikrein inhibitor, or phenyl methyl sulfonyl fluoride (PMSF; Sigma), which may be used individually or in combination as necessary to inhibit cellular protease activity (as evidenced by successful preparation by the complete three-step extraction procedure of HFK-ECM capable of adhering HFF or HT1080 cells in a manner inhabitable with antibodies to the $\alpha_3\beta_1$ integrin; see below; Example 6, "Functional Properties of Epithelial Ligand"). (These same protease inhibitors were used at the same concentrations in the solutions used in the second and third steps, below.) The second step, in the three-step extraction procedure, involves solubilizing and removing nuclear and cytoskeletal components with a solution containing 2 M urea (ammonium-free), 1 M NaCl, and protease inhibitors; and the third step involves solubilization of any residual cellular components with a solution of 8 M urea and protease inhibitors. The ECM remaining attached to the culture dish after the three-step extraction procedure of HFK culture dishes, or HFF culture dishes, is referred to as HFK-ECM or HFF-ECM, respectively.

HFK-ECM can be solubilized into 0.5% w/v SDS by scraping the culture dishes with a rubber policeman; its constituent glycoproteins consist essentially of four to five covalently linked disulfide-bonded glycoproteins with an apparent Mr>450 kDa; i.e., they do not enter an 8% SDS-PAGE (12), traverse the upper 3.5% stacking gel, and stop at the 8% gel interface; and the four to five covalently linked glycoproteins can be separated by reduction and SDS-PAGE run under reducing conditions (12) into components with apparent Mr of 200 kDa, 170 kDa, 145 kDa, 135 kDa and 36 kDa. In contrast, the matrix produced by cultured fibroblasts consists essentially of a non-covalently linked dissociable complex of type I collagen, fibronectin, and heparin-containing and chondroitin-sulfate-containing proteoglycans (108), most of which is extracted by the three-step sequential extraction procedure.

7. Example 2

Process for Preparing Antibody Binding Partners to Epiligrin as Exemplified by Rabbit Antisera and Monoclonal Antibody Specific for Epiligrin Glycoprotein Complex Useful antigens for producing monoclonal and polyclonal antibodies include HFK cells, and also include HFK-ECM (prepared as described in Example 1), or individual glycoproteins present in HFK-ECM which are physically separable by techniques obvious to those skilled in the art including at least SDS-PAGE.

Various procedures well known in the art are useful for the production of polyclonal antibodies to antigenic epitopes in HFK-ECM. Various host animals can be immunized by injection with HFK-ECM proteins, fragments thereof, or synthetic peptides constructed to mimic the amino acid sequence in an HFK-ECM protein. Adjuvants may be used to augment the immune response and immunogenicity of small proteins, and peptides may be enhanced by coupling them to larger "carrier" molecules.

Monoclonal antibodies for therapeutic use may be human monoclonal antibodies or chimeric human-mouse (or other species) of monoclonal antibodies. Human monoclonals may be made by numerous techniques known in the art and the subject of many reviews and detailed techniques manuals, e.g., Olsson et al., *Methods in Enzymology* 92:3–16 (1982). Similarly, techniques are well known by which chimeric antibody molecules may be prepared containing a mouse V-region antigen binding domain with human constant regions. Molecular cloning of antibodies may also be used to construct recombinant DNA molecules which encode monoclonal antibody, and chimeric monoclonal antibodies from different species, and these methods are also well known to those skilled in the art.

HFK cells for use as an immunogen to produce monoclonal antibodies were prepared as follows. First, HFK cells were seeded in plastic tissue culture dishes. After 7 days the cells were detached from the substrata and collected by centrifugation. The cell pellet was resuspended in PBS and mixed with an equal volume of Complete Freund's Adjuvant. 0.2 ml was injected into each of 2sc and 2im sites in RBF/Dr mice. Third, the animals were boosted after 14 and 21 days.

HFK-ECM was collected from the surface of culture dishes by scraping with a rubber policeman into 0.5% SDS and dialyzing against PBS to remove the SDS. This HFK-ECM aggregated protein suspension was mixed with an equal volume of Complete Freund's Adjuvant and 100 µl of the adjuvant solution was injected at each of 2sc and 2im sites in New Zealand white rabbits. The animals were boosted at 14 and 21 days.

Immune spleen cells from HFK-immunized mice were prepared and fused with NS-1 /FOX-NY murine myeloma cells using polyethylene glycol as described (59, 99, 100). (These and the following methods (below) are also useful for producing monoclonal antibodies from mice immunized with HFK-ECM and individual glycoproteins present in HFK-ECM). Viable heterokaryons were selected in RPMI 1640 supplemented with adenine/aminopterin/thymidine (AAT; 100). Heterokaryons producing antibodies (termed "hybridomas") specific for HFK-ECM and not binding to HFF-ECM were selected. The clones designated P1E1 and P1H8 were derived, as an example, by this method.

Other immunochemical methods for selecting positive hybridomas producing antibodies reacting with epithelial ligand glycoprotein complexes will be obvious to those skilled in the art, including at least selection by ELISA, RIA, and Western blotting using purified epithelial ligand antigens (Example 3, below) and/or HFK-ECM and HFF-ECM.

It will also be understood that antibodies other than monoclonal antibodies may be produced (e.g., by immunizing rabbits, goats, or other animals), and will be equally useful.

The specific immunochemical properties of monoclonal (or other) antibodies specific for epiligrin antigens are detailed below in Example 5.

8. Example 3

Process for Preparing Epiligrin

Epiligrin (epithelial ligand complex) was substantially purified by mechanically scraping HFK-ECM (prepared in Example 1) into 0.5% SDS. When subject to reduction of disulfide bonds, e.g., with DTT or 2-mercaptoethanol, the epithelial ligand complex prepared in this manner exhibited epithelial ligand glycoproteins with apparent molecular sizes of 200 kDa (E200), 170 kDa (E170), 145 kDa (E145), 135 kDa (E135), and 36 kDa (E36) when reduced and electrophoresed under reducing conditions on 8% SDS-PAGE with a 3.5% stacking gel (12).

A mixture containing predominantly a covalently-linked epithelial ligand glycoprotein complex was substantially purified from the conditioned medium of HFK cells as outlined in FIG. 3. This was accomplished in a stepwise fashion involving, first, affinity purification of MAb P1E1 from hybridoma culture medium on Protein G-sepharose using the methods recommended by the manufacturer (Pharmacia, Piscataway, N.J.). Second, the P1E1 antibody was immobilized on a matrix i.e., to form a P1E1-affinity-column) by covalently coupling purified monoclonal antibody to Affigel-10 according to the manufacturer's instructions (Bio-Rad Laboratories, Richmond, Calif.). Third, conditioned medium from confluent cultures of HFK cells was passed over a gelatin-sepharose column (Pharmacia) to remove fibronectin. Fourth, the flow-through from the gelatin-sepharose column was passed over the P1E1-affinity-column; unbound protein was removed by washing with PBS until the wash had an OD280 of less than 0.001 units; the bound epithelial ligand glycoprotein complex was eluted with 3 M KSCN, and the fractions containing the eluted protein were pooled and dialyzed overnight at 4° C. against at least 10 volumes of PBS. The substantially-purified covalently-linked epithelial ligand glycoprotein complex purified in this manner (i.e., from conditioned media) comprised predominantly E170, E145, E135, and E36, although low levels of E200 and E100 were also present by SDS-PAGE.

It will be understood by those skilled in the art that MAb P1E1 is purified sing affinity chromatography on other chromatographic resins containing compositions binding murine Ig (i.e., protein A-sepharose, or anti-IgG or protein M-sepharose); or alternatively, by specific binding of MAb P1E1 to epithelial ligand complex or epithelial ligand glycoprotein covalently bound to a matrix (e.g., Affigel-10, Bio-Rad or CNBr-sepharose, Pharmacia).

It is also obvious to those skilled in the art that the relatively large molecular size of the epithelial ligand glycoprotein complex (calculated to at least greater than 450 kDa to 650 kDa, assuming equimolar amounts of each epithelial ligand glycoprotein), and insolubility of HFK-ECM glycoproteins in aqueous solutions will be used to advantage in purification schemes designed to separate these complexes from numerous smaller soluble cellular components. Purification of epithelial ligand glycoprotein complex from HFK-ECM or HFK-conditioned medium by conventional column chromatography was not possible due to the relatively poor solubility of the complex and its large molecular weight. It is also obvious that reduction and alkylation of the disulfide bonds will be useful for producing epithelial ligand glycoproteins, where intramolecular cross-linking (leading to formation of aggregates) is inhibited by 2 mM n-ethyl malaeimide and similar chemical agents. However, it was also discovered that reduction and alkylation leads to inactivation of the epiligrin adherence-promoting activity and it is apparent that preserving the secondary structure of epithelial ligand glycoproteins is important to preserving their functional activity.

The epiligrin (E170) protein was substantially purified from either HFK-ECM or the affinity-purified epithelial ligand glycoprotein complex by SDS-PAGE. It is understood by those skilled in the art that epithelial ligand for integrins is also purified by other conventional means from conditioned media of other epithelial cells under other conditions of growth.

The physical, immunochemical, and functional properties of the epithelial ligand glycoprotein complex epiligrin is detailed in Examples 4, 5, and 6, respectively, below.

9. Example 4

Physical Properties of HFK-ECM, and Epithelial Ligand Glycoprotein Complex

HFKs were seeded into 7.5 mm plastic tissue culture dishes, as described in Example 1, and incubated in KGM medium (supplemented as described in Example 1) and containing $^{35}$S-methionine or alternatively $^3$H-glucosamine. HFK-ECM was prepared according to Example 1, which includes sequential extraction with 1% Triton X-100, 2 M urea/1 M NaCl, and then 8 M urea, These conditions are known by those skilled in the art to frequently be sufficient to dissociate non-covalently associated proteins, and also, to be sufficient to denature other proteins. HFK-ECM is also stable to extraction with 6 M guanidine hydrochloride and 4 M sodium trichloroacetate. Thus, it may be said that the epiligrin complex is relatively stable to denaturing conditions, and relatively resistant to extraction from the plastic tissue culture substrata (although it has been observed that some low levels of epithelial ligand glycoprotein complex are extracted with 8 M urea).

$^{35}$S-methionine biosynthetically-radiolabeled HFK-ECM glycoproteins (above) and non-radiolabeled HFK-ECM glycoproteins were solubilized into 0.5% SDS (w/v) (sodium dodecyl sulfate; Bio-Rad) by mechanical scraping of the tissue culture dishes with a rubber policeman, and the glycoproteins solubilized in this manner were then subjected to SDS-PAGE essentially according to Laemmli (12) op. cit. on 8% gels under non-reducing and reducing conditions using a 3.5% stacking gel. Non-radiolabeled glycoproteins were visualized by staining with Coomassie Brilliant Blue (Bio-Rad) and the radiolabeled glycoproteins were visualized by fluorography although other methods known to those skilled in the art for detecting biosynthetically radiolabeled glycoproteins are equally useful. Under reducing conditions five glycoproteins were visualized in epiligrin complex with apparent molecular sizes in the 8% gel of 200 kDa (E200), 170 kDa (E170), 145 kDa (E145), 135 kDa (E135) and 36 kDa (E36), (FIG. 1, lanes 4 and 6, $^{35}$S-methionine biosynthetically radiolabeled); lane 9 ($^3$H glucosamine-radiolabeled); and lane 8 (nonradiolabeled). The five glycoproteins appeared to be present in about equal amounts in the biosynthetically radiolabeled HFK-ECM samples (FIG. 1, lanes 4 and 9). An approximate combined Mr for the non-reduced epithelial ligand glycoprotein complex was calculated to be at least 450 kDa–650 kDa (excluding any contribution of proteoglycan to the molecular weight, see below). The non-radiolabeled sample of HFK-ECM appeared to contain lesser amounts of the E200 precursor (relative to E170, E145, or E135) than that present in biosynthetically-radiolabeled samples. This may be because there are differences in the amounts of E200 in the epithelial ligand glycoprotein complexes at different stages in HFK cell growth (e.g., subconfluent vs. confluent). It is also possible that (1) recently synthesized E200 may be covalently associated with the epithelial ligand glycoprotein complex and that (2) with time, reduction of the disulfide bonds (e.g., with glutathione or disulfide-exchange) may lead to liberation of processed peptides from the complex, leaving behind a 170 kDa protein. Under nonreducing conditions the epithelial ligand complex in HFK-ECM was visualized as a high molecular weight complex which did not enter the 8% gel. (FIG. 1, lane 5).

The five glycoproteins in the epithelial ligand complex were not biosynthetically radiolabeled with $^{35}SO_4^{-2}$ (FIG. 1, lane 10) indicating that they are not sulfated proteoglycans. However, independent of the epithelial ligand complex the HFK-ECM (biosynthetically radiolabeled for 15 hours with 50 $\mu$Ci/ml of $^{35}SO_4^{-2}$ in KGM containing 1 mg/ml HD-BSA as a carrier protein) contained three high-Mr sulfated proteoglycans that were associated with the HFK-ECM (FIG. 1, lane 10) and thus with the epithelial ligand complex in the HFK-ECM (FIG. 1, lane 9). The first sulfated proteoglycan did not enter the 3.5% stacking gel and the second barely entered the stacking gel but did not enter the 8% running gel.

10. Example 5

Immunochemical Properties of Epithelial Ligand Antigen, Epithelial Ligand Complex, and Monoclonal Antibody to Epiligrin Monoclonal antibodies P1E1 and P1H8 selected (above, Example 2) for specific binding to HFK-ECM and not to HFF-ECM, e.g., P1E1, bound to $^{35}$S-methionine radiolabeled epiligrin complex in HFK-conditioned media (prepared as in Example 3, above) and the immunoprecipitate formed by adding a second antibody (i.e., rabbit or goat anti-murine IgG and IgM H and L chain sera) with carrier proteins (e.g., diluted murine sera containing murine IgG and IgM) contained E200, E170,E145,E135 and E36. (FIG. 2, lanes marked "P1E1").

P1E1 did not bind to any of the epithelial ligand glycoproteins when they had been reduced and subjected to SDS-PAGE under reducing conditions, suggesting that the P1E1 antigenic epitope may be conformational and denatured in these treatments.

The glycoproteins immunoprecipitated by P1E1 include relatively greater amounts of E170 than E135, E145, or E200. These findings indicate: a) that E170 may contain the P1E1-reactive antigenic epitope in the epiligrin complex; and b) that E170 may also exist in HFK-conditioned media as a glycoprotein independent of the epiligrin complex.

P1H8, while binding to HFK-ECM and soluble epiligrin complex in HFK-conditioned media, did not bind to the endogenous epiligrin complex in HFK cells unless the plasma membrane was permeabilized to allow entry of antibodies into the cytoplasm. P1H8 immunoprecipitated E36 from HFK-conditioned media in amounts relatively greater than E200, E170, E145 or E135 indicating: a) that E36 contains the P1H8 antigenic epitope of the epiligrin glycoprotein complex; and b) that E36 is also present in HFK-conditioned media as a glycoprotein independent of the epithelial ligand complex.

Verification that monoclonal (or polyclonal) antibody is directed to epiligrin complex is obtained by $^{35}$S-methionine or 3H-glucosamine biosynthetically-radiolabeling HFK cells, collecting the conditioned medium, and using the antibody in question to form an immunoprecipitate with the biosynthetically radiolabeled antigens in the conditioned medium. Antigens in the epiligrin complex exhibit characteristic molecular weights of 170±20 kDa, 145±20 kDa, 135±20 kDa, 36±15 kDa (with variable amounts of E200±20 kDa) under reducing conditions on 8% SDS-PAGE and when run according to Laemmli (12).

Additional verification that monoclonal (or polyclonal) antibody is directed to epiligrin can be obtained by examining the pattern of staining of cells in epithelial tissues by immunoperoxidase staining with cryostat sections of tissues (prepared as described above, see "Epithelial Ligand Localization in Normal Epithelial BM") (see "Epithelial Ligand, $\alpha_3\beta_1$, and $\beta_4$ localization at the cell-BM Junction"). Antibodies to epiligrin stain basement membrane materials in normal skin, tonsil, and lung essentially as described (see "Epiligrin Localization in Normal Epithelial BM"; "Epiligrin Localization in Lymphoid Tissues"; "Epiligrin Localization in Lung Tissues"; above). Antibodies to epiligrin do not stain BM materials of heart muscle, mesothelium, brain, or glomerulus and tubules in kidney (see "Epiligrin Localization in Other Tissues and Organs").

When HFK cells are grown on BSA-coated surfaces the epiligrin complex is contained within characteristic "ring structures" in the ECM that are visualized by immunofluorescent staining with P1E1 (see, "Epiligrin Distribution in Motile and Non-motile HFKs"). An example of these characteristic "ring structures" formed by epithelial ligand glycoprotein complex in HFK-ECM is provided in FIGS. 4A, 4C, and 4F. Confirmation that "ring structures" produced by other cells of epithelial origin (i.e., Epith-ECM; i.e., other than HFK) contain epiligrin will be possible using monoclonal antibodies to epiligrin, such as P1E1, and as a preferred embodiment, using these anti-epiligrin antibodies in a double antibody immunofluorescence microscopic technique with antibodies binding $\alpha_6\beta_4$ integrin (e.g., FIGS. 4B and 4D) or BPA (e.g., FIG. 4G). In the latter case, the simultaneous presence of epiligrin antigens and $\alpha_6\beta_4$ or BPA in a "ring structure" will confirm that the ECM structure contains the epiligrin complex. Additional verification that the "ring structures" identified in this manner contain epiligrin will be obtained by extracting the epithelial-ECM sequentially with 1% Triton X-100, 2 M urea/1M NaCl, and then 8 M urea as described in Example 1, above, and in connection with FIGS. 5A–5F. The "ring structures" containing epiligrin complex will be stable under these conditions, in a manner similar to those in HFK-ECM (FIGS. 5A–5E).

11. Example 6

Functional Properties of Epiligrin Complex: Cell Adhesion Assays

Test cells which express functional $\alpha_3\beta_1$ integrin will bind to ligand in the epiligrin complex, and if epiligrin is coated onto the surface of a normally non-adhesive substratum (epithelial ligand-coated substratum) the interaction between the epiligrin and the $\alpha_3\beta_1$ integrin is sufficient to modulate adhesion of the test cells, in this case, by increasing their adhesion to the epiligrin-coated substratum. The adhesion of the test cells to the substratum will be optimal after 24 hours of incubation at 37° C. to allow washing to remove non-adherent cells, and the relative number of adherent cells will be determined by microscopically counting the adherent test cells or by radiolabeling the test cells prior to incubation in the assay, such as with $Na^{51}CrO_4$ or other suitable label known to those skilled in the art. The preferred embodiments relate to test cells which do not express the $\alpha_6\beta_4$ receptor or epiligrin in amounts sufficient to be detected by immunofluorescence microscopy, and HFF and HT1080 fibrosarcoma cells are examples of such test cells. Polystyrene plastic petri dishes (i.e., bacteriological grade petri dishes as opposed to tissue culture plastic dishes) are examples of a non-adhesive substratum which will be useful for coating with epiligrin. The epiligrin coating on the non-adhesive substrate may be applied by any of a variety of means known to those skilled in the art (e.g., by soaking, spraying, dipping, etc.) using a concentration of protein sufficient to accomplish the desired result of test cell adhesion to the epiligrin-coated substratum. Epiligrin useful for coating the non-adhesive substratum will be, as an example, the epithelial ligand glycoprotein complex purified in Example 3, above, from HFK-conditioned medium, although other cellular sources, preparative purification methods, and substantially equivalent epithelial ligand compositions will also be useful. To verify that the adherence of the test cells to the epiligrin-coated substratum involves a specific binding interaction between $\alpha_3 \oplus_1$ integrin and the epiligrin, it will be obvious to one skilled in the art that controls will be required including at least non-coated non-adhesive substrata incubated for the same period of time with the test cells. In addition, it will be useful to test the specificity of the adherence of test cells to the epiligrin-coated substratum utilizing reagents specifically binding to either the receptor (e.g., monoclonal antibodies, such as P1 B5 to the $\alpha_3\beta_1$ integrin, or MAb to the $\alpha_3$ or $\beta_1$ chains; or peptide portions of the epiligrin complex which will competitively or non-competitively inhibit specific binding of the receptor), or alternatively, to the ligand (e.g., monoclonal antibodies to epiligrin which will inhibit adhesion of test cells in a specific manner or peptide portions of $\alpha_3\beta_1$ integrin polypeptide chains which will inhibit the adhesion of test cells in a specific manner).

As an additional test for epithelial ligand complexes, the ability of such ligands to co-distribute on epithelial cells with $\alpha_3\beta_1$, $\alpha_6\beta_4$, or BPA antigens will be useful. Examples of these embodiments of the invention can be found above (see "Epiligrin Distribution in Motile and Non Motile HFKs" and "Epiligrin is a Ligand for $\alpha_3\beta_1$-FAs").

12. Example 7

Epiligrin Adherence of Lymphoid Test Cells

Human peripheral blood lymphocytes lack cellular $\alpha_3\beta_1$ integrin but acquire this receptor when they are activated in tissue culture with Interleukin-2 and Interleukin-3 (59). Such tissue cultures contain a class of nonspecific "killer" lymphocyte commonly referred to as LAK cells (lymphokine-activated killer cells). LAK have been tested, previously by others, for their potential therapeutic antitumor effects in cancer patients by intravenous fusion. One observed property of LAK cells infused in this manner was a capacity to localize nonspecifically in epithelial tissues.

Activated lymphoid cells expressing a $\alpha_3\beta_1$ receptors bind in a specific manner to epiligrin-coated non-adhesive substrata in the cell adhesion assay described in Example 6, above, or Example 11, below. The binding of activated lymphoid cells to epiligrin-coated substrata is inhibited in a specific manner by reagents specifically binding to either the $\alpha_3\beta_1$, receptor or to epiligrin, such as that described in Example 6, above and Example 11, below. One of ordinary skill in the art is able to use the test cell assay described here with activated lymphoid cells to screen for reagents (e.g., peptides mimicking the receptor binding domain in epithelial ligand, or alternatively, integrin peptides mimicking the receptor domain which specifically inhibit binding of activated lymphoid cells to epiligrin). These reagents are also useful for specifically inhibiting the binding of activated lymphoid cells at sites of chronic and acute inflammation, for example, but not limited to, autoimmune dermatological diseases, rheumatoid arthritis, graft-versus-host disease and transplant rejection sites. Embodiments of the invention relate to activated lymphoid cells which include but are not limited to LAK cells; interleukin, cytokine, and specific antigen-activated T- and B-lymphocytes; and activated mononuclear phagocytes (e.g., but not limited to, treatment with LPS), and/or antigen-activated mast cells (e.g., but not limited to, treatment with allergens).

13. Example 8

Wound Healing Compositions

Wound strength depends on cellular and molecular factors which include granulation tissue deposition, deposition of extracellular matrix, and re-epithelialization. Re-epithelialization depends upon migration of epithelial cells from the periphery of the wound site in a migratory tongue into the wound site. This migratory process is encouraged and promoted by epiligrin complex, epiligrin component glycoproteins, and portions thereof; particularly $\alpha_6\beta_4$ and $\alpha_3\beta_1$ receptor binding portions of epiligrin glycoproteins. Agents which stimulate increased expression of $\alpha_6\beta_4$ and $\alpha_3\beta_1$ integrins on cells also promote cellular migration, which is advantageous in wound healing.

The epiligrin compositions and receptor binding portions disclosed herein promote the formation of SACs, and the proliferation of basal (stem) cells in epithelial tissues by cytokines, since they act as "second signals" to potentiate the action of cytokines. The binding of $\alpha_6\beta_4$ and $\alpha_3\beta_1$ receptors to the epiligrin complex serves as a nucleation site for the formation of SACs, and stimulates synthesis of epiligrin glycoproteins which ultimately results in a migratory cell becoming stationary. Thus, migratory behavior also promoted by agents which down-regulate epiligrin glycoprotein synthesis, or interfere with formation of the epiligrin complex. These agents and compositions are within the scope of the embodiments of the invention, and the methods and processes of the invention provide examples of how these agents may be identified.

The premature terminal differentiation of basal (stem) cells in wound sites slows the process of wound healing and contributes to wounds having lesser tensile strength than wounds in which terminal differentiation of epithelial cells can be slowed or completely retarded to allow proliferation of basal (stem) cells. Also, epiligrin complex provides a natural basement membrane material for basal (stem) cells and epithelial tissue explants which favors terminal differentiation of the epithelial cells into complex structures such as sweat glands and hair follicles, this process is not currently possible with existing wound healing compositions. Epiligrin is also useful for screening reagent compositions in vitro that promote wound healing and epithelial cell growth in vivo, for example, but not limited to, cytokines and growth factors, epithelial ligand peptides, and $\alpha_3\beta_1$ receptor binding partners, such as described in Example 6, above, and in Examples 10 and 11, below.

14. Example 9

Role for Epiligrin in Polarized Asymmetric Cell Division, and Growth and Differentiation of Cells of Epithelial Origin Asymmetric cell division of epithelial basal cells is characterized by retention of one proliferative daughter cell at the BM (the first daughter cell) and dissociation of the other differentiating daughter (second daughter cell) from the basal layer with movement into the upper layers (i.e., the Malpighian layer of the skin and spinous strata in nervous tissue) (109). In general, $\alpha_3\beta_1$ and epiligrin are associated with proliferating basal cells (57, 110, 111), and epiligrin synthesis ceases as cells leave the basal layer. Cellular control of asymmetric cell division is manifest through cytoplasmic polarization created by asymmetrical localization of adhesion sites (e.g., SACs and FAs) on the cell plasma membrane of the basal stem cells. Such asymmetry involves cytoplasmic glycoproteins associated with SACs and FAs and their interactions with epiligrin and the $\alpha_3\beta_1$ and $\alpha_6\beta_4$ integrins in these structures, e.g., cytoplasmic actin and the 36±15 kDa epithelial ligand associated glycoprotein. These (and other) cytoplasmic glycoprotein components of SACs and FAs bind to cytoplasmic cytoskeletal elements and create the cytoplasmic polarization sufficient to create a first daughter cell which is distinctly different in cytoplasmic organization from the second daughter cell. $\alpha_6\beta_4$ and $\alpha_3\beta_1$ interact with epiligrin in the proliferative first daughter at the basal surface of the cell (i.e., in association with BM). $\alpha_3\beta_1$ relocates to proximal sites of intercellular cell-cell adhesion in the basal cell which creates an asymmetrical force upon the differentiating second daughter cell. The lack of physical binding of the second daughter cell to the basement membrane, the down-regulation of epiligrin synthesis, and increased cell-cell adhesion in the upper Malpighian or spinous layers creates a physical force to draw the differentiating second daughter away from the proliferative first daughter. Regulation of these polarized adhesion functions facilitates separation of the daughter cells and the resultant polarized/asymmetric cell division in epithelial tissues. Epiligrin functions to maintain the proliferative functions of the basal (stem) cells through dual roles in anchoring the cell to the substratum and promoting (as a second signal) the activities of cytokines. Lack of epiligrin functions to create the class of "second daughter cells" committed to differentiation. Thus, the epiligrin complex, epithelial ligand glycoproteins, and portions thereof (particularly ligand portions which interact with the $\alpha_3\beta_1$ and the $\alpha_6\beta_4$ integrins) are useful for promoting basal (stem) cell growth in epithelial cells and modulation of epiligrin synthesis promotes differentiation of epithelial cells such as cancer cells, cells in autoimmune disease states, and cells in psoriasis. Thus, the differentiation of these cells reverses the processes by which the cells cause disease. In addition, $\alpha_3\beta_1$ receptor specific binding partners, such as (for example) antibody to the receptor, promotes aggregation of cells lacking epiligrin, and this also is useful for mimicking the effects of epiligrin in inducing proliferation and differentiation of epithelial cells.

15. Example 10

Use of Epiligrin to Identify the Receptor Binding Portions of the $\alpha_3\beta_1$ and $\alpha_6\beta_4$ Integrins An alignment of the adjusted $\alpha_6$ amino acid sequence (as reported by Tamura, 56) with the $\alpha_3$ amino acid sequence as they appear in GeneBank results in 37% identity, a value greater than with any other integrin chain. Amino acid sequence of a protein that is related to the functional properties of the protein are frequently evolutionarily conserved. The present finding that epiligrin complex binds to both $\alpha_3\beta_1$ and $\alpha_6\beta_4$ provides for the first time a relationship between these two integrins and a functional basis for regions of conserved amino acid sequence(s). Knowing that there is a 37% sequence identity between $\alpha_3$ and $\alpha_6$, and that both $\alpha_3\beta_1$ and $\alpha_6\beta_4$ bind to epiligrin, one can select and employ conserved peptide sequence(s) to modulate binding of epiligrin to the $\alpha_3\beta_1$ and $\alpha_6\beta_4$ integrins as follows. "Limited sequence portions" of the ($\alpha_3$ and $\alpha_6$ chains, i.e., peptides which are at least 30% homologous or identical over at least 3 to 30 amino acids, are identified by direct comparison of the aligned amino acid sequences. From these template "limited sequence portions" in $\alpha_3$ and $\alpha_6$ chains, homologous peptides are constructed ("$\alpha_3$ or $\alpha_6$ test peptides") which are composed of amino acid sequences that are at least 30% homologous and/or identical to the amino acid sequence in the "limited sequence portions." Such "limited sequence portions" and/or "$\alpha_3$ and $\alpha_6$ test peptides" are then assayed pursuant to this disclosure to determine and select "reagent peptides" which will function as inhibitors ("$\alpha_3$ and $\alpha_6$ inhibitory test peptides"), antagonists, and agonists of the natural binding of $\alpha_3\beta_1$ and $\alpha_6\beta_4$ integrins to the epiligrin.

In a representative example, cellular adhesion assays such as those described in Example 6, above, are used to determine and select which of the "limited sequence portions" and "$\alpha_3$ and $\alpha_6$, inhibitory test peptides" inhibit cellular adhesion by at least 20% to epiligrin-coated substrata at a physiologically significant molar concentration (i.e., to determine the "$\alpha_3$ or $\alpha_6$ inhibitory peptides"). Test cells are allowed to adhere to epiligrin-coated substrata in tissue culture medium within 2 to 24 hours, and preferably 2 to 18 hours, and this adherence of the test cells is inhibited by at least 20% when the "$\alpha_3$ or $\alpha_6$ inhibitory test peptide" is added to the tissue culture medium at a physiologically significant molar concentration, i.e., of $10^{-5}$ M to $10^{-10}$ M and preferably $10^{-6}$ M to $10^{-10}$ M. A plurality of assays with a plurality of test cells and "$\alpha_3$ or $\alpha_6$ inhibitory test peptides" are run to identify the "$\alpha_3$ or $\alpha_6$ inhibitory peptide(s)" which inhibit test cell adherence in the assay by at least 20% at a physiologically significant molar concentration.

The selected inhibitors, antagonists, and agonists may be engineered to, e.g., improve their stability, half-life in blood or binding affinity for ligands. Such improvements are made either by substitution of one or more amino acid(s) in the "$\alpha_3$ or $\alpha_6$ inhibitor peptide" for a "natural amino acid" (the "natural amino acid" is that amino acid that is present more than 40% of the time at that particular position when the $\alpha_3$ and $\alpha_6$ chains from at least 5 different animal species are properly aligned). Improvements are also made by biochemical or chemical modification of the "$\alpha_3$ or $\alpha_6$ inhibitor peptide" to create at least one synthetic amino acid, or a plurality of synthetic amino acids, in the amino acid sequence of the "$\alpha_3$ or $\alpha_6$ inhibitor peptide" to produce "$\alpha_3$ and $\alpha_6$ inhibitor analogues." Alternatively, by conformationally modeling the "$\alpha_3$ and $\alpha_6$ inhibitor peptides" and their interaction with epiligrin, it is possible to construct an "$\alpha_3$ or $\alpha_6$ inhibitor mimetic" which mimics the "$\alpha_3$ or $\alpha_6$ inhibitor peptide" interaction with epiligrin by filling at least 50% of the three-dimensional fluid space occupied by the "$\alpha_3$ or $\alpha_6$ inhibitor peptide" in tissue culture medium at physiological pH and ionic strength when the "$\alpha_3$ or $\alpha_6$ inhibitor peptide" is interacting with the epiligrin complex.

16. Example 11

Use of $\alpha_3$ and $\alpha_6$ Inhibitor Peptides; $\alpha_3$ and $\alpha_6$ Inhibitor Analogues; and $\alpha_3$ and $\alpha_6$ Inhibitor Mimetics for Inhibiting the Binding of Lymphoid Test Cells to Epithelial Basement Membrane Compositions Certain of the compositions described in Example 10 are useful for inhibiting the binding of activated T lymphocytes through the integrins to basement membrane compositions having at least epiligrin. Using the test cell assay disclosed in Example 7 (above), it is possible to assay a plurality of the inhibitor, antagonist, and agonist compositions disclosed in Example 10 to determine which compositions inhibit by at least 20% the adherence of lymphoid test cells at a physiologically meaningful concentration, e.g., between $10^{-5}$ M to $10^{-10}$ M (i.e., "lymphoid inhibitory compositions"). The "lymphoid inhibitory compositions" are useful for preventing and slowing the accumulation of activated lymphoid cells (as defined in Example 7) at sites of chronic or acute inflammation, for example (but not limited to) in graft vs. host disease, transplant rejection, autoimmune dermatological and rheumatic diseases, such as rheumatoid and non-rheumatoid arthritis, bullous pemphigoid, CP, and EBA.

17. Example 12

Use of Epiligrin to Identify Autoantibodies in Patient Sera

Epiligrin complex and its constituent antigens (as described in Examples 1–3 and as, for example, prepared according to Example 3) are useful for identifying autoantibody in patients with autoimmune disease, for example (but not limited to) greater than 50% of the patients with cicatrical pemphigoid and less than 20% of the patients with BP or EBA; they are useful for distinguishing CP from BP and EBA.

Immunochemical diagnostic assay formats, for example, which are useful include at least enzyme-linked immunoadsorbent assays (ELISA), radioimmunoassays (RIA), fluorescence immunoassays (FIA), Western immunoblot assays, time-resolved fluorescence assays (TRF), particle agglutination assays (e.g., latex, red cell, etc.). In these assays the bound antibody (or antigen) is separated from free antibody (or antigen) by physical means involving, for example, the use of a solid-phase adsorption of antibody (or antigen) in tubes, microtiter plates, and on polymeric membranes, dipsticks, and beads (e.g., magnetic beads or polystyrene or nylon-66-tm beads); or, alternatively, bound antibody (or antigen) is separated from free antibody (or antigen) through the use of a washing step wherein the assays are run in steps involving at least binding of antibody (or antigen), separation of bound antibody (or antigen) from the free antibody (or antigen) with washing, and assaying for the amount (or presence) of bound antibody (or antigen).

18. Example 13

Epiligrin Complex for Promoting the Growth of Epithelial Basal (Stem) Cells in Biopsy Materials: Use for Transplantation Epiligrin-complex-coated substratum is optimal for promoting the growth of epithelial basal (stem) cells and for preventing the differentiation of this population of cells into other cell types, such as keratinocytes in the skin. For example, primary cultures of epithelial cells, e.g., from biopsy samples, are grown on epiligrin-coated substrata in KGM medium (e.g., keratinocyte growth medium, containing growth factors such as PDGF, EGF, FGF, and insulin, and serum, such as 1–10% fetal bovine serum), and the basal (stem) cells in the samples continue to exhibit mitotic activity. To confirm the mitotic activity of basal (stem) cells in these cultures, and to distinguish from the mitotic activity of other contaminating cell types (e.g., fibroblasts in skin biopsy samples) it is possible to observe the basal (stem) cells microscopically after fixing, staining, and embedding the cell layer for autoradiography, e.g., using a photographic emulsion. Basal (stem) cells cultured on epiligrin-coated substrata retain their mitotic activity for a period of time which is longer than that of biopsy samples grown on control substrata, i.e., HD-BSA; 7 to 14 days is a convenient length of time for assessing this activity (although it is also possible to visually assess the cultures on a daily basis by inverted microscopy, and those skilled in the art are readily able to determine the optimal time for determining mitotic activity in an individual experiment). The mitotic activity is microscopically visible in the autoradiograph as increased numbers of silver grains over the nucleus of the basal (stem) cells. In any cases where doubt may exist as to the nature of the cells in the mitosis assay, it is possible to combine autoradiographic analysis with the uses of immunochemical or other differentiation markers and in these cases, the basal (stem) cells lack the differentiation marker and are thus distinguished.

The ability of epiligrin-complex-coated substrata to support mitosis and growth of epithelial basal (stem) cells creates, for the first time, the opportunity to establish tissue cultures of continuously proliferating and differentiating epithelia that mimic normal biological processes and provides a superior source of epithelial cell sheets for transplantation. Such cell sheets are obtained from any epithelial tissue; for example, in the case of skin they are useful for skin transplants; in the case of epithelial cells in the bone marrow and lymphoid tissues they are useful in bone marrow transplantation methods; and, in the case of gastrointestinal ulcers, the cell sheets are useful for repopulating denuded areas of ulcerated tissues through noninvasive transplantation procedures, such as through the use of a catheter.

19. Example 14

Therapeutic Compositions

The subject epiligrin complex, and epiligrin glycoproteins and peptide compositions may be administered to a human patient or other mammalian host in need of treatment by a variety of conventional routes of administration, including orally, parenterally, intravenously, intraperitoneally, intradermally, subcutaneously or intramuscularly. Compositions may also be administered transdermally (as in a lipid-soluble vehicle for a timed-release skin patch), or by nasal or oral instillation into the lungs (as with a nebulizer). In general, these compounds will be administered at dosages between 1 and 250 mg per kg body weight of the subject to be treated per day. However, some variation in dosage will necessarily occur depending on the condition of the patient being treated, and the physician will, in any event, determine the appropriate dose for the individual patient.

Pharmaceutically acceptable salts can be readily prepared from sorbinil and sorbinil analogs by conventional methods. Thus, such salts may be prepared by treating the sorbinil or sorbinil analog with an aqueous solution of the desired pharmaceutically acceptable metallic hydroxide or other metallic base and evaporating the resulting solution to dryness, preferably under reduced pressure. Alternatively, a lower alkanoic solution of the sorbinil or sorbinil analog may be mixed with an alkoxide of the desired metal, and the solution subsequently evaporated to dryness. The pharmaceutically acceptable hydroxides, bases, and alkoxides include those with cations that form metal salts with the acidic compounds of sorbinil and its analogs and that are nontoxic at the dosages administered to a patient in need of treatment. Suitable cations for this purpose include, but are not limited to, potassium, sodium, ammonium, calcium and magnesium.

The compounds may be administered alone or in combination with pharmaceutically acceptable carriers, in either single or multiple doses. Suitable pharmaceutical carriers include inert solid diluents or fillers, sterile aqueous solutions and various nontoxic organic solvents. The pharmaceutical compositions formed by combining the sorbinil or sorbinil analog with the pharmaceutically acceptable carrier are then readily administered in a variety of dosage forms, such as tablets, powders, lozenges, syrups, injectable solutions and the like. These pharmaceutical compositions can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrrolidine, sucrose, gelatin and acacia. Additionally, lubricating agents, such as magnesium stearate, sodium lauaryl sulfate, and talc are often useful for tableting purposes. Solid compositions of a similar type may also be employed as fillers in salt and hard-filled gelatin capsules; preferred materials for this purpose include lactose or milk sugar and high molecular weight polyethylene glycols. When aqueous suspensions of elixirs are desired for oral administration, the essential active ingredient therein may be combined with various sweetening or flavoring agents, colored matter or dyes, and, if desired, emulsifying or suspending agents, together with diluents such as water, ethanol, propylene glycol, glycerin, and combinations thereof. For parenteral administration, solutions of the sorbinil or sorbinil analog in sesame or peanut oil or in aqueous propylene glycol may be employed, as well as sterile aqueous solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well known to those skilled in the art. Additionally, it is also possible to administer the aforesaid compounds topically via an appropriate solution suitable for the present purposes at hand.

The subject compounds, when formulated as described above, will typically be packaged with printed instructions specifying their use as anti-cancer or anti-inflammatory compounds, e.g., for reestablishing normal growth control in carcinoma cells, or for inhibiting adhesion of activated lymphoid cells to epithelium, respectively.

20. Materials and Methods

20.1 Cells and Cell Culture

Normal newborn human foreskin keratinocytes (HFKs) were prepared as described by Boyce and Ham (1985) and maintained in serum-free Keratinocyte Growth Medium (KGM; Clonetics, San Diego, Calif.) containing insulin, epidermal growth factor (10 ng/ml), hydrocortisone, and bovine pituitary extract. The FE-A, FEPE1L-8 and FE-H18L cell lines are HFKs that have been transfected with transforming genes E6 and E7 from human papilloma virus 16 and 18 (94; 95).

Primary cultures of human foreskin fibroblasts (HFFs) were prepared by collagenase digestion of neonatal foreskins (e.g., Methods in Enzymology). HT1080 human fibrosarcoma cells were obtained from the American Type Culture Collection (Rockville, Md.). Tera-2 cells, human embryonal carcinoma, were obtained from Dr. Bruce Fenderson (Biomembrane Institute, Seattle, Wash.). OVCAR-4 cells (human ovarian carcinoma and T-47D cells (human mammary tumor) were obtained as gifts from Dr. Arnoud Sonnenberg (Central Lab. of Netherlands Red Cross, Amsterdam Holland). Peroxidase-, fluorescein-, and rhodamine-conjugated (goat) anti-mouse and anti-rat IgG and IgM (H and L chains) or peroxidase and rhodamine-conjugated (goat) anti-rabbit IgG and IgM (H and L chains) were obtained from Tago, Inc. (Burlingame, Calif.).

20.2 Antibodies and Immunochemical Reagents

Peroxidase-, fluorescein-, and rhodamine-conjugated (goat) anti-mouse and anti-rat IgG and IgM (H and L chains) or peroxidase and rhodamine-conjugated (goat) anti-rabbit IgG and IgM (H and L chains) were obtained from Tago, Inc. (Burlingame, Calif.). Fluorescein-conjugated avidin was from Vector Labs (Burlingame, Calif.). N-hydroxysuccinimido-Biotin was from CalBiochem (La Jolla, Calif.).

MAbs to the integrins $\alpha_3\beta_1$ (P1B5, P1F2), $\alpha_2\beta_1$ (P1H5), $\alpha_5\beta_1$ (P1D6), and $\beta_1$ (P4C10) have been described (20, 21, 57, 59, 96). P1H5 and P1D6 inhibit fibroblast, keratinocyte, and platelet adhesion to collagen-coated and fibronectin-coated substrates, respectively (21, 57, 59, 97). MAb P4C10 reacts with all $\beta_1$-containing integrins and inhibits cell adhesion to laminin, collagen, and fibronectin (20, 21). SP2 is a control-conditioned culture medium from the SP2 mouse melanoma. Monoclonal anti-tenascin, F9A5, was prepared in this lab (Maxwell and Carter, unpublished results). Monoclonal anti-$\alpha_6$ (GoH3) was from Dr. Arnoud Sonnenberg (Amsterdam, Holland) and inhibits platelet adhesion to laminin via $\alpha_6\beta_1$, (Sonnenberg et al., 1988) and carcinoma adhesion to laminin via $\alpha_6\beta_4$ (63). Rabbit anti-laminin (R5922) and anti-fibronectin were prepared as previously described (59 and 98, respectively). Mouse MAb 3E1 against integrin $b_4$ was a gift from Dr. Eva Engvall (La Jolla Cancer Res. Ctr., La Jolla, Calif.). Rabbit polyclonal antiserum against the carboxy terminus of the bullous pemphigoid antigen (BPA; R1086) was a gift from Dr. John R. Stanley (Dermatology Branch of the National Institutes of Health, Bethesda, Md.). Rabbit polyclonal anti-entactin was from Upstate Biotechnology, Inc. (Lake Placid, N.Y.).

20.3 Extracellular Matrix Adhesive Ligands

Mouse laminin (derived from EHS sarcoma, grown in mice) was purchased from Collaborative Research Inc. (Bedford, Mass.) or prepared in this lab. Plasma fibronectin and collagen type I were prepared as described (Wayner et al., 1988). Entactin was from Upstate Biotechnology, Inc. (Lake Placid, N.Y.). Tenascin and pepsinized human placental laminin were from Telios (San Diego, Calif.).

20.4 Cellular Adhesion to Extracellular Matrix Adhesive Ligand-Coated Substrates For immunofluorescence and interference reflection microscopy HFK-ECM was prepared by growing HFKs (or HFF) for three days in KGM on acid-washed glass cover slips (25 mm diameter). The adherent cells were removed by a three-step sequential extraction procedure: first, with 1% v/v Triton x-100 detergent (Sigma) in 10 mM sodium phosphate, buffered, pH 7.4, 0.14 M saline (PBS); second, with 2 M urea/1 M NaCl; and, third, with 8 M urea. The HFK-ECM was digested with DNase I for 30 minutes in 1% w/v HD-BSA (Sigma)/PBS. The resulting cover slips were washed with PBS, and blocked with HD-BSA (i.e., to avoid nonspecific binding of test antibody to the glass).

To test adhesion of cells to purified extracellular matrix ligands, acid-washed glass cover slips (25 mm diameter) were derivatized with dimethyldichlorosilane (Pierce, Rockford, Ill.); then coated with purified ligands (1 to 10 "N" symbol protein/ml); and finally blocked with 1% w/v HD-BSA in PBS as previously described (20, 21). Cells were adhered to the cover slips in KGM medium for periods of 1 hour to 3 days.

21. Example 15

Complete Nucleotide Sequence Transcripts and Polypeptide Corresponding to E170 Epiligrin Glycoprotein As disclosed above, epiligrin is a major component of epithelial basement membranes that mediates basal cell adhesion via integrin $\alpha_3\beta_1$. In an effort to further characterize epiligrin glycoproteins, a cDNA expression library was screened using a polyclonal rabbit antibody prepared against the extracellular matrix of human foreskin keratinocytes, i.e., HFK-ECM. A lambda gt11 expression library generated from human keratinocytes was screened with an affinity purified polyclonal antibody prepared against HFK-ECM using a method previously described (124). A 600 base pair cDNA clone, referred to as Ep-1 (deposited at the American Type Culture Collection, Rockville, N. Mex. and assigned ATCC No. 75540) was isolated, plaque purified, and used for additional studies.

Ep-1 was shown by two independent immunological methods to express a polypeptide immunologically indistinguishable from the 170 kDa component of epiligrin, herein referred to as E170. First, Ep-1 cDNA was expressed as a fusion protein, and the fusion protein was shown to serve as a specific antigen in preparation of immunosorbents that affinity purified anti-epiligrin antibodies from a polyclonal anti-HFK-ECM serum. For these experiments the Ep-1 fusion protein was immobilized on nitrocellulose and then incubated with anti-HFK-ECM polyclonal antiserum. The nitrocellulose blot was washed and the bound antibody eluted using 0.1 M glycine-HCl, pH 3.0. The eluate was neutralized using 1 M Tris-HCl, pH 7.4, and dialyzed against 0.1 M phosphate buffer, pH 7.4, 0.14 M saline (PBS). Finally, the Ep-1-expressed fusion-protein-adsorbed antibodies were tested for immunoreactivity against epiligrin, in this case purified by affinity chromatography on monoclonal P1E1 (as described in the Examples above). The adsorbed EP-1 fusion protein-reactive antibodies bound specifically to E170 in epiligrin after electrophoresis in SDS-PAGE (under reducing conditions) and following blotting of the polypeptide onto nitrocellulose (i.e., in a Western blot).

Second, polyclonal immune serum was raised to the Ep-1 fusion protein and shown to react specifically in immunoblot analysis with the E170 epiligrin glycoprotein. For these experiments Ep-1 cDNA was cloned into pGEX-1N (Amrad Corporation, Australia), which expresses a portion of the glutathione S-transferase gene. The fusion protein encoded by the chimeric construct was purified using glutathione agarose beads and then SDS-PAGE. An SDS-PAGE gel band containing the purified fusion protein was used to immunize a rabbit, and the resulting anti-serum was tested for immunoreactivity to purified epiligrin by Western blot analysis against the Ep-1 fusion protein, HFK-ECM (under reducing conditions), and P1E1-purified epiligrin. Anti-GST-Ep-1 fusion protein serum bound specifically to E170 in these Western blot analyses.

The experiments depicted in FIGS. 16A–16B illustrate the experiments showing that Ep-1 fusion protein expressed in pGEX-$^1$N can purify antibodies that recognize the 170-kDa subunit of epiligrin. The left panel (PROTEIN) shows a Coomassie Blue stain of purified epiligrin (P1E1 Ag) under reducing (+2-ME) and nonreducing conditions (−2-ME). The subunits of epiligrin are designated E170, E150, E135, and E100, based on molecular size in kilodaltons. "A" identifies high molecular mass disulfide-bonded aggregates of epiligrin. The right panel (IMMUNOBLOT) shows that the fusion protein expressed by the clone (Ep-1) can immunopurify antibodies from anti-HFK ECM polyclonal antiserum that react specifically with the 170-kDa subunit of epiligrin (P1E1 Ag). A second band of slightly lower molecular weight is detectable and may correspond to a degradation product or a second related polypeptide. The negative control antibody (CONTROL) showed no reactivity to epiligrin. B, Ep-1 fusion protein was used to generate a rabbit polyclonal antiserum. The Ep-1 immune serum reacts specifically with the 170-kDa subunit of epiligrin on an immunoblot containing purified epiligrin (P1E1 Ag) and HFK-conditioned culture media (Cond. Media). A nonspecific band was detected by the preimmune serum in the lane containing conditioned media. It should be noted that this band does not comigrate with the second band of slightly lower molecular weight that is detected by the Ep-1 immune serum. The negative control (Pre-Immune Serum) showed no reactivity to purified epiligrin (P1E1 Ag).

Heterogeneity of transcripts hybridizing to Ep-1 probe. Northern blot analysis was conducted using RNAs from human foreskin keratinocytes, fibroblasts, and transformed keratinocytes with $^{32}$P-DNA full length Ep-1 cDNA used as the probe. The results of these experiments showed (as expected) no expression of Ep-1 mRNA in fibroblasts.

Interestingly, in HFK cells Ep-1 transcripts were present as a doublet of bands at about 5 kb and about 6 kb, indicating two mRNA species for E170, and the possibility of alternatively spliced forms of E170. To further elucidate these two forms of transcript, the cDNA probe Ep-1 was used to examine factors that affect expression of epiligrin mRNA in cultured cells (FIGS. 17A–17B). Total cellular RNA was isolated by the guanidine isothiocyanate/ultracentrifugation method (Kingston et al., 1991), run on a 1% denaturing agarose gel, and transferred to nitrocellulose (Brown, 1993). DNA was radiolabeled with $^{32}$P by random priming, hybridized overnight at 42° C. in 50% formamide solution (#118, Maniatis), and washed at 54° C. in 0.1×SSC, 0.1% SDS.

This mRNA analysis revealed two different-sized $\alpha3_{Ep}$ transcripts (approximately 5 and 6 Kb in size) to be present in HFK RNA (FIG. 17A, lane 1). Lanes 2 and 3 indicate respectively that both $\alpha3_{Ep}$ transcripts were present at lower levels in RNA isolated from FEP18-11 and FEP1L-8, two lines of HFK that have been immortalized with human papilloma virus (FIG. 17A) (Kaur and McDougall, 1988; Kaur et al, 1989). These papilloma virus transformed cells lines display altered adhesive capabilities (ref. to Carter et al, 1990b; Kaur and Carter, 1992) which may be due in part to the down regulation of epiligrin mRNA that has been observed by the inventors. HFF cells, which do not express epiligrin, were included in lane 4 as a control (FIG. 17A). Positive hybridization to tubulin mRNA indicates that comparable amounts of RNA were loaded in FIG. 17A, lanes 1–4.

These observations were consistent with the results of multiple sequence alignments which had indicated that there are two distinct $\alpha_3$ transcripts that display variability within domain IIIa (see FIGS. 18A–18B; SEQ ID NOS:25 and 27). First, the cDNA clone 5-4-1 was independently isolated and shown to encode an amino-terminal domain which is different from that presented in FIGS. 19A–19R (SEQ ID NO:24). This second distinct transcript, referred to as $\alpha3_{EpB}$, maintains homology to $\alpha1$ laminin throughout domain III1 and into domain IV (FIG. 18B; SEQ ID NO:27 and 28). Second, PCR was performed in order to determine if both the $\alpha_3$ transcripts are expressed. Briefly, primer 11, which corresponds to a region of nondivergent sequence in cDNA clones 3-1-1, 5-4-1, and 5-4-2, was used to synthesize cDNA from mRNA using reverse transcriptase. Next, primers 11 and 14, as well as primers 11 and 16, were used to amplify distinct PCR products. A control RNA sample was included to ensure that the PCR products were generated from reverse-transcribed cDNA and not genomic DNA. DNA sequencing of the PCR products generated from reverse-transcribed mRNA confirmed that both the $\alpha_3$ message forms are present in HFK mRNA. Since the cDNA clones 5-4-1, 5-4-2, and 3-1-1 contain sequences which are absolutely identical throughout the 3' end of each clone (FIG. 18C; SEQ ID NO:29 and 30), the most reasonable explanation is that they represent two different products of the same gene. Third, sequencing of genomic clones corresponding to the LamA3 gene contained sequences for both the $\alpha3_{EpA}$ and the $\alpha3_{EpB}$ transcripts. It should be noted that the sequence provided in FIG. 18B (SEQ ID NO:27) was deduced from sequencing of the cDNA clone 5-4-1 and does not correspond to the 5' end of the $\alpha3_{EpB}$ transcript. A 5' RACE experiment was performed, and the size of the anchored PCR product revealed that the 5' end of the $\alpha3_{EpB}$ transcript extends approximately 2.0 kb beyond the sequence presented in FIG. 18B (SEQ ID NO:27). Preliminary sequencing of the RACE product revealed that the $\alpha3_{EpB}$ transcript maintains similarity to $\alpha1$ laminin and encodes a second EGF-like region upstream of domain IV. Despite the sequence of the $\alpha3_{EpB}$ transcript being incomplete, these data show clearly that the differential expression of the two $\alpha3_{Ep}$ transcripts would produce variability in domain IIIa, leading to the presence of two $\alpha_3$ epiligrin chains with different amino-terminal sequences.

The Applicants also examined the effect of differentiation in HFK cells on the level of $\alpha3_{Ep}$ transcripts. FIG. 17B shows that when proliferating HFK cells are induced to differentiate by adding calcium (1.3 mM Ca++, lane 2) or by increased cell density (lane 3), $\alpha3_{Ep}$ expression is concomitantly down regulated. In contrast, RNA isolated from subconfluent cultures expressed significantly higher levels of $\alpha3_{Ep}$ mRNA (FIG. 17B, lane 1). Under these conditions, a third transcript was detectable that appeared to be migrating behind the 7.5 Kb molecular weight marker (lane 1). Therefore, while the 6 Kb transcript appears to be the most abundant, there are clearly additional $\alpha3_{Ep}$ transcripts present in HFK RNA. As shown below, the Applicants have succeeded in isolating cDNA clones corresponding to at least two distinct $\alpha3_{EpA}$ transcripts.

These findings indicate that expression of E170 epiligrin glycoprotein (as measured with antibodies to E170 and probes for E170 mRNA) is an early marker for commitment of cells to differentiate into a cells of the epithelial lineage. In normal epithelial differentiation E170 is down-regulated so that mature basal epithelial stem cells (and their progeny) express only low levels of E170 mRNA. Basal stem cells, however, retain the capacity to express E170 following wounding (as described in Example 16, below), and E170 expression is increased in the epithelial "tongue" of cells that are migrating into wound sites. Thus, E170 is a useful marker for assessing damage to, and regeneration of, epithelial tissues.

Elucidation of nucleotide sequences encoding E170. As disclosed above, the first cDNA isolated that encodes a E170 epiligrin glycoprotein (Ep-1), was obtained by expression screening with polyclonal antibody. Since the experiments described above (e.g., FIGS. 16A–16B) provided convincing evidence that Ep-1 encodes a portion of the 170 kDa subunit of epiligrin, the inventors utilized Ep-1 as a probe to identify additional cDNA clones by screening cDNA libraries. Additional overlapping cDNA clones were isolated also by using the 5' RACE system. Both of these methods are discussed below, and are schematically depicted in FIG. 10A.

Analysis of the overlapping cDNA clones revealed two distinct transcripts that share some degree of sequence and structural homology, with the $\alpha1$ chain of laminin (see FIGS. 10B–10C). To maintain consistence with the laminin nomenclature proposed by Burgeson et al., the gene for epiligrin A chain has been designated as LamA3 and the two distinct transcripts as $\alpha3_{EpA}$ and $\alpha3_{EpB}$.

As compared with $\alpha3_{EpA}$, $\alpha3_{EpB}$ mRNA encodes a larger amino-terminal domain and contains additional EGF repeats and sequences corresponding to domain IV of $\alpha1$ laminin (FIG. 18B; SEQ ID NO:27). FIGS. 18A (SEQ ID NO:26) and 18B (SEQ ID NO:28), compare the partial amino-terminal sequences of proteins encoded by the $\alpha3_{EpA}$ and $\alpha3_{EpB}$ cDNAs. FIG. 18C (SEQ ID NO:30) depicts the common protein domain of $\alpha3_{EpA}$ and $\alpha3_{EpB}$, which is encoded by cDNA clones 3-1-1, 5-4-1, and 5-4-2 (FIG. 10F; SEQ ID NO:21). Nucleic acid sequencing of PCR products showed that HFK cells contain two distinct $\alpha_3$ transcripts in which either sequences A and C are continuous or sequences B and C are continuous.

Sequence Encoding E170

(1) 5' RACE system (GIBCO BRL, Gathersburg, Md.). Primer MR-3 (FIGS. 12A–12B; SEQ ID NOS:1–8) was used to prepare cDNA from total cellular RNA using reverse transcriptase. The cDNA clones that were generated were then tailed with dCTP using terminal transferase. Next, PCR was performed using an anchor primer (i.e., a primer hybridizing to the polyC tail) and primer MR-4 (FIGS. 12A–12B; SEQ ID NOS: 1–8). The resulting PCR product (also referred to herein as the "race-product") was shown by sequencing and hybridization in Northern and Southern blots to overlap with the original Ep-1 cDNA clone. The steps involved in this RACE method are depicted in FIG. 14.

(2) Library screening with nucleic acid probes. Primers MR4 and MR-8 (FIGS. 12A–12B; SEQ ID NOS:1–8) were used to synthesize a 650 bp fragment that overlaps with the Ep-1 cDNA. This 650 bp fragment was then labeled with $^{32}P$ and used to rescreen the cDNA library (FIG. 10A). Over 100 potential positive clones hybridized on a primary screening. Since this number of positive clones seemed too high, it was assumed that the amplified sequence was also hybridizing with a common sequence in several gene products. To impart specificity to the screening method the same filters were rescreened using $^{32}P$-radiolabeled Ep-1 as a probe. Four positive clones were identified in this screening and were isolated for further testing: cDNA clones "1-1" (about 2 kb in size), "2-3" (about 1.1 kb), "8-2" (about 1 kb), and "8-6" (about 1.6 kb). Clones 1-1 and 2-3 contain cDNA overlapping with each other and with cDNA in clone Ep-1, as well as with the 650 bp PCR product (above).

By nucleotide sequencing, Ep-1 was shown to contain 600 bp encoding a helix region of the E170 polypeptide. A cloning artifact was also identified in the first 150 bp of the clone sequence, namely, ribosomal RNA nucleotide sequence unrelated to E170. (The compiled nucleotide sequence in FIGS. 11A–11C (SEQ ID NO:22) and 15A–15F (SEQ ID NO:23) were edited to remove the unrelated rRNA sequence.)

The overlapping cDNAs used to compile the E170 nucleotide sequence (FIGS. 15A–15F; SEQ ID NO:23) are shown in FIG. 10D. Sequence analysis revealed that clone Ep-1 encodes a helix region of E170 glycoprotein; clone "1-1" an EGF-like region of E170 (FIG. 10F; SEQ ID NO:21); and, clone "8-6" encodes a potentially globular region of E170. The complete E170 nucleotide and protein sequences are shown in FIGS. 15A–15F (SEQ ID NO:23) and the composite nucleotide sequence of E170 as contained in 1-1, the Race-product (above), and EP-1 is shown in FIGS. 11A–11C (SEQ ID NO:22).

Characterization of the E170 transcript and the protein it encodes. The composite sequence provided in FIGS. 15A–15F (SEQ ID NO:23) depict the entire $\alpha 3_{EpA}$ transcript. The adenine residue presented as nucleotide 1 (FIG. 15A; SEQ ID NO:23) is based on sequence analysis of a 5' RACE product that showed this residue to correspond to the 5' end of the $\alpha 3_{EpA}$ transcript.

The open reading frame shown in FIGS. 15A–15F (SEQ ID NO:23) corresponds to the $\alpha 3_{EpA}$ transcript and encodes a probable signal peptide followed by domains IIIa, II/I, and G. FIGS. 15A–15F depict the nucleotide sequence and FIGS. 19A–19R (SEQ ID NO:24) the polypeptide sequence. The initiator methionine (amino acid 1) was designated as such because it is followed by a sequence that likely corresponds to the signal peptide (FIG. 19A; SEQ ID NO:24), and it is flanked by a nucleotide sequence that is consistent with the consensus sequence reported for translation initiation of vertebrate mRNAs (#137). The proposed signal peptide is followed by a short protein domain and then by a cysteine-rich domain comprised of multiple EGF repeats with similarity to those found in domain IIIa of the laminin α1 chain (ref. Sasaki et al., 1988). Domain IIIa (FIGS. 19B–19C; SEQ ID NO:24, residues 46–201) of the $\alpha 3_{EpA}$ translation product contains two complete EGF repeats that show conserved spacing between cysteine residues 1, 2, and 8 and between cysteine residues 5, 6, and 7. This conserved spacing is strictly maintained in the EGF repeats that have been identified in all three laminin chains (Sasaki et al., 1987, 1988; Sasaki and Yamada, 1987). The last EGF repeat of the $\alpha 3_{EpA}$ chain diverges from the α1 chain of laminin and is a partial repeat containing 4 cysteine residues that conform with the arrangement described by Sasaki et al., (1988). The sequence identity in domain IIIa between the human $\alpha_3$ and $\alpha_1$ (Nissinen et al., 1991) laminin chains was found to be 46%, whereas a comparison of the human $\alpha_3$ and $\alpha_2$ merosin chains (Ehrig et al., 1990; Vuolteenaho et al., 1994) revealed a slightly higher sequence identity (48%). Regions of high sequence homology across domain III were also observed upon comparison of the $\alpha_3$ chain of epiligrin with a Drosophila α chain homologue (ref., Garrison et al., 1991). In particular, a differentially expressed region encoding the first one-half EGF repeat of domain IIIa in the $\alpha 3_{EpB}$ transcript (FIG. 18B; SEQ ID NO:27) showed high conservation across the Drosophila and vertebrate α chain homologues. The sequence identity between the $\alpha_3$ and $\alpha_1$ laminin chains is only 22% in domains I and II; however, the structural similarity is maintained.

FIGS. 19A–19R (SEQ ID NO:24) diagram several features of the translated amino acid sequence of $\alpha 3_{EpA}$. The proposed signal peptide (S.P.) is identified in FIG. 19A (SEQ ID NO:24). Structural protein domains and the 3'-untranslated sequence (3' UTR) are shown in FIGS. 19B–C, 19D–H, 19I–J, 19K–L, 19M–N, 19O–P, and 19Q–R (SEQ ID NO:24). Cysteine residues are shown as "Cys". The first cysteine residue of the EGF-repeats are marked with a black triangle and the first two cysteine residues in domains I/II are marked with a black diamond. Potential glycosylation sites are boxed, and consensus sequences for adhesion recognition sites are shaded.

The $\alpha_3$ chain of epiligrin contains a series of heptad repeats (FIGS. 19D–H; SEQ ID NO:24, residues 202–793) which are characteristic of proteins that form an α-helical coiled coil structure (ref., Cohen and Parry, 1986; Beck et al., 1990). The presence of an α-helical domain in the $\alpha_3$ chain of epiligrin suggests that it is capable of interacting with laminin chains to form a heterodimeric coiled structure (Hunter, 1990). The two cysteine residues which are found at the beginning of domain II (residues 202 and 205) could stabilize epiligrin heterotrimers by forming intermolecular disulfide bonds as was proposed previously for EGS laminin (Sasaki et al., 1988). These cysteine residues are also present in the $\beta_3$ chain of laminin-5 (B1k; Gerecke et al., 1994) and K2 chain (B2t; Kallunki et al., 1992) suggesting that they may be important for stabilizing the isoforms of laminin that are found in skin.

The $\alpha_3$ chain of epiligrin contains two potential cell adhesion recognition sequences, RGD (FIG. 19G; SEQ ID NO:24, residues 658–660) and LDV (FIG. 19D; SEQ ID NO:24, residues 313–314), within the α-helical domain. These sequences were shown to mediate cell adhesion to fibronectin through integrin $\alpha_5\beta_1$ (Wayner et al., 1989; Guan and Hunes, 1989; Komoriya et al., 1991), respectively. A sequence SKVAV (FIG. 19H; SEQ ID NO:24, residues 765–769) was also identified at the carboxyl-terminal end of the α-helical domain which is homologous in sequence and position to a regulatory sequence in the laminin α1 chain (SIKVAV) that mediated cell growth (Kubota et al., 1992) and metastases (Kanemoto et al., 1990).

Amino acids 794 through 1713 (FIG. 19I; SEQ ID NO:24), comprise the G domain of the $\alpha 3_{EpA}$ transcript. In EHS sarcoma laminin, the G domain has been shown to have an internal repeating structure composed of five tandem repeats with approximately 180 amino acids per repeat (Sasaki et al., 1988). Data compiled from a multiple sequence alignment (Schuler et al., 1991) indicated that the $\alpha_3$ chain of epiligrin contains five subdomains which are individually related to the Drosophila and vertebrate α chains. A Dotplot analysis (Maizel and Lenk, 1981; Wilbur, 1983) comparing the $\alpha_3$ chain to itself and to other α chains revealed that the $\alpha_3$ subdomains (G1–G5) are more closely related across different α chains than they are to one another. This is consistent with a report by Garrison (1991) which compared the sequence of the G domain form Drosophila with other laminin α chains. A BLAST protein search (Altschul et al., 1990) revealed that the G4 and G5 subdomains of epiligrin are also related to the heparin sulfate proteoglycan core protein (Noonan et al., 1991) and the neurexin family of proteins (Ushkaryov et al., 1992).

Although multiple sequence alignments (Schuler et al., 1991; Altschul et al., 1990) identified five G subdomains in $\alpha_3$ epiligrin (FIGS. 19I–R; SEQ ID NO:24, subdomains G1–G5) that are related to G subdomains described by Sasaki et al. (1988), there is evidence of increased sequence divergence in the $\alpha_3$ chain. A comparison of the $\alpha_3$ G domain to either the α1 (Nissenen et al., 1991) or α2 (merosin; Ehrig et al., 1990) G domains revealed less than 25% identity. In contrast, when the α1 and α2 chains are compared with one another, they share 41.8% sequence identity across the G domain (Vuolteenaho et al., 1994). This suggests that the $\alpha_3$ chain of epiligrin may represent a new category of functionally distinct α chain homologues.

The structure of E170 glycoprotein deduced from the nucleotide sequence of FIGS. 15A–15F (SEQ ID NO:23) have overall similarity to the structure found in laminin A chain, but (as shown in the Examples, above) antibodies to laminin fail to bind to epiligrin, P1E1 fails to bind to laminin, polyclonal antibodies raised to epiligrin fail to bind to laminin, and $^{32}$P-radiolabeled full length Ep-1 used as probe in Northern blots fails to detect any species of mRNA other than 5 kb and 6 kb transcripts that are appropriate in size for E170 glycoprotein.

As disclosed in the Examples, E170 polypeptide, antibodies to E170, and E170 mRNA are markers useful in identifying abnormal patterns of epiligrin expression and thus monitoring basal cell differentiation in the epithelium. For instance, epiligrin is not expressed in basal cell carcinoma and skin diseases such as junctional epidermolysis bullosa gravis (as disclosed in the Examples, above; and also independently confirmed, 114).

Moreover, the amino acid sequences shown in FIGS. 19A–R (SEQ ID NO:24) provide one skilled in the art with the information needed to create synthetic polypeptides whose properties resemble those of epiligrin E170. Synthetic polypeptides of the invention comprise at least 5 amino acids, corresponding to at least 15 consecutive nucleic acids from the sequence of FIGS. 15A–15F (SEQ ID NO:23). Methods are well known to those skilled in the art for synthesizing polypeptides having a predetermined amino acid sequence.

Epiligrin expression in healing wounds. To further examine changes in the patterns of expression of epiligrin in regenerating tissues, expression of Ep-1 mRNA was investigated in wound sites using in situ hybridization and immunochemical staining. For the in situ work, Ep-1 (600 bp) was cloned in both orientations into a Bluescript expression vector (Stratagene, La Jolla, Calif.) so that sense and antisense cRNA probes could be synthesized using the T7 promoter. cRNA probes were labeled with digoxigenin-11-UTP (Boehringer Mannheim Biochemicals, St. Louis, Mo.) and then cleaved by alkaline hydrolysis to an average size of 100–150 nucleotides. Probes were incubated with tissue slides containing formaldehyde-fixed cryostat sections of punch biopsies from wounded epidermis (including adjacent non-wounded epidermis), and processed for immunohistochemical staining. Bound probes were visualized using affinity purified anti-digoxigenin antibody coupled to alkaline phosphatase and a colorimetric assay was used to localize bound probe within the tissue. (Ep-1 sense probes were used as a control and they showed no signal above background on the indicated tissues.)

The highest observed steady state of $\alpha 3_{EP}$ mRNA observed by the inventors has been in subconfluent keratinocytes that are still actively migrating. Taking this observation one step further, the inventors used the above-described methods to examine the expression of this mRNA in human skin harvested 55 h after the introduction of a wound. The wounding of skin results in the transition of keratinocytes from a sedentary to a migratory state (Grinnell, 1992). As shown in FIG. 20A, the antisense cRNA probe localized $\alpha 3_{EP}$ mRNA to keratinocytes in the wound site, but not to keratinocytes flanking the wound site (FIG. 20B). The sense probe (FIGS. 20C–20D) was negative as expected. An antisense probe for keratin 14 (FIGS. 20E–20F) showed that keratin 14 mRNA is detectable in the basal cells of both wounded and normal epidermis. FIGS. 20E and 20H illustrate the localization of epiligrin and integrin $\alpha_3\beta_1$ in the wound site. Immunoperoxidase staining using anti-epiligrin (MAb P1E1, FIG. 20G) and anti-$\alpha_3$ antibodies (MAb P1F2, FIG. 20H) shows that epiligrin protein is present in the newly synthesized basement membrane (BM) (FIG. 20E, arrows), and integrin $\alpha_3\beta_1$ relocalizes from the apical and lateral surfaces to the basal surface (FIG. 20H, arrows). The epidermis and dermis are marked as E and D, respectively.

The localization of the $\alpha 3_{EP}$ transcript in the wound site is correlated with the reorganization of integrin $\alpha_3\beta_1$ from the apical and lateral to the basal surface of the keratinocytes (FIG. 20H) in contact with the newly synthesized epiligrin present in the basement membrane (FIG. 20G). The reorganization of integrin $\alpha_3\beta_1$ suggests that keratinocytes may utilize integrin $\alpha_3\beta_1$ in cell/substrate adhesion mediated by epiligrin for motility during wound repair. Thus, expression of E170 epithelial ligand glycoprotein in epidermal tissues distinguishes between regenerating epithelial tissues (where expression is high) and non-regenerative epithelial tissues or malignant tissues (where expression is low). Many situations exist in histopathological examination where it would be most helpful to be able to distinguish between a normal regenerative event in an epithelial tissue (e.g., resulting from traumatic injury or infection) and an abnormality that might be a neoplastic or preneoplastic event. Examining E170 epiligrin glycoprotein expression (e.g., using immunochemical techniques or in situ hybridization) provides a way in which normal regenerative events can be distinguished from premalignant and malignant events.

22. Materials and Methods for Example 15

22.1 DNA Sequencing. cDNA inserts were amplified using Taq Polymerase (Perkin-Elmer Cetus), purified on an agarose gel, and directly sequenced using either the Taq DyeDeoxy™ Terminator Cycle Sequencing Kit (Applied Biosystems, Inc., Foster City, Calif.) or a modified version of Sanger et al. (120) with Sequenase (USB, Cleveland, Ohio). Deduced amino acid sequence was compared to the available data bases through searches with both Blast/ncbi.nlm.nih.gov. and Blitz/EMBL-heidelberg.de using the homology matrix described by Henikoff and Henikoff (115).

22.2 Northern Blot Analysis. Human foreskin keratinocytes, fibroblasts, and transformed keratinocytes were prepared as previously described (113; 166–117). Total cellular RNA from each of these cell types was isolated by the guanidine isothyocyanate method, run on a 1% denaturing agarose gel, and transferred to nitrocellulose (118). Ep-1 cDNA (0.6 kb) was radiolabeled with $^{32}$P by random priming, hybridized overnight at 42° C. in 50% formamide solution (118), and washed at 54° C. in 0.1×SSC/0.1% SDS.

22.3 In situ Hybridization. Ep-1 (600 bp) was cloned in both orientations into a Bluescript expression vector (Stratagene, La Jolla, Calif.) so that sense and antisense cRNA probes could be synthesized using the T7 promoter. cRNA probes were synthesized using T7 RNA polymerase and labeled with digoxigenin-1 1-UTP (Boehringer Mannheim Biochemicals, St. Louis, Mo.). Full length probes were then cleaved by alkaline hydrolysis to an average size of 100–150 nucleotides. Probes were incubated with slides containing formaldehyde-fixed cryostat sections overnight at 50° C. in hybridization buffer (50% formamide/5×SSC/1 mg/ml yeast tRNA/100 μg/ml heparin/1× Denhardts/0.1%

Tween 20/0.1% CHAPS). Slides were treated for 30 minutes at 37° C. with 20 µg/ml of RNase A, washed twice at room temperature with 2× SSC for 30 minutes, and washed twice at 50C in 0.1× SSC for 30 minutes. Next, slides were equilibrated in PBS and processed for immunohistochemical staining. An affinity purified anti-digoxigenin antibody coupled to alkaline phosphatase (Boehringer Mannheim Biochemicals) followed by a colorimetric assay was used to localize bound probe within the tissue.

22.4 Tissue Preparation. Punch biopsies of wounded epidermis, including adjacent non-wounded epidermis, was taken from a human volunteer at several different time points (22, 55, and 79 hours) and then embedded directly in OCT. Cryostat sections (12 µm) were placed on aminoalkylsilane-treated slides, fixed in 4% paraformaldehyde, treated with 0.25% acetic anhydride in 0.1 M triethanolamine, rinsed in 2× SSC, and then dehydrated through a series of alcohol solutions (30%, 50%, 70%, 95%, 100%).

23. Example 16

Regulation of Epiligrin Expression: Effects of Cell Density, Wounding, Oncogenic Transformation and Growth Factors Epidermal wound healing is characterized by migration of the regenerating epithelium in a migratory tongue across a bed of newly formed granulation tissue. Using immunochemical techniques and several different monoclonal antibodies directed to epiligrin, it has been observed that epiligrin is deposited in the basement membrane at the leading edge of the migratory tongue of epithelium 24, 48, and 72 hours after wounding in normal human volunteers. In these wound sites epiligrin and $\alpha_3\beta_1$ were localized to the basal surface of the cells in the migrating epithelial tongue. In situ hybridization with antisense cRNA probes specific for E170 identified elevated E170 mRNA levels in the epithelial cells in the wound site (see, e.g., FIG. 20A). These data suggest that $\alpha_3 \beta_1$ and epiligrin are involved in wound repair, perhaps in relation to deposition and assembly of epiligrin in the basement membrane upon which the epithelial cells must migrate. Further, when the migrating epithelial tongue reestablished contact with the surrounding epidermis, the level of epiligrin expression observed immunocytochemically was decreased. Thus, epiligrin expression may serve to limit migration of the epithelial tongue and prevent keloid formation in the epidermis. In contrast to the findings with epiligrin, laminin and $\alpha_6\beta_4$ were reduced in the cells at the leading edge of the migratory epidermal tongue, consistent with a possible role of laminin in forming stable (i.e., non-migratory) hemidesmosome structures for non-migrating cells.

Cell-cell contact down-regulates expression of certain cellular proteins in normal cells, but not tumor cells, and is commonly studied by establishing cell cultures at different cell densities. A comparison was made of E170 expression in HFK cells grown at low and high cell density (i.e., confluence) using Northern blot analysis to examine the levels of expression (FIG. 17B). E170 expression was dramatically increased in cells grown at low density, and expression was decreased in confluent cells. Further, detachment of HFK cells from the substratum in vitro caused a decrease in the level of epiligrin expression observed immunohistochemically. Oncogenic transformation of HFK cells, i.e., using retroviral vectors encoding HPV E6 and E7, resulted in decreased expression of E170 (FIG. 17A). Considering these findings in the light of epiligrin expression during wound healing (above) and disease, it seems likely that lowering cell density at an epithelial site (i.e., by wounding) may induce increased epiligrin expression, and detachment of the epidermis from dermis (e.g., in blistering diseases) may inhibit expression of epiligrin. In the latter case, decreasing cell density and restoring epithelial cell contact with a material containing epiligrin may prove useful for therapeutic intervention in epithelial dysjunction diseases such as acquired and genetic epidermal disorders, ulcerative colitis, Crohns disease, and cholera. It should also be noted that decreased expression of epiligrin in transformed cells contrasts markedly with the observed expression in wound sites, and that pathological metastasis of malignant cells into tissue sites may be distinguished from normal regeneration by examining the level of epiligrin expression in the cells (e.g., using in situ hybridization or immunocytochemical methods). In the latter case normal regenerating cells have high levels of epiligrin expression and tumor cells have low levels.

The combined results (above) suggest that interaction of epiligrin with the $\alpha_3\beta_1$ receptor regulates migration and growth of epithelial cells. Additional experiments were conducted in which the receptor-ligand interaction was disrupted and the effects were observed. Incubation of keratinocytes in vitro with anti-$\alpha_3\beta_1$ was observed to inhibit cell adhesion to epiligrin, stop migration of the cells on the tissue culture surface, and induce cell-cell adhesion that resulted in rounded balls of aggregated cells. The differentiative state of the cells in the keratinocyte aggregates was examined using immunohistochemical identification of involucrin, a marker for epithelial cell differentiation. Keratinocytes in the cellular aggregates exhibited increased involucrin expression, and a subcellular morphology consistent with differentiation. Thus, the results are consistent with the notion that inhibition of epiligrin binding to $\alpha_3\beta_1$ induces terminal differentiation in keratinocytes. The observed effects of epiligrin are contrasted with those of fibronectin, which interacts with $\alpha_5\beta_1$ receptors in cells to induce decreased (rather than increased) expression of involucrin. Because fibronectin is expressed in wounded epidermis, and not in normal regenerating epidermis, it is most likely that $\alpha_5\beta_1$-fibronectin interactions inhibit differentiation during wound repair, while the $\alpha_3$ $\beta_1$-epiligrin interaction plays a role in normal epithelial regeneration by preventing basal stem cells from differentiating (i.e., while in contact with epithelial ligand) and by stimulating terminal differentiation in progeny cells (i.e., when released from contact with epiligrin).

The role of the $\alpha_3\beta_1$-epiligrin interaction in regenerating epidermis was studied further by testing the effects of dermal growth factors, i.e., TGF$\alpha$ and TGF$\beta$, on expression of epiligrin in vitro as measured by Northern blotting for E170 mRNA. For these experiments, HFK cells were established in cell culture and grown to approximately 75% confluency so that expression was down-regulated and the cells assumed a resting state. Next, to determine whether dermal growth factors could induce expression of epiligrin, 30 ng/ml of TGF$\alpha$, or 20 ng/ml of TGF$\beta$, were added to separate cultures and the cells were cultured for an additional 24 hrs. A control culture was included in which the medium was changed but no growth factors were added. Finally, epithelial ligand expression was measured by Northern blotting for E170 mRNA. The results obtained showed about a 2-fold increase in epiligrin expression with either TGF$\alpha$ or TGF$\beta$ over the level of expression seen in the control culture.

24. Example 17

Chromosomal Localization of the Human LamA3 Gene

Fluorescent in situ hybridization was performed using the P1 genomic clone DMPC-HFF#1-1034F10 which contained coding sequences for the human LamA3 gene. The results, shown in FIG. 21, localized the human LamA3 gene to chromosome 18q11.2. The human laminin $\alpha_1$ chain (LamA1) was also found on chromosome 18 but mapped to 18p11.3 (Nagayoshi et al., 1989), a locus distinct from that of LamA3.

The probe for the chromosomal localization was prepared by nick-translation with biotin label and was hybridized to normal human metaphase cells as described previously (VanDevanter and Yirdaw, 1993). Hybridized probe was detected with Texas red avidin and chromosomes were identified by fluorescence R-banding with chromomycin A3/distamycin A (VanDevanter et al., 1994). Texas red and chromomycin A3 signals were excited independently using a Nikon Optiphot-2 epifluorescence microscope and captured as 8-bit black and white digital TIFF images using an intensified CCD camera and a SAMBA 4000 image analysis system (Imaging Products International, Chantilly, Va.). Chromomycin A3 intensities were linearly reduced to generate gray countersignals, digitally added to Texas red signals collected from the same fields, and printed as black and white images on a Phaser IISDX dye sublimation printer (Techtronix, Beaverton, Oreg.).

25. Example 18

Novel Assay for Epiligrin Function

25.1 Trypsin-treated HFK-ECM: "Epiligrin-ECM"

As described above, differential extraction with Triton X-100 and urea may be used to prepare a tissue culture surface coated with substantially purified epiligrin complex. The yield of epiligrin coated matrices is relatively low, and so studies were conducted to determine whether detaching HFK from ECM with trypsin (i.e., as cells were passaged) left an epiligrin that might be suitable for use in adhesion assays. To distinguish epiligrin made in this manner from those of previous methods the preparations are referred to herein as "epiligrin-ECM" was an adhesive substrate in adhesion assay, and surprisingly, the substrate adhered cells more rapidly (i.e., more than >90% of HFK were attached in less than 5 minutes) and tightly (i.e., not easily removed with strong shaking) than epiligrin substrates.

As a first step, the relative role of epiligrin in the attachment was investigated using anti-epiligrin monoclonal antibody and $\alpha_3$-transfected K562 cells ($\alpha_3$-K562). Weitzman et al. (1993) reported that expression of $\alpha_3$ integrin in K562 was sufficient for adhesion to HFK-ECM differentially extracted to prepare an epiligrin-coated substratum. These findings were confirmed and extended in the present studies. When $^{51}$Cr-labeled $\alpha_3$-K562 were incubated with different ECM ligands, the cell preferentially attached and spread on the epiligrin-ECM$^t$. EHS laminin, collagen type I (COL; $\alpha_2\beta_1$-mediated) and BSA failed to support adhesion of $\alpha_3$-K562. A partially purified laminin preparation from human placental basement membranes also failed to induce adhesion. Adhesion of $\alpha_3$-K562 to epiligrin-ECM$^t$ was inhibited with anti-$\alpha_3\beta_1$ (P1H8) and anti-$\beta_1$ (P4C10) monoclonal antibodies, confirming the involvement of both the transfected $\alpha_3$ and the $\beta_1$ subunits in attachment (i.e., the $\alpha_5$ and $\beta_1$ subunits are biosynthetic products of K562 cells, and adhesion of $\alpha_3$-K562 cells to fibronectin was inhibited by anti-$\alpha_5$ confirming the existence of the $\alpha_5\beta_1$ receptor). Anti-$\alpha_5$ had no effect on adhesion to epiligrin-ECM$^t$.

As a second step, the adhesion of HFK to epiligrin-ECM$^t$ was tested. While the results with $\alpha_3$-K562 (above) followed a relatively predictable pattern, a surprising observation was made with HFKs. Adhesion of HFKs to epiligrin-ECM$^t$ was not inhibited with anti-$\alpha_3$ or anti-$\beta_1$, (i.e., suggesting the involvement of a receptor other than $\alpha_3\beta_1$) but, spreading of HFK on epiligrin-ECM$^t$ was inhibited with both anti-$\alpha_3$ and anti-$\beta_1$. These combined results suggested that $\alpha_3\beta_1$ mediated spreading of HFK but some other receptor mediated attachment.

25.2 Dual Roles of $\alpha_3\beta_1$ and $\alpha_6\beta_4$ in Attachment and Spreading of HFK As described above, adhesion of human foreskin keratinocytes (HFK) to epiligrin is mediated through $\alpha_3\beta_1$ in focal adhesions and $\alpha_6\beta_4$ in hemidesmosomes. Studies were conducted in which the relative roles of $\alpha_3\beta_1$ and $\alpha_6\beta_4$ were determined i) by investigating epiligrin-ECM$^t$ adhesion of $\alpha_3$-transfected K562, human fibroblasts, and HT1080 cells, (all of which have only the $\alpha_3\beta_1$ receptor) and comparing the results with those obtained with HFK (having both the $\alpha_3\beta_1$ and $\alpha_6\beta_4$ receptors); and, ii) by evaluating $\alpha_6\beta_4$ mechanisms at 4° C., (i.e., a condition that inhibits $\alpha_3\beta_1$-dependent cell adhesion). The results obtained in these experiments are summarized below.

For $\alpha_3\beta_1$ mediated adhesion, attachment and motility of $\alpha_3$-transfected K562, human fibroblasts, and HT1080 cells were blocked by monoclonal antibodies to $\alpha_3\beta_1$, and epiligrin, or by culture at 4° C.; in the latter case, 4° C. inhibits energy metabolism required for actin rearrangement in the cytoskeleton and test cells that express $\alpha_3\beta_1$, but not $\alpha_6\beta_4$ (e.g., HFF, HFM, and HT1080), adhere to epiligrin-ECM$^t$ and collagen at 37° C. but not to any ligand at 4° C. Adhesion to epiligrin via $\alpha_3\beta_1$ induced transmembrane signaling through tyrosine-phosphorylation of a focal adhesion kinase (FAK; 125 kDa).

For $\alpha_6\beta_4$ mediated adhesion, the attachment of HFK occurred without spreading at 4° C., did not require energy metabolism and actin cytoskeletal rearrangement, and was inhibited by anti-$\alpha_6$ alone. Thus, $\alpha_6\beta_4$ was capable of mediating attachment of HFK independent of $\alpha_3\beta_1$. Hemidesmosome adhesion structures assembled on epiligrin at 4° C. contained $\alpha_6$, $\beta_4$ and bullous pemphigoid antigen I (BPA1) as a Triton X-100-insoluble complex. $\alpha_6\beta_4$ mediated adhesion of HFK to epiligrin was distinguished from that mediated by $\beta_1$ integrins in the following manner: (1) it was more rapid; (2) it occurred at 4° C.; (3) it did not result in cell spreading; (4) it did not induce phosphorylation of FAK; (5) it did not induce formation of Triton X-100 detergent-insoluble adhesion structures (i.e., the type involved when both $\alpha_3\beta_1$, and $\alpha_6\beta_4$ mediate adhesion, below). At 4° C. HFK failed to adhere to fibronectin and EHS laminin, indicating that under these conditions the assay is specific for $\alpha_6\beta_4$ receptors, and that the $\alpha_6\beta_4$ receptors form stable adhesion contact only with epiligrin at 4° C.

For $\alpha_3\beta_1$ and $\alpha_6\beta_4$ mediated adhesion, HFK attachment and motility at 37° C. required both $\alpha_3\beta_1$ and $\alpha_6\beta_4$; monoclonal antibodies to $\alpha_3$ blocked spreading but not attachment; and, anti-$\alpha_6$ blocked neither spreading nor attachment, but the combination of anti-$\alpha_3$ and anti-$\alpha_6$ successfully blocked both spreading and attachment. In addition, both $\alpha_3\beta_1$ and $\alpha_6\beta_4$ appeared to mediate their effects through epiligrin, since anti-epiligrin monoclonal antibodies blocked adhesion through both receptors.

Thus, epithelial cells, in contrast to many other cells that express only $\alpha_3\beta_1$ receptors, control motility on epiligrin (i.e., through $\alpha_3\beta_1$ and transmembrane signaling) and stable anchorage on epiligrin (i.e., through $\alpha_6\beta_4$) by differential expression of these two integrin receptors in hemidesmosomes.

The foregoing may be better understood in connection with FIGS. 22A–22B. As shown in FIG. 22A, suspended cells (1) that express $\alpha_3\beta_1$ (including $\alpha_3$-K562 cells, melanocytes, HT1080 cells, and fibroblasts) attach and spread on epiligrin via $\alpha_3\beta_1$ at 37° C. (3), but not at 4° C. (2) or in the presence of anti-$\alpha_3$ or anti-epiligrin. Attachment and spreading involves formation of FAs and phosphorylation of FAK (FAK→P-FAK). As shown in FIG. 22B, suspended cells (1) that express $\alpha_3\beta_1$, and $\alpha_6\beta_4$ (including HFKs) utilize $\alpha_3\beta_1$ for motility (attachment, spreading and migration) at 37° C. (3) and $\alpha_6\beta_4$ for stable anchorage without spreading at 4° C. (2) and 37° C. (3). Adhesion at either temperature is blocked with anti-epiligrin monoclonal antibodies. HFKs anchored at 4° C. via $\alpha_6\beta_4$ (2) will spread via $\alpha_3\beta_1$ when warmed to 37° C. (3). This spreading is blocked with anti-$\alpha_3\beta_1$. Anchorage via $\alpha_6\beta_4$ at 4° C. does not require phosphorylation of FAK while spreading via $\alpha_3\beta_1$ induces tyrosine phosphorylation of FAK (3).

25.3 The $\alpha_6\beta_4$ Receptor Participates in Adhesion and HDs in Migratory HFK at 37° C.

The effects of anti-$\alpha_6$ on the distribution of the $\alpha_6$, $\beta_4$, BPA1, epiligrin, Talin protein components of HDs and FAs was examined using immunohistochemical techniques and interference reflection microscopy to identify co-localization of the proteins in FAs and HDs. Anti-$\alpha_6$-treated cells continued to adhere and spread, but failed to form colonies and acquired an elongate morphology indicative of migratory cells. Anti-$\alpha_6$ did not disrupt localization of $\alpha_3$ or Talin in FAs, but did disrupt the co-localization of $\alpha_6$, $\beta_4$, and BPA1 (a cytoplasmic component of HDs) in FAs. These results confirm that at 37° C. $\alpha_6$ associates with $\beta_4$ and BPA1 in immature HDs and contributes to adhesion of HFKs on epiligrin-ECM$^t$.

25.4 Domain-Specific Anti-Epiligrin Antibodies

It was considered highly likely that the epiligrin ligand protein amino acid sequence domain involved in integrin $\alpha_3\beta_1$ receptor binding to epiligrin-ECM$^t$ were different than those involved in $\alpha_3\beta_1$ or $\alpha_6\beta_4$ binding to non-trypsin-treated epiligrin. To identify the additional functional domain in epiligrin, monoclonal antibodies were selected that inhibited binding of cells to epiligrin-ECM$^t$. For these experiments HFK were grown on cellophane sheets, and the HFK-ECM deposited on the sheets by the cells was used as an antigen for immunization of BALB/c mice. Hybridoma clones were selected based on immunoreactivity in a solid phase ELISA with epiligrin (i.e., solid phase antigen). Three monoclonal antibodies from the resulting library of clones were selected for additional testing for their ability to immunoprecipitate $^{35}$S-methionine biosynthetically-radiolabeled HFK-ECM proteins (i.e., in the presence of Staphlococcal Protein A). Anti-epiligrin monoclonal antibody P1E1 was used as a control. Immunoprecipitated proteins were evaluated on SDS-PAGE under reducing (i.e., using 2-mercaptoethanol) or non-reducing conditions. The results showed that monoclonal antibodies P1E1, C2-9, G3-3, and B4-6 specifically immunoprecipitate a disulfide-bonded high molecular mass complex from HFK-ECM (non-reduced) that contained only E170, E135, and E100/145 (i.e., following reduction). Monoclonal antibodies C2-9, G3-3, and B4-6 were not reactive with human or mouse laminin, tenascin, thrombospondin, collagen types I, IV or VII, fibronectin, human placental basement membrane proteins, or BSA.

Next, monoclonal antibodies capable of inhibiting adhesion and spreading of HFK on epiligrin-ECM$^t$ were identified using $^{51}$Cr-radiolabeled test cells, and the assays described in the Examples above in regard to P1E1. Adhesion of $\alpha_3$-transfected K562 cells to epiligrin-ECM$^t$ (i.e., via the $\alpha_3\beta_1$ receptor) was inhibited to about 43% (of the control level of cpm bound) by monoclonal antibody C2-9, but not by D3-4, B4-6, G3-3 or P1E1. Control experiments demonstrated that C2-9 had no inhibitory effect on binding of the $\alpha_3$-K562 to collagen (i.e., through the $\alpha_5\beta_1$ receptor). Thus, monoclonal antibody C2-9 identifies an amino acid sequence domain present in epiligrin-ECM$^t$, and epiligrin, that is a functional requisite for binding by at least $\alpha_3\beta_1$ integrin receptors.

25.5 Kinetics of Binding of Epiligrin at 4° C. and 37° C.

Kinetic binding assays were conducted wherein the binding of $\alpha_6\beta_4$-receptor bearing test cells (i.e., HFK) to epiligrin-ECM$^t$ was evaluated at 4° C. and 37° C. The rate of adherence of HFK test cells, or HFF control cells, to epiligrin-ECM$^t$ was determined using $^{51}$Cr-radiolabeled HFK and the test cell assays described above. The results are presented in TABLE 3, below.

TABLE 3

| Time (minutes) | 4° C. Assay (% Adherent Cells) | | 37° C. Assay (% Adherent Cells) | |
|---|---|---|---|---|
| | HFF | HFK | HFF | HFK |
| 0 | 1–2 | 30 | 0 | 0 |
| 2 | 1–2 | 28 | 4 | 10 |
| 5 | 1–2 | 28 | 6 | 10 |
| 10 | 1–2 | 25 | 8 | 20 |
| 15 | 1–2 | 37 | 18 | 26 |
| 25 | 1–2 | 35 | 29 | 36 |
| 30 | 1–2 | 31 | 30 | 38 |
| 45 | 1–2 | 30 | 38 | 50 |
| 60 | 1–2 | 35 | 57 | 60 |

Adherence of HFK test cells to epiligrin-ECM$^t$ was rapid, occurring to maximal values within 2 minutes, and adherence was specific for $\alpha_6\beta_4$-receptor bearing test cells, i.e., $\alpha_6\beta_4$-receptor-negative HFF control cells did not adhere under these conditions. Similar results were obtained with HT1080 control cells.

25.6 Composition of ECM Assembled by HFK at 4° C. and 37° C.

Previous studies indicated that detergent extraction (i.e., Triton X-100, as above) solubilizes $\alpha_3\beta_1$, but not $\alpha_6$, $\beta_4$ or BPA1 that are associated with SACs formed at 37° C. Since HFKs attached but did not spread at 4° C., a question arose as to the composition of the ECM under these conditions. HFK were allowed to adhere overnight at 4° C. to epiligrin-ECM$^t$. The next day the cells were removed with Triton X-100 and fluorescence microscopy was used to examine the detergent-insoluble cellular skeletons left by cells, with the following findings: namely, $\alpha_6$, $\beta_4$ and BPA1 were co-localized within the residual detergent insoluble ECM material. $\alpha_3\beta_1$ was not detected in the extracted ECM. These results suggest that HFK adhesion to epiligrin at 4° C. is mediated via $\alpha_6\beta_4$ in HDs that results in the formation of Triton-insoluble SACs.

25.7 A Specific Assay for Identification of Functional Epiligrin in Tissues

The binding of cells containing $\alpha_6\beta_4$ receptors to epiligrin-ECM$^t$ at 4° C., described above, formed the functional basis for a novel microscopic epiligrin-specific "rosetting" assay. In this assay cryostat sections of normal human skin were incubated at 4° C. with fluorescently-labeled $\alpha_6\beta_4$-receptor bearing HFK cells (i.e., HFK containing cytoplasmic FITC). Functional epiligrin in tissues was identified by binding of the labeled cells at 4° C. to only the basal stem cell basement membrane layer in the human epidermis. In contrast, at 37° C. the labeled cells bound to so many different cells types that no definitive structures could be identified. Thus, the 4° C. assay provides a simple and definitive test for identifying functional epiligrin ligand in normal and diseased epithelial tissues including e.g. epithelia in skin, gastric mucosa, lung, organs, endocrine glands, and the like. Suitable $\alpha_6\beta_4$-receptor bearing test cells that have been used in the assay include HFK and human papilloma virus transformed immortalized HFKs (i.e., E1L-8; Kaur et al., 1992). As a negative control, (e.g., for maintaining a constant 4° C. temperature during the assay), it may be desirable to use an $\alpha_6\beta_4$-receptor-negative control cell on a parallel cryostat section of tissue. Suitable negative control cells that have been used include HFFs, melanocytes, HT1080 cells, and $\alpha_3$-K562 cells. As a positive control, (e.g., for the overall health of the tissue section and for the activity of the $\alpha_6\beta_4$-receptor on the test cells), $\alpha_6\beta_4$-receptor bearing test cells were incubated with the cryostat tissue section at 37° C. (i.e., to allow both the $\alpha_6\beta_4$ and $\alpha_3\beta_1$-receptor).

Epidermal basal stem cells in patients with junctional epidermolysis bullosus (JEB) gravis are defective in epiligrin synthesis (Domloge-Hultsch et al.) and the patients exhibit a lethal blistering disease. It is thought highly likely that patients who synthesize functionally defective epiligrin (e.g., mutant epiligrin) will present clinically in a wide variety of seemingly unrelated skin diseases, which upon testing according to the assay of the invention will share a common underlying epiligrin-related etiology. Skin biopsy samples collected from patients exhibiting less severe forms of blistering and skin diseases, e.g., non-lethal JEB, psoriasis, and the like, may be processed as follows. First, pieces of the biopsy sample are quick frozen in preservative and prepared for cryostat sectioning according to routine procedures. Second, the 4° C. epiligrin-rosetting assay (developed above with FITC-labeled HFK cells), is used to identify locations in the patient tissue where functional epiligrin, (i.e., capable of binding an $\alpha_6\beta_4$-receptor positive test cell), is resident. It may be convenient to use a tissue sample of similar type from a normal individual as a positive control in the assay. Patients lacking a normal functional epiligrin are identified by qualitative and/or quantitative difference in the binding of the labeled $\alpha_6\beta_4$-receptor positive test cells. For example, the biosynthesis of a functionally defective epiligrin in a patient may be identified by fewer test cells binding, or a decreased rate of binding, at histological locations that would normally bind large numbers of test cells (i.e., in a normal tissue). Decreased numbers of test cells may be observed binding in the basement membrane zone in a skin biopsy sample within a 5 minute time interval. (In a similar manner, patients having autoimmune anti-epiligrin antibodies may show decreased binding of the test cells in tissues as a result of auto-antibodies blocking epiligrin ligand binding sites for the $\alpha_6\beta_4$-receptors on the test cells.) Alternatively, qualitative alterations in the distribution of epiligrin can be identified according to the assay, and these may result from defects in FA, HD, or SAC formation in the tissues of a patient, e.g., an actin cytoskeletal defect (or related energy metabolism defect) that prevents epiligrin from co-localizing with $\alpha_6$, $\beta_4$, and BPA1 in HDs.

26. Citations

1. Kefalides, N.A., Int. Rev. Connect. Tissue Res. 6:63–104, 1973.
2. Vracko, R., Am. J. Pathol. 77:314–338, 1974.
3. Timpl, R. and Martin, G., IN: Immunochemistry of Collagen (Furthmayr, H., Ed., vol. 11, pp- 119–150, CRC Press, Boca Raton, Fla.) 1982.
4. Laurie, G. W. and C. P. Leblond, Histochem. Cytochem. 31:159–163, 1983.
5. Yurchenko, P. and J. C. Schittny, FASEB J. 4:1577–1590, 1990.
6. Orkin, R. W., P. Gehron, E. B. McGoodwin, G. R. Martin, T. Valentine, and J. R. Swarm, J. Exp. Med. 145:204–220, 1977
7. Timpl, R., H. Rohde, P. Gehron Robey, S. Rennard, J. M. Roidat and G. R. Martin, J. Biol. Chem. 254:9933–9937, 1979.
8. Chung, A. E., R. Juffe, J. L. Freeman, J. P. Vergness, K. E. Broginski, and B. Carlin, Cell 16:277–287, 1979.
9. Carlin, B., R. Jaffe, B. Bender, and A. E. Chung, J. Biol. Chem. 256:5209–5214, 1981.
10. Kanwar, Y. S. and M. G. Farquhar, Proc. Natl. Acad Sci., USA, 76:4493–4497, 1979.
11. Hassell, J. R., W. C. Leyshon, S. R. Ledbetter, B. Tyree, S. Suzuki, K. Masoto, K. Kimata, and H. K. Kleinman, J. Biol. Chem. 260:8098–8105, 1985.
12. Laemmli, U. K., Nature 227:680–685, 1970
13. Kleinman, H. K. et al., Biochemistry 25:312–318, 1986.
14. Staehlin, L. A., Int. Rev. Cytol. 39:191–283, 1974.
15. Jones, J. C. R., K. M. Yokoo, and R. D. Goldman, Cell Motil. and Cytoskeleton 6:560–569, 1986.
16. Shienvold, F. L. and D. E. Kelly, Cell Tissue Res. 172:289–307, 1976.
17. Griepp, E. B. and E. S. Robbins, Epithelium in Cell and Tissue Biology. (Ed. L. Weiss), Urban & Swarzenburg, Inc., Baltimore, Md., 1988.
18. Burridge, K., K. Fath, T. Kelly, G. Nuckolls, and G. Turner, Ann. Rev. Cell Biol., 4:487–525, 1988.
19. Stepp et al., Pro. Natl. Acad. Sci. 87:8970–8974, 1990.
20. Carter, W. G., J. Cell Biol. 111:3141–3154, 1990.
21. Carter, W. G., E. A. Wayner, T. S. Bouchard, and P. Kaur, 1990, J. Cell Biol., 110:1387–1404.
22. Keene, D. R., L. Y. Sakai, G. P. Lunstrum, N. P. Morris, and R. E. Burgeson, J. Cell Biol. 104:611–620, 1987.
23. Keene et al., 1988.
24. Sakai, L. Y., D. R. Keene, N. P. Morris, and R. E. Burgeson, J. Cell Biol. 103:1577–1586, 1986.
25. Gipson et al., 1983.
26. Stanley, J. R. Clin. Invest. 94:617–623, 1989.
27. Tanaka, T., N. J. Korman, H. Shimizu, R. A. J. Eady, V. Klaus-Kovtun, K. Cehrs, and J. R. Stanley, J. Invest. Dermatol. 94:617–623, 1990.
28. Green, H. and J. G. Rheinwald, U.S. Pat. No. 4,016,036 (1977).
29. Green, H. et al., U.S. Pat. No. 4,304,866 (1981).
30. Green, H. et al., Proc. Nat. Acad. Sci., USA, 76:5665–5668, 1979.
31. Rheinwald and H. Green, Nature 265:421–424; 1977
32. Kamalti, T., M. Howard, and R. F. Brooks, Development 106:283–293, 1989.
33. Kamalti, T., Z. McIvor, M. Howard, and M. R. Green, Exp. Cell Res. 185:453–463, 1989.
34. Haake, A. R. and A. T. Lane, In vitro Develop. Biol. 25:592–560, 1989.
35. Pillai, S., D. D. Bikle, M. Hincenbergs, and P. M. Elias, J. Cell Physiol. 134(2):229–237, 1988.
36. Wilke, M. S., M. Edens, and R. E. Scott, J. Natl. Cancer Inst. 80:1299–1304, 1988.

37. Adams, J. C. and F. M. Watt, J. Cell Biol. 107(5):1927–1938, 1988.
38. Michel, S., R. Schmidt, S. M. Robinson, B. Shroot, and U. Reichert, J. Invest. Dermatol. 88:301–305, 1987.
39. Eckert, R. L. and H. Green, Cell 46:583–589, 1986.
40. Eckert, R. L. and E. A. Rorke, Environ. Health Perspect. 80:109–116, 1989.
41. Watt, F. M., J. Invest. Dermatol. 81 (1 Suppl.):100s–103s, 1983.
42. Murphy, G. F., T. C. Flynn, R. H. Rice, and G. S. Pinkus, J. Invest. Dermatol. 82:453–457, 1984.
43. Simon, M. and H. Green, J. Invest. Dermatol. 92:721–724,1989.
44. Parentau, N. L., R. L. Eckert, and R. H. Rice, Proc. Natl. Acad. Sci., USA 84:7571–7575, 1987.
45. Hronis, T. S., M. L. Steinberg, V. Defendi, and T. T. Sun, Cancer Res. 44:5797–5804, 1984.
46. Cline, P. R. and R. H. Rice, Canc. Res. 43:3203–3207, 1983
47. Watt, F. M., J. Invest. Dermatol. 81(1 Suppl.):100s–103s, 1983.
48. Simon, M. and H. Green, Cell 36:827–834, 1984.
49. Simon, M. and H. Green, Cell 40:677–683, 1985.
50. Martin, G. and R. Timpl, Ann. Rev. Cell Biol. 3:57–85, 1987.
51. Beck, K., L. Hunter, and J. Engel, FASEB, 4:148–160, 1990.
52. Hynes, R. O., Cell, 48:549–554, 1987.
53. Rouslahti, E., Ann. Rev. Biochem. 57:375–413, 1988.
54. Hemler, M. E., Immunol. Today 9:109,1988.
55. Buck, C. F. and A. F. Horwitz, Ann. Rev. Cell Biol. 3:179–205, 1990.
56. Tamura, R. N., C. Rozzo, L. Starr, J. Chambers, L. Reichardt, H. M. Cooper, and V. Quaranta, J. Cell. Biol. 111:1593–1604, 1990.
57. Wayner, E. A., W. G. Carter, R. S. Piotrowicz, and T. J. Kunicki, J. Cell Biol., 107:1881–1897, 1988.
58. DeLuca, M., R. N. Tamura, S. Kajiji, S. Bondanza, P. Rossino, R. Cancedda, P. C. Marchisio, and V. Quaranta, Proc. Natl. Acad. Sci. USA, 87:6888–6892, 1990.
59. Wayner, E. A. and W. G. Carter, J. Cell. Biol. 105:1873–1884, 1987.
60. Santoro, 1986.
61. Elices, M. J. and M. E. Hemler, Proc. Natl. Acad. Sci. USA 86:9906–9910, 1989.
62. Langvino et al., 1989.
63. Lotz, M. M., C. A. Korzelius, and A. M. Mercurio, Cell Regulation 1:249–257, 1990.
64. Sonnenberg, A., C. J. Linders, P. W. Modderman, C. H. Damsky, M. Aumailley, and R. Timpl, J. Cell Biol. 110:2145–2155, 1990.
65. Gehlsen, KR., K. Dickerson, W. S. Argraves, E. Engvall, and E. Rouslahti, J. Biol. Chem. 264:19034–19038, 1989.
66. Adams, J. C. and F. M. Watt, Cell 63:425–435, 1990.
67. Stanely, J. R., J. Clin. Invest. 83:1443–1448, 1989.
68. Kaufmann, R., D. Frosch, C. Westphal, L. Weber, and C. Klein, J. Cell Biol. 109:1807–1815, 1989.
69. Larjava, H., J. Peltonen, S. K. Akiyama, H. R. Gralnick, J. Uitto, and K. M. Yamada, J. Cell Biol. 110:803–815, 1990.
70. Hadley et al., J. Cell. Biol. 101:1511–1522, 1985.
71. Madison et al., 1985.
72. Carey, D. and M. Todd, unpublished results and L. Reid, unpublished results cited in Kleinman et al., # 13, above.
73 Bernard, B. A., S. M. Robinson, A. Semat, and M. Carmon, Canc. Res. 45:1707–1716, 1985.
74. Said, J. M., A. F. Sassoon, I. P. Shintaku, and S. Banks-Schlegel, J. Invest. Dermatol. 82:449–452, 1984.
75. Murphy, G. F., M. J. Warhol, and R. H. Rice, J. Invest. Dermatol. 82:453–457, 1984.
76. Levitt, M. L., A. F. Gazdar, H. K. Oie, H. Schulter, and S. M. Thacker, Cancer Res. 50:120–128, 1990.
77. Peterson, L. L., J. G. Zettergren, and K. D. Wuepper, J. Invest. Dermatol. 81(1 Suppl.):45s–100s, 1983.
78. Kvedar, J. C., J. Fewkes, and H. P. Baden, Arch. Pathol. Lab. Med. 110:183–188, 1986.
79. Elsayed, A., R. M. Richart, and C. P. Crum, Gynecol. Oncol. 26:25–34, 1987.
80. Harris, H. and M. E. Bramwell, J. Cell Sci. 87:383–388, 1987.
81. Bernard, B. A., S. M. Robinson, S. Vandaele, J. N. Mansbridge, and M. Darmon, Br. J. Dennatol. 112:647–653, 1985.
82. Schaumberg-Lever, W. F., J. Invest. Dermatol. 64:47–49, 1979.
83. Holubar, K., K. Wolfe, E. H. Beutner, J. Invest. Dermatol. 64:220–225, 1975.
84. Honigsmann, H., G. Stingl, K. Holubar, E. Wolff-Schreiner, K. Konrad, and K. Wolff, J. Invest. Dermatol. 66:262, 1976.
85. Nieboer, C., D. M. Boorsma, and M. J. Woerdeman, Br. J. Hematol. 106:419–422, 1983.
86. Fine, J. D., G. R. Neises, and S. I. Katz, J. Invest. Dermatol. 82:39–43, 1984.
87. Yaoita, H., R. A. Briggaman, T. J. Lawley, T. T. Provost, and S. I. Katz, J. Invest Dermatol. 76:288–292, 1981.
88. Stanley, J. R., P. Hawley Nelson, S. H. Yuspa, E. M. Sherach, and S. I. Katz, Cell 24:897–903, 1981.
89. Nisengard, R. J., S. Jablonska, E. H. Beutner, S. Shu, T. P. Chorzelski, M. Jarzabek, M. Blascyk and G. Rzesa, Oral Surgery 40:365–375, 1975.
90. Woodley, D. T., R. A. Briggaman, E. J. O'Keefe, A. O. Inman, L. L. Queen, and W. R. Gammon, N. Engl. J. Med. 310:1007–1013, 1984.
91. Stanley, J. R., P. Hawley Nelson, S. H. Yuspa, E. M. Shevach, and S. I. Katz, Cell 24:897–903, 1981.
92. Fine, J. D., J. Invest. Dermatol. 82:39–43, 1984.
93. Fine, J. D., Collagen Rel. Res. 5:369–377, 1985.
94. Kaur, P. and J. K. McDougall, J. Virol. 62:1917–1924, 1988.
95. Kaur, P., J. K. McDougall, and R. Cone, J. Gen. Virol. 70:1261–1266, 1989.
96. Wayner, E. A. et al., J. Cell Biol. 109:1321–1330, 1989.
97. Kunicki et al., 1988.
98. Carter, W. G., J. Biol. Chem. 257:13805–13815, 1982.
99. Oi and L. Herzenberg, IN: *Selected Methods in Cellular Immunology* (B. B. Mishell and S. M. Shiigi, Eds.), W. H. Freeman & Co. Publishers, San Francisco, Calif., pp. 351–373, 1980.
100. Taggart and Samloff, Science 219:1228–1230, 1983.
101. Neylakh, A. A., I. S. Tint, T. M. Svitkina, A. D. Bershadsky, and V. I. Gelfand, Exp. Cell. Res. 149:387–396, 1983.
102. Aumailley, M., R. Timpl, and A. Sonnenberg, Exp. Cell Res. 188:55–60, 1990.
103. Katz, S. I., J. Amer. Acad. Dermatol. 11:1025–1037, 1984.
104. Haber et al., J. Amer. Acad. Dermatol. 12:836–844, 1985.
105. Mar, H. and T. N. Wight, IN: *Colloidal Gold: Principles, Methods, and Applications*, vol. 2, (Ed. M. A. Hayat), Acad. Press, Inc., N.Y., 1989.
106. Boyce, S. T. and R. G. Ham, J. Tiss. Cult. Meth. 9:83–93, 1985.
107. Towbin et al., Proc. Natl. Acad. Sci. USA 76:4350–4354, 1979.

108. Michel, S. R. et al., J. Invest. Dermatol. 88:301–305, 1987.
109. Wolpert, L., J. Cell Sci., Suppl. 10:1–9, 1988.
110. Plantefaber, L. C. and R. O. Hynes, Cell 56:281–290, 1989.
111. Hemler, M. E., Immunol. Today 9:109,1988.
112. Carter, W. G., Wayner, E. A., Bouchard, T. S., and Kaur, P. (1990) J. Cell Biol. 110: 1387–1404.
113. Carter, W. G., Ryan, M. C., and Gahr, P. J. (1991) Cell 65:599–610.
114. Domloge-Hultsch, N., Gamnon, W. R., Griggaman, R. A., Gil, S. G., Carter, W. G., and Yancey, K. B. (1992) J. Clin. Invest. 90:1628–1633.
115. Henikoff, S. and Henikoff, J. G. (1992) Proc. Natl. Acad. Sci. USA 89:10915–10919.
116. Kaur, P. and McDougall, J. K. (I 988) J. Virol. 62:12917–1924.
117. Kaur, P., McDougall, J. K., and Cone, R. (1989) J. Gen. Virol. 70:1261–1266.
118. Maniatis, T., Fritsch, E. F., and Sambrook, J. (1982) Molecular Cloning: A Laboratory Manual; pp. 149–184, 382–387. Cold Spring Harbor Laboratory, Cold Spring Harbor, New York.
119. Rousselle, P., Lunstrum, G. P., Keene, D. R., and Burgeson, R. E. (1991) J. Cell Biol. 116:567–576.
120. Sanger, F., Nicklen, S., and Coulson, A. (1977) Proc. Natl. Acad. Sci. USA 74:5463–5467.
121. Verrando, P., Hsi, B-L., Yeh, C-J., Pisani, A., Serieys, N., and Ortonne, J-P. (1987) Exp. Cell. Res. 170:116–128.
122. Verrando, P., Blanchet-Bardon, C., Pisani, A., Thomas, L., Cambazard, F., Eady, R. A. J., Schofield, O., and Ortonne, J-P. (1991) Lab. Invest. 64:85–92.
123. Wayner, E. A., Gil, S. G., Murphy, G. F., Wilke, M. S., and Carter, W. G. (1993) J. Cell Biol. 121:1141–1152.
124. Young, R. A. and Davis, R. W. (1983) Proc. Natl. Aca. Sci. USA 80:1194–1198.
125. Burgeson, R. E., Chiquet, M., Deutzmann, R., Ekblom, P., Engel, J., Kleinman, H., Martin, G. R., Meneguzzi, G., Paulsson, M., Sanea, J., Timpl, R., Trygguason, U., Yamada, Y., and Yurchenco, P. D. (1994). Matrix Biology 14:209–211, 1994.
126. Gil, S. G., Brown, T. A., Ryan, M. C., and Carter, W. G., J. Invest. Dermatol. 103 (5 Suppl):31S–38S, 1994.
127. Fine, J. D., Bauer, E. A., Briggman, R. A., Carter, D. M., Eady, R. A. J., Esterly, N. B., Holbrook, K. A., Hurwitz, S., Johnson, L., Lin, H., Pearson, R., and Sybert, V. P., J. Am. Acad. Dermatol. 24:119–135, 1991.
128. Uitto, J., and Christiano, A. M., J. Clin. Invest. 90:687–692, 1992.
129. Weitzman, J. B., Pasqualin, R., Takada, Y., and Hemler, M. E., J. Biol. Chem268:8651–8657, 1993.
130. Niessen, E. H. M., Kuikman, I., and Sonnenber, A., Exp. Cell Res. 211:360–367, 1994.
131. Rouselle, P, and Aumailley, M., J. Cell Biol. 125:205–214, 1994.
132. [no entry]
133. Ryan, M. C., Tizard, R., VanDevanter, D. R., and Carter, W. G. J. Biol. Chem. 269 (in press).
134. Verrando, P., Pisani, A., and Ortonne, J.-P. Biochem. Biophys. Acta 942:45–56, 1988.
135. Baudoin, C., Aberdam, D., Ortonne, J.-P., and Meneguzzi, G. J. Invest. Dermatol. 102:549 (abstr.), 1994.
136. Altschul et al., J. Mol. Biol. 214:403–410, 1990
137. Brown, T., in Current Protocols in Molecular Biology, Vol. I, pp. 4.9.2–4.9.6, 1993
138. Carter, W. et al., in The Integrins: The Biological Problems (Takada, Y., ed.), 1994
139. Cohen, C., and Parry, A. D., Trends Biochem. Sci. 11:245–248, 1986.
140. Ehrig., K., et al., Proc. Natl. Acad. Sci. USA 87:3264–3268, 1990.
141. Garrison, K., et al., J. Biol. Chem. 266:22899–22904, 1992.
142. Gerecke, D. R. et al., J. Biol. Chem. 269:11073–11080, 1994.
143. Grinnell, F., J. Cell. Sci. 101:1–5, 1992.
144. Guan, J. L., and Hynes, R. O., Cell 60:53–61, 1989.
145. Hunter, I., et al., Eur. J. Biochem. 188:205–211, 1990.
146. Kallunki, P., et al., J. Cell Biol. 119:679–693, 1992.
147. Kanemoto, T., et al., Proc. Natl. Acad. Sci. USA 87:2279–2283, 1990.
148. Kaur, P., and Carter, W. G., J. Cell Sci. 103:755, 1992.
149. Komoriya, A., et al., J. Biol. Chem. 266:15075, 1991.
150. Kozak, M., J. Cell. Biol. 115:887, 1991.
151. Kubota, S., et al., J. Biol. Chem. 267:4285, 1992.
152. Maizel, J. V., and Lenk, R. P., Proc. Natl. Acad. Sci. USA 78:7665, 1981.
153. Marinkovich, M. P., et al., Lab. Invest. 69:295, 1993.
154. Nagayoshi, T., et al., Genomics 5:932, 1989.
155. Nissenen, M. et al., Biochem. J. 276:369, 1991.
156. Noonan, et al., J. Biol. Chem. 266:22939, 1991.
157. Rouselle, P., and Aumailley, M., J. Cell Biol. 125:205, 1994.
158. Sasaki, M., and Yamada, Y, J. Biol. Chem. 262:17111, 1987.
159. Sasaki, M., et al., Proc. Natl. Acad. Sci. USA 84:935, 1987.
160. Sasaki, M., et al., J. Biol. Chem. 263:16536, 1988.
161. VanDevanter, D. R., and Yirdaw, G., Genes Chromosomes & Cancer 6:190, 1992.
162. VanDevanter, D. R., et al., Proc. Natl. Acad. Sci. USA, 91:5858, 1994.
163. Vuolteenaho, R., et al., J. Cell Biol. 124:381, 1994.
164. Wayner, E. A., et al., J. Cell Biol. 109:1321, 1989.
165. Wilbur, Wj., and Lipman, D. J., Proc. Natl. Acad. Sci., USA 80:726, 1983.

The embodiments of the invention in which an exclusive property or privilege is claimed are defined as follows:

1. An isolated nucleic acid having a length of at least 15 nucleotides capable of hybridizing under stringent conditions to the nucleotide sequence shown in SEQ ID NO:23, or its complement.

2. The nucleic acid of claim 1, capable of hybridizing under stringent conditions to the nucleotide sequence shown in SEQ ID NO:21.

3. The nucleic acid of claim 1, capable of hybridizing under stringent conditions to the nucleotide sequence shown in SEQ ID NO:22.

4. The nucleic acid of claim 1, capable of hybridizing under stringent conditions to at least one nucleotide sequence selected from the group consisting of Ep-1 (ATCC No. 75540), 1-1 (ATCC No. 75539), and 8-6 (ATCC No. 75538).

5. A vector molecule comprising the nucleic acid of claim 1.

6. A cell transduced or transfected with a vector molecule comprising the nucleic acid of claim 1.

7. The cell of claim 6, which expresses a E170 epiligrin glycoprotein.

8. A method for isolating from cellular nucleic acid a nucleic acid encoding a E170 epiligrin glycoprotein, comprising the steps of:

isolating single-stranded cellular nucleic acid;

selecting two or more of primers selected from the group consisting of SEQ ID NOS:1–20;

binding the selected primers under stringent hybridization conditions to the isolated single-stranded cellular nucleic acid;

extending the bound primers with Taq polymerase to form a duplex cellular nucleic acid;

amplifying the duplex cellular nucleic acid by PCR cycling; and, cDNA cloning the product of the PCR cycling and identifying cDNAs hybridizing to the nucleotide sequence depicted in SEQ ID NO:23.

* * * * *

UNITED STATES PATENT AND TRADEMARK OFFICE
CERTIFICATE OF CORRECTION

PATENT NO. : 6,120,991
DATED : September 19, 2000
INVENTOR(S) : W.G. Carter et al.

It is certified that error appears in the above-identified patent and that said Letters Patent is hereby corrected as shown below:

Title page,
Item [56], References Cited, OTHER PUBLICATIONS, after "Kefalides, NA.," insert -- Aberdam, D. et al., "Assignment of mouse nicein genes to Chromosomes 1 and 18," *Mamm. Genome* 5:229-233, 1994. --
"Kanwar, Y.S. and Farquhar, M.G." reference after "*Natl.*" insert -- *Acad.* --
"Griepp, E.B. and Robbins, E.S.," reference before "L. Weiss," insert -- ( --
"Engall, E. et al.," reference "Engall," should read -- Engvall, --
"Green H., et al.," reference "*Nat.*" should read -- *Natl.* --

Column 1,
Line 3, insert the following paragraph -- This invention was supported by grants from the National Institutes of Health under grants numbers CA 49259 and GM 15085. The government has certain rights in the invention. --

Column 6,
Line 30, after "$\alpha_3\beta_1$" delete ","
Line 47, "$\beta_2\beta_1$" should read -- $\alpha_2\beta_1$ --
Line 52, after "$\alpha_2\beta_1$" delete ","

Figure 5D:
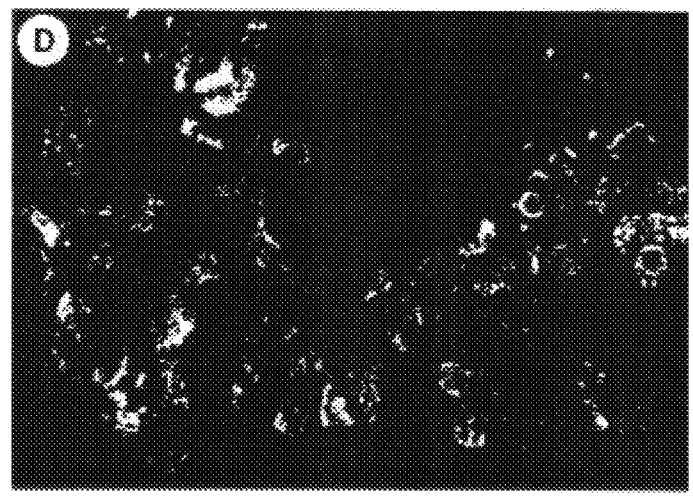
Figure 5E:
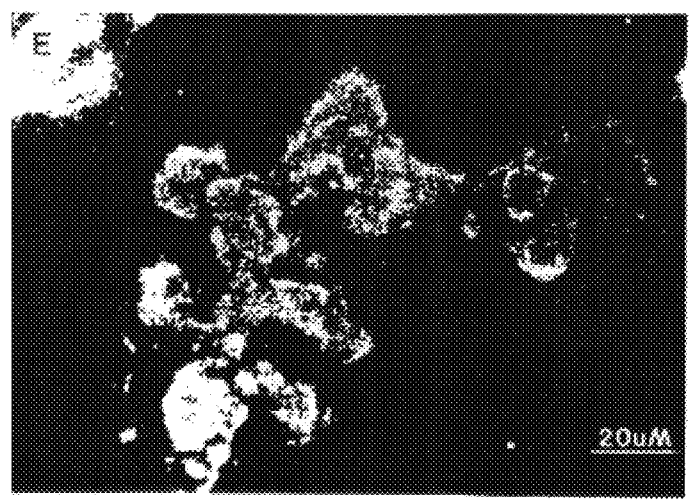
Figure 5F:
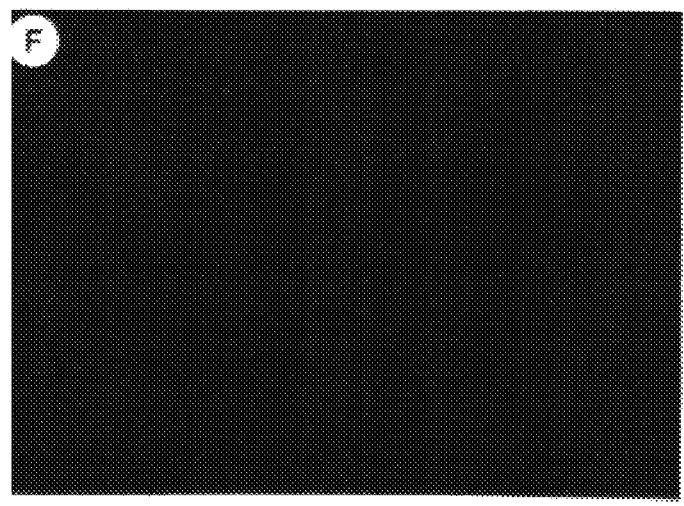

Column 9,
Line 36, "he subject" should read -- the subject --
Line 37, before "FIG. 5D)," insert -- ( --
Line 37, "P1 F2," should read -- P1F2, --
Line 38, "FK-ECM" should read -- HFK-ECM --
Line 40, after "fibroblasts" insert -- to --

Column 10,
Line 52, "20FFF." should read -- 20F. --

Column 11,
Line 6, "$\alpha_3\beta_4$" should read -- $\alpha_3\beta_1$ --
Line 8, "$\alpha_3 \beta_1$" should read -- $\alpha_3\beta_1$ --

Column 12,
Line 35, after "$\alpha_3\beta_1$" delete ","
Line 49, "epithelia" should read -- epithelial --

Column 13,
Line 49, after "$\alpha_3\beta_1$" delete ","

UNITED STATES PATENT AND TRADEMARK OFFICE
CERTIFICATE OF CORRECTION

PATENT NO. : 6,120,991
DATED : September 19, 2000
INVENTOR(S) : W.G. Carter et al.

It is certified that error appears in the above-identified patent and that said Letters Patent is hereby corrected as shown below:

Column 14,
Line 3, "$\alpha_3\alpha_1$" should read -- $\alpha_3\beta_1$ --

Column 17,
Line 11, "form" should read -- formed --
Line 35, "bum" should read -- burn --

Column 19,
Line 46, "C-41/CRL1595" should read -- C-4I/CRL1595 --

Column 24,
Line 10, "anti-$\alpha_3 \beta_1$," should read -- anti-$\alpha_3\beta_1$ --
Line 65, "microscopy. of" should read -- microscopy. Of --

Column 25,
Lines 12 and 22, after "$\alpha_3\beta_1$" delete "."
Line 20, "$\alpha_3 \beta_1$" should read -- $\alpha_3\beta_1$ --

Column 26,
Line 1, "(FN)" should read -- (FN; --
Line 26, after "$\alpha_5\beta_1$" delete ","
Line 26, after "$\alpha_6\beta_1$" delete ","

Column 27,
Line 35, after "$\alpha_3\beta_1$" delete ","

Column 29,
Line 15, "CO2" should read -- $CO_2$ --

Column 30,
Line 28, "mono
        clonal" should read -- mono-
        clonal --
Line 52, "HFK-ECM)." should read -- HFK-ECM.) --

Column 31,
Line 47, "sing" should read -- using --

Column 32,
Line 31, "urea, These" should read -- urea. These --

UNITED STATES PATENT AND TRADEMARK OFFICE
CERTIFICATE OF CORRECTION

PATENT NO. : 6,120,991
DATED : September 19, 2000
INVENTOR(S) : W.G. Carter et al.

It is certified that error appears in the above-identified patent and that said Letters Patent is hereby corrected as shown below:

Column 33,
Line 44, "E170,E145,E135" should read -- E170, E145, E135 --
Line 45, "marked "P1E1")." should read -- marked "P1E1".) --

Column 34,
Line 3, "3H-glucosamine" should read -- $^3$H-glucosamine --

Column 35,
Line 25, "$α_3⊕_1$" should read -- $α_3β_1$ --
Lines 32-33, the term "P1
             B5" should not break across a paragraph
Line 56, after "tested" delete ","
Line 57, "after "other" delete ","
Line 61, "a $α_3β_1$ receptors" should read -- $α_3β_1$ receptors --
Line 67, after "$α_3β_1$" delete ","

Column 38,
Line 5, "($α_3$" should read -- $α_3$ --
Line 22, after "$α_6$" delete ","

Column 42,
Line 8, after "carcinoma" insert -- ) --
Line 26, "(P4C10)" should read -- (P4C10) --
Line 37, "after "$α_6β_1$" delete ","
Line 41, "b$_4$" should read -- $β_4$ --

Column 43,
Line 15, "Sequence Transcripts" should read -- Sequence, Transcripts, --

Column 44,
Lines 57-58, "cells lines" should read -- cell lines --
Line 59, "al," should read -- al. --

Column 45,
Line 8, "NO:27" should read -- NOS:27 --
Line 23, "NO:29" should read -- NOS: 29 --
Line 61, "a cells" should read -- cells --

UNITED STATES PATENT AND TRADEMARK OFFICE
CERTIFICATE OF CORRECTION

PATENT NO.    : 6,120,991
DATED         : September 19, 2000
INVENTOR(S)   : W.G. Carter et al.

It is certified that error appears in the above-identified patent and that said Letters Patent is hereby corrected as shown below:

<u>Column 46,</u>
Line 37, "Gathersburg," should read -- Gaithersburg, --
Line 50, "MR4" should read -- MR-4 --

<u>Column 47,</u>
Line 28, "after "15A-15F" insert -- (SEQ ID NO:23) --
Line 57, "Drosophila" should read -- *Drosophila* --
Line 61, "Drosophila" should read -- *Drosophila* --

<u>Column 48,</u>
Line 6, "are marked" should read -- is marked --
Line 24, "K2 chain" should read -- γ2 chain --
Line 48, "Drosophila" should read -- *Drosophila* --
Line 50, "a chains" should read -- α chains --
Line 54, "Drosophila" should read -- *Drosophila* --

<u>Column 49,</u>
Line 13, before "probe" insert -- a --

<u>Column 50,</u>
Lines 61-62, "Man-
          nheim" should break as follows
          -- Mann-
          heim --

<u>Column 51,</u>
Line 4, "50C" should read -- 50°C --
Line 38, "$\alpha_3 \beta_1$" should read -- $\alpha_3\beta_1$ --

<u>Column 52,</u>
Line 39, "$\alpha_3 \beta_1$-epiligrin" should read -- $\alpha_3\beta_1$-epiligrin --

<u>Column 53,</u>
Line 28, ""Epiligrin-ECM" should read -- "Epiligrin-ECM" --
Line 39, ""epiligrin-ECM" should read -- "epiligrin-ECM$^b$" --

UNITED STATES PATENT AND TRADEMARK OFFICE
CERTIFICATE OF CORRECTION

PATENT NO. : 6,120,991
DATED : September 19, 2000
INVENTOR(S) : W.G. Carter et al.

It is certified that error appears in the above-identified patent and that said Letters Patent is hereby corrected as shown below:

Column 54,
Line 39, "$\alpha_6,\beta_4$" should read -- $\alpha_6\beta_4$ --
Line 47, after "$\alpha_3\beta_1$" delete ","

Column 55,
Line 9, after "$\alpha_3\beta_1$" delete ","
Line 52, "Staphlococcal" should read -- Staphylococcal --

Column 57,
Line 5, "cells types" should read -- cell types --
Line 8, "including e.g." should read -- including, e.g., --
Line 43, after "epiligrin" delete ","

Column 58,
Line 6, "pp-" should read -- pp. --
Line 48, after "J.R." insert -- , --

Column 59,
Line 2, "107(5)
　　　:1927-1938," should break as follows -- 107(5):
　　　1927-1938, --
Line 9, "(1 Suppl.).
　　　:100s-103s," should break as follows -- (1 Suppl.):
　　　100s-103s, --
Line 29, "9:109,1988" should read -- 9:109, 1988 --
Line 51, "KR," should read -- K.R., --

Column 61,
Line 6, "9:109,1988" should read -- 9:109, 1988 --
Lines 16-17, "(I 988) J. Virol. 62:12917-1924." should read -- (1988) J. Virol. 62:12917-12924. --
Line 35, "Aca." should read -- Acad. --
Line 51, "Chem268:8651-8657," should read -- Chem. 268:8651-8657, --

UNITED STATES PATENT AND TRADEMARK OFFICE
CERTIFICATE OF CORRECTION

PATENT NO. : 6,120,991
DATED : September 19, 2000
INVENTOR(S) : W.G. Carter et al.

It is certified that error appears in the above-identified patent and that said Letters Patent is hereby corrected as shown below:

Column 62,
Line 9, "G.J." should read -- G.J., --
Line 52, "Wj., and Lipman," should read -- W.J., and Lipman, --
Line 53, after "USA" insert -- , --

Column 104,
Line 57, "Taq" should read -- *Taq* --

Signed and Sealed this

Sixth Day of May, 2003

JAMES E. ROGAN
*Director of the United States Patent and Trademark Office*